(12) United States Patent
Kelly et al.

(10) Patent No.: US 8,906,681 B2
(45) Date of Patent: Dec. 9, 2014

(54) RELIABLE STABILIZATION OF N-LINKED POLYPEPTIDE NATIVE STATES WITH ENHANCED AROMATIC SEQUONS LOCATED IN POLYPEPTIDE TIGHT TURNS

(75) Inventors: Jeffery W. Kelly, LaJolla, CA (US); Joshua L. Price, Vineyard, UT (US); Elizabeth K. Culyba, Arlington, MA (US); Evan T. Powers, San Diego, CA (US)

(73) Assignee: The Scripps Research Institute, LaJolla, CA (US)

( * ) Notice: Subject to any disclaimer, the term of this patent is extended or adjusted under 35 U.S.C. 154(b) by 0 days.

(21) Appl. No.: 13/565,502

(22) Filed: Aug. 2, 2012

(65) Prior Publication Data

US 2013/0034547 A1 Feb. 7, 2013

Related U.S. Application Data

(60) Provisional application No. 61/514,202, filed on Aug. 2, 2011.

(51) Int. Cl.
| | |
|---|---|
| *C12N 5/07* | (2010.01) |
| *C07K 1/00* | (2006.01) |
| *C07K 16/00* | (2006.01) |
| *C07K 14/00* | (2006.01) |
| *C07K 1/107* | (2006.01) |
| *A61K 38/00* | (2006.01) |

(52) U.S. Cl.
CPC ............. *C07K 14/00* (2013.01); *C07K 2319/70* (2013.01); *C07K 16/00* (2013.01); *A61K 38/00* (2013.01); *C07K 1/1077* (2013.01)
USPC .......... 435/326; 530/402; 530/387.1

(58) Field of Classification Search
None
See application file for complete search history.

(56) References Cited

U.S. PATENT DOCUMENTS 6,491,916 B1 * 12/2002 Bluestone et al. ......... 424/133.1
8,084,584 B2   12/2011 Sugo et al.

2003/0096281 A1 * 5/2003 Venkataraman et al. ......... 435/6
2007/0041979 A1   2/2007 Raju et al.
2010/0286067 A1 * 11/2010 DeFrees ....................... 514/20.9

OTHER PUBLICATIONS

Bowie et al, 1990, Science 247:1306-1310.*
Wells, 1990, Biochemistry 29:8509-8517.*
Ngo et al., 1994, The Protein Folding Problem and Tertiary Structure Prediction, Merz et al., eds, Birkhauser, Boston, pp. 433-506.*
Wang et al 2001. J. Biol Chem. 276:49213-49220.*
WO 2012/039954 Search Report.
WO 2012/039954 Written Opinion.
Chou, *Anal Biochem* 286, 1-16 (2000).
Richardson, *Adv Protein Chem* 34, 167-339 (1981).
Price et al., *J Am Chem Soc* 132, 15359-15367 (2010).
Culyba et al., *Science* 331, 571-575 (Feb. 4, 2011).
Price et al., *Proc Natl Adad Sci*, USA 108(34), 14127-14132 (Aug. 23, 2011).
Chen et al., *J Am Chem Soc* 135, 9877-9884 (2013).
Anon., *C&ENews*, Am. Chem Soc., p. 26 (Feb. 7, 2011).
Prabakaran et al., *Acta Cryst*. D64:1062-1067 (2008).
Voynov et al., *PLoS One*, (Dec. 2009) 4(12):e8425, p. 2
Valliere-Douglass et al., *J Biol Chem* 284(47):32493-32506 (2009).

* cited by examiner

*Primary Examiner* — Shulamith H Shafer
(74) *Attorney, Agent, or Firm* — Husch Blackwell, LLP

(57) ABSTRACT

A chimeric therapeutic polypeptide of a pre-existing therapeutic polypeptide is disclosed, as are a method of enhancing folded stabilization and a pharmaceutical composition of the glycosylated chimer. The pre-existing and chimeric polypeptides have substantially the same length, substantially the same amino acid residue sequence, and exhibit at least one tight turn containing a sequence of four to about seven amino acid residues in which at least two amino acid side chains extend on the same side of the tight turn and are within less than about 7 Å of each other. The chimeric therapeutic polypeptide has the sequon Aro-(Xxx)n-(Zzz)p-Asn-Yyy-Thr/Ser (SEQ ID NO:001) within that tight turn sequence such that the side chains of the Aro, Asn and Thr/Ser amino acid residues project on the same side of the turn and are within less than about 7 Å of each other. That sequon is absent from the pre-existing therapeutic polypeptide.

25 Claims, 9 Drawing Sheets

FIG. 1
Fig. 1A
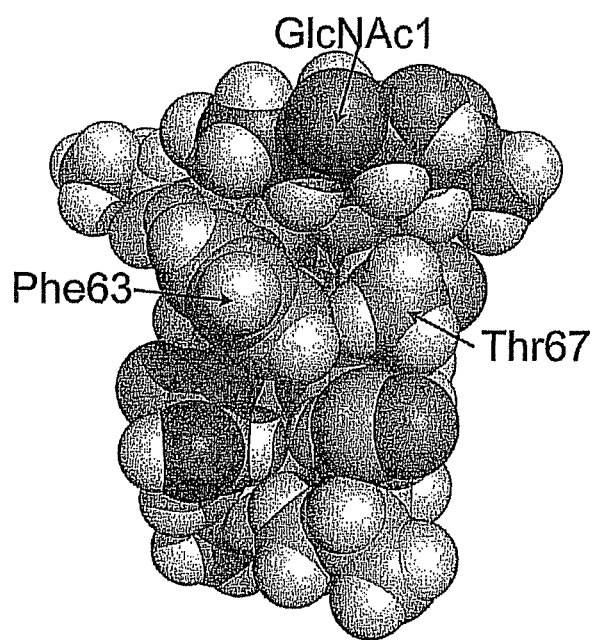
Fig. 1B
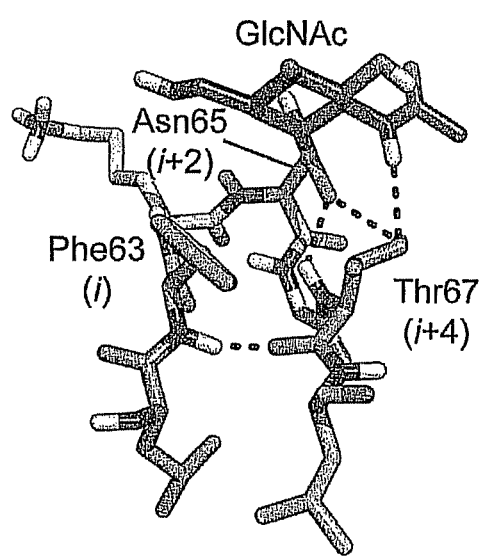

type II β-turn
in a six-residue loop five-residue
type I β-bulge turn four-residue
type I' β-turn FIG. 5
Fig. 5A
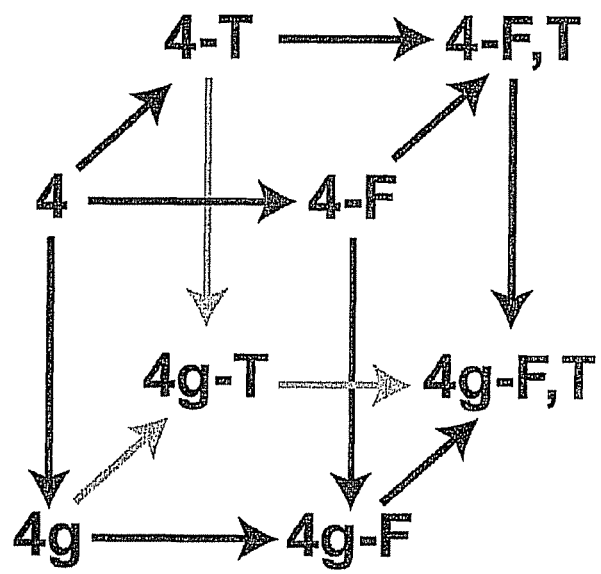
Fig. 5B
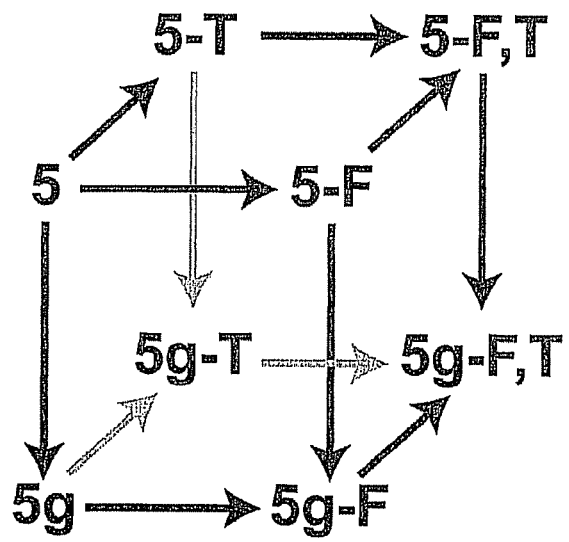

RELIABLE STABILIZATION OF N-LINKED POLYPEPTIDE NATIVE STATES WITH ENHANCED AROMATIC SEQUONS LOCATED IN POLYPEPTIDE TIGHT TURNS

CROSS-REFERENCE TO RELATED APPLICATION

This application claims priority from provisional application No. 61/514,202, filed Aug. 2, 2011 whose disclosures are incorporated herein by reference.

GOVERNMENTAL SUPPORT

The present invention was made with governmental support under Contract Nos. GM051105 and GM086039 awarded by the National Institutes of Health. The government has certain rights in this invention.

BACKGROUND ART

Nearly one-third of the eukaryotic proteome traverses the cellular secretory pathway [Imperiali, *Acc. Chem. Res.* 30, 452-459 (1997)]. Many of these proteins are co-translationally N-glycosylated at Asn residues within the conserved $Asn^1$-$Yyy^2$-$Thr^3$/$Ser^3$ sequon, where Yyy is any amino acid residue other than proline and is located at position 2 between an asparagine (Asn) at the amino-terminal end of the sequon and a threonine or serine (Thr/Ser) at the carboxy-terminal end of the sequon. N-Glycosylation can increase the stability of proteins, however the molecular basis for this is enhanced stability is incompletely understood.

As the ribosome inserts polypeptide chains into the endoplasmic reticulum (ER), the enzyme oligosaccharyl transferase (OST) attaches the highly conserved $Glc_3Man_9GlcNAc_2$ (where Glc is glucose, Man is mannose, and GlcNAc is N-acetylglucosamine) glycan (oligosaccharide) en bloc to the N atom of the Asn side chain in a subset of Asn-Xxx-Thr/Ser sequons [Kornfeld et al., *Annu Rev Biochem* 54, 631-664 (1985); and Kelleher et al., *Glycobiology* 16:47 R-62R (2006)]. N-linked glycans have important extrinsic effects on folding in the ER by allowing glycoproteins to enter the calnexin/calreticulin (CNX/CRT) folding/degradation pathway [Molinari, *Nat Chem Biol* 3, 313-320 (2007); Helenius et al., *Science* 291, 2364-2369 (2001)]. N-glycans can also have intrinsic effects on protein folding by enhancing protein folding efficiency in cells, even when the CNX/CRT pathway is absent [Banerjee et al., *Proc Natl Acad Sci USA* 104, 11676-11681 (2007); Trombetta, *Glycobiology* 13, 77R-91R (2003)] or when the N-glycan does not allow CNX/CRT interactions [Stanley et al., *FASEB J* 9, 1436-1444 (1995)], consistent with reports that N-glycans stabilize protein structure, accelerate folding, and reduce aggregation in vitro [Wormald et al., *Structure with Folding & Design* 7, R155-R160 (1999); Jitsuhara et al., *J Biochem* 132, 803-811 (2002); Mitra et al., *Trends in Biochemical Sciences* 31, 156-163 (2006)].

The increased use of protein therapeutics has made issues such as stabilized polypeptide structure, accelerated folding, and reduced aggregation of paramount importance to the pharmaceutical industry [Li et al., *Curr Opin Biotechnol* 20, 678-684 (2009); Sinclair et al., *J Pharm Sci* 94, 1626-1635 (2005); Sola et al., *BioDrugs* 24, 9-21 (2010); Walsh et al., *Nat Biotechnol* 24, 1241-1252 (2006)]. The therapeutic benefits of N-glycosylation are exemplified in darbepoetin alfa (an erythropoietin variant with two additional N-glycans) [Egrie et al., *Exp Hematol* 31, 290-299 (2003), interferon β [Runkel et al., *Pharm Res* 15, 641-649 (1998)], and follicle stimulating hormone [Perlman et al., *J Clin Endocrinol Metab* 88, 3227-3235 (2003)].

A number of types of tight turns within secondary protein or polypeptide sequences have described in the literature. These structures are referred to as a δ-turn that encompasses two amino acid residues, a γ-turn that involves three residues, a β-turn that involves four amino acid residues, an α-turn that involves five residues and a π-turn that involves six residues. [Chou, *Anal Biochem* 286, 1-16 (2000).]

A β-turn or reverse turn contains a sequence of four consecutive amino acid residues that are designated i, i+1, i+2 and i+3, in the direction from N-terminus toward C-terminus of the polypeptide. The five residues of an α-turn are designated i, i+1, i+2, i+3 and i+4. Most, but not all reverse turns and α-turns contain a hydrogen bond between the first and fourth or first and fifth residues, respectively, in which the residue designated i contains a peptide bond (peptidyl) carbonyl group (>C=O), whereas the fourth residue, i+3, or the fifth residue, i+4, contains the peptidyl —NH— group whose hydrogen is hydrogen-bonded to the carbonyl oxygen of the i residue. Residues bonded to the amino group of the i residue (toward the amino-terminus from the i residue) are designated i−1, i−2, i−3, etc.

Another way to define a reverse turn and an α-turn motif is by the close approach, less than 7 Å, of $C^\alpha$ atoms (alpha-carbon atoms) of the residues of the motif. Thus, one can define a β-turn and an α-turn by the close approach of $C^\alpha$ atoms of residues I and i+3 or i and i+4, respectively. [Chou, *Anal Biochem* 286, 1-16 (2000).] This distance implies a particular geometry of the corresponding backbone, which turns back on itself or, more generally, that corresponds to a change of direction, and that the residue side chains are on the same side of the backbone chain.

The β-turns are usually described as orienting structure because they orient α-helices, and β-sheets, indirectly defining the topology of proteins. They are one of the most abundant secondary structures.

Several types of reverse turns have been identified and are designated types I, I', II, III, IV, V and VI. Types I and II are the most common reverse turns, the essential difference between them being the orientation of the peptide bond between residues at i+1 and i+2. The i+2 residue of the type II turn can substantially only be occupied by glycine because of steric interference of the carbonyl group of the i+1 residue.

It was recently shown that naturally occurring N-glycosylation at a single Asn residue comprising a reverse turn within the adhesion domain of human glycoprotein CD2 (HsCD2ad) stabilizes the protein by −3.1 kcal $mol^{-1}$, makes folding four times faster, and makes unfolding 50 times slower in vitro [Hanson et al., *Proc Natl Acad Sci USA* 106, 3131-3136 (2009)]. However, introducing N-glycans into proteins that are not normally glycosylated (naïve proteins) has previously rarely led to substantially improved folding energetics [Hackenberger et al., *J Am Chem Soc* 127, 12882-12889 (2005); Wang et al., *Biochemistry* 35, 7299-7307 (1996); Elliott et al., *J Biol Chem* 279, 16854-16862 (2004)].

The present inventors and co-workers recently showed that glycosylation of an Asn residue within the sequence Aro-(Xxx)n-(Zzz)p-Asn-Yyy-Thr/Ser, where Aro is an aromatic amino acid residue such as histidine, phenylalanine, tyrosine or tryptophan, n is zero, 1, 2, 3 or 4, Xxx is an amino acid residue other than an aromatic residue, p is zero or one, Zzz is any amino acid residue, Asn is asparagine, Yyy is any amino acid residue other than proline, Thr/Ser is one or the other of the amino acid residues threonine and serine, stabilizes the glycosylation-naïve rat CD2 adhesion domain (RnCD2ad)

and human muscle acylphosphatase (AcyP2) by about −2 kcal mol$^{-1}$, provided that Asn is located at the i+2 position of a type I β-turn with a G1 β-bulge using the terminology of Sibanda et al., *J Mol Biol* 206(4), 759-777 (1989); Richardson, *Adv Protein Chem* 34, 167-339 (1981), hereafter called a type I β-bulge turn [Culyba et al., *Science* 331, 571-575 (2011); Application Ser. No. 61/380,967, filed 8 Sep. 2010].

Published structural data [Wyss et al., *Science* 269, 1273-1278 (1995)] from the human ortholog of RnCD2ad (HsCD2ad, FIG. 1A) suggest that placement of an N-glycan at i+2 in the type I β-bulge turn context permits the α-face of GlcNAc1 of the N-glycan to engage in stabilizing hydrophobic interactions with the aromatic ring of Phe at the i position, and the side-chain methyl group of Thr at the i+4 position {a stabilizing C—H/π interaction may also play a role [Laughrey et al., *J Am Chem Soc* 130(44), 14625-14633 (2008)]}.

Thus, it is hypothesized that the substantial energetic benefits of glycosylating a protein such as HsCD2ad depend on both the reverse turn context of the glycosylation site and the surrounding amino acid sequence. Some results showing the correctness of this hypothesis as applied to therapeutic polypeptides are shown and discussed hereinafter.

BRIEF DESCRIPTION OF THE INVENTION

A chimeric therapeutic polypeptide of a pre-existing therapeutic polypeptide is contemplated. Such a therapeutic chimeric polypeptide is often present in isolated and purified form.

The pre-existing therapeutic polypeptide has a length of about 15 to about 1000, preferably about 25 to about 500, and more preferably about 35 to about 300, amino acid residues, and exhibits a secondary structure that comprises at least one tight turn containing a sequence of four to about seven amino acid residues in which at least two amino acid side chains extend on the same side of the tight turn and are within less than about 7 Å of each other. The pre-existing therapeutic polypeptide lacks the sequon, in the direction from left to right and from N-terminus to C-terminus, Aro-(Xxx)n-(Zzz)p-Asn-Yyy-Thr/Ser [SEQ ID NO:001], within that sequence of four to about seven amino acid residues. In that sequon, Aro is an aromatic amino acid residue such as histidine, phenylalanine, tyrosine or tryptophan, n is zero, 1, 2, 3 or 4, Xxx is an amino acid residue other than an aromatic residue, p is zero or one, Zzz is any amino acid residue, Asn is asparagine, Yyy is any amino acid residue other than proline, Thr/Ser is one or the other of the amino acid residues threonine and serine. Except for the four to about seven residues within the tight turn, a contemplated chimeric therapeutic polypeptide has the same length, at least one tight turn and substantially the same amino acid residue sequence as the pre-existing therapeutic polypeptide. The two sequences differ by the presence in the chimeric therapeutic polypeptide of the sequon, Aro-(Xxx)n-(Zzz)p-Asn-Yyy-Thr/Ser (SEQ ID NO:001) as defined above. That sequon is located at the same position in the tight turn as the sequence of four to about seven amino acid residues such that the side chains of the Aro, Asn and Thr/Ser amino acid residues project on the same side of the turn and are within less than about 7 Å of each other. In one preferred embodiment, "n" is 1 and "p" is 1 and the chimeric polypeptide contains a Type II β-turn in a six-residue loop.

In another preferred embodiment, "n" is 1 and "p" is zero. The two polypeptide sequences differ by the presence in the chimeric therapeutic polypeptide of the sequon, Aro-Xxx-Asn-Yyy-Thr/Ser (SEQ ID NO:002) as defined above. The chimeric polypeptide preferably contains a five-residue type I β-bulge turn.

In still another preferred embodiment, "n" is zero and "p" is zero. The two sequences differ by the presence in the chimeric therapeutic polypeptide of the sequon, Aro-Asn-Yyy-Thr/Ser (SEQ ID NO:003) as defined above. Here, a preferred chimeric polypeptide contains a four-residue type I' β-turn.

In preferred practice, when the sequon is glycosylated, the therapeutic chimeric polypeptide exhibits a folding stabilization enhancement by about −0.5 to about −4 kcal/mol compared to the before-mentioned pre-existing therapeutic polypeptide in non-glycosylated form.

It is to be understood that substantially any and every therapeutic polypeptide that contains a tight turn in its secondary structure is contemplated herein. For example, substantially all of the Fc portions of human IgG antibodies contain one or two tight turn sequences to which the present invention can be applied. One of those sequences is often glycosylated, whereas the other is not glycosylated.

In some preferred embodiments, the sequon has the sequence, in the direction from left to right and from N-terminus to C-terminus, -Lys-(Zzz)m-Aro-(Xxx)n-(Zzz)p-Asn-Yyy-Thr/Ser (SEQ ID NO:004), wherein m is zero, 1, 21, or 3, n is 0, 1, 2, 3, or 4, p is zero or one, and Lys is lysine, and Zzz, Aro, Xxx, Asn, Yyy and Thr/Ser are as defined above.

A method of enhancing folded stabilization of a therapeutic polypeptide is also contemplated. A contemplated therapeutic polypeptide has a sequence of about 15 to about 1000, preferably about 25 to about 500, and more preferably about 35 to about 300, amino acid residues, and exhibits a secondary structure that comprises at least one tight turn in which the side chains of two residues in a preferably glycosylation-free sequence of four to about seven amino acid residues within the tight turn project on the same side of the turn and are within less than about 7 Å of each other. In accordance with the method, a therapeutic chimeric polypeptide is prepared. That therapeutic chimeric polypeptide has the same length and substantially same amino acid sequence as the therapeutic polypeptide, and exhibits a secondary structure containing at least one tight turn at the same sequence position within the tight turn of the therapeutic polypeptide except that the sequence of preferably glycosylation-free four to about seven amino acid residues is replaced with the sequon, in the direction from left to right and from N-terminus to C-terminus, Aro-(Xxx)n-(Zzz)p-Asn(Glycan)-Yyy-Thr/Ser (SEQ ID NO:005), wherein Aro is an aromatic amino acid residue, n is zero, 1, 2, 3 or 4, Xxx is an amino acid residue other than an aromatic residue, p is zero or one, Zzz is any amino acid residue, Asn(Glycan) is glycosylated asparagine, Yyy is any amino acid residue other than proline, Thr/Ser is one or the other of the amino acid residues threonine and serine, and the side chains of the Aro, Asn(Glycan) and Thr/Ser amino acid residues project on the same side of the tight turn and are within less than about 7 Å of each other.

In some embodiments, a therapeutic chimeric polypeptide is prepared by expressing a nucleic acid sequence that encodes the polypeptide sequence of the therapeutic chimeric polypeptide in a host cell that glycosylates the amino acid residue sequence Aro-(Xxx)n-(Zzz)p-Asn-Yyy-Thr/Ser (SEQ ID NO:001) when present in a polypeptide sequence expressed therein to form a polypeptide containing the amino acid residue sequence Aro-(Xxx)n-(Zzz)p-Asn(Glycan)-Yyy-Thr/Ser (SEQ ID NO:005). In other embodiments, a therapeutic chimeric polypeptide is prepared by in vitro peptide synthesis.

Another embodiment is a pharmaceutical composition that comprises an effective amount of a before-discussed chimeric therapeutic polypeptide dissolved or dispersed in a pharmaceutically acceptable diluent composition. That pharmaceutical composition typically also contains water, at least when administered.

The present invention has several benefits and advantages. One benefit is that a therapeutic polypeptide whose folding is thermodynamically more stable by the preparation of glycosylated chimer whose amino acid residue sequence is almost identical to that of the therapeutic polypeptide.

An advantage of the invention is that the preparation of a glycosylated chimeric therapeutic polypeptide is readily accomplished.

Still further benefits and advantages will be apparent to those of skill in the art from the disclosures that follow.

BRIEF DESCRIPTION OF THE DRAWINGS

In the drawings forming a portion of this disclosure,

FIG. 1 in five parts illustrates that matching enhanced aromatic sequons with reverse turn hosts that can facilitate stabilizing interactions among Phe, Asn(GlcNAc1), and Thr. FIG. 1A shows a space-filling model of the Phe63-Asn65-GlcNAc-Thr67 interaction of a glycosylated five-residue type I β-bulge turn from the adhesion domain of the human protein CD2 [PDB accession code: 1GYA; Wyss et al., *Science* 269, 1273-1278 (1995)]; FIG. 1B illustrates the same sequence using different models; FIGS. 1C-1D are from variants of the WW domain of human protein Pin1 having incorporated components of the enhanced aromatic sequon. Structures are rendered in PyMOL (a user-sponsored molecular visualization system on an open-source foundation) with dotted lines depicting hydrogen bonds. Interatomic distances between the side-chain beta carbons (Cβ's) in Å are depicted.

FIGS. 2B and 2C show stabilities and folding kinetics of the eight RnCD2* sequences required for the thermodynamic cycle were determined by equilibrium denaturation and stopped-flow kinetic studies; FIG. 2D is a western blot showing that the relative ratio of N-glycosylated to non-glycosylated polypeptides from Sf9 insect cells is substantially higher for a RnCD2* variant having a Phe residue in the tight turn relative to a variant that lacks the Phe residue; tabulated data are shown in FIG. 2E (N refers to N-glycosylated Asn); and FIG. 2F illustrates contact of the Phe and Thr side chains with the first GlcNAc, of the N-glycan of four polypeptides found in a PDB search of proteins that contain type I β-bulge turns with a Phe at the i position, a glycosylated Asn residue at the i+2 position, and a Thr at the i+4.

FIG. 3B shows data from a equilibrium denaturation study for determining folding free energy; FIG. 3C illustrates the sequences at positions 41-47 of four AcyP2* variants, AcyP2*(SEQ ID NO:174); g-AcyP2* (SEQ ID NO:175); AcyP2*-F (SEQ ID NO:176); g-AcyP2*-F (SEQ ID NO:177), that differ in the identity of the side chain at position 43 (Phe or Thr) and in the presence or absence of a glycan at Asn45; and FIG. 3D is a western blot showing that the relative ratio of N-glycosylated to non-glycosylated polypeptides from Sf9 insect cells is substantially higher for a AcyP2* variant having a Phe residue in the tight turn relative to a variant that lacks the Phe residue.

FIG. 4B shows melting curves of a glycosylated (g-WW-F,T) and non-glycosylated (WW-F,T) variants; FIGS. 4D and 4E show illustrative plots from variable temperature circular dichroism spectroscopy and laser temperature jump studies; and FIG. 4F tabulates the thermal stability and folding rate data for the eight Pin WW variants studied.

DEFINITIONS

Figure 1C:
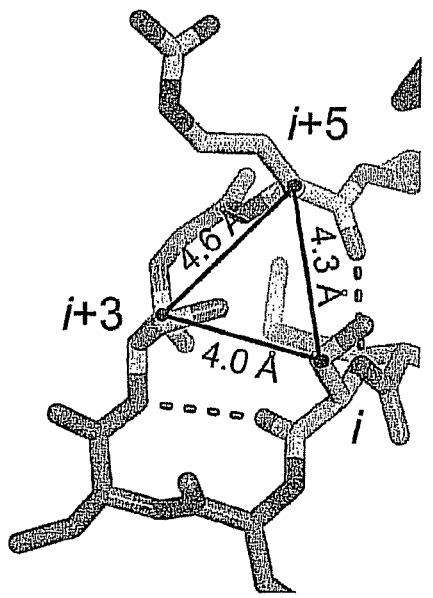
FIG. 1C illustrates a Type II β-turn in a six-residue loop [PDB accession code: 1PIN; Ranganathan et al., *Cell* 89, 875-886 (1997)]

To facilitate understanding of the invention, a number of terms are defined below.

The term "antibody" refers to a molecule that is a member of a family of glycosylated proteins called immunoglobulins, which can specifically bind to an antigen.

The term "chimer" or "chimeric" is used to describe a polypeptide that is man-made and does not occur in nature. A contemplated chimeric polypeptide is encoded by a nucleotide sequence made by a splicing together of two or more complete or partial genes or cDNA, or by synthetically constructing such a polypeptide by in vitro methods. The pieces used can be from different species. In the present instance, the sequence of the sequon Aro-(Xxx)n-(Zzz)p-Asn-Yyy-Thr/Ser (SEQ ID NO:001), as defined before, is typically spliced into a tight turn present in a pre-existing therapeutic polypeptide using genetic engineering techniques.

The term "polypeptide" is used herein to denote a sequence of about 15 to about 1000 peptide-bonded amino acid residues. A whole protein as well as a portion of a protein having the stated minimal length is a polypeptide.

The term "tight turn" is used herein as defined in Chou, *Anal Biochem* 286, 1-16 (2000) to mean a polypeptide site where (i) a polypeptide chain reverses its overall direction, and (ii) the amino acid residues directly involved in forming the turn are no more than six. Tight turns are generally categorized as δ-turn, γ-turn, β-turn, α-turn, and π-turn, which are formed by two-, three-, four-, five-, and six-amino-acid residues, respectively. According to the folding mode, each of such tight turns can be further classified into several different types. β-Turns also known as "reverse turns" are of most interest herein, and of those tight turns, the tight turns referred to as a type-I β-bulge turn, a type-I' β-turn and a type-II β-turn are of particular interest. Methods for predicting the presence of β-turns in polypeptides are provided in the citations of Chou, *Anal Biochem* 286, 1-16 (2000), and are otherwise well known in the art.

All amino acid residues identified herein are in the natural L-configuration. In keeping with standard polypeptide nomenclature, *J. Biol. Chem.*, 243, 3557-3559 (1969), abbreviations for amino acid residues are as shown in the following Table of Correspondence:

| TABLE OF CORRESPONDENCE SYMBOL | | |
|---|---|---|
| 1-Letter | 3-Letter | AMINO ACID |
| Y | Try | L-tyrosine |
| G | Gly | glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Trp | L-tryptophan |
| R | Arg | L-arginine |
| D | Asp | L-aspartic acid |
| N | Asn | L-asparagine |
| C | Cys | L-cysteine |

DETAILED DESCRIPTION OF THE INVENTION

The present invention contemplates a therapeutic chimeric polypeptide that is typically present in isolated and purified form, and is a chimer of a pre-existing therapeutic polypeptide. The pre-existing therapeutic polypeptide has a length of about 15 to about 1000, preferably about 25 to about 500, and more preferably about 35 to about 300 amino acid residues.

A pre-existing therapeutic polypeptide is a polypeptide used as a pharmaceutical or nutraceutical that is administered to a human or other animal. A contemplated pre-existing therapeutic polypeptide is typically prepared exogenously of the recipient's body, but can be an endogenous polypeptide. A contemplated chimeric therapeutic polypeptide is typically prepared as an exogenous polypeptide, but can be produced endogenously via gene therapy.

A contemplated pre-existing therapeutic polypeptide exhibits a secondary structure that comprises at least one tight turn containing a sequence of four to about seven amino acid residues in which at least two amino acid side chains extend on the same side of the tight turn and are within less than about 7 Å of each other. The four to about seven amino acid residues present do not necessarily participate in the formation of the tight turn, but are present in the turn.

A contemplated chimeric therapeutic polypeptide has substantially the same length, at least one tight turn and substantially the same amino acid residue sequence as the pre-existing therapeutic polypeptide. However, a contemplated chimer is different in its total amino acid sequence from the pre-existing polypeptide, and can be longer or shorter by one to about three residues than the pre-existing therapeutic polypeptide (substantially the same length), but is preferably the same length. The two sequences differ by the presence in the chimeric therapeutic polypeptide of the sequon, in the direction from left to right and from N-terminus to C-terminus, Aro-(Xxx)n-(Zzz)p-Asn-Yyy-Thr/Ser, (SEQ ID NO:001)

wherein Aro is an aromatic amino acid residue such as histidine, phenylalanine, tyrosine or tryptophan, of which phenylalanine, tyrosine and tryptophan are preferred, n is zero, 1, 2, 3 or 4, Xxx is an amino acid residue other than an aromatic residue, p is zero or one, Zzz is any amino acid residue, Asn is asparagine, Yyy is any amino acid residue other than proline, and Thr/Ser is one or the other of the amino acid residues threonine and serine, of which threonine is preferred.

The above sequon is located at the same position in the tight turn as the sequence of four to about seven amino acid residues present in the pre-existing polypeptide such that the side chains of three amino acid residues—Aro, Asn and Thr/Ser—project on the same side of the turn and are within less than about 7 Å of each other.

The sequence of four to about seven amino acid residues present in the pre-existing polypeptide is preferably glycosylation-free. In preferred practice, the above sequon is glycosylated. When the sequon is glycosylated, the therapeutic chimeric polypeptide exhibits a folding stabilization enhancement by about −0.5 to about −4 kcal/mol compared to the pre-existing therapeutic polypeptide in non-glycosylated form.

Returning to the formula for the above-mentioned sequon, it is seen that the length can be four residues when n=p=zero, five residues when n=zero and p=1 or when n=1 and p=0, and ten residues when n=4 and p=1. Of course, intermediate lengths between four and nine residues are also contemplated. It is additionally preferred that the residues Xxx, Yyy and Zzz be other than cysteine.

The above Aro-(Xxx)n-(Zzz)p-Asn-Yyy-Thr/Ser (SEQ ID NO:001) sequence is referred to herein as an "enhanced aromatic sequon" because of its increased propensity to form a stabilizing compact structure upon glycosylation, relative to the canonical Asn-Yyy-Thr sequon, and because it is more efficiently glycosylated by eukaryotic cells than the Asn-Yyy-Thr sequon [Culyba et al., *Science* 331, 571-575 (2011)].

The sequon Asn-Yyy-Thr/Ser is a sequon recognized by the enzyme oligosaccharyl transferase (OST). OST attaches the highly conserved $Glc_3Man_9GlcNAc_2$ glycan en bloc to the N atom of the Asn amido side chain. A glycan bonded to the amido nitrogen of an asparagine side chain is illustrated herein as "Asn(Glycan)" to denote any glycan.

During the translocation of a glycosylated polypeptide through the endoplasmic reticulum (ER), several sugars including each glucose (Glc) and several of the mannose (Man) groups are removed from the glycan portion. The specific resulting glycan is dependent upon the plant or animal in which the polypeptide is expressed, and at what stage after expression the glycopolypeptide is recovered.

Illustrative glycosylated Asn residues include those with one N-acetylglucosamine [Asn (GlcNAc)], two N-acetylglucosamines [Asn(GlcNAc2)], with one mannose and two N-acetylglucosamines [Asn(ManGlcNAc2)], and with three mannoses and two N-acetylglucosamines that is referred to as "paucimannose" (Man3GlcNAc2) that forms the glycosylated residue Asn(Man3GlcNAc2), and the like. Additionally, glycosylated asparagine residues can be utilized in an in vitro polypeptide synthetic scheme.

In another embodiment, the sequon contemplated has the formula, from left to right and in the direction from N-terminus to C-terminus, -Lys-(Zzz)$_m$-Aro-(Xxx)n-(Zzz)p-Asn-Yyy-Thr/Ser, (SEQ ID NO:002)

wherein m is zero, 1, 2, or 3, and

Lys is lysine, and

Zzz, Aro, Xxx, n, p, Yyy and Thr/Ser are as defined previously.

Again, as in the previous discussion, this sequon is positioned in the tight turn sequence of the chimeric polypeptide at the same position in the tight turn as the sequence of four to about seven amino acid residues present in the pre-existing polypeptide such that the side chains of four amino acid residues—Lys, Aro, Asn and Thr/Ser—project on the same side of the turn and are within less than about 7 Å of each other. That is, each of the Lys, Aro and Thr/Ser residue side chains interacts with the glycan of the Asn residue after proper folding, as for example, after expression and passage of the expressed polypeptide through the ER.

Another way to identify the position of the about four to seven residue amino acid residues present in the pre-existing polypeptide is through use of the numbering system utilized for the location of residues present in a hydrogen bonded sequence of a β-turn, even though a hydrogen bond need not be present in a contemplated tight turn. In this system, the N-terminal residue of the sequence that participates in the hydrogen bond is designated the "i" residue. Going in the direction toward the C-terminus of the sequence, the residues are numbered "i+1", "i+2", "i+3", "i+4", "i+5", etc. Residues to the N-terminal side of residue "i" are numbered "i−2", "i−3", "i−4", "i−5", etc.

Illustrative examples of this type of nomenclature can be seen hereinafter such as in work regarding the type-I β-bulge turn present in the non-therapeutic genetically-engineered polypeptide rat glycoprotein CD2 (RnCD2*). The sequon in that type-I n-bulge turn was engineered to be Asn-Gly-Thr, within the seven residue sequence Glu-Ile-Leu-Ala-Asn-Gly-Thr (SEQ ID NO:006) and was replaced in the chimeric polypeptide by the sequon -Lys-(Zzz)$_m$-Aro-(Xxx)n-(Zzz)p-Asn-Yyy-Thr/Ser (SEQ ID NO:004), where m=1, n=3 and p=zero, Lys-Ile-Phe-Ala-Asn-Gly-Thr (SEQ ID NO:007). The pre-existing sequence in the pre-existing RnCD2* is Asn-Gly-Thr, where the Asn is at the i position, whereas the Gly is at the i+1, and Thr is at the i+2 position. In the chimeric polypeptide, the Asn, Gly and Thr are as before, and the Lys, Ile, Phe, and Ala are at positions i−4, i−3, i−2, and i−1, respectively.

In the above polypeptide Lys-Ile-Phe-Ala-Asn-Gly-Thr (SEQ ID NO:007)} the Phe, Thr and Asn(Glycan) interact, and the Lys also appears to interact with those residues. As a result, looking from the viewpoint of the chimeric therapeutic polypeptide, one can base the numbering nomenclature upon the Phe as the i residue, the Ala as i+1, the Asn as i+2, the Gly as i+3, and the Thr as i+4. Both methods of numbering are used herein.

Turning again to the before-discussed preferred sequon,

Aro-(Xxx)n-(Zzz)p-Asn-Yyy-Thr/Ser (SEQ ID NO:001), in one preferred embodiment, "n" is 1 and "p" is 1 and the chimeric polypeptide contains a Type II β-turn in a six-residue loop. The resulting enhanced aromatic sequon present in the chimeric polypeptide has the sequence:Aro-Xxx-Zzz-Asn-Yyy-Thr/Ser (SEQ ID NO:008).

In another preferred embodiment, "n" is 1 and "p" is zero. The pre-existing and chimeric polypeptide sequences differ by the presence in the chimeric therapeutic polypeptide of the sequon, Aro-Xxx-Asn-Yyy-Thr/Ser (SEQ ID NO:002) as defined above. The chimeric polypeptide preferably contains a five-residue type I β-bulge turn.

In still another preferred embodiment, "n" is zero and "p" is zero. The pre-existing and chimeric polypeptide sequences differ by the presence in the chimeric therapeutic polypeptide of the sequon, Aro-Asn-Yyy-Thr/Ser (SEQ ID NO:003) as defined above. Here, a preferred chimeric polypeptide contains a four-residue type I' β-turn.

One group of exemplary pre-existing therapeutic polypeptides is constituted of therapeutic antibodies, and particularly the heavy chains of human antibodies. The heavy chain of all IgG-type antibodies has three constant domains: CH1, CH2, and CH3. The CH2 and CH3 domains form what is called the Fc fragment, or the crystallizable fragment. A complete human antibody heavy chain contains about 450 amino acid residues, of which about one-half are present in the Fc portion.

The following Table A provides a list of USAN names of therapeutic antibodies that are approved or at some point in clinical trials. The CH2 and CH3 domains of human antibody Fc portions contain reverse turns, each of which can be modified to form one or two enhanced aromatic sequons. The pre-existing tight turn sequence of illustrative antibodies or antibody Fc portions such as those below and exemplary replacement sequons contemplated herein that can provide enhanced folding stability are provided in Table B thereafter.

TABLE A

USAN Names of Therapeutic Antibodies

"abagovomab", "adalimumab", "alemtuzumab",
"apolizumab", "basiliximab", "basliximab",
"belimumab", "bevacizumab", "canakinumab",
"catumaxomab", "certolizumab", "cetuximab",
"cixutumumab", "conatumumab", "consumab",
"daclizumab", "dalotuzumab", "denosumab", "dermab",
"eculizumab", "edrecolomab", "efalizumab",
"efungumab", "elotuzumab", "epratuzumab",
"ertumaxomab", "etaracizumab", "figitumumab",
"galiximab", "ganitumab", "gemtuzumab", "genmab",
"golimumab", "ibalizumab", "ibritumomab",
"infliximab", "ipilimumab", "lexatumumab",
"lintuzumab", "lumiliximab", "mapatumumab",
"matuzumab", "mepolizumab", "milatuzumab",
"motavizumab", "natalizumab", "necitumumab",
"nimotuzumab", "ofatumumab", "omalizumab",
"oregovomab", "otelixizumab", "palivizumab",
"panitumumab", "pertuzumab", "ramucirumab",
"ranibizumab", "reslizumab", "rituximab",
"siplizumab", "sonepcizumab", "tanezumab",
"tefibazumab", "teplizumab", "ticilimumab",
"tocilizumab", "tositumomab", "trastuxumab",
"trastuzumab", "tremelimumab", "tucotuzumab",
"ustekinumab", "veltuzumab", "visilizumab",
"volociximab", "zalutumumab"

TABLE B

| Drug Bank ID Number | USAN Name | Polypeptide Identity | Native Sequence [SEQ ID NO] | Exemplary Sequon [SEQ ID NO] |
|---|---|---|---|---|
| DB00078 | Ibritumomab | Mouse Anti-CD20 Heavy chain 1 | DYNST [009] | FYNST [010] |
| " | " | Mouse Anti-CD20 Heavy chain 1 | DSDGS [011] | YSNGS [012] |
| DB00078 | Ibritumomab | Mouse Anti-CD20 Heavy chain 2 | DYNST [013] | FYNSS [014] |
| " | " | Mouse Anti-CD20 Heavy chain 2 | DSDGS [015] | YSNGT [016] |
| DB00028 | Immune globulin | IgG1 | QYNST [017] | YYNST [018] |
| " | Immune globulin | " | DSDGS [019] | YSNGS [020] |
| DB00005 | Etanercept | TNF receptor 2 fused to human Fc of IgG1 | QYNST [021] | WYNST [022] |
| " | " | TNF receptor 2 fused to human Fc of IgG1 | DSDGS [023] | HSNGT [024] |
| DB00087 | Alemtuzumab | 1CE1:H CAMPATH-1H:Heavy Chain 1 | DSDGS [025] | WSNGT [026] |
| " | " | 1CE1:H CAMPATH-1H:Heavy Chain 2 | DSDGS [027] | FSNGT [028] |
| DB00113 | Arcitumomab | 1clo:Anti-CEA heavy chain 1 | DYNST [029] | FYNST [030] |
| " | " | 1clo:Anti-CEA heavy chain 1 | DSDGS [031] | FSNGT [032] |
| DB00113 | Arcitumomab | 1clo:Anti-CEA heavy chain 2 | DYNST [033] | FYNST [034] |
| " | " | 1clo:Anti-CEA heavy chain 2 | DSDGS [035] | WSNGS [036] |
| DB00043Anti | Omalizumab | IgE antibody VH domain chain 1 | QYNST [037] | WYNST [038] |
| DB00043Anti | " | IgE antibody VH domain chain 1 | DSDGS [039] | YSNGT [040] |
| DB00043Anti | Omalizumab | IgE antibody VH domain chain 2 | QYNST [041] | HYNST [042] |
| DB00043Anti | " | IgE antibody VH domain chain 2 | DSDGS [043] | YSNGS [044] |
| DB00057 | Satumomab Pendetide | Heavy chain 1 B72.3 | DYNST [045] | FYNST [046] |
| " | Satumomab Pendetide | Heavy chain 1 B72.3 | DSDGS [047] | HSNGT [048] |
| DB00057 | Satumomab Pendetide | Heavy chain 2 B72.3 | DYNST [049] | WYNST [050] |
| " | Satumomab Pendetide | Heavy chain 2 B72.3 | DSDGS [051] | YSNGS [052] |
| DB00092 | Alefacept | Human LFA fused to human Fc | QYNST [053] | WYNST [054] |
| " | " | Human LFA fused to human Fc | DSDGS [055] | YSNGT [056] |
| DB00111 | Daclizumab | Humanized Anti-CD25 Heavy Chain 1 | QYNST [057] | FYNST [058] |
| " | " | Humanized Anti-CD25 Heavy Chain 1 | DSDGS [059] | YSNGS [060] |
| DB00111 | Daclizumab | Humanized Anti-CD25 Heavy Chain 2 | QYNST [061] | HYNST [062] |
| " | " | Humanized Anti-CD25 Heavy Chain 2 | DSDGS [063] | FSNGS [064] |
| DB00002 | Cetuximab | Anti-EGFR heavy chain 1 | DSDGS [065] | WSNGS [066] |
| DB00002 | Cetuximab | Anti-EGFR heavy chain 2 | DSDGS [067] | WSNGT [068] |
| DB00081 | Tositumomab | Mouse-Human chimeric Anti-CD20 heavy chain 1 | QYNST [069] | FYNST [070] |
| " | " | Mouse-Human chimeric Anti-CD20 heavy chain 1 | DSDGS [071] | FSNGT [072] |
| DB00081 | Tositumomab | Mouse-Human chimeric Anti-CD20 heavy chain 2 | QYNST [073] | FYNSS [074] |

TABLE B-continued

| Drug Bank ID Number | USAN Name | Polypeptide Identity | Native Sequence [SEQ ID NO] | Exemplary Sequon [SEQ ID NO] |
|---|---|---|---|---|
| " | " | Mouse-Human chimeric Anti-CD20 heavy chain 2 | DSDGS [075] | WSNGT [076] |
| DB00072 | Trastuzumab | Anti-HER2 Heavy chain 1 | QYNST [077] | FYNST [078] |
| " | " | Anti-HER2 Heavy chain 1 | DSDGS [079] | WSNGS [080] |
| DB00072 | Trastuzumab | Anti-HER2 Heavy chain 2 | QYNST [081] | FYNST [082] |
| " | " | Anti-HER2 Heavy chain 2 | DSDGS [083] | WSNGS [084] |
| DB00075 | Muromonab | 1SY6:H OKT3 Heavy Chain 1 | QYNST [085] | WYNST [086] |
| " | " | 1SY6:H OKT3 Heavy Chain 1 | DSDGS [087] | FSNGS [088] |
| DB00075 | Muromonab | 1SY6:H OKT3 Heavy Chain 2 | QYNST [089] | HYNST [090] |
| " | " | 1SY6:H OKT3 Heavy Chain 2 | DSDGS [091] | YSNGS [092] |
| DB00054 | Abciximab | 1TXV:H ReoPro-like antibody Heavy Chain 1 | QYNST [093] | WYNST [094] |
| " | " | 1TXV:H ReoPro-like antibody heavy Chain 1 | DSDGS [095] | WSNGT [096] |
| DB00054 | Abciximab | 1TXV:H ReoPro-like antibody Heavy Chain 2 | QYNST [097] | FYNST [098] |
| " | " | 1TXV:H ReoPro-like antibody Heavy Chain 2 | DSDGS [099] | FSNGT [100] |
| DB00074 | Basiliximab | 1MIM:H Anti-CD25 antibody heavy CHIMERIC chain 1 | QYNST [101] | YYNST [102] |
| " | " | 1MIM:H Anti-CD25 antibody heavy CHIMERIC chain 1 | DSDGS [103] | FSNGT [104] |
| DB00074 | Basiliximab | 1MIM:H Anti-CD25 antibody heavy CHIMERIC chain 2 | QYNST [105] | WYNST [106] |
| " | " | 1MIM:H Anti-CD25 antibody heavy CHIMERIC chain 2 | DSDGS [107] | FSNGS [108] |
| DB00073 | Rituximab | Mouse-Human chimeric Anti-CD20 Heavy Chain 1 | QYNST [109] | HYNSS [110] |
| " | " | Mouse-Human chimeric Anti-CD20 Heavy Chain 1 | DSDGS [111] | YSNGS [112] |
| DB00073 | Rituximab | Mouse-Human chimeric Anti-CD20 Heavy Chain 2 | QYNST [113] | FYNSS [114] |
| " | " | Mouse-Human chimeric Anti-CD20 Heavy Chain 2 | DSDGS [115] | WSNGS [116] |

Another group of exemplary pre-existing therapeutic polypeptides is hormones. Illustrative of such hormones are erythropoietin, darbepoetin alfa (an erythropoietin variant with two additional N-glycans), interferon beta, and follicle stimulating hormone, follitropin beta, peginterferon alfa-2b, becaplermin, sermorelin, somatropin, pramlintide, sargramostim, insulin, thyrotropin alfa, choriogonadotropin alfa, lepirudin, lutropin alfa, secretin, bivalirudin, corticotrophin, exenatide and the like.

Yet another group of exemplary pre-existing therapeutic polypeptides is enzymes. Illustrative of such enzymes are laronidase, collagenase, pancrelipase, streptokinase, urokinase, imiglucerase, reteplase, coagulation factor VII, coagulation factor VII, coagulation factor IX, alglucerase, agalsidase beta, asparaginase, hyaluronidase, tenecteplase, pegademase bovine, dornase alfa, anistreplase, pegaspargase, alteplase, and the like.

Further pre-existing polypeptides include denileukin diftitox, botulinum toxin type B, nesiritide, pegfilgrastim, human serum albumin, mecasermin, aldesleukin, antihemophilic factor, aprotinin, palifermin, peginterferon alfa-2a, teriparatide, urofollitropin, anakinra, menotropins, OspA lipoprotein, pegvisomant, thymalfasin, follitropin beta, peginterferon alfa-2b, alpha-1-proteinase inhibitor, filgrastim, oprelvekin, rasburicase, darbepoetin alfa, enfuvirtide and the like.

Table C, below, illustrates five residue native sequences within tight turns of two of the above polypeptides, the alpha chain of follitropin beta, which has a type VI β-turn, and imiglucerase, which has a type I β-bulge turn. Also illustrated for each of those polypeptides are replacement sequon sequences for the illustrated native five residue sequences.

TABLE C

| Drug Bank ID Number | USAN Name | Polypeptide Identity | Native Sequence [SEQ ID NO] | Exemplary Sequon [SEQ ID NO] |
| --- | --- | --- | --- | --- |
| DB00066 | Follitropin beta | Human follicle alpha chain stimulating hormone | VMGGF [117] | FMNGT [118] |
| " | Follitropin beta | Human follicle alpha chain stimulating hormone | VMGGF [117] | WMNGT [119] |
| " | Follitropin beta | Human follicle alpha chain stimulating hormone | VMGGF [117] | YMNGT [120] |
| " | Follitropin beta | Human follicle alpha chain stimulating hormone | VMGGF [117] | HMNGT [121] |
| " | Follitropin beta | Human follicle alpha chain stimulating hormone | VMGGF [117] | FMNGS [122] |
| " | Follitropin beta | Human follicle alpha chain stimulating hormone | VMGGF [117] | WMNGS [123] |
| " | Follitropin beta | Human follicle alpha chain stimulating hormone | VMGGF [117] | YMNGS [124] |
| " | Follitropin beta | Human follicle alpha chain stimulating hormone | VMGGF [117] | HMNGS [125] |
| DB00053 | Imiglucerase | Human Beta-glucocidase | HPDG [126] | FPNGT [127] |
| " | " | Human Beta-glucocidase | HPDGS [126] | WPNGT [128] |
| " | " | Human Beta-glucocidase | HPDGS [126] | YPNGT [129] |
| " | " | Human Beta-glucocidase | HPDGS [126] | HPNGT [130] |
| " | " | Human Beta-glucocidase | HPDGS [126] | FPNGS [131] |
| " | " | Human Beta-glucocidase | HPDGS [126] | WPNGS [132] |
| " | " | Human Beta-glucocidase | HPDGS [126] | YPNGS [133] |
| " | " | Human Beta-glucocidase | HPDGS [126] | HPNGS [134] |

Nearly 9% of the reverse turns in the Protein Data Bank (PDB) are type I β-bulge turns [Sibanda et al., *J Mol Biol* 206(4), 759-777 (1989); and Oliva et al., *J Mol Biol* 266(4), 814-830 (1997)], so installing the Aro-(Xxx)n-(Zzz)p-Asn-Yyy-Thr/Ser (SEQ ID NO:001) enhanced aromatic sequon could be an attractive strategy for increasing the stability of the many proteins that harbor type I β-bulge turns. Identifying other suitable reverse turn types that could position Phe, GlcNAc1, and Thr close enough to facilitate a tripartite interaction would further expand the number of proteins that could benefit from the increased stability and possibly the increased glycosylation efficiency afforded by the enhanced aromatic sequon.

Illustrative glycosylated Asn residues include those with one N-acetylglucosamine [Asn(GlcNAc)], two N-acetylglucosamines [Asn(GlcNAc2)], with one mannose and two N-acetylglucosamines [Asn(ManGlcNAc2)], and with three mannoses and two N-acetylglucosamines that is referred to as "paucimannose" (Man3GlcNAc2) that forms the glycosylated residue Asn(Man3GlcNAc2), and the like. Additionally, glycosylated asparagine residues can be utilized in an in vitro polypeptide synthetic scheme.

Preparation of a Chimeric Therapeutic Polypeptide

A method of method of enhancing folded stabilization of a chimeric therapeutic polypeptide compared to a pre-existing therapeutic polypeptide is also contemplated. The pre-existing therapeutic polypeptide comprises a sequence of about 15 to about 1000 amino acid residues, preferably about 25 to about 500 residues, and more preferably about 35 to about 300 residues, and exhibits a secondary structure that comprises at least one tight turn in which the side chains of two residues in a sequence of four to about seven amino acid residues within the tight turn project on the same side of the turn and are within less than about 7 Å of each other. Those four to about seven amino acid residues are preferably glycosylation-free. In accordance with that method, a therapeutic chimeric polypeptide is prepared that is of the same length and substantially same sequence as the therapeutic polypeptide and exhibits a secondary structure comprising at least one tight turn at the same sequence position within the tight turn as in the therapeutic polypeptide, except that said sequence of four to about seven amino acid residues is replaced with the sequon, in the direction from left to right and from N-terminus to C-terminus, Aro-(Xxx)n-(Zzz)p-Asn(Glycan)-Yyy-Thr/Ser, (SEQ ID NO:005)

wherein

Aro is an aromatic amino acid residue, n is zero, 1, 2, 3 or 4,

Xxx is an amino acid residue other than an aromatic residue, p is zero or 1,

Zzz is any amino acid residue,

Asn(Glycan) is glycosylated asparagine,

Yyy is any amino acid residue other than proline,

Thr/Ser is one or the other of the amino acid residues threonine and serine, and the side chains of the Aro, Asn(Glycan) and Thr/Ser amino acid residues project on the same side of the turn and are within less than about 7 Å of each other.

In some embodiments, the Asn(Glycan) is Asn(GlcNAc)1. In other embodiments, Asn(Glycan) is Asn(GlcNAc)2, whereas in other embodiments Asn(Glycan) is Asn(GlcNAc)$_2$Man$_1$. In still other embodiments, the glycan of Asn(Glycan) is paucimannose.

A contemplated polypeptide can be prepared in a number of manners. Longer polypeptides, such as those of about 50 residues and longer, are most readily prepared by genetic engineering following well known techniques. Thus, for example, a therapeutic chimeric polypeptide is prepared by expressing a nucleic acid sequence that encodes the polypeptide sequence of the therapeutic chimeric polypeptide in a host cell that glycosylates the amino acid sequence Aro-(Xxx)n-(Zzz)pAsn-Yyy-Thr/Ser (SEQ ID NO:003) when present in a polypeptide sequence expressed therein to form the sequence Aro-(Xxx)n-(Zzz)p-Asn(Glycan)-Yyy-Thr/Ser (SEQ ID NO:005). Examples of such preparations are illustrated hereinafter.

In such a preparation, any of eukaryotic several host cells can be utilized for the preparation of a glycosylated chimeric therapeutic polypeptide. For example, yeast cells such as *Saccharomyces cerevisiae, Pichia pastoris*, mammalian cells such as CHO cells, insect cells such as *Spodoptera frugiperda* (Sf9) cells, and in plant cells such as those of tobacco (Nicotiana tobaccum M38) or *Arabidopsis thaliana*. Unstablized (unglycosylated or non-glycosylated) therapeutic polypeptides useful for comparative purposes can be expressed in bacterial cells that do not gylcosylate their expressed polypeptides such as *E. coli*.

In the following examples, an illustrative polypeptide is expressed as a fusion protein that contains isolation and purification sequences. One such sequence is a 6-residue hexahistidine sequence at the N-terminus of the polypeptide to assist in purifying and isolating the desired chimer via binding to a Nickel affinity ligand on a solid support. Additional affinity tags include the 9-residue FLAG-tag and the myc-tag that are bound by solid-support-linked antibody binding sites. The so-called Strep-tag® II, which consists of a streptavidin-recognizing octapeptide, can be affinity-purified using a matrix with a modified streptavidin and eluted with a biotin analog.

Because it is desirable to remove most tags at the end of the purification process, considerable advances have been made in design of affinity tags so that they can be cleaved without leaving any residues behind and also to simplify the entire process of purification and cleavage. One such system is the "Profinity eXact™" fusion-tag system (Bio-Rad Laboratories, Hercules, Calif.), which uses an immobilized subtilisin protease to carry out affinity binding and tag cleavage. The protease is not only involved with the binding and recognition of the tag, but upon application of the elution buffer, it also serves to precisely cleave the tag from the fusion protein directly after the cleavage recognition sequence. This delivers a native, tag-free polypeptide in a single step. Another system for simple purification of proteins is based on elastin-like polypeptides (ELP) and intein. ELP consist of several repeats of a peptide motif that undergo a reversible transition from soluble to insoluble upon temperature upshift. The fusion protein is purified by temperature-induced aggregation and separation by centrifugation, and intein is used for tag removal. No affinity columns are needed for initial purification.

Solubility-enhancing tags are generally large peptides or proteins that increase the expression and solubility of fusion proteins. Fusion tags like GST and MBP also act as affinity tags and as a result, they are very popular for protein purification. Other fusion tags like NusA, thioredoxin (TRX), small ubiquitin-like modifier (SUMO), and ubiquitin (Ub), on the other hand, require additional affinity tags for use in protein purification.

An expressed polypeptide also preferably includes a peptide cleavage site so that a purified polypeptide can be cleaved from any tags utilized in its purification and isolation. This cleavage or tag-removal step almost always involves using a protease to cleave a specific peptide bond between the tag and the protein of interest. A small number of highly specific proteases are routinely used for this purpose. These include the tobacco etch virus (TEV) protease; thrombin (factor IIa, fIIa) and factor Xa (fXa) from the blood coagulation cascade; an enzyme involved in the cleavage or activation of trypsin in the mammalian intestinal tract, enterokinase (EK); proteases involved in the maturation and deconjugation of SUMO, SUMO proteases (Ulp1, Senp2, and SUMOstar); and a mutated form of the *Bacillus subtilis* protease, subtilisin BPN' (Bio-Rad's Profinity eXact system). Many of these enzymes have been genetically engineered to enhance their stability (e.g., AcTEV™, ProTEV) or their specificity, (e.g. SUMOstar, Profinity). With the exception of the SUMO proteases, all of these enzymes have the potential to cleave within the protein of interest. The SUMO proteases recognize not only their specific cleavage site, but also the tertiary structure of SUMO itself, giving them a very high degree of specificity.

A desired polypeptide can also be prepared by one or more of the well known in vitro polypeptide synthesis techniques, particularly solid phase synthesis. This mode of synthesis is also illustrated hereinafter.

Pharmaceutical Compositions

In yet another embodiment of the invention, a contemplated chimeric therapeutic polypeptide is an active ingredient in a pharmaceutical composition for administration to a human patient or suitable animal host such as a chimpanzee, mouse, rat, horse, sheep or the like.

Thus, a contemplated chimeric therapeutic polypeptide is dissolved or dispersed in a pharmaceutically acceptable diluent composition that typically also contains water. When administered to a host animal in need of the polypeptide, such as a mammal (e.g., a mouse, dog, goat, sheep, horse, bovine, monkey, ape, or human) or bird (e.g., a chicken, turkey, duck or goose), the polypeptide provides the benefit of the pre-existing polypeptide.

The amount of chimeric therapeutic polypeptide present in a pharmaceutical composition is referred to as an effective amount and can vary widely, depending inter alia, upon the polypeptide used and the presence of adjuvants and/or other excipients present in the composition. The amount of chimeric therapeutic polypeptide that constitutes an effective amount varies with the polypeptide and the condition to be treated. Starting dosages are taken from the literature or the product label of the corresponding pre-existing therapeutic polypeptide usage, and are typically ultimately some what less than that used for the pre-existing therapeutic polypeptide.

The preparation of pharmaceutical compositions that contain proteinaceous materials as active ingredients is well understood in the art. Typically, such compositions are prepared as parenterals, either as liquid solutions or suspensions; solid forms suitable for solution in, or suspension in, liquid prior to injection can also be prepared. The preparation can also be emulsified.

Once purified, a contemplated chimeric therapeutic polypeptide is typically recovered by lyophilization. A pharmaceutical composition is typically prepared from a recovered chimeric therapeutic polypeptide by dispersing the polypeptide, preferably in particulate form, in a physiologically tolerable (acceptable) diluent vehicle such as water, saline, phosphate-buffered saline (PBS), acetate-buffered saline (ABS), Ringer's solution, or the like to form an aqueous composition. Alternatively, the lyophilized polypeptide is mixed with additional solid excipients and stored as such for constitution with water, saline and the like as discussed above.

Excipients that are pharmaceutically acceptable and compatible with the active ingredient are often mixed with the solid polypeptide, or can be predissolved in the liquid medium. Suitable excipients are, for example, water, saline, dextrose, glycerol, ethanol, or the like and combinations thereof. In addition, if desired, a composition can contain minor amounts of auxiliary substances such as wetting or emulsifying agents, pH buffering agents that enhance the effectiveness of the composition.

ILLUSTRATIVE EXAMPLES

The adhesion domain of human glycoprotein CD2 (HsCD2ad), a non-therapeutic polypeptide, is glycosylated at Asn65, within the Asn65-Gly66-Thr67 sequon (FIG. 1A). NMR and crystallographic data demonstrate that Asn65 occupies the i+2 position of a five-residue type I β-bulge turn that spans from Phe63 (i) to Thr67 (i+4; FIG. 1B), with Gly66 occupying the i+3 bulge position [Wyss et al., Science 269, 1273-1278 (1995); Wang et al., Cell 97, 791-803 (1999)]. Nuclear Overhauser effects (NOEs) suggest that the side chain of Phe63 at the i position interacts with the hydrophobic face of the first GlcNAc residue of the glycan (Asn65-GlcNAc1-GlcNAc2-), which also packs into the side chain methyl group of Thr67 (see FIG. 1C for a space-filling view of this cluster).

NOE evidence also suggests the possibility of a stabilizing protein-glycan interaction between GlcNAc2 of the glycan and Lys61 [Wyss et al., Science 269, 1273-1278 (1995)]. Wyss et al. hypothesized that this interaction disperses the positive charge present in a cluster of five Lys residues, but the energetics of this interaction were not probed [Wyss et al., Science 269, 1273-1278 (1995)]. Previous kinetic studies of glycan-dependent HsCD2ad folding suggest that the N-glycan does much more than attenuate unfavorable electrostatic interactions [Hanson et al., Proc Natl Acad Sci USA 106: 3131-3136 (2009)].

Bioinformatic analysis of the protein data bank (PDB) has revealed that aromatic residues are overrepresented two residues before Asn in occupied sequons [Petrescu et al., Glycobiology 14, 103-114 (Februaru, 2004)], leading us to hypothesize that the unusually large stabilizing effect of glycosylation on HsCD2ad folding is largely due to a tripartite Phe63-GlcNAc1-Thr67 interaction. Because nonglycosylated HsCD2ad is unfolded, we used the structurally homologous rat ortholog of HsCD2ad (RnCD2ad) to test this hypothesis as RnCD2ad does not require N-glycosylation to fold. Residues 63-67 of the RnCD2ad retain the same five-residue type I β-bulge turn geometry found in HsCD2ad (FIG. 2A, inset) [Jones et al., Nature 360, 232-239 (1992)].

We installed the Asn65-Gly66-Thr67 glycosylation sequon from HsCD2ad into the β-bulge turn of RnCD2 by mutating Asp67 to Thr (residues 65 and 66 in the wild-type RnCD2ad sequence are already Asn and Gly, respectively). To generate a version of RnCD2ad that would be glycosylated only within this turn context, we removed three naturally occurring N-glycosylation sequons (by mutating Asn72, Asn82 and Asn89 to Gln, Gln and Asp, respectively). This modified RnCD2ad sequence (which contains only one glycosylation site at Asn65) is referred to as RnCD2*.

Figure 2:
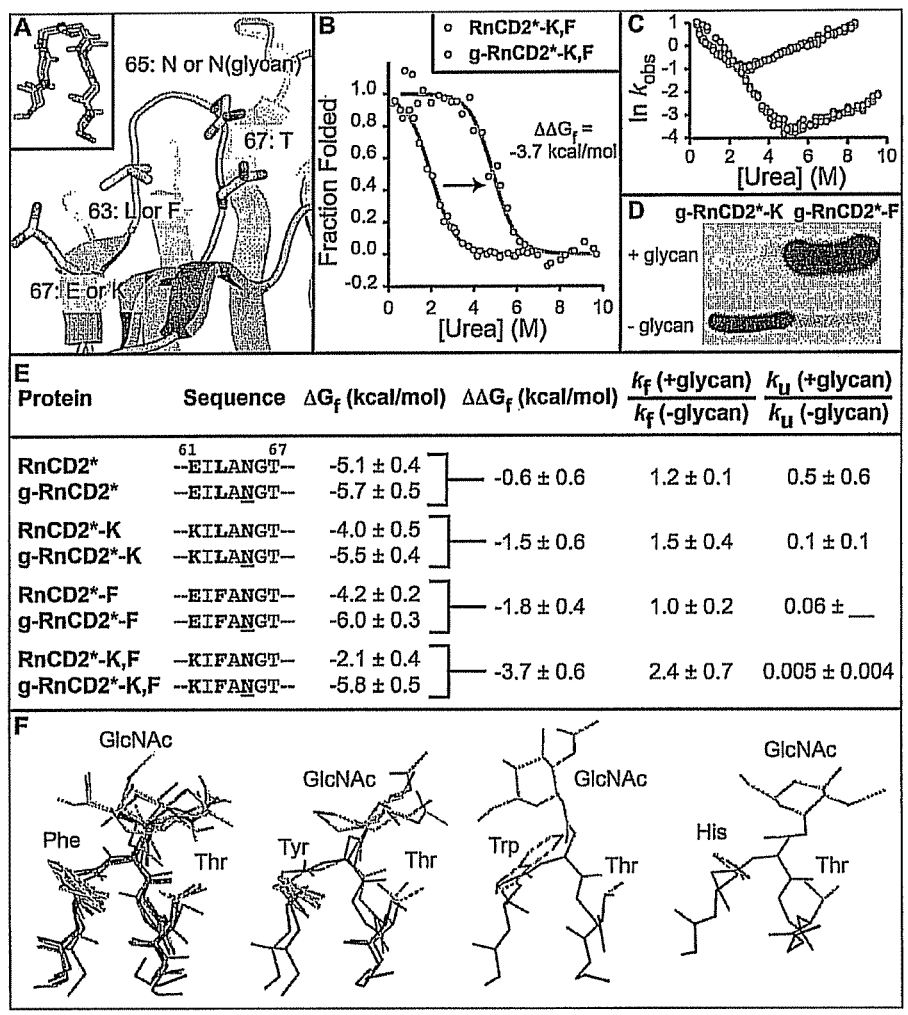
FIG. 2 in six parts shows in FIG. 2A that residues 63-67 of the RnCD2ad retain the same five-residue type I β-bulge turn geometry found in HsCD2ad but RnCD2ad does not require N-glycosylation to fold.

RnCD2* folds in the absence of glycosylation (expressed in E. coli), and has Glu at position 61 and Leu at position 63 in contrast to the Lys61 and Phe63 in HsCD2ad (FIG. 2A). These differences make RnCD2* an ideal sequence in which to study the kinetic and thermodynamic consequences of the interactions between the N-glycan, Lys61, and Phe63, using a triple mutant thermodynamic cycle [Jones et al., Nature 360, 232-239 (1992)]. The stabilities and folding kinetics of the eight RnCD2* sequences required for the cycle were determined by equilibrium denaturation and stopped-flow kinetic studies (see FIGS. 2B,C for representative data) and tabulated data are shown in FIG. 2E (N refers to N-glycosylated Asn). Glycosylated (g-RnCD2*) variants appended with $Man_{6-8}$ oligomannose glycans (determined by ESI-MS; Fig SX) were expressed in Sf9 insect cells.

Glycosylation stabilizes g-RnCD2* by −0.6 kcal $mol^{-1}$ relative to RnCD2*, which is −2.5 kcal $mol^{-1}$ less than the increase in stability observed upon glycosylation of HsCD2ad. g-RnCD2*-K (Glu61Lys), and g-RnCD2*-F (Leu63Phe) are stabilized by −1.5 and −1.8 kcal $mol^{-1}$ relative to the corresponding non-glycosylated variants, respectively. These effects are each about −1 kcal $mol^{-1}$ greater than the observed increase in stability upon glycosylation of the unmodified RnCD2*, suggesting that Lys61 and Phe63 in these RnCD2* variants are each able to form stabilizing interactions with the N-glycan at position 65 that are putatively similar to the interactions observed in the NMR structure of HsCD2ad.

The N-glycan-dependent contributions of Lys61 ($\Delta\Delta G_f$[RnCD2*-K]-$\Delta\Delta G_f$[RnCD2*]) and Phe63 ($\Delta\Delta G_f$[RnCD2*-F]-$\Delta\Delta G_f$[RnCD2*]) to RnCD2* stability. are comparable: −0.9 kcal $mol^{-1}$ and −1.2 kcal $mol^{-1}$, respectively. Notably, these interactions are synergistic: according to the data in the triple mutant cycle, this synergy amounts to −1.0 kcal $mol^{-1}$. A comparison of kinetic measurements shows that glycosylated variants that contain Phe63 unfold 20 to 200 times more slowly than the corresponding nonglycosylated variants, suggesting that an interaction between Phe63 and the N-glycan at position 65 stabilizes the native state of RnCD2* (FIG. 2E).

Unlike the interaction of the N-glycan with Lys61, which may depend on the presence of a nearby cluster of positively charged residues, the stabilizing tripartite interaction between Phe-i, Asn-N-glycan-i+2 and Thr-i+4 in RnCD2* and HsCD2ad appears to be a self-contained structural module, which we call an enhanced aromatic sequon. We next explored whether incorporating this "enhanced aromatic sequon" into reverse turns in other glycosylation-naïve proteins would also result in substantial increases to stability.

A PDB search supports this possibility by revealing four additional proteins that contain type I β-bulge turns with a Phe at the i position, a glycosylated Asn residue at the i+2 position, and a Thr at the i+4. In each case, the Phe and Thr side chains contact the first GlcNAc of the N-glycan (FIG. 2F). Furthermore, we identified glycosylated type I β-bulge turns in four additional proteins in which aromatic residues other than Phe (Tyr, Trp, or His) occupy the i position, making analogous contacts. This observation highlights the view that aromatic amino acid side chains other than Phe can also enhance glycosylation sequons by engaging in similarly stabilizing interactions with N-glycans in reverse turns.

As is disclosed in detail hereinafter, we demonstrate that placing a Phe two or three residues prior to (up stream of or toward the amino-terminus from) a glycosylated Asn in certain reverse turn-contexts leads to substantial stabilization in three different proteins, and constitutes a portable method for increasing glycoprotein stability.

The portability of the stabilization conferred by the enhanced aromatic sequon was tested by integrating it into a glycosylation-naïve reverse turn in human muscle acylphosphatase (AcyP2), a two-layer α/β protein, in which two α-helices pack against a four-stranded β-sheet [Pastore et al., J Mol Biol 224, 427-440 (1992)]. Reverse turn residues 43 to 47 are not well-enough defined in the NMR structure of AcyP2 to discern their precise conformation, but homologous residues in the crystal structure of common type acylphosphatase (57% identical to AcyP2) adopt a type I β-bulge turn conformation [Yeung et al., Acta Crystallogr Sect F Struct Biol Cryst Commun 62, 80-82 (2006)].

Figure 3:
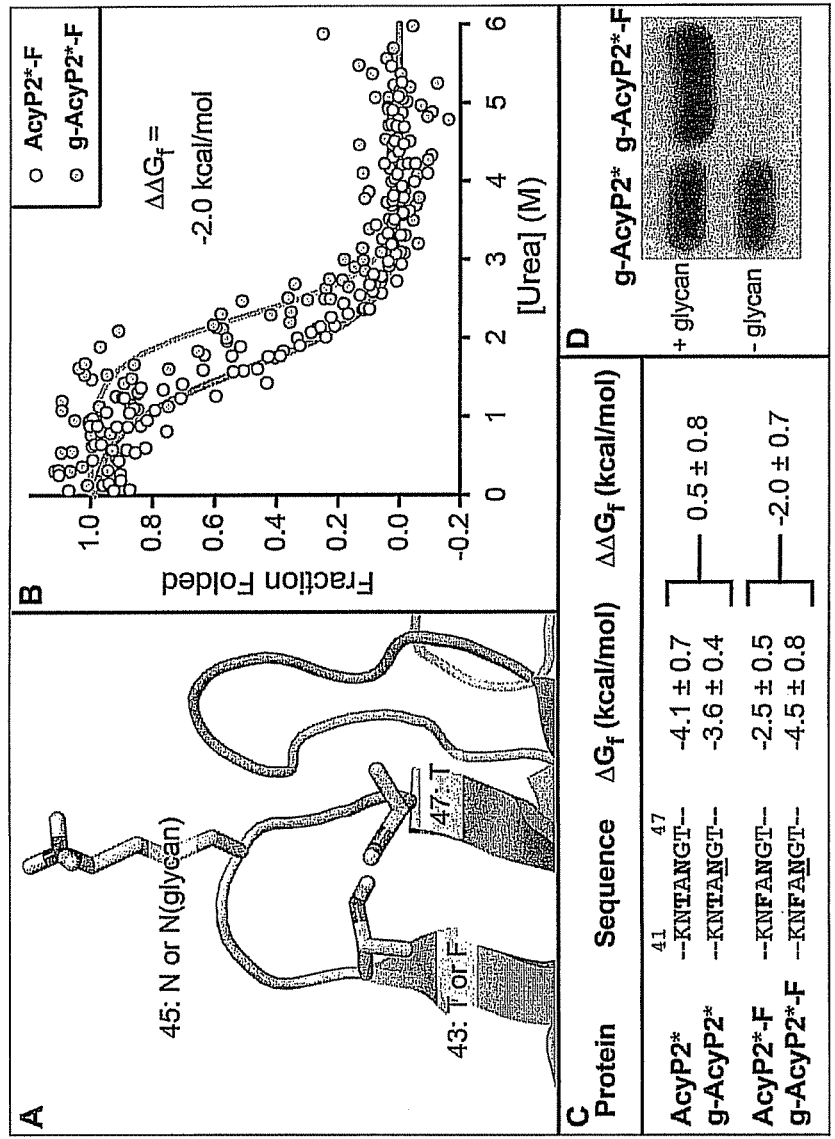
FIG. 3 in four parts illustrates in FIG. 3A that the Thr43Phe (i) and Lys45Asn (i+2) mutations in the β-bulge turn human muscle acylphosphatase (AcyP2) create an enhanced aromatic sequon in that the i+4 position is already Thr.

Thus, Thr43Phe (i) and Lys45Asn (i+2) mutations in the β-bulge turn create the enhanced aromatic sequon (the i+4 position is already Thr; FIG. 3A). The three additional sequons present in wild-type AcyP2 (but which are not normally glycosylated, as AcyP2 is a cytosolic protein) were removed by Ser to Ala mutations at positions 44, 82 and 95 to create a modified variant of AcyP2 (AcyP2*; SEQ ID NO:174) that is N-glycosylated only at Asn45.

Four AcyP2* variants, differing in the identity of the side chain at position 43 (Phe or Thr) and in the presence or absence of a glycan at Asn45 (FIGS. 3A,C) were prepared. The 43T→F mutant is AcyP2*-F (SEQ ID NO:176), the glycosylated variant is g-AcyP2*-F (glycosylated AcyP2*-F; SEQ ID NO:177). Glycoproteins g-AcyP2* (SEQ ID NO:175) and g-AcyP2*-F (SEQ ID NO:177) with predominantly fucosylated paucimannose glycans were expressed in Sf9 insect cells.

The folding free energies of each variant were determined by equilibrium denaturation (see FIG. 3B for representative data). Glycoprotein g-AcyP2*-F is stabilized by −2 kcal mol$^{-1}$ relative to nonglycosylated AcyP2*-F from *E. coli*. In contrast, glycoprotein g-AcyP2* is destabilized relative to the non-glycosylated AcyP2* by +0.5 kcal mol$^{-1}$. Thus, the estimated N-glycan-dependent contribution of the Phe-glycan interaction is −2.5 kcal mol$^{-1}$, suggesting that an interaction between Phe43 and the N-glycan at position 45 (and putatively Thr47) stabilizes the reverse turn, and thus the protein.

In fact, the contribution of Phe-glycan interaction in AcyP2* is about −1 kcal mol$^{-1}$ larger than was observed in RnCD2* (FIG. 2E). Even in the absence of structural data for g-AcyP2*-F, it is clear the enhanced aromatic sequon is a portable module that can stabilize proteins, like RnCD2* and AcPy2*, whose glycosylation-naïve reverse turns have not been tailored by evolution for optimal protein-glycan interactions.

In addition to the stabilization, conferred by the enhanced aromatic sequon, cellular glycosylation efficiency was consistently enhanced. The ratio of N-glycosylated to non-glycosylated proteins from Sf9 insect cells is substantially higher for both RnCD2* and AcyP2* variants relative to variants that lack the Phe residue (FIG. 2D and FIG. 3D), suggesting that the enhanced glycosylation sequon may be a better substrate for glycosylation by OST. This observation should prove useful for enhancing glycoprotein yields, as sequon occupancy can be variable. The enzymology of this observation merits further investigation, but it is tempting to speculate that OST may have evolved to favor sequences, like the enhanced aromatic sequon, that stabilize proteins upon glycosylation.

The structural information in the PDB suggests that the origin of the enhanced aromatic sequon effect depends on the Phe$^i$-Xxx-Asn(Glycan)-Gly-Thr$^{i+4}$-type I β-bulge turn substructure, which allows the Phe, GlcNAc and Thr side-chains to interact optimally.

Several features of this substructure are also likely to be important. The Thr side chain accepts a H-bond from the NH of the first GlcNAc residue and the C=O of the i+2 Asn residue accepts a H-bond from the backbone NH of Thr at the i+4 position. These H-bonds, and the characteristic H-bond between the >C=O of the i+4 Thr and the NH of the i position Phe are largely solvent occluded and may contribute additional enthalpic stabilization to this portable stabilizing substructure.

In principle, reverse turns other than the type I β-bulge turn could also benefit from the tripartite stabilizing interaction between Phe, Thr and Asn-glycan. This hypothesis was tested using a portion of the 34-residue WW domain from human Pin 1 (Pin WW), a glycosylation-naïve β-sheet protein in which three anti-parallel β-strands are connected by two loops. In wild-type WW, loop 1 adopts an unusual six-residue hydrogen-bonded loop harboring an internal type II β-turn (FIG. 1B); 0.1% of the reverse turns in the PDB have this conformation [Oliva et al., *J Mol Biol* 266(4):814-830 (1997)].

In the Pin1 WW crystal structure, the side chains of Ser16, Ser19, and Arg21 all project on the same side of loop 1, such the side-chain β-carbons (Cβ's) at each position are within 5-6 Å [Ranganathan et al., *Cell* 89, 875-886 (1997)]. Those distances are close enough to facilitate a stabilizing interaction between Phe, GlcNAc1 and Thr, similar to the interactions observed in the glycosylated type I β-bulge turn of HsCD2ad (FIG. 1A) [Wang et al., *Cell* 97, 791-803 (1999)]. The similar Cβ-Cβ distances in HsCD2ad suggest that positions 16, 19, and 21 might be suitable locations for incorporating the individual elements of the enhanced sequon (Phe at position 16, Asn-linked glycan at position 19, and Thr at position 21, FIG. 4A). In this version of the enhanced aromatic sequon, Phe is at the −3 position relative to the glycosylated Asn, instead of at the −2 position, as in the examples above.

Pin1 WW can be synthesized chemically, enabling us to examine the contributions of the Thr side chain to N-glycan dependent stabilization of Pin WW, in addition to the Phe-glycan interaction explored above. Here, a simple Asn-GlcNAc side chain is used. Eight Pin WW variants were synthesized (FIG. 4E), which contain all possible combinations of the Ser16Phe, Asn19Asn-GlcNAc, and Arg21Thr mutations, enabling triple mutant thermodynamic cycle analysis. WW (SEQ ID NO:204), g-WW (SEQ ID NO:205), WW-F (SEQ ID NO:197), g-WW-F (SEQ ID NO:198), WW-T (SEQ ID NO:199), g-WW-T (SEQ ID NO:200), WW-F,T, (SEQ ID NO:201) and g-WW-F,T (SEQ ID NO:202). The thermal stability and folding rates of these variants were determined by variable temperature circular dichroism spectroscopy and laser temperature jump studies, respectively (see FIG. 3B-D for representative data and Table D, E for the remaining data) and tabulated data appear in FIG. 4E.

Chemical glycosylation of the Phe-Xxx-Zzz-Asn-Yyy-Thr sequon (SEQ ID NO:135) (with a single GlcNAc, GlcNAc1) in the six-residue loop of WW increased the stability of the resulting WW variant by −0.7 kcal mol$^{-1}$ [herein and in Culyba et al., *Science* 331, 571-575 (2011)], a smaller effect than observed for the Phe-Xxx-Asn-Yyy-Thr (SEQ ID NO:136) sequon in the type I β-bulge turns of RnCD2 and AcyP2 ($\Delta\Delta G_f$=−1.8 kcal mol$^{-1}$, −2.5 kcal mol$^{-1}$, respectively).

One possible interpretation of these results is that the type II β-turn within the six-residue loop does not promote the stabilizing tripartite interaction between Phe, GlcNAc, and Thr as effectively as does the five-residue type I β-bulge turn. However, key host context differences between the WW, RnCD2, and AcyP2 proteins could also be partially responsible for these observations, including differences in folding topology and mechanism [Nickson et al., *Methods* 52(1), 38-50 (2010)], and differences in the amino acids that flank the glycosylated reverse turns [Culyba et al., *Science* 331, 571-575 (2011)].

Moreover, because the WW domain is synthesized chemically via a solid-phase strategy, the N-glycan in WW (GlcNAc) is much smaller than the N-glycans in RnCD2 (oligomannose) and AcyP2 (fucosylated paucimannose). Interactions between the host sequences and these extended glycans could also contribute to the stabilization associated with glycosylating the Phe-Xxx-Asn-Yyy-Thr (SEQ ID NO:136) sequon in the type I β-bulge turns within RnCD2 and AcyP2.

The N-glycan-dependent contribution of Phe16 to Pin WW stability is −0.19 kcal mol$^{-1}$ in the absence of Thr21, but is −0.62 kcal mol$^{-1}$ in the presence of Thr 21. Similarly, the N-glycan-dependent contribution of Thr21 to Pin WW stability is −0.18 kcal mol$^{-1}$ in the absence of Phe16, but is −0.63 kcal mol$^{-1}$ in the presence of Phe16.

These results strongly suggest the presence of a stabilizing tripartite interaction between Phe16, Asn19-GlcNAc, and Thr21 and provide evidence that the enhanced aromatic sequon can be successfully applied in reverse turn contexts other than the type I β-bulge turns present in HsCD2ad, RnCD2* and AcyP2*. Significant slowing of the unfolding rate in g-WW-F,T relative to WW-F,T suggests that the Phe-GlcNAc-Thr interaction stabilizes the Pin WW native state. Notably, both the kinetic and thermodynamic data provide strong evidence for the importance of Thr in this reverse turn context. Thr has long been known to play a crucial role in the biology of the OST-mediated glycosylation, but this is the first clear demonstration of its energetic importance.

It is well established that N-glycosylation can enhance glycoprotein stability, but it was not previously possible to know where to put a glycan to achieve predictable stabilization. Our findings indicate that the Asn-N-glycan, Phe and Thr side chains contribute key interactions that significantly stabilize glycoproteins when appropriately placed in reverse turn contexts, even those that are not normally glycosylated. This observation may account in part for the high frequency of glycosylation in the reverse turns of secreted proteins [Petrescu et al., *Glycobiology* 14, 103-114 (2004); Zielinska et al., *Cell* 141, 897-907 (2010)].

The results obtained herein are useful for predicting with increased accuracy whether N-glycosylation at a given site is likely to stabilize a protein, and whether that site is likely to be glycosylated efficiently, information that is critical for glycoprotein engineering. That the enhanced aromatic sequon in a type I β-bulge turn context is found in the PDB with all possible aromatic residues at the i position indicates that aromatics other than Phe are useful.

The WW domain from human Pin 1 also conveniently provides a single protein into which several types of enhanced aromatic sequons and their corresponding reverse turn types can be inserted without changing the overall structure or the flanking sequences. The WW domain is ideal for these requirements: many WW variants harboring different reverse turn types in loop 1 have been structurally characterized [Ranganathan et al., *Cell* 89, 875-886 (1997); Jäger M, et al. *Proc. Natl. Acad. Sci. USA* 103, 10648-106531 (2006); and Fuller et al. *Proc. Natl. Acad. Sci. USA* 106, 11067-11072 (2009)] and biophysically [Jäger et al. *Proc. Natl. Acad. Sci. USA* 103, 10648-106531 (2006); Fuller et al. *Proc. Natl. Acad. Sci. USA* 106, 11067-11072 (2009); Jäger et al., *J. Mol. Biol.* 311, 373-393 (2001); and Kaul et al., *J. Am. Chem. Soc.* 123, 5206-5212 (2001)].

Figure 1D:
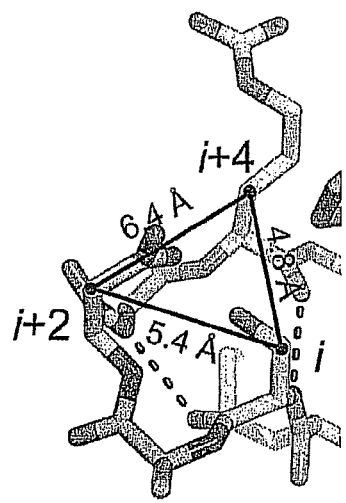
FIG. 1D shows a five-residue type I β-bulge turn [PDB accession code: 2F21; Jäger et al., *Proc. Natl. Acad. Sci. USA* 103, 10648-10653 (2006)]
Figure 1E:
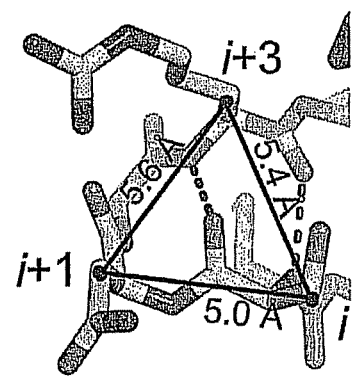
FIG. 1E illustrates a four-residue type I' β-turn [PDB accession code: 1ZCN; Jäger et al., *Proc. Natl. Acad. Sci. USA* 103, 10648-10653 (2006)].

Crystal structures exist for WW domains harboring a type II β-turn in a six-residue loop (FIG. 1B), a five-residue type I β-bulge turn (FIG. 10), and a four-residue type I' β-turn (FIG. 1D) as loop 1. It is thought that a type I' β-turn, which makes up 11% of the reverse turns in the PDB [Oliva et al., *J Mol Biol* 266(4), 814-830 (1997)], would also be an additional conformational host for a complementary enhanced aromatic sequon: the Cβ's of the side chains at the i, i+1, and i+3-positions are close enough (<5.6 Å; see FIG. 1D) to support a stabilizing tripartite interaction among Phe, Asn(GlcNAc1), and Thr. Importantly, the chemical synthesis of homogeneously glycosylated [Bertozzi et al., *Science* 291, 2357-2364 (2001)] WW domains is efficient [Culyba et al., *Science* 331, 571-575 (2011); and Price et al., *J. Am. Chem. Soc.* 132, 15359-15367 (2010)] enabling numerous analogs to be prepared, each having an identical N-glycan (in this case, GlcNAc1).

The data herein show that type I' β-turns are suitable conformational hosts for a stabilizing enhanced aromatic sequon. This result significantly expands the scope of protein stabilization by glycosylating enhanced aromatic sequons. Furthermore, these data show that the order of stabilization by glycosylating enhanced aromatic sequons in the different turn types is: type I β-bulge turns>type II β-turns in a six-residue loop>type I' β-turns.

Because enhanced aromatic sequons in proper turn contexts are stabilizing and may be preferred OST substrates, engineering glycoproteins with these sequences is a useful tool for protein evolution. Thermodynamic stabilization has proven essential for the discovery of mutants with enhanced activity where functional requirements might be at odds with optimal folding energetics. The enhanced aromatic sequon design concepts outlined within should also be immediately applicable to pharmacologic proteins, including antibodies, which could benefit from additional thermodynamic stabilization (and thus increased against proteolysis and aggregation) beyond the numerous other benefits of N-glycosylation such as improved serum half-life; solubility; and lowered immunogenicity [Li et al., *Curr Opin Biotechnol* 20, 678-684 (2009); Sinclair et al., *J Pharm Sci* 94, 1626-1635 (2005); Sola et al., *BioDrugs* 24, 9-21 (2010); Walsh et al., *Nat Biotechnol* 24, 1241-1252 (2006)].

Using the before noted the ideal platform offered by Pin 1 WW domain loop 1 reverse turn types, four-, five-, and six-residue reverse turns comprising loop 1 of WW were converted to their corresponding enhanced aromatic sequons by replacing the amino acid at position 16 (Ser in all cases) with Phe, replacing the amino acid at position 19 (Asn, Asp, or Ser, respectively) with Asn(GlcNAc1), and replacing the amino acid at position 21 (Arg in all cases) with Thr [Jäger et al. *Proc. Natl. Acad. Sci. USA* 103, 10648-106531 (2006); and Jäger et al., *J Mol Biol* 311, 373-393 (2001)].

Note that the same number is used to indicate amino acid residues in analogous positions in WW variants with different loop 1 lengths [Jäger et al. *Proc. Natl. Acad. Sci. USA* 103, 10648-106531 (2006); and Fuller et al. *Proc. Natl. Acad. Sci. USA* 106, 11067-11072 (2009)]. Thus, the sequences of the enhanced aromatic sequons in the four-, five-, and six-residue reverse turns comprising loop 1 include Phe16-Asn (GlcNAc1)19-Gly20-Thr21 (SEQ ID NO:137), Phe16-Ala18-Asn(GlcNAc1)19-Gly20-Thr21 (SEQ ID NO:138), and Phe16-Arg17-Ser18-Asn(GlcNAc1)19-Gly20-Thr21 (SEQ ID NO:139), respectively.

The stabilizing effect of glycosylating enhanced aromatic sequons can be quantified by comparing the stabilities of WW variants with glycosylated enhanced aromatic sequons to the stabilities of their non-glycosylated counterparts. The contributions of two- and three-way interactions amongst the Phe16, Asn19(GlcNAc1) and Thr21 side chains to the overall stabilizing effect of glycosylation can be estimated using triple mutant cycle analyses, done previously [Culyba et al., *Science* 331, 571-575 (2011)]. This parsing of stabilization energies through energetic comparisons was accomplished by replacing Phe16, Asn19(GlcNAc1) and Thr21 by Ser16, Asn19, and Arg21, respectively, in every possible combination, for a total of eight proteins in each of the three correlated enhanced aromatic sequon-reverse turn contexts. The results of these analyses are described hereinafter The WW variants are named by the number of amino acids in the loop 1 reverse turn, followed by the letter "g" if the variant is N-glycosylated on Asn19, the letter "F" if it has Phe at position 16, and the letter "T" if it has Thr at position 21. The lack of the letters g, F, and/or T indicates that the variant is not N-glycosylated on Asn19, that position 16 is Ser, and/or that position 21 is Arg, respectively. For example, variant 4g-F,T has a 4-residue loop 1 type I' β-turn, with Asn (GlcNAc1) at position 19, Phe at position 16, and Thr at position 21. Variant 4 has a 4-residue loop 1 type I' β-turn, with Asn at position 19, Ser at position 16, and Arg at position 21 (see the table hereinafter for the names of the WW variants studied).

Stabilization from Glycosylating Enhanced Aromatic Sequons

To quantify the stabilizing effect of glycosylating enhanced aromatic sequons in loop 1 of the corresponding four-, five-, and six-residue reverse turns, we used variable temperature circular dichroism (CD) spectropolarimetry to analyze the thermodynamic stability of WW variants 4-F,T, 4g-F,T, 5-F,T, 5g-F,T, 6-F,T, and 6g-F,T. CD data for 6-F,T and 6g-F,T and their derivatives (described below) have been published previously at a protein concentration of 50 μM [Culyba et al., *Science* 331, 571-575 (2011)], but were further studied herein at a protein concentration of 10 μM (the energetic data are comparable at both concentrations) to facilitate direct comparisons with 4-F,T, 4g-F,T, 5-F,T, and 5g-F,T and their derivatives (some of which were not completely soluble at 50 μM).

The table below shows the melting temperature $T_m$ and free energy of folding free energies ($\Delta G_f$) (at 65° C.) for each protein and corresponding glycoprotein, along with the effect of glycosylation on the $T_m$ and $\Delta G_f$ (at 65° C.) for each protein. A reference temperature of 65° C. was used because it is within

TABLE D

| WW Variant [SEQ ID NO] | Sequence# 15   21 | $T_m$ (° C.) | $\Delta T_m$ (° C.) | $\Delta G_f$ (kcal/mol) | $\Delta\Delta G_f$ (kcal/mol) |
|---|---|---|---|---|---|
| 4 [140]      | MS--NGR  | 64.4 ± 0.4 | 2.2 ± 0.6  | 0.06 ± 0.04  | -0.23 ± 0.06 |
| 4g [141]     | MS--N̲GR  | 66.6 ± 0.4 |            | -0.17 ± 0.04 |              |
| 4-F [142]    | MF--NGR  | 66.7 ± 0.5 | 1.5 ± 0.7  | -0.18 ± 0.08 | -0.18 ± 0.08 |
| 4g-F [143]   | MF--N̲GR  | 68.2 ± 0.5 |            | -0.36 ± 0.05 |              |
| 4-T [144]    | MS--NGT  | 62.2 ± 0.4 | -0.8 ± 0.6 | 0.30 ± 0.04  | 0.07 ± 0.07  |
| 4g-T [145]   | MS--N̲GT  | 61.4 ± 0.5 |            | 0.37 ± 0.05  |              |
| 4-F,T [146]  | MF--NGT  | 63.5 ± 0.3 | 3.2 ± 0.7  | 0.18 ± 0.03  | -0.39 ± 0.09 |
| 4g-F,T [147] | MF--N̲GT  | 66.7 ± 0.6 |            | -0.21 ± 0.08 |              |
| 5 [148]      | MS-ANGR  | 68.7 ± 0.2 | 0.6 ± 0.3  | -0.38 ± 0.02 | -0.07 ± 0.04 |
| 5g [149]     | MS-AN̲GR  | 69.3 ± 0.2 |            | -0.46 ± 0.03 |              |
| 5-F [150]    | MF-ANGR  | 65.2 ± 0.3 | 5.0 ± 0.4  | -0.02 ± 0.03 | -0.55 ± 0.04 |
| 5g-F [151]   | MF-AN̲GR  | 70.3 ± 0.2 |            | -0.58 ± 0.02 |              |
| 5-T [152]    | MS-ANGT  | 68.9 ± 0.2 | 2.4 ± 0.3  | -0.42 ± 0.02 | -0.23 ± 0.03 |
| 5g-T [153]   | MS-AN̲GT  | 71.3 ± 0.3 |            | -0.65 ± 0.03 |              |
| 5-F,T [154]  | MF-ANGT  | 66.0 ± 0.2 | 9.2 ± 0.2  | -0.11 ± 0.02 | -0.94 ± 0.03 |
| 5g-F,T [155] | MF-AN̲GT  | 75.2 ± 0.2 |            | -1.05 ± 0.02 |              |
| 6 [156]      | MSRSNGR  | 56.2 ± 0.3 | -2.6 ± 0.4 | 0.95 ± 0.04  | 0.21 ± 0.06  |
| 6g [157]     | MSRSN̲GR  | 53.6 ± 0.3 |            | 1.16 ± 0.04  |              |
| 6-F [158]    | MFRSNGR  | 51.0 ± 0.3 | 0.7 ± 0.4  | 1.45 ± 0.06  | -0.17 ± 0.08 |
| 6g-F [159]   | MFRSN̲GR  | 51.7 ± 0.3 |            | 1.28 ± 0.04  |              |
| 6-T [160]    | MSRSNGT  | 52.5 ± 0.3 | -0.2 ± 0.5 | 1.22 ± 0.05  | 0.04 ± 0.07  |
| 6g-T [161]   | MSRSN̲GT  | 52.3 ± 0.3 |            | 1.26 ± 0.05  |              |
| 6-F,T [162]  | MFRSNGT  | 47.4 ± 0.4 | 7.6 ± 0.5  | 1.72 ± 0.09  | -0.70 ± 0.10 |
| 6g-F,T [163] | MFRSN̲GT  | 55.0 ± 0.3 |            | 1.02 ± 0.04  |              |

*Tabulated data are given as mean ± standard error at 65° C. for WW variants at 10 μM in 20 mM aqueous sodium phosphate, pH 7.
N̲ = Asn(glycan).

the transition regions of all the variants studied herein. Extrapolating $\Delta G_f$ to temperatures outside the transition region using thermodynamic parameter estimates from fits to variable temperature CD data is unreliable (because errors in $\Delta C_p$, the least-well defined parameter from such fits, become magnified outside the transition region). For sets of proteins with similar $\Delta C_P$ values, the differences between their $T_m$ values should reflect the differences between their $\Delta G_f$ values both at 65° C. and at lower temperatures.

The $T_m$ of glycoprotein 4g-F,T is 3.2±0.7° C. higher than that of protein 4-F,T ($\Delta\Delta G_f=-0.39\pm0.09$ kcal mol$^{-1}$ at 65°C.), indicating that glycosylating the Phe-Asn-Yyy-Thr (SEQ ID NO:164) enhanced aromatic sequon in the context of a four-residue type I' β-turn stabilizes WW. Glycosylating the Phe-Xxx-Asn-Yyy-Thr (SEQ ID:136) sequon in the context of the five-residue type I β-turn also stabilizes WW ($\Delta T_m=9.2\pm0.2°$ C., $\Delta\Delta G_f=-0.94\pm0.03$ kcal mol$^{-1}$ at 65° C.), as does glycosylating the Phe-Xxx-Zzz-Asn-Yyy-Thr (SEQ ID NO:135) sequon in the type II β-turn in a six-residue loop ($\Delta T_m=7.6\pm0.5°$ C., $\Delta\Delta G_f=-0.70\pm0.10$ kcal mol$^{-1}$ at 65° C.). These data indicate that the Phe-Xxx-Asn-Yyy-Thr (SEQ ID NO:136) enhanced aromatic sequon corresponding to the five-residue type I β-bulge turn is, overall, the best for stabilizing WW amongst those studied here.

Figure 5C:
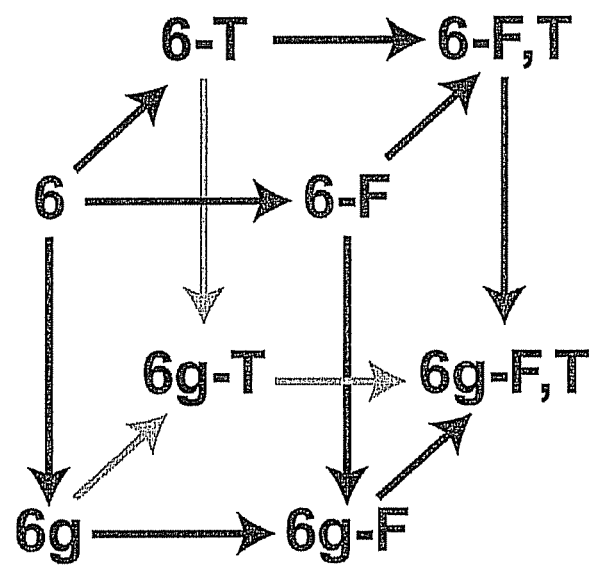
FIG. 5 in three parts illustrates triple mutant cycle cubes formed by protein 4, glycoprotein 4g, and their derivatives (FIG. 5A); Protein 5, glycoprotein 5g, and their derivatives (FIG. 5B); and Protein 6, glycoprotein 6g, and their derivatives (FIG. 5C).

Interaction Energies in Enhanced Aromatic Sequons from Triple Mutant Cycle Analysis To determine whether Phe, Asn(GlcNAc1) and Thr side chains interact similarly in each correlated enhanced aromatic sequon/reverse turn context, the thermodynamic stabilities of each WW variant were measured in the four-, five-, and six-residue reverse turn groups in the table above. The data from each group of eight WW variants comprise a triple mutant cycle (FIG. 5). Triple mutant cycles contain more information than conventional double mutant cycles, because each of the six "faces" of a triple mutant cycle "cube" is itself a double mutant cycle [Horovitz et al., *J Mol Biol* 224(3), 733-740 (1992)]. Whereas double mutant cycles provide information about the energetic impact of an interaction between two residues, a triple mutant cycle provides information about the energetic impact of the two- and three-way interactions.

Extracting this information from a triple mutant cycle is straightforward, and begins with analyzing the double mutant cycle faces of the triple mutant cycle cube (FIG. 5). The double mutant cycle formed by proteins 4 and 4-F and glycoproteins 4g and 4g-F (the front face of the triple mutant cycle cube in FIG. 5A), reveals that glycosylation of Asn19 (in the presence of Arg21) stabilizes glycoprotein 4g relative to protein 4 ($\Delta\Delta G_{f,1}=-0.23\pm0.06$ kcal mol$^{-1}$ at 65° C.). Similarly, glycosylation of Asn19 (in the presence of Arg 21) stabilizes 4g-F relative to 4g ($\Delta\Delta G_{f,2}=-0.18\pm0.08$ kcal mol$^{-1}$ at 65° C.). The difference between $\Delta\Delta G_{f,2}$ and $\Delta\Delta G_{f,1}$ ($\Delta\Delta\Delta G_{f,front}=0.05\pm0.10$ kcal mol$^{-1}$ at 65° C.) indicates that changing Ser16 to Phe16 (while keeping Arg21 constant) does not significantly change the effect of glycosylating Asn19 in the four-residue type I' β-turn. In other words, Phe16 and Asn(GlcNAc1)19 do not interact favorably in 4g-F.

Changing Arg21 to Thr21 changes this trend. The double mutant cycle formed by proteins 4-T, 4g-T, 4-F,T, and 4g-F,T (the back face of the triple mutant cycle "cube" shown in FIG. 5A) reveals that in the presence of Thr21 (instead of Arg21), Phe16 and Asn(GlcNAc1) interact favorably ($\Delta\Delta\Delta G_{f,back}=-0.46\pm0.11$ kcal mol$^{-1}$ at 65° C.). The difference between the front and back double mutant cycles is an estimate of the energy of the three-way interaction between Phe16, Asn(GlcNAc1)19, and Thr21. The large difference between $\Delta\Delta\Delta G_{f,back}$ and $\Delta\Delta\Delta G_{f,front}$ for the four-residue type I' β-turn ($\Delta\Delta\Delta\Delta G_f=-0.51\pm0.15$ kcal mol$^{-1}$ at 65° C.) indicates that Phe16, Asn(GlcNAc1)19 and Thr21 engage in a favorable three-way interaction in 4g-F,T.

Similar analyses of the triple mutant cycles formed by proteins 5 and 6 and their derivatives (FIGS. 5B, 5C) reveal a favorable interaction between Phe16, Asn(GlcNAc1)19, and Thr21 in the five-residue type I β-bulge turn ($\Delta\Delta\Delta\Delta G_f=-0.23\pm0.07$ kcal mol$^{-1}$ at 65° C.) and in the type II β-turn in a six-residue loop ($\Delta\Delta\Delta\Delta G_f=-0.36\pm0.15$ kcal mol$^{-1}$ at 65° C.). This three-way interaction between Phe16, Asn(GlcNAc1) 19, and Thr21 is similarly favorable in each reverse turn context (perhaps more favorable in the type I' β-turn than in the type I β-bulge turn, but recall that this is only part of the overall stabilizing effect of N-glycosylation).

The attribution of $\Delta\Delta\Delta G_{f,front}$ and $\Delta\Delta\Delta G_{f,back}$ values to the interaction between Phe16 and Asn(GlcNAc1)19, and of $\Delta\Delta\Delta\Delta G_f$ to the tripartite interaction among Phe16, Asn (GlcNAc1)19, and Thr21, assumes that the Ser16 side chain does not interact with the side chains at positions 19 or 21, and that the Arg21 side chain does not interact with the side chains at positions 16 or 19, in any variant. This assumption is, to a first approximation, consistent with the available structural data. Crystal structures of WW in the context of the full-length Pin1 protein [Ranganathan et al., (1997) *Cell* 89:875-886; and Jäger et al., (2006) *Proc. Natl. Acad. Sci. USA* 103:10648-10653] show that the side chains at positions 16, 19, and 21 generally interact only with solvent or the main chain (see, FIG. 1B-1D).

The lone exception is an interaction between the side chain hydroxyl of Ser16 and the side chain carboxylate of Asp19 in the type I β-bulge turn (FIG. 1C). However, the equivalent interaction (between the Ser16 hydroxyl and the Asn19 side chain carbonyl) in the variants of 5 that have Ser at position 16 (5, 5g, 5-T, and 5g-T) should be the same whether Asn19 is N-glycosylated or not, and thus should not affect the analysis.

It is also noted that the reverse turn structures are likely to depend primarily on loop length and the identities of a few key residues (e.g., Asn19 and Gly20 in the variants of 4 and Gly20 in the variants of 5, because these amino acids are strongly favored in these positions of type I' β-turns and type I β-bulge turns, respectively) [Sibanda et al., *J Mol Biol* 206(4), 759-777 (1989); and Jäger et al. *Proc. Natl. Acad. Sci. USA* 103, 10648-10653 (2006). Because these factors are kept constant within the variants that make up each triple mutant cycle, the corresponding reverse turn structures should remain roughly constant as well.

Least-squares regression was used to extract additional information about interactions amongst Phe, Asn(GlcNAc1), and Thr from the triple mutant cycles formed by WW variant groups 4, 5, and 6. The folding free energy data (at 65° C.) from the triple mutant cycle formed by 4 and its derivatives were fit to the following Equation (A):

$$\Delta G_f = \Delta G_f^0 + C_F \cdot W_F + C_N \cdot W_N + C_T \cdot W_T + C_{F,N} \cdot W_F \cdot W_N + \qquad (A)$$
$$C_{F,T} \cdot W_F \cdot W_T + C_{N,T} \cdot W_N \cdot W_T + C_{F,N,T} \cdot W_F \cdot W_N \cdot W_T$$

Equation A shows how the $\Delta G_f$ of a given variant of 4 is related to the average $\Delta G_f^0$ of 4, plus a series of correction terms that account for the interactions amongst the amino acids at positions 16, 19, and 21. Each correction term is a product of one or more indicator variables W (that reflect whether a mutation is present in the given variant) and a free energy contribution factor C. $W_F$ is 0 when position 16 is Ser or 1 when it is Phe; $W_N$ is 0 when position 19 is Asn or 1 when it is Asn(GlcNAc1); $W_T$ is 0 when position 21 is Arg or 1 when it is Thr. $C_F$, $C_N$, and $C_T$ describe the energetic consequences of the Ser16 to Phe16, Asn19 to Asn(GlcNAc1)19, and Arg21 to Thr21 mutations, respectively. These energies are thought to reflect the difference in conformational preferences between Ser and Phe at position 16, Asn and Asn(GlcNAc1) at position 19, and Arg and Thr at position 21.

$C_{F,N}$, $C_{F,T}$, and $C_{N,T}$ describe the free energies of the two-way interactions between Phe16 and Asn(GlcNAc1)19, between Phe16 and Thr21, and between Asn(GlcNAc1)19 and Thr21, respectively. $C_{F,N,T}$ describes the energetic impact of the three-way interaction between Phe16, Asn(GlcNAc1) 19, and Thr21. $C_{F,N}$, $C_{F,T}$, $C_{N,T}$, and $C_{F,N,T}$ are essentially equivalent to the two- and three-way interaction energies ($\Delta\Delta\Delta G_f$ and $\Delta\Delta\Delta\Delta G_f$ values) that could be calculated by a conventional analysis (e.g., as in the preceding section) of the triple mutant cycle data [Horovitz et al., (1992) *J Mol Biol* 224(3):733-740], but obtaining them by regression is more convenient, and can provide their standard errors in the regression output. Similar analyses for triple mutant cycle analysis of folding free energy data at 65° C. (338.15 K) for glycosylated and non-glycosylated WW variants harboring either a four-, five-, or six-residue reverse turn in loop 1 were performed and the results are shown in the table below. Note that the caveats

TABLE E

|  | Type I' β-turn | Type I β-bulge turn | Type II β-turn in six-residue loop |
|---|---|---|---|
| $\Delta G_f°$ | 0.06 ± 0.06 (0.287) | −0.38 ± 0.04 (0.000) | 0.95 ± 0.04 (0.000) |
| $C_F$ | −0.24 ± 0.08 (0.005) | 0.36 ± 0.06 (0.000) | 0.50 ± 0.06 (0.000) |
| $C_N$ | −0.23 ± 0.08 (0.009) | −0.07 ± 0.06 (0.248) | 0.21 ± 0.06 (0.000) |
| $C_T$ | 0.23 ± 0.08 (0.010) | −0.04 ± 0.06 (0.557) | 0.27 ± 0.06 (0.000) |
| $C_{F,N}$ | 0.05 ± 0.11 (0.661) | −0.48 ± 0.09 (0.000) | −0.38 ± 0.08 (0.000) |
| $C_{F,T}$ | 0.15 ± 0.11 (0.168) | −0.05 ± 0.09 (0.562) | 0.00 ± 0.08 (0.983) |
| $C_{N,T}$ | 0.31 ± 0.12 (0.015) | −0.16 ± 0.09 (0.088) | −0.17 ± 0.08 (0.051) |
| $C_{F,N,T}$ | −0.54 ± 0.15 (0.001) | −0.23 ± 0.12 (0.078) | −0.36 ± 0.11 (0.006) |

* Parameters are given as mean ± standard error. P values given in parentheses indicate the probability that random sampling error accounts for the difference between zero and the observed value of the parameter.

to the conventional analysis of triple mutant cycle data mentioned in the preceding section apply to this analysis as well.

Figure 6:
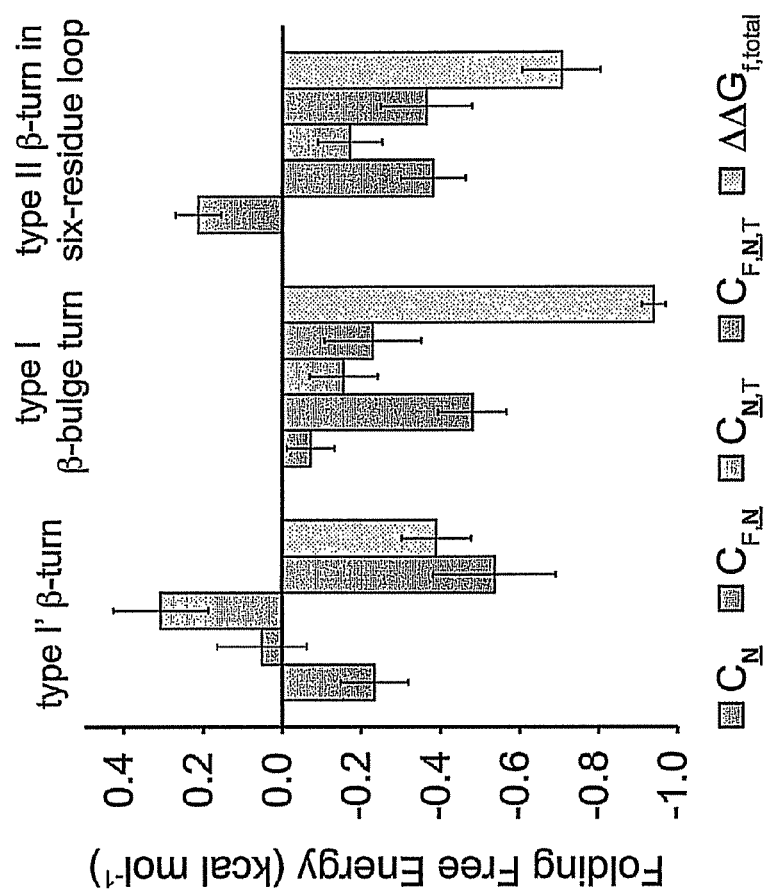
FIG. 6 is a graph showing the origin of the increase in stability of Pin1 protein derivatives 4-F,T, 5-F,T, and 6-F,T upon glycosylation. $\Delta G_{f,total}$ is the sum of the energetic effects of (1) the Asn19 to Asn(GlcNAc)19 mutation ($C_N$); (2) the two-way interaction between Phe16 and Asn(GlcNAc)19 ($C_{F,N}$); (3) the two-way interaction between Asn(GlcNAc)19 and Thr21 ($C_{N,T}$); and (4) the three-way interaction between Phe16, Asn(GlcNAc)19, and Thr21 ($C_{F,N,T}$). $C_N$, $C_{F,N}$, $C_{N,T}$, and $C_{F,N,T}$ are parameters obtained from least-squares regression of Equation A; error bars represent the corresponding standard errors.

According to Equation A, the stabilizing effect of glycosylating the enhanced aromatic sequon in 4-F,T [$\Delta\Delta G_f = \Delta G_f(4g\text{-}F,T) - \Delta G_f(4\text{-}F,T)$] is equal to the sum of the corresponding values of $C_N$, $C_{F,N}$, $C_{N,T}$, and $C_{F,N,T}$. The same is true for 5-F,T and 6-F,T. Thus, by comparing $C_N$, $C_{F,N}$, $C_{N,T}$, and $C_{F,N,T}$ values one can trace the origins of the stabilizing effect of glycosylating the enhanced aromatic sequon in each reverse turn context (FIG. 6).

Changing Asn19 to Asn(GlcNAc1)19 affects each turn type differently: it stabilizes the four-residue type I' β-turn ($C_N$=−0.23±0.08 kcal mol$^{-1}$), does not affect the five-residue type I β-bulge turn substantially ($C_N$=−0.07±0.06 kcal mol$^{-1}$), and destabilizes the type II β-turn within a six-residue loop ($C_N$=0.21±0.06 kcal·mol$^{-1}$). It is possible that Asn (GlcNAc1) has backbone dihedral angle preferences that are more compatible with the i+1 position of a type I' β-turn than with the i+2 position of a I β-bulge turn or with the i+3 position of a type II β-turn. If so, such preferences would differ substantially from those of Asn itself [Hovmoller et al., *Acta Crystallogr D* 58, 768-776 (2002)], which is favored at i+1 in a type I' β-turn, and at i+2 in a type I β-turn, but not at i+3 in a type II β-turn [Hutchinson et al., *Protein Sci* 3(12), 2207-2216 (1994)].

The two-way interaction between Phe16 and Asn (GlcNAc1)19 stabilizes the five-residue type I β-bulge turn ($C_{F,N}$=−0.48±0.09 kcal mol$^{-1}$) and the type II β-turn within a six-residue loop ($C_{F,N}$=−0.38±0.08 kcal mol$^{-1}$), but does not substantially change the stability of the four-residue type I' β-turn ($C_{F,N}$=0.05±0.11 kcal mol$^{-1}$). These differences appear not to correlate with differences among the Cβ-Cβ distances between positions 16 and 19 in the four-, five-, and six-residue turns (FIG. 1B-D), although it is possible that the backbone flexibility and/or direction of the Cα-Cβ bond vectors in the five- and six-residue turns permit better two-way interactions between Phe16 and Asn(GlcNAc1)19 than are possible in the four-residue turn.

The two-way interaction between Asn(GlcNAc1)19 and Thr21 stabilizes the five- and six-residue turns ($C_{N,T}$=−0.16±0.09 kcal mol$^{-1}$ and −0.17±0.08 kcal mol$^{-1}$, respectively), but substantially destabilizes the four-residue turn ($C_{N,T}$=0.31±0.12 kcal mol$^{-1}$). Published structural data [Wyss et al., *Science* 269, 1273-1278 (1995)] indicate that the glycosylated enhanced aromatic sequon in an analogous type I β-bulge turn in HsCD2ad involves three hydrogen bonds between Thr and Asn(GlcNAc1): one between the Thr side-chain oxygen and the amide proton of the 2-acetamido group of GlcNAc, and two between the Asn side-chain amide carbonyl oxygen and the backbone amide and side-chain hydroxyl protons of Thr (FIG. 1A). The differences observed here between the $C_{N,T}$ values in the four-, five-, and six-residue turn contexts could reflect the presence of analogous hydrogen bonds in the type I β-bulge turn of 5g-F,T and in six-residue loop of 6g-F,T, but not in the type I' β-turn of 4g-F,T.

The $C_{F,N,T}$ values for the four-residue type I' β-turn ($C_{F,N,T}$=−0.54±0.15 kcal mol$^{-1}$), the five-residue type I β-bulge turn ($C_{F,N,T}$=−0.23±0.12 kcal mol$^{-1}$), and the type II β-turn within a six-residue loop ($C_{F,N,T}$=−0.36±0.11 kcal mol$^{-1}$) mirror the $\Delta\Delta\Delta\Delta G_f$ values obtained by comparison of the front and back double mutant cycles in each triple mutant cube in FIG. 5, confirming that the three-way interaction between Phe16, Asn(GlcNAc1)19, and Thr21 stabilizes each reverse turn type by similar amounts.

Discussion

Glycosylating an enhanced aromatic sequon in its correlated reverse turn context is stabilizing. However, the origins of this stabilizing effect differ amongst the enhanced aromatic sequon/reverse turn pairs (FIG. 6).

In the type I' β-turn, this effect comes predominantly from the three-way interaction between Phe16, Asn(GlcNAc1)19, and Thr21 ($C_{F,N,T}$) and from the Asn19 to Asn(GlcNAc1)19 mutation ($C_N$), offset by an unfavorable two-way interaction between Asn(GlcNAc1)19 and Thr21 ($C_{N,T}$).

In the type I β-bulge turn, the two-way interaction between Phe16 and Asn(GlcNAc1)19 ($C_{F,N}$) contributes more than does the three-way interaction between Phe16, Asn (GlcNAc1)19, and Thr21 ($C_{F,N,T}$). In the type II β-turn within a six-residue loop, the two-way interaction between Phe16 and Asn(GlcNAc1)19 ($C_{F,N}$) and the three-way interaction between Phe16, Asn(GlcNAc1)19 and Thr21 ($C_{F,N,T}$) contribute similar amounts, offset by the unfavorable effect of the Asn19 to Asn(GlcNAc1)19 mutation ($C_N$). Despite these differences, the results provided here show that each reverse turn type is a suitable host for its corresponding enhanced aromatic sequon.

Adding N-glycans to naïve sites in proteins can be an attractive strategy for increasing their stability. This approach has been used in the development of protein drugs [Walsh et al., *Nat Biotechnol* 24(10), 1241-1252 (2006); Sinclair et al., *J Pharm Sci-Us* 94(8), 1626-1635 (2005); Li et al., *Curr Opin Biotech* 20(6), 678-684 (2009); and Sola et al., *Biodrugs* 24(1), 9-21 (2010)], where new N-glycans can extend serum half-life [Egrie et al., *Exp Hematol* 31(4), 290-299 (2003); Su et al., *Int J Hematol* 91(2), 238-244 (2010); and Ceaglio et al., *Biochimie* 90(3), 437-449 (2008)] and shelf-life, owing in part to increased protease resistance [Raju et al., *Biochem Bioph Res Co* 341(3), 797-803 (2006)], decreased aggregation propensity, and compensation for the destabilizing effect of methionine oxidation [Liu et al., *Biochemistry* 47(18), 5088-5100 (2008)]. Historically, efforts to increase protein stability via N-glycosylation have depended on a trial-and-error approach [Ceaglio et al., *Biochimie* 90(3), 437-449 (2008); and Elliott et al., *J. Biol. Chem.* 279, 16854-16862 (2004)], which resulted in unpredictable energetic consequences [Price et al., *J. Am. Chem. Soc.* 132, 15359-15367 (2010); Hackenberger et al., *J. Am. Chem. Soc.* 127, 12882-12889 (2005); and Chen et al. *Proc. Natl. Acad. Sci. USA* 107(52), 22528-22533 (2010).

By matching each enhanced aromatic sequon to an appropriate reverse turn conformation, the present invention has provided engineering guidelines by which N-glycosylation can reliably stabilize proteins. These matches include Phe-Asn-Yyy-Thr (SEQ ID NO:164) for type I' β-turns, Phe-Xxx-Asn-Yyy-Thr (SEQ ID NO:136) for type I β-bulge turns, and Phe-Xxx-Zzz-Asn-Yyy-Thr (SEQ ID NO:135) for type II β-turns within a six-residue loop. Each appears to facilitate native-state stabilizing interactions between Phe, Asn (GlcNAc) and Thr in glycosylation-naïve proteins that have not evolved to optimize protein-carbohydrate interactions [Culyba et al., *Science* 331, 571-575 (2011)]. The structure-stability relationships unveiled by this work also enable investigators to better predict which glycans can be removed from a glycoprotein to increase crystallization propensity, without yielding an unfolded or destabilized protein.

As noted earlier, the type I β-bulge turn and the type II β-turn in a six-residue loop (in which the Phe-Xxx-Asn-Yyy-Thr (SEQ ID NO:136) and Phe-Xxx-Zzz-Asn-Yyy-Thr (SEQ ID NO:135) sequons were previously applied, respectively) comprise less than 9% of all reverse turns in the PDB [Sibanda et al., *J Mol Biol* 206(4), 759-777 (1989); and Oliva et al., *J Mol Biol* 266(4), 814-830 (1997)]. By successfully applying the new Phe-Asn-Yyy-Thr (SEQ ID NO:164) enhanced aromatic sequon to the type I' β-turn (which comprises nearly 11% of all reverse turns in the PDB), the number of candidate proteins in which enhanced aromatic sequons can be employed without altering the conformation or the number of residues comprising the native reverse turn is doubled [DeGrado et al., *Annu Rev Biochem* 68, 779-819 (1999); and Gellman, *Curr Opin Chem Biol* 2(6), 717-725 (1998)].

Materials and Methods

General

Unless otherwise noted, chemicals and products were purchased from Fisher Scientific or Sigma-Aldrich. Phosphate buffered saline (PBS) was prepared from PBS tablets (SIGMA P-4417) and maintained at pH 7.2 with 0.5 mM TCEP and 0.01% sodium azide. 50 mM acetate buffer was prepared from a 4× solution made from 4× solutions of acetic acid (Acros Organic 124040025) and sodium acetate trihydrate (SIGMA 236500) to achieve a final pH of 5.5. Acetate buffer was also prepared with 0.5 mM TCEP and 0.01% sodium azide. All buffer solutions were filtered (Millipore 0.2 µM). Protein was concentrated using Amicon centrifugation devices, MWCO 3 kDa (Millipore). Final concentrations of RnCD2* and AcyP2* variants were determined by evaluation of absorbance at 280 nm using calculated extinction coefficients (ExPASy, ProtParam tool, Swiss Institute of Bioinformatics). All oligonucleotides for site directed mutagenesis were purchased from Integrated DNA Technologies (IDT), 25 nmole DNA oligo normalized to 100 µM in IDTE pH 8.0. Wild type RnCD2 and AcyP2 gene constructs were ordered from IDT as miniGenes in pZErO-2 vectors (Kan resistant).

RnCD2 Amino Acid Sequence

The sequence of wild type RnCD2 used for site directed mutagenesis to produce mutant sequences used:

```
                                         (SEQ ID NO: 165)
HHHHHHENLYFQS  DYKDDDDKIEGR  ADCRDSGTVW

GALGHGINLN     IPNFQMTDDI    DEVRWERGSTLV

AEFKRKMKPF     LKSGAFEILA    NGDLKIKNLT

RDDSGTYNVTVY   STNGTRILDK    ALDLRILEM

RnCD2.
```

The first 6 residues are a 6× Histidine-tag, which was included for Nickel affinity chromatography purification. This tag is followed by a 7-residue Tobacco Etch Virus protease cleavage site (TEVs) tag. This tag/protease cleavage site combination is followed by a 9-residue FLAG-tag, which in turn is followed by the 4-residue Factor Xa cleavage site (Xas) that was included so that all of the tags could be removed from the expressed gene construct (which was done before all measurements were taken).

All residues are numbered to correspond to homologous residues in human CD2ad. Thus, the numbering begins with 3; i.e., Ala3, and all following residue numbers increase sequentially. It should also be noted that some sequence changes were made to all mutants to ensure that the protein was only glycosylated at the desired position (Asn65) when expressed in Sf9 cells.

The wild type RnCD2 sequence contains three glycosylation sequons. The asparagines in these positions, Asn72, Asn82, and Asn89, were mutated to glutamine, glutamine, and aspartic acid (underlined), respectively. Finally, to confer glycosylation at Asn65 (bold), Asp67 (bold and underlined) was mutated to threonine:

```
                                         (SEQ ID NO: 166)
HHHHHHENLYFQS  DYKDDDDKIEGR  ADCRDSGTVW

GALGHGINLN     IPNFQMTDDI    DEVRWERGSTLV

AEFKRKMKPF     LKSGAFEILA    NGTLKIKELT

RDDSGTYEVTVY   STDGTRILDK    ALDLRILEM

RnCD2*.
```

AcyP2 Amino Acid Sequence

The sequence of wild type AcyP2 used for site directed mutagenesis to produce mutant sequences used:

```
                                         SEQ ID NO: 173
HHHHHHENLYFQS  DYKDDDDKIEGR  MSTAQSLKSV

DYEVFGRVQG     VCFRMYTEDE    ARKIGVVGWV
```

-continued

```
KNTSKGTVTG   QVQGPEDKVN   SMKSWLSKVG

SPSSRIDRTN   FSNEKTISKL   EYSNFSIRY
```

The same purification/protease site tag used in the RnCD2* variants was used for AcyP2* variants and as with RnCD2* the entire tag was remove via Factor Xa cleavage prior to all studies. Note that the residues are numbered starting with the first residue (Met) after the Factor Xa cleavage site. It should also be noted that some sequence changes were made to all mutants to ensure that the protein was only glycosylated at the desired position (45) when expressed in Sf9 cells. The wild type AcyP2 sequence contains three glycosylation sequons. The serines in these positions, Ser44, Ser82, and Ser96 (underlined), were mutated to alanine. Finally, to confer glycosylation at position 45, Lys45 (bold and underlined) was mutated to asparagine.

```
                              SEQ ID NO: 174
HHHHHHENLYFQS   DYKDDDDKIEGR   MSTAQSLKSV

DYEVFGRVQG      VCFRMYTEDE     ARKIGVVGWV

KNTANGTVTG      QVQGPEDKVN     SMKSWLSKVG

SPSSRIDRTN      FANEKTISKL     EYSNFAIRY
```

Pin1 Amino Acid Sequence

Peptidyl-prolyl cis-trans isomerase NIMA-interacting 1 (Pin1) is an enzyme (EC 5.2.1.8) that regulates mitosis presumably by interacting with NIMA and attenuating its mitosis-promoting activity. The enzyme displays a preference for an acidic residue N-terminal to the isomerized proline bond. The enzyme catalyzes pSer/Thr-Pro cis/trans isomerizations, and its amino acid residue sequence in single letter code is shown below, from left to right and from N-terminus to C-terminus.

```
                              SEQ ID NO: 178
MADEEKLPPG   WEKRMSRSSG   RVYYFNHITN

ASQWERPSGN   SSSGGKNGQG   EPARVRCSHL

LVKHSQSRRP   SSWRQEKITR   TKEEALELIN

GYIQKIKSGE   EDFESLASQF   SDCSSAKARG

DLGAFSRGQM   QKPFEDASFA   LRTGEMSGPV

FTDSGIHIIL   RTE
```

Pin1 WW Domain Amino Acid Sequence

Residues 6 through 44 at the N-terminus constitute the WW domain of Pin1 [Ranganathan et al., *Cell* 89, 875-886 (1997)]. The WW domain sequences used as illustrative herein are from position-6 through position-38. Amino acid residue position changes made to the WW domain are designated with the original amino acid residue position from the N-terminus. The amino acid residue sequences utilized herein are shown in the tables below along with their expected and observed MALDI-TOF [M+H$^+$] values.

TABLE F

| Protein | Sequence* 6  10   15    20    25    30    35   39 | SEQ ID NO |
|---|---|---|
| 4 | KLPPG WEKRM S--NG RVYYF NHITN ASQFE RPSG | 179 |
| 4g | KLPPG WEKRM S--NG RVYYF NHITN ASQFE RPSG | 180 |
| 4-F | KLPPG WEKRM F--NG RVYYF NHITN ASQFE RPSG | 181 |
| 4g-F | KLPPG WEKRM F--NG RVYYF NHITN ASQFE RPSG | 182 |
| 4-T | KLPPG WEKRM S--NG TVYYF NHITN ASQFE RPSG | 183 |
| 4g-T | KLPPG WEKRM S--NG TVYYF NHITN ASQFE RPSG | 184 |
| 4-F, T | KLPPG WEKRM F--NG TVYYF NHITN ASQFE RPSG | 185 |
| 4g-F, T | KLPPG WEKRM F--NG TVYYF NHITN ASQFE RPSG | 186 |
| 5 | KLPPG WEKRM S-ANG RVYYF NHITN ASQFE RPSG | 187 |
| 5g | KLPPG WEKRM S-ANG RVYYF NHITN ASQFE RPSG | 188 |
| 5-F | KLPPG WEKRM F-ANG RVYYF NHITN ASQFE RPSG | 189 |
| 5g-F | KLPPG WEKRM F-ANG RVYYF NHITN ASQFE RPSG | 190 |
| 5-T | KLPPG WEKRM S-ANG TVYYF NHITN ASQFE RPSG | 191 |
| 5g-T | KLPPG WEKRM S-ANG TVYYF NHITN ASQFE RPSG | 192 |
| 5-F, T | KLPPG WEKRM F-ANG TVYYF NHITN ASQFE RPSG | 193 |
| 5g-F, T | KLPPG WEKRM F-ANG TVYYF NHITN ASQFE RPSG | 194 |
| 6 | KLPPG WEKRM SRSNG RVYYF NHITN ASQFE RPSG | 195 |
| 6g | KLPPG WEKRM SRSNG RVYYF NHITN ASQFE RPSG | 196 |
| 6-F | KLPPG WEKRM FRSNG RVYYF NHITN ASQFE RPSG | 197 |

TABLE F-continued

| | Sequence* | | | | | | | SEQ ID |
|---|---|---|---|---|---|---|---|---|
| Protein | 6 10 | 15 | 20 | 25 | 30 | 35 | 39 | NO |
| 6g-F | KLPPG | WEKRM | FRS<u>N</u>G | RVYYF | NHITN | ASQFE | RPSG | 198 |
| 6-T | KLPPG | WEKRM | SRS<u>N</u>G | TVYYF | NHITN | ASQFE | RPSG | 199 |
| 6g-T | KLPPG | WEKRM | SRS<u>N</u>G | TVYYF | NHITN | ASQFE | RPSG | 200 |
| 6-F, T | KLPPG | WEKRM | FRS<u>N</u>G | TVYYF | NHITN | ASQFE | RPSG | 201 |
| 6g-F, T | KLPPG | WEKRM | FRS<u>N</u>G | TVYYF | NHITN | ASQFE | RPSG | 202 |

\* N = Asn(GlcNAc), Dash = deletion

TABLE G

| | MALDI-TOF [M + H⁺] | |
|---|---|---|
| Protein | Expected [M + H⁺] (amu)† | Observed [M + H⁺] (amu) |
| 4 | 3766.9 | 3766.8 |
| 4g | 3969.9 | 3972 |
| 4-F | 3826.9 | 3826.4 |
| 4g-F | 4030.0 | 4030.5 |
| 4-T | 3711.8 | 3711.8 |
| 4g-T | 3914.9 | 3916.3 |
| 4-F,T | 3771.9 | 3770.8 |
| 4g-F,T | 3974.9 | 3975.1 |
| 5 | 3837.9 | 3837.4 |
| 5g | 4041.0 | 4041.7 |
| 5-F | 3897.9 | 3898.1 |
| 5g-F | 4101.0 | 4101.6 |
| 5-T | 3782.9 | 3783.2 |
| 5g-T | 3985.9 | 3986.2 |
| 5-F,T | 3842.9 | 3842.7 |
| 5g-F,T | 4046.0 | 4045.4 |
| 6 | 4010.0 | ‡ |
| 6g | 4213.1 | ‡ |
| 6-F | 4070.0 | ‡ |
| 6g-F | 4273.1 | ‡ |
| 6-T | 3954.9 | ‡ |
| 6g-T | 4158.0 | ‡ |
| 6-F,T | 4015.0 | ‡ |
| 6g-F,T | 4218.1 | ‡ |

*N = Asn(GlcNAc);
†Monoisotopic masses;
‡Determined previously [Culyba et al., Science 331, 571-575 (2011)].

Structural Coordinates

RnCD2 structural coordinates were obtained from the PDB (accession code 1HNG). AcyP2 structural coordinates were obtained from the PDB for horse muscle acylphosphatase (accession code 1APS.pdb), which shares 94% sequence homology with the human protein. Coordinates were manipulated and rendered using PyMOL software (Schrödinger LLC).

Molecular Biology

All PCR was performed using Pfu Turbo® DNA polymerase (Stratagene) using recommended conditions. Restriction enzymes were obtained from New England Biolabs and applied as indicated. DNA fragments were ligated with standard conditions supplied for T4 ligase (Roche). Amplified and digested DNA was purified using 1% agarose (molecular biology grade gel prepared in TAE buffer. DNA isolation/purification steps, including genomic isolation, plasmid isolation, restriction digestion clean-up, and PCR purification were performed with Qiagen kits. Clones were transformed, amplified, and maintained in DH5a E. coli. All clones were verified for accuracy by sequencing.

Protein Purification Steps on FPLC

All FPLC procedures were carried out on an AKTA FPLC from GE Healthcare. HisTrap™ HP columns (1 mL) were run in 25 mM sodium phosphate, 300 mM NaCl, 5-300 mM imidazole, pH 8.0 at a flow rate of 3 mL/minute at room temperature. A Superdex™ 75 10/300 GL column (24 mL) was run in PBS (RnCD2*) or acetate (AcyP2*) at a flow rate of 0.4 mL/minute at room temperature (retention times: RnCD2* with glycan 12.5 minutes, RnCD2* without glycan 12.75 minutes, AcyP2* with glycan 14.75 minutes, AcyP2* without glycan 15 minutes).

Fluorescence Spectrometry

Both RnCD2* and AcyP2* have at least one tryptophan residue buried in the hydrophobic core allowing for an intrinsic fluorescence that depends on the folding status. Fluorescence measurements for RnCD2* and AcyP2 variants were obtained using either a CARY Eclipse (Varian) or an ATF-105 (Aviv) fluorescence spectrometer. Measurements were made in quartz cuvettes, at 25° C., at protein concentrations of 5-30 µg/mL, unless otherwise noted. Fluorescence emission spectra were collected from 315 to 400 nm, following excitation at 280 nm.

CD Spectrometry

CD measurements were made using an Aviv™ 62A DS spectropolarimeter, using quartz cuvettes with path lengths of 0.1 or 1 cm. WW domain solutions were prepared in 20 mM sodium phosphate buffer, pH 7; protein solution concentrations were determined spectroscopically from tyrosine and tryptophan absorbance at 280 nm in 6 M guanidine hydrochloride+20 mM sodium phosphate ($\epsilon_{Trp}$=5690 M⁻¹ cm⁻¹, $\epsilon_{Tyr}$=1280 M⁻¹ cm⁻¹) as described previously [Price et al., J. Am. Chem. Soc. 132, 15359-15367 (2010); and Edelhoch Biochemistry 6, 1948-1954 (1967)]. CD spectra were obtained by monitoring molar ellipticity from 340 to 200 nm in 1 nm increments, with 5-second averaging times. Variable temperature CD data were obtained by monitoring molar ellipticity at 227 nm from 0.2 to 98.2° C. at 2° C. intervals, with 90 second equilibration time between data points and 30 second averaging times. The variable temperature CD data were fit to obtain $T_m$ and $\Delta G_f$ values for each protein, as described previously [Price et al., J. Am. Chem. Soc. 132, 15359-15367 (2010)], and elsewhere herein.

Preparation of RnCD2* and AcyP2* Variants

Construction of Non-Glycosylated Variant Genes

Genes for non-glycosylated versions of RnCD2* and AcyP2* were subcloned into pT7-7 expression vectors using the PIPES method [Klock et al., Methods Mol Biol 498, 91-103 (2009)], to create pHisFLAG-RnCD2b and pHisFLAG-AcyP2b with native sequons removed sequences. The total N- to C-protein coding region is: Met-6His-TEVs-FLAGtag-FXas-RnCD2* or AcyP2*.

Site Directed Mutagenesis:

All mutant variants were engineered from these constructs using quick change site directed mutagenesis.

Expression of Non-Glycosylated Variants in *E. coli* (Rich Medium)

Bacterial RnCD2* and AcyP2* were expressed as described previously [Hanson et al., *Proc Natl Acad Sci USA* 106, 3131-3136 (2009)].

Nickel Affinity Purification

Cells were thawed and resuspended in an appropriate purification buffer (RnCD2* variants: 25 mM sodium phosphate, 300 mM NaCl, 5 mM imidazole, 0.5 mM TCEP, pH8.0; AcyP2* variants: same as above with 25 mM TrisHCl in place of phosphate) in $\frac{1}{20}^{th}$ of the original growth volume. Protease inhibitors (1 tablet/50 mL; Roche EDTA-free) were added. Cells were lysed by sonication. The cell lysate was spun down (15,000 rpm, 30 minutes, 4° C.), the soluble fraction (supernatent) was separated from the insoluble fraction (pellet) and used for Ni-NTA purification. In the case of RnCD2* variants RnCD2*K and RnCD2*KF and AcyP2* variant AcyP2*-F the insoluble fraction was treated with 6 M guanidine hydrochloride (GdnHCl) in the appropriated binding buffer and subjected to for Ni-NTA purification under denaturing conditions (6 M GdnHCl).

Superflow™ Ni-NTA resin was used to affinity purify proteins via the 6×His tag, using conditions described in the Qiagen manual. Denaturing purification was performed similarly with the addition of 6 M GdnHCl to all solutions. Eluted fractions were exchanged into Factor Xa cleavage buffer (50 mM TrisHCl, 100 mM NaCl, pH 7.9) and concentrated in Amicon centrifugation devices.

Factor XA Cleavage of N-Terminal Tags from Non-Glycosylated Proteins 5 mM $CaCl_2$ was added to concentrated protein in 50 mM TrisHCl, 100 mM NaCl, pH 7.9 before Factor Xa (New England Biolabs) treatment (1 µg Factor Xa: 100 µg of RnCD2 of mAcP). For RnCD2* variants, the protease reaction was carried out at 4° C. for 12 hours. For AcyP2* variants, the protease reaction was carried out at 25° C. for 2 hours. The cleavage mixture was quenched with 100 µM PMSF and separated and buffer exchanged by FPLC (Superdex® 75). RnCD2* final buffer: PBS, 0.5 mM TCEP, 0.01% sodium azide, pH 7.2. AcyP2* final buffer: 50 mM Acetate, 0.5 mM TCEP, 0.01% sodium azide, pH 5.5. HisFLAG-free RnCD2* ESI MS found: 11578; RnCD2*-K ESI MS found: 11576; RnCD2*-F ESI MS found: 11612; RnCD2*-KF ESI MS found: 11611. HisFLAG-free AcyP2* ESI MS found: 11078; AcyP2*-F ESI MS found: 11124.

Glycosylated Variants

Cloning for RnCD2 and AcyP2 Into an Insect Shuttle Vector

A 5' SacI site (gagctc) and 3' KpnI (ggtacc) site and a preprotrypsin leader sequence (PLS, for excretion into the medium) were designed into both the RnCD2 and AcyP2 genes ordered from IDT. Digestion (SacI and KpnI) and ligation of the products and the insect shuttle vector pFastBac™ (Invitrogen), yielded clone pPLSHisFLAG-RnCD21 and pPLSHisFLAG-AcyP21 (sometimes referred to as RnCD21 and AcyP21, respectively, herein).

Site Directed Mutagenesis

All mutant variants were engineered from these constructs [in the pFastBac™ vector (Invitrogen)] using quick change site directed mutagenesis.

Expression of RnCD2* and AcyP2* in Sf9 (Insect) Cells

Expression in insect cells was carried out as previously described [Hanson et al., *Proc Natl Acad Sci USA* 106, 131-3136 (2009)]. After expression, growth medium was collected and 0.2 µM filtered. Protease inhibitors (1 tablet/200 mL; Roche EDTA-free), 0.5 mM TCEP, and 1 mM EDTA were added to the filtered growth media extract.

Ammonium Sulfate Precipitation of Glycosylated Variants

Growth medium was incubated for 1 hour with ammonium sulfate (30% wt/vol) at 4° C. with constant stirring and precipitating species were removed. Addition of more ammonium sulfate (80% total wt/vol) to the soluble fraction for 1 hour at 4° C. resulted in the precipitation of either RnCD2* or AcyP2* variants from the medium. The precipitate was collected with centrifugation followed by vacuum filtration (Whatman Grade 5 qualitative filter paper). Precipitate was stored at −80° C.

Purification of Glycosylated Variants by Nickel Affinity Chromatography

Superflow® Ni-NTA resin (Qiagen) was used to affinity-purify proteins via the 6×His tag, using conditions described in the Qiagen manual. Briefly, precipitated protein was resuspended in ¼ of expression volume of lysis buffer (same as non-glycosylated variants) stirred for 1 hour at 4° C. and 0.2 µM filtered. Filtered medium was applied to a gravity Ni-NTA column in appropriate lysis buffer, and washed with 10 column volumes of lysis buffer and 50 column volumes of washing buffer (18 mM imidazole). Bound protein was removed with 4 column volumes of elution buffer (20 mM TrisHCl, 300 mM imidazole, pH 8.0 for all variants).

Alternatively, an FPLC HisTrap HP column (1 mL) was used for purification with the same buffer conditions as above. Eluted fractions were exchanged into Concanavilin A (ConA) binding buffer (25 mM TrisHCl, 500 mM NaCl, 1 mM $MnCl_2$, 1 mM $CaCl_2$, pH 7.4) and 0.5 mM TCEP and concentrated in Amicon centrifugation devices.

Isolation of Glycosylated Protein by Lectin Chromatography

Lectin chromatography with Concanavilin A (ConA) was performed on Nickel column eluate with the ConA Glycoprotein Isolation Kit (Pierce), following the protocols described therein. High mannose and paucimannose species were separated from the non-glycosylated protein found in every expression. Elution and wash fractions that contained only glycosylated protein were pooled and exchanged into Factor Xa cleavage buffer (50 mM TrisHCl, 100 mM NaCl, pH 7.9).

Factor Xa Cleavage of N-Terminal Tags from Glycosylated Proteins 5 mM $CaCl_2$ was added to concentrated protein in 50 mM TrisHCl, 100 mM NaCl, pH 7.9 before Factor Xa (New England Biolabs) treatment (1 µg Factor Xa: 100 µg of RnCD2* or AcyP2*). For RnCD2* variants the protease reaction was carried out at 4° C. for 12 hours. For AcyP2* variants the protease reaction was carried out at 25° C. for 2 hours. The cleavage mixture was quenched with 100 µM PMSF and separated and buffer exchanged by FPLC (Superdex® 75). RnCD2* variant final buffer: PBS, 0.5 mM TCEP, 0.01% sodium azide, pH 7.2. AcyP2* variant final buffer: 50 mM acetate, 0.5 mM TCEP, 0.01% sodium azide, pH 5.5. If cleavage was incomplete Nickel-NTA resin was used to remove uncleaved protein.

ESI-MS Characterization

Liquid Chromatography Mass Spectrometry (LCMS)

LCMS analysis was performed using an Agilent 1100 LC coupled to an Agilent 1100 single quad ESI mass spectrometer. LC was performed with a 4.6 mm×50 mm ZORBAX 08 column (Agilent Technologies, Inc.).

TABLE

MS characterization of glycosylated RnCD2* and AcyP2* variants

| Variant | $MW_{expected}$ | $MW_{found}$ | % | Structure |
|---|---|---|---|---|
| g-RnCD2* | 12956 | 12956 | 25 | $Man_6GlcNAc_2$ |
| (SEQ ID NO: 203) | 13119 | 13118 | 44 | $Man_7GlcNAc_2$ |
|  | 13282 | 13282 | 31 | $Man_8GlcNAc_2$ |
| g-RnCD2*-K | 12468 | 12469 | 6 | $Man_3GlcNAc_2$ |
| (SEQ ID NO: 168) | 12792 | 12793 | 13 | $Man_5GlcNAc_2$ |
|  | 12955 | 12956 | 22 | $Man_6GlcNAc_2$ |
|  | 13118 | 13118 | 43 | $Man_7GlcNAc_2$ |
|  | 13281 | 13280 | 16 | $Man_8GlcNAc_2$ |
| g-RnCD2*-F | 12990 | 12991 | 23 | $Man_6GlcNAc_2$ |
| (SEQ ID NO: 170) | 13153 | 13153 | 54 | $Man_7GlcNAc_2$ |
|  | 13316 | 13315 | 23 | $Man_8GlcNAc_2$ |
| g-RnCD2*-KF | 12989 | 12989 | 21 | $Man_6GlcNAc_2$ |
| (SEQ ID NO: 172) | 13152 | 13151 | 33 | $Man_7GlcNAc_2$ |
|  | 13315 | 13314 | 46 | $Man_8GlcNAc_2$ |
| AcyP2* | 12117 | 12116 | 100 | $Man_3GlcNAc_2$ (Fuc) |
| (SEQ ID NO: 175) |  |  |  |  |
| AcyP2* | 12163 | 12162 | 100 | $Man_3GlcNAc_2$ (Fuc) |
| (SEQ ID NO: 175) |  |  |  |  |

Details for the Characterization of RnCD2* Variants Folding Kinetics and Thermodynamics General PBS buffer (1×, 0.5 mM TCEP, 0.01% sodium azide, pH 7.2) was made fresh daily from a 10× stock and filtered. Urea and guanidine solutions were prepared fresh daily in 1×PBS, filtered, and concentrations were confirmed my index of refraction (IOR). Subsequent dilutions of urea or guanidine were made with 1×PBS and concentrations were checked by IOR. Constants defined in equations include the universal gas constant (R) and temperature (T). The value of RT at 25° C. was taken to be 0.592 kcal/mol. Data were imported and fitted in Mathematica® 7 software (Wolfram Research). Urea was used, exclusively, as the chaotrope for all RnCD2* variants except for L63F variants. Due to the high thermodynamic stability of the L63F variants and the saturation point of urea at 25° C., all measurements were also taken in guanidine hydrochloride solutions for this mutant (variants g-RnCD2*-F and RnCD2*-F). Further data can be found in Culyba et al., *Science* 331, 571-575 (2011).

Folding Kinetics of RnCD2* Variants

Fluorescence measurements related to kinetic studies were obtained using an AVIV® ATF-105 stopped-flow fluorimeter for single-mixing studies. The set-up consisted of two syringes (syringe 1:1 mL, syringe 2:2 mL) that permitted up to a 25-fold dilution of the components of syringe 1 with syringe 2, in a minimum of 80 μL, of which the flow cell holds 40 μL. The dead time between start of mixing and acquisition of data was estimated to be 50-100 ms; in general, only data after the first 200 ms were used for fitting.

Excitation was set at 280 nm (bandwidth: 2 nm) and emission was measured at 330 nm (bandwidth: 8 nm). The photomultiplier voltage was set to 1000 V and data was recorded for 20-200 seconds.

For unfolding studies, the decrease in intensity at 330 nm was monitored after native protein in PBS or low concentrations of urea or guanidine in syringe 1 was mixed with varying volumes of concentrated urea or guanidine solutions in syringe 2. For refolding studies, the increase in intensity at 330 nm was monitored after denatured protein in a urea or guanidine solution in syringe 1 was diluted with varying volumes of PBS buffer or low concentrations of urea or guanidine from syringe 2. All shots of a particular dilution were typically repeated at least 4 times.

Continuous irradiation of RnCD2* at 280 nm led to a decrease in fluorescence intensity over time that correlated with the excitation bandwidth, indicating that photobleaching was taking place. The fluorescence intensity at 330 nm ($F_{330}$) was therefore fit to a double exponential containing a photobleaching ($k_{pb}$) component and a folding/unfolding component ($k_{obs}$):

$$F_{330} = e^{-k_{pb}t}(c_1 + c_2 e^{-k_{obs}}) \quad [1]$$

where t is time, $c_1$ is the fluorescence intensity at t=0, and $c_2$ is the difference in fluorescence between the initial and final states. Note that $c_2$ was positive in unfolding studies and negative in refolding studies. There was no indication in any of the kinetic studies performed that Eq. 1 was inadequate to describe the observed folding kinetics. Thus, after accounting for photobleaching, folding was a monoexponential process for all variants.

Thermodynamic Stability of RnCD2* Variants Using Chaotrope Denaturation

All fluorescence measurements for equilibrium chaotrope denaturation studies were taken on a CARY Eclipse fluorescence spectrophotometer. The temperature at reading was kept constant at 25° C. using a CARY single cell Peltier accessory (Agilent Technologies).

For equilibrium denaturation studies, solutions of RnCD2* variants were prepared in PBS and high concentration of urea or guanidine (in 1×PBS) at matched protein concentrations (15-20 μg/mL). The solutions were mixed to produce approximately thirty 120 μL samples at regular intervals of urea or guanidine concentrations. Solutions were permitted to equilibrate for at least 30 minutes before fluorescence emission spectra were scanned, the average of three scans was taken.

Global Fit to Kinetic and Equilibrium Data

Plots of the natural logarithm of the observed rate of equilibration between the folded and unfolded states of a protein, ln ($k_{obs}$), vs. denaturant concentration have characteristic V-shapes (hence the term "chevron plot"). The quantity $k_{obs}$ is equal to the sum of the unfolding and folding rate constants, $k_u$ and $k_f$. Chevron plots therefore result from the dependence of ln $k_u$ and ln $k_f$ on urea concentration. The unfolding rate constant dominates $k_{obs}$ at high denaturant concentrations, where the chevron plots for several of the RnCD2* variants are slightly curved. Curvature in the unfolding arm of a chevron plot is often attributed to changes in the structure of the folding transition state. This behavior is accounted for by assuming that ln $k_u$ has a quadratic dependence on denaturant concentration:

$$\ln k_u = \ln k_{u,0} + m_{u1}[D] + m_{u2}[D]^2 \quad [2]$$

where [D] is denaturant concentration, $k_{u,0}$ is the unfolding rate constant at [D]=0, and $m_{u1}$ and $m_{u2}$ are the coefficients of the linear and squared terms in the dependence of ln $k_u$ on [D]. The folding rate constant dominates $k_{obs}$ at low denaturant concentrations, where, again, the chevron plots for many of the RnCD2* variants are curved. This has been observed previously by Parker et al. [Parker et al., *Biochemistry* 36, 13396-13405 (1997)], and was attributed to the rapid formation of an off-pathway intermediate. Thus, the effective folding rate constant, $k_f^*$, depends as follows on denaturant concentration:

$$k_f^* = f_u k_f = \frac{e^{\ln k_{f,0} + m_f[D]}}{1 + e^{\ln K_{i,0} + m_i[D]}} \quad [3]$$

where $f_u$ is the fraction of not-yet-folded protein that is in the unfolded state (instead of the off-pathway intermediate state;

i.e, $f_u=[U]/([U]+[I])=1/(1+K_i))$, $k_f$ is the true folding rate constant at a given denaturant concentration, [D] is denaturant concentration, $k_{f,0}$ is the true folding rate constant at [D]=0, $m_f$ is the slope of the dependence of ln $k_f$ on [D], $K_{i,0}$ is the equilibrium constant for formation of the off-pathway intermediate at [D]=0, and $m_i$ is the slope of the dependence of ln $K_i$ on [D]. Summing the expressions for $k_f^*$ and $k_u$ yields an equation for $k_{obs}$:

$$\ln k_{obs} = \ln(k_u + k_f^*) = \ln\left(e^{\ln k_{u,0}} e^{m_{u1}[D]+m_{u2}[D]^2} + \frac{e^{\ln k_{f,0}+m_f[D]}}{1+e^{\ln K_{i,0}+m_i[D]}}\right) \quad [4]$$

This equation can be fit to folding kinetics vs. denaturant concentration data to get the parameters of interest (primarily $k_{f,0}$ and $k_{u,0}$). However, the robustness of the fit can be improved by simultaneously fitting kinetics and equilibrium data. The folding equilibrium constant at a given denaturant concentration ($K_f$) is related to the parameters above as follows:

$$K_f = \frac{k_f}{k_u} = \frac{e^{\ln k_{f,0}+m_f[D]}}{e^{\ln k_{u,0}} e^{m_{u1}[D]+m_{u2}[D]^2}} \quad [5]$$

This expression can be inserted into the equation for fluorescence-detected equilibrium denaturation:

$$F = F_{f,0} + \varphi_f[D] + \frac{\Delta F + \Delta\varphi[D]}{1+K_f} = \quad [6]$$
$$F_{f,0} + \varphi_f[D] + \frac{\Delta F + \Delta\varphi[D]}{1+\frac{e^{\ln k_{f,0}+m_f[D]}}{e^{\ln k_{u,0}} e^{m_{u1}[D]+m_{u2}[D]^2}}}$$

where F is the total fluorescence, $F_{f,0}$ is the fluorescence of the folded protein at [D]=0, $\phi_f$ is the slope of the fluorescence of the folded state vs. [D], $\Delta F$ is the difference in fluorescence between the unfolded and folded states, and $\Delta\phi$ is the difference between the slopes of the fluorescences of the folded and unfolded states vs [D]. Some of the same parameters occur in the models for the dependence on [D] of the folding kinetics and equilibrium. This circumstance enables the simultaneous fitting of kinetic and equilibrium data mentioned above.

To ensure that the kinetic and equilibrium data had equal influence on the parameter estimates, the equilibrium data were weighted as follows: 1) the equilibrium and kinetic data were fit separately to their models; 2) the root mean squared residuals for the two fits were calculated; 3) the ratio of the kinetic and equilibrium RMS residuals was calculated (RMS$_{kinetic}$/RMS$_{equilibrium}$); 4) the equilibrium data points were multiplied by this ratio. The combined kinetic and (weighted) equilibrium data sets were then fit simultaneously to the combined kinetic and equilibrium model using Mathematica® 7.0 (Wolfram Research). The fit yielded estimates for $k_{f,0}$ and $k_{u,0}$ which were converted to a folding free energy ($\Delta G_{f,0}$) through the relation:

$$\Delta G_{f,0} = -RT \ln K_{f,0} = -RT \ln k_{f,0}/k_{u,0} \quad [7]$$

The slope of the dependence of $\Delta G_{f,0}$ on [D] at [D]=0, $m_{eq,0}$, was determined from the values of $m_f$ and $m_{u1}$ through the relation:

$$m_{eq,0} = -RT(m_f - m_{u1}) \quad [8]$$

Further data from these studies can be found in Culyba et al., Science 331, 571-575 (2011).

Details for the Characterization of AcyP2* Variants Thermodynamics

General

Acetate buffer (50 mM Acetate, 0.5 mM TCEP, 0.01% sodium azide, pH 5.5; Acetate) was made fresh daily from a 4× stock and filtered. Urea solutions were prepared fresh daily in 1× Acetate, filtered, and concentrations were confirmed my index of refraction (IOR). Subsequent dilutions of urea were made with 1× Acetate and concentrations were checked by IOR. Constants defined in equations include the universal gas constant (R) and temperature (T). The value of RT at 25° C. was taken to be 0.592 kcal/mol. Data were imported and fit in Microsoft Excel.

Thermodynamic Stability of AcyP2* Variants Using Chaotrope Denaturation

All fluorescence measurements for equilibrium chaotrope denaturation studies were taken on a CARY Eclipse fluorescence spectrophotometer. The temperature at reading was kept constant at 25° C. using a CARY single cell Peltier accessory (Agilent Technologies). Each chaotrope denaturation study was repeated at least three times for each variant.

For equilibrium denaturation studies, solutions AcyP2* variants were prepared in Acetate and high concentration of urea (in 1× Acetate) at matched concentrations (15-30 μg/mL). The solutions were mixed to produce approximately thirty 120 μL samples at regular intervals of urea or guanidine concentrations. Solutions were permitted to equilibrate for at least 30 minutes before fluorescence emission spectra were scanned, an average of three scans was taken. Like RnCD2*, AcyP2* unfolding in response to increasing concentrations of urea or guanidine causes a shift and intensity change in fluorescence spectrum. Thus, plots of fluorescence intensity at single wave lengths ($F_\lambda$), versus chaotrope concentration were plotted to demonstrate unfolding. $\Delta G_{f,0}$ and $m_{eq}$ values for AcyP2* were estimated by fitting fluorescence intensity at 330 nm ($F_{330}$) vs. urea concentration data to:

$$F = F_{f,0} + \varphi_f[D] + \frac{\Delta F + \Delta\varphi[D]}{1 + e^{-(\Delta G_{f,0}+m_{eq}[D])/RT}} \quad [9]$$

where F is the total fluorescence, $F_{f,0}$ is the fluorescence of the folded protein at [D]=0, $\phi_f$ is the slope of the fluorescence of the folded state vs. [D], $\Delta F$ is the difference in fluorescence between the unfolded and folded states, and $\Delta\phi$ is the difference between the slopes of the fluorescences of the folded and unfolded states vs [D].

$\Delta G_{f,0}$ and $m_{eq}$ values derived from single chaotrope denaturation studies were averaged to give the $\Delta G_{f,0}$, and $m_{eq}$ values and fits reported.

Polypeptide Synthesis

General

Pin1 WW domain proteins were synthesized as C-terminal acids, employing a solid phase peptide synthesis approach using a standard Fmoc Nα protecting group strategy either manually (protein WW) or via a combination of manual and automated methods (proteins g-WW (SEQ ID NO:205), WW-F (SEQ ID NO:197), g-WW-F (SEQ ID NO:198), WW-T (SEQ ID NO:199), g-WW-T (SEQ ID NO:200), WW-F,T, (SEQ ID NO:201) and g-WW-F,T (SEQ ID NO:202) were synthesized on an Applied Biosystems 433A automated peptide synthesizer except for the manual coupling of Fmoc-Asn(Ac$_3$GlcNAc)-OH; as discussed below). See also, Price et al., J. Am. Chem. Soc. 132, 15359-15367 (2010).

Amino acids were activated by 2-(1H-benzotriazole-1-yl)-1,1,3,3-tetramethyluronium hexafluorophosphate (HBTU, purchased from Advanced ChemTech) and N-hydroxybenzotriazole hydrate (HOBt, purchased from Advanced ChemTech). Fmoc-Gly-loaded NovaSyn® TGT resin and all Fmoc-protected α-amino acids (with acid-labile side-chain protecting groups) were purchased from EMD Biosciences, including the glycosylated amino acid Fmoc-Asn(Ac₃GlcNAc)-OH {N-α-Fmoc-N-β-[3,4,6-tri-O-acetyl-2-(acetylamino)-deoxy-2-β-glucopyranosyl]-L-asparagine} [Meldal et al., *Tetrahedron Lett.* 31, 6987-6990 (1990); Otvos et al., *Tetrahedron Lett.* 31, 5889-5892 (1990)]. Piperidine and N,N-diisopropylethylamine (DIEA) were purchased from Aldrich, N-methylpyrrolidinone (NMP) was purchased from Applied Biosystems, and N,N-dimethylformamide (DMF) was obtained from Fisher.

A general protocol for manual solid phase peptide synthesis follows: Fmoc-Gly-loaded NovaSyn® TGT resin (217 mg, 50 μmol at 0.23 mmol/g resin loading) was aliquotted into a fritted polypropylene syringe and allowed to swell in $CH_2Cl_2$ and dimethylformamide (DMF). Solvent was drained from the resin using a vacuum manifold. To remove the Fmoc protecting group on the resin-linked amino acid, 2.5 mL of 20% piperidine in DMF was added to the resin, and the resulting mixture was stirred at room temperature for 5 minutes. The deprotection solution was drained from the resin with a vacuum manifold. Then, an additional 2.5 mL of 20% piperidine in DMF was added to the resin, and the resulting mixture was stirred at room temperature for 15 minutes. The deprotection solution was drained from the resin using a vacuum manifold, and the resin was rinsed five times with DMF.

For coupling of an activated amino acid to a newly deprotected amine on resin, the desired Fmoc-protected amino acid (250 μmol, 5 eq.) and HBTU (250 μmol, 5 eq.) were dissolved by vortexing in 2.5 mL 0.1 M HOBt (250 μmol, 5 eq.) in NMP. To the dissolved amino acid solution was added 87.1 μmol DIEA (500 μmol, 10 eq.). Only 1.5 eq. of amino acid were used during the coupling of the expensive Fmoc-Asn(Ac3GlcNAc)-OH monomer, and the required amounts of HBTU, HOBT, and DIEA were adjusted accordingly. The resulting mixture was vortexed briefly and allowed to react for at least 1 minute.

The activated amino acid solution was then added to the resin, and the resulting mixture was stirred at room temperature for at least 1 hour. Selected amino acids were double coupled as needed to allow the coupling reaction to proceed to completion. Following the coupling reaction, the activated amino acid solution was drained from the resin with a vacuum manifold, and the resin was subsequently rinsed five times with DMF. The cycles of deprotection and coupling were alternately repeated to give the desired full-length protein.

Acid-labile side-chain protecting groups were globally removed and proteins were cleaved from the resin by stirring the resin for about 4 hours in a solution of phenol (0.5 g), water (500 μL), thioanisole (500 μL), ethanedithiol (250 μL), and triisopropylsilane (100 μL) in trifluoroacetic acid (TFA, 8 mL). Following the cleavage reaction, the TFA solution was drained from the resin, the resin was rinsed with additional TFA, and the resulting solution was concentrated under Ar. Proteins were precipitated from the concentrated TFA solution by addition of diethyl ether (about 45 mL). Following centrifugation, the ether was decanted, and the pellet (containing the crude protein) was stored at −20° C. until purification.

Acetate protecting groups were subsequently removed from the 3-, 4-, and 6-hydroxyl groups of GlcNAc in Asn (GlcNAc)-containing proteins by hydrazinolysis, as described previously [Price et al., *J. Am. Chem. Soc.* 132, 15359-15367 (2010); and Ficht et al., *Chem. Eur. J.* 14, 3620-3629 (2008)] and elsewhere herein. The WW domains were purified by reverse-phase HPLC on a 018 column using a linear gradient of water in acetonitrile with 0.2% v/v TFA. The identity of each WW domain was confirmed by matrix-assisted laser desorption/ionization time-of-flight spectrometry (MALDI-TOF), and purity was evaluated by analytical HPLC.

Removal of Acetate Protecting Groups on Asn-Linked GlcNAc Residues in Glycosylated Pin1 WW Domain Proteins Acetate protecting groups were removed from the 3-, 4-, and 6-hydroxyl groups on the Asn-linked GlcNAc residues in proteins g-WW, g-WW-F, g-WW-T, and g-WW-F,T via hydrazinolysis as described previously [Ficht et al., *Chem. Eur. J.* 14, 3620-3629 (2008)]. Briefly, the crude protein was dissolved in a solution of 5% hydrazine solution in 60 mM aqueous dithiothreitol (sometimes containing as much as 50% acetonitrile, to facilitate dissolution of the crude protein) and allowed to stand at room temperature for about 1 hour with intermittent agitation. The deprotection reaction was quenched by the addition of about 1 mL TFA and about 20 mL water. The quenched reaction mixture was frozen and lyophilized to give the crude deprotected protein as a white powder.

Purification and Characterization

Immediately prior to purification, the crude proteins were dissolved in either 1:1 water:acetonitrile, DMSO, or 8 M GdnHCl (depending on solubility of the crude protein—8 M GdnHCl was frequently required to dissolve the crude glycosylated proteins even though these proteins were readily soluble in water after purification). Proteins were purified by preparative reverse-phase HPLC on a C18 column using a linear gradient of water in acetonitrile with 0.2% v/v TFA. HPLC fractions containing the desired protein product were pooled, frozen, and lyophilized. Polypeptides were identified by matrix-assisted laser desorption/ionization time-of-flight spectrometry (MALDI-TOF) and purity was established by analytical HPLC. Further data from these studies can be found in Culyba et al., *Science* 331, 571-575 (2011).

Circular Dichroism Spectroscopy

Measurements were made with an Aviv 62A DS Circular Dichroism Spectrometer, using quartz cuvettes with a 0.1 cm path length. Protein solutions were prepared in 10 mM sodium phosphate buffer, pH 7, and protein concentrations were determined spectroscopically based on tyrosine and tryptophan absorbance at 280 nm in 6 M guanidine hydrochloride+20 mM sodium phosphate ($\epsilon_{Trp}$=5690 M$^{-1}$ cm$^{-1}$, $\epsilon_{Tyr}$=1280 M$^{-1}$ cm$^{-1}$) [Price et al., *J. Am. Chem. Soc.* 132, 15359-15367 (2010); and Edelhoch Biochemistry 6, 1948-1954 (1967)]. CD spectra were obtained by monitoring molar ellipticity from, 340 to 200 nm, with 5 second averaging times. Variable temperature CD data were obtained by monitoring molar ellipticity at 227 nm from 0.2 to 98.2° C. at 2° C. intervals, with 90 seconds equilibration time between data points and 30 second averaging times.

Variable temperature CD data were fit to the following model for two-state thermally induced unfolding transitions:

$$[\theta] = \frac{(D_0 + D_1 \cdot T) + K_f(N_0 + N_1 \cdot T)}{1 + K_f} \quad (10)$$

where T is temperature in Kelvin, $D_0$ is the y-intercept and $D_1$ is the slope of the post-transition baseline; $N_o$ is the y-intercept and $N_1$ is the slope of the pre-transition baseline; and $K_f$ is the temperature-dependent folding equilibrium constant. $K_f$ is related to the temperature-dependent free energy of folding $\Delta G_f(T)$ according to the following equation:

$$K_f = \exp\left[\frac{-\Delta G_f(T)}{RT}\right] \quad (11)$$

where R is the universal gas constant (0.0019872 kcal/mol/K). The midpoint of the thermal unfolding transition (or melting temperature $T_m$) was calculated by fitting $\Delta G_f(T)$ to either of two equations. The first equation is derived from the van't Hoff relationship:

$$\Delta G_f(T) = \frac{\Delta H(T_m)}{T_m}(T_m - T) + \Delta C_p\left[T - T_m - T\ln\left(\frac{T}{T_m}\right)\right] \quad (12)$$

where $\Delta H(T_m)$ is the enthalpy of folding at the melting temperature and $\Delta C_p$ is the heat capacity of folding ($\Delta H(T_m)$, $\Delta C_p$, and $T_m$ are parameters of the fit). The second equation represents $\Delta G_f(T)$ as a Taylor series expansion about the melting temperature:

$$\Delta G_f(T) = \Delta G_0 + \Delta G_1 \times (T-T_m) + \Delta G_2 \times (T-T_m)^2 \quad (13)$$

in which $\Delta G_0$, $\Delta G_1$, and $\Delta G_2$ are parameters of the fit and $T_m$ is a constant obtained from the van't Hoff fit (in equation 12). The $\Delta G_f$ values displayed in FIG. 4F for each Pin WW domain protein were obtained by averaging the $\Delta G_f$ values (calculated at 328.15 K using equation 13) from each of three or more replicate variable temperature CD studies on the same protein.

CD spectra and variable-temperature CD data for proteins Pin WW domain proteins WW, g-WW, WW-F, g-WW-F, WW-T, g-WW-T, WW-F,T, and g-WW-F,T appear in the Supplemental Information along with parameters from equations 12 and 13 that were used to fit the variable temperature CD data. The standard error for each fitted parameter is also shown. These standard parameter errors were used to estimate the uncertainty in the average $\Delta G_f$ values, along with the uncertainty in the folding and unfolding rate ratios shown in FIG. 4F by propagation of error. Further data from these studies can be found in Culyba et al., Science 331, 571-575 (2011).

Laser Temperature Jump Studies

Relaxation times following a rapid laser-induced temperature jump of about 12° C. were measured by monitoring Trp fluorescence of 50 μM solution of Pin WW domain proteins WW, g-WW, WW-F, g-WW-F, WW-T, g-WW-T, WW-F,T, and g-WW-F,T in 20 mM sodium phosphate (pH 7) using a nanosecond laser temperature jump apparatus, as described previously [Ballew et al., Rev. Sci. Instrum. 67, 3694-3699 (1996); Ballew et al., Proc. Natl. Acad. Sci. USA 93, 5759-5764 (1996); Ervin et al., J. Photochem. Photobiol. sect. B 54, 1-15 (2000); Jäger et al., J. Mol. Biol. 311, 373-393 (2001)] to monitor the fluorescence decay of a Trp residue in each protein after a laser-induced temperature jump at each of several temperatures.

The relaxation traces represent the average of at least 10 individual temperature-jump studies, and were obtained by fitting the shape f of each fluorescence decay at time t to a linear combination of the fluorescence decay shapes before $f_1$ and after $f_2$ the temperature jump:

$$f(t) = a_1(t) \cdot f_1 + a_2(t) \cdot f_2, \quad (14)$$

where $a_1(t)$ and $a_2(t)$ are the coefficients of the linear combination describing the relative contributions of $f_1$ and $f_2$ to the shape of the fluorescence decay at time t [Jäger et al., J. Mol. Biol. 311, 373-393 (2001)]. Then, the relaxation of the protein to equilibrium at the new temperature following the laser-induced temperature jump can be represented as $\chi_1(t)$:

$$\chi_1(t) = \frac{a_1(t)}{a_1(t) + a_2(t)}, \quad (15)$$

plotted as a function of time for each protein at several temperatures [Ballew et al., Proc. Natl. Acad. Sci. USA, 93, 5759-5764 (1996); and Ervin et al., J. Photochem. Photobiol. sect. B 54, 1-15 (2000)].

The relaxation traces at each temperature were then fit to the following equation:

$$\chi(t) = C_1 \cdot \exp\left[\frac{-(t-x_0)}{\tau}\right] + C_2, \quad (16)$$

where $C_1$ and $C_2$ are constants describing the amplitude of the fluorescence decay, $x_0$ is a constant that adjusts the measured time to zero after the instantaneous temperature jump, and $\tau$ is the relaxation time, which is the inverse of the observed rate constant $k_{obs}$ ($k_{obs} = 1/\tau$). Using the temperature-dependent equilibrium constant $K_f$ for each protein (from the variable temperature CD studies), folding $k_f$ and unfolding $k_u$ rate constants can be extracted from $k_{obs}$ according to the following equations:

$$k_{obs} = k_f + k_u \quad (17)$$

$$K_f = \frac{k_f}{k_u} \quad (18)$$

$$k_f = k_{obs} \cdot \left[1 - \frac{1}{K_f + 1}\right] \quad (19)$$

The folding rates for each protein can then be fit as a function of temperature to the following Kramers model [Kramers, Physica 7, 284 (1940); Lapidus et al., Proc. Natl. Acad. Sci. USA 97, 7220-7225 (2000); Hanggi et al., Rev. Mod. Phys. 62, 251-341 (1990)] equation:

$$k_f(T) = \nu(59° \text{ C.}) \cdot \frac{\eta(59° \text{ C.})}{\eta(T)} \exp\left[-\frac{\Delta G_0 + \Delta G_1 \cdot (T-T_m) + \Delta G_2 \cdot (T-T_m)^2}{RT}\right], \quad (20)$$

in which the temperature-dependent free energy of activation $\Delta G^{\ddagger}_f$ is represented as a second order Taylor series expansion about the melting temperature $T_m$, and $\Delta G^{\ddagger}_0$, $\Delta G^{\ddagger}_1$, and $\Delta G^{\ddagger}_2$ are parameters of the fit. The pre-exponential term in equation S11 represents the viscosity-corrected frequency $\nu$ of the characteristic diffusional folding motion at the barrier [Bieri et al., Proc. Natl. Acad. Sci. USA 96, 9597-9601 (1999); Ansari et al., Science 256, 1796-1798 (1992) at 59° C., $\nu = 5 \times$ $10^5$ s$^{-1}$) [Fuller et al., *Proc. Natl. Acad. Sci. USA* 106, 11067-11072 (2009)]. $\eta(59°$ C.) is the solvent viscosity at 59° C. and $\eta(T)$ is the solvent viscosity at temperature T, both calculated with equation 21:

$$\eta(T) = A \cdot 10^{\frac{B}{T-C}} \quad (21)$$

where A=2.41×10$^5$ Pas, B=247.8 K, and C=140 K [Weast, *CRC Handbook of Chemistry and Physics*; CRC Press: Boca Raton, 1982].

Figure 4:
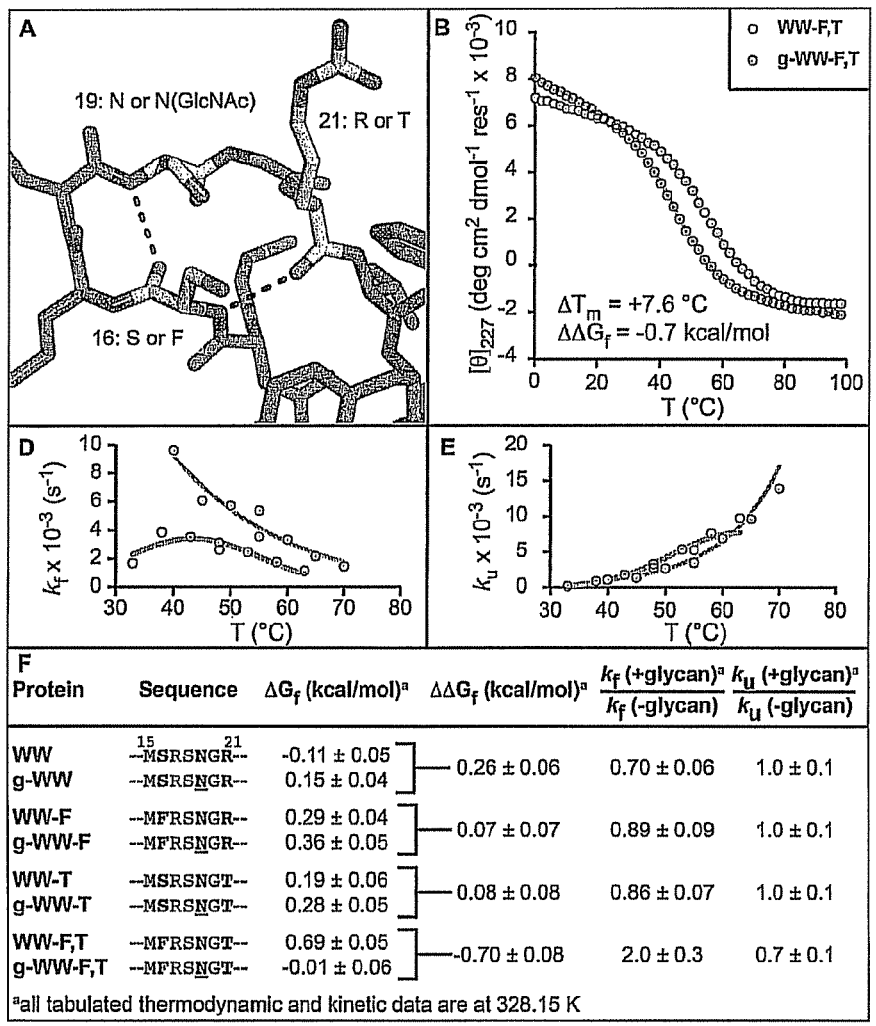
FIG. 4 in five parts illustrates in FIG. 4A the residues of loop 1 of the 34-residue WW domain from human Pin 1 (Pin WW or Pin1 WW), a glycosylation-naïve β-sheet protein, that contains a four residue type II β-turn within a larger six-residue H-bonded loop. WW is SEQ ID NO:204, g-WW is SEQ ID NO:205, WW-F is SEQ ID NO:197, g-WW-F is SEQ ID NO:198, WW-T is SEQ ID NO:199, g-WW-T is SEQ ID NO:200, WW-F,T is SEQ ID NO:201 and g-WW-F,T is SEQ ID NO:202.

The parameters for equations 13 and 20 were used to calculate the folding and unfolding rate ratios at 328.15 K for Pin WW domain proteins WW, g-WW, WW-F, g-WW-F, WW-T, g-WW-T, WW-F,T, and g-WW-F,T shown in FIG. 4F.

Each of the patents, patent applications and articles cited herein is incorporated by reference. The use of the article "a" or "an" is intended to include one or more.

The foregoing description and the examples are intended as illustrative and are not to be taken as limiting. Still other variations within the spirit and scope of this invention are possible and will readily present themselves to those skilled in the art.

SEQUENCE LISTING

```
<160> NUMBER OF SEQ ID NOS: 327

<210> SEQ ID NO 1
<211> LENGTH: 9
<212> TYPE: PRT
<213> ORGANISM: Artificial Sequence
<220> FEATURE:
<223> OTHER INFORMATION: Engineered enhanced sequon
<220> FEATURE:
<221> NAME/KEY: MISC_FEATURE
<222> LOCATION: (1)..(1)
<223> OTHER INFORMATION: Xaa at position 1 is an aromatic amino acid
      His, Phe, Trp, or Tyr.
<220> FEATURE:
<221> NAME/KEY: MISC_FEATURE
<222> LOCATION: (2)..(5)
<223> OTHER INFORMATION: Xaa at positions 2-5 are present or absent
      and are Alanine, Cysteine, Aspartic Acid , Glutamic Acid, Glycine,
      Isoleucine, Lysine, Leucine, Methionine, Asparagine, Proline,
      Glutamine, Arginine, Serine, Threonine or Valine.
<220> FEATURE:
<221> NAME/KEY: MISC_FEATURE
<222> LOCATION: (6)..(6)
<223> OTHER INFORMATION: Xaa at position 6 is present or absent and is
      any amino acid residue.
<220> FEATURE:
<221> NAME/KEY: MISC_FEATURE
<222> LOCATION: (8)..(8)
<223> OTHER INFORMATION: Xaa at position 8 is Alanine, Cysteine,
      Aspartic Acid , Glutamic Acid, Phenylalanine, Glycine,
      Histidine, Isoleucine, Lysine, Leucine, Methionine, Asparagine,
      Glutamine, Arginine, Serine, Threonine, Valine, Tryptophan, or
   Tyrosine.
<220> FEATURE:
<221> NAME/KEY: MISC_FEATURE
<222> LOCATION: (9)..(9)
<223> OTHER INFORMATION: Xaa at position 9 is Serine or Threonine.
<300> PUBLICATION INFORMATION:
<301> AUTHORS: Culyba EK, Price JL, Hanson SR, Dhar A, Wong CH, Gruebele
      M, Powers ET, Kelly JW
<302> TITLE: Protein native-state stabilization by placing aromatic side
      chains in N-glycosylated reverse turns.
<303> JOURNAL: Science
<304> VOLUME: 331
<305> ISSUE: 6017
<306> PAGES: 571-575
<307> DATE: 2011-02-04
<313> RELEVANT RESIDUES IN SEQ ID NO: (1)..(9)

<400> SEQUENCE: 1

Xaa Xaa Xaa Xaa Xaa Xaa Asn Xaa Xaa
1               5

<210> SEQ ID NO 2
<211> LENGTH: 5
<212> TYPE: PRT
<213> ORGANISM: Artificial Sequence
<220> FEATURE:
<223> OTHER INFORMATION: Engineered enhanced sequon
<220> FEATURE:
```

```
<221> NAME/KEY: MISC_FEATURE
<222> LOCATION: (1)..(1)
<223> OTHER INFORMATION: Xaa at position 1 is Histidine, Phenylalanine,
      Tryptophan, or
      Tyrosine.
<220> FEATURE:
<221> NAME/KEY: MISC_FEATURE
<222> LOCATION: (2)..(2)
<223> OTHER INFORMATION: Xaa at position 2 is Alanine, Cysteine,
      Aspartic Acid , Glutamic Acid, Glycine, Isoleucine, Lysine,
      Leucine, Methionine, Asparagine, Proline, Glutamine, Arginine,
      Serine, Threonine or Valine.
<220> FEATURE:
<221> NAME/KEY: MISC_FEATURE
<222> LOCATION: (4)..(4)
<223> OTHER INFORMATION: Xaa at position 4 is Alanine, Cysteine,
      Aspartic Acid , Glutamic Acid, Phenylalanine, Glycine, Histidine,
      Isoleucine, Lysine,  Leucine, Methionine, Asparagine, Glutamine,
      Arginine, Serine, Threonine, Valine, Tryptophan, or Tyrosine.
<220> FEATURE:
<221> NAME/KEY: MISC_FEATURE
<222> LOCATION: (5)..(5)
<223> OTHER INFORMATION: Xaa at position 5 is Serine or Threonine.

<400> SEQUENCE: 2

Xaa Xaa Asn Xaa Xaa
1               5

<210> SEQ ID NO 3
<211> LENGTH: 4
<212> TYPE: PRT
<213> ORGANISM: Artificial Sequence
<220> FEATURE:
<223> OTHER INFORMATION: Engineered enhanced sequon
<220> FEATURE:
<221> NAME/KEY: MISC_FEATURE
<222> LOCATION: (1)..(1)
<223> OTHER INFORMATION: Xaa at position 1 is Histidine, Phenylalanine,
      Tryptophan, or Tyrosine.
<220> FEATURE:
<221> NAME/KEY: MISC_FEATURE
<222> LOCATION: (3)..(3)
<223> OTHER INFORMATION: Xaa at position 3 is Alanine, Cysteine,
      Aspartic Acid , Glutamic Acid, Phenylalanine, Glycine, Histidine,
      Isoleucine, Lysine, Leucine, Methionine, Asparagine, Glutamine,
      Arginine, Serine, Threonine, Valine, Tryptophan, or Tyrosine.
<220> FEATURE:
<221> NAME/KEY: MISC_FEATURE
<222> LOCATION: (4)..(4)
<223> OTHER INFORMATION: Xaa at position 4 is Threonine or Serine

<400> SEQUENCE: 3

Xaa Asn Xaa Xaa
1

<210> SEQ ID NO 4
<211> LENGTH: 31
<212> TYPE: PRT
<213> ORGANISM: Artificial Sequence
<220> FEATURE:
<223> OTHER INFORMATION: Engineered enhanced sequon
<220> FEATURE:
<221> NAME/KEY: MISC_FEATURE
<222> LOCATION: (2)..(22)
<223> OTHER INFORMATION: Xaa at residues 2-22 are present or absent and
      if present there are 1, 3, or 21 residues that are any amino acid
      residue.
<220> FEATURE:
<221> NAME/KEY: MISC_FEATURE
<222> LOCATION: (23)..(23)
<223> OTHER INFORMATION: Xaa at residue 23 is Histidine, Phenylalanine,
      Tryptophan, or Tyrosine.
<220> FEATURE:
<221> NAME/KEY: MISC_FEATURE
<222> LOCATION: (24)..(27)
```

```
<223> OTHER INFORMATION: Xaa at residues 24-27 are present or absent and
      if present are Alanine, Cysteine, Aspartic Acid , Glutamic Acid,
      Glycine, Isoleucine, Lysine, Leucine, Methionine, Asparagine,
      Proline, Glutamine, Arginine, Serine, Threonine, or Valine.
<220> FEATURE:
<221> NAME/KEY: MISC_FEATURE
<222> LOCATION: (28)..(28)
<223> OTHER INFORMATION: Xaa at residue 28 is present or absent and if
      present is any amino acid residue
<220> FEATURE:
<221> NAME/KEY: MISC_FEATURE
<222> LOCATION: (30)..(30)
<223> OTHER INFORMATION: Xaa at residue 30 is present or absent and is
      Alanine, Cysteine, Aspartic Acid , Glutamic Acid, Phenylalanine,
      Glycine, Histidine, Isoleucine, Lysine, Leucine, Methionine,
      Asparagine, Glutamine, Arginine, Serine, Threonine, Valine,
      Tryptophan, or Tyrosine.
<220> FEATURE:
<221> NAME/KEY: MISC_FEATURE
<222> LOCATION: (31)..(31)
<223> OTHER INFORMATION: Xaa at residue 31 is Serine or Threonine.

<400> SEQUENCE: 4

Lys Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Asn Xaa Xaa
            20                  25                  30

<210> SEQ ID NO 5
<211> LENGTH: 9
<212> TYPE: PRT
<213> ORGANISM: Artificial Sequence
<220> FEATURE:
<223> OTHER INFORMATION: Engineered enhanced sequon
<220> FEATURE:
<221> NAME/KEY: MISC_FEATURE
<222> LOCATION: (1)..(1)
<223> OTHER INFORMATION: Xaa at residue 1 is Histidine, Phenylalanine,
      Tryptophan, or Tyrosine.
<220> FEATURE:
<221> NAME/KEY: MISC_FEATURE
<222> LOCATION: (2)..(5)
<223> OTHER INFORMATION: Xaa at positions 2-5 are present or absent and
      are Alanine, Cysteine, Aspartic Acid , Glutamic Acid, Glycine,
      Isoleucine, Lysine, Leucine, Methionine, Asparagine, Proline,
      Glutamine, Arginine, Serine, Threonine or Valine.
<220> FEATURE:
<221> NAME/KEY: MISC_FEATURE
<222> LOCATION: (6)..(6)
<223> OTHER INFORMATION: Xaa at position 6 is present or absent and if
      present is any amino acid residue.
<220> FEATURE:
<221> NAME/KEY: CARBOHYD
<222> LOCATION: (7)..(7)
<223> OTHER INFORMATION: The Asparagine at position 7 is glycosylated
<220> FEATURE:
<221> NAME/KEY: MISC_FEATURE
<222> LOCATION: (8)..(8)
<223> OTHER INFORMATION: Xaa at position 8 is Alanine, Cysteine,
      Aspartic Acid , Glutamic Acid, Phenylalanine, Glycine, Histidine,
      Isoleucine, Lysine, Leucine, Methionine, Asparagine, Glutamine,
      Arginine, Serine, Threonine, Valine, Tryptophan, or Tyrosine.
<220> FEATURE:
<221> NAME/KEY: MISC_FEATURE
<222> LOCATION: (9)..(9)
<223> OTHER INFORMATION: Xaa at position 9 is Serine or Threonine.

<400> SEQUENCE: 5

Xaa Xaa Xaa Xaa Xaa Xaa Asn Xaa Xaa
1               5

<210> SEQ ID NO 6
<211> LENGTH: 7
<212> TYPE: PRT
```

```
<213> ORGANISM: Artificial Sequence
<220> FEATURE:
<223> OTHER INFORMATION: Engineered sequon
<220> FEATURE:
<221> NAME/KEY: MISC_FEATURE
<222> LOCATION: (1)..(8)
<223> OTHER INFORMATION: type-I beta-bulge turn present in the non-
      therapeutic genetically-engineered polypeptide rat glycoprotein
      CD2 (RnCD2*); the sequon in that type-I beta-bulge turn was
      engineered to be Asn-Gly-Thr here

<400> SEQUENCE: 6

Glu Ile Leu Ala Asn Gly Thr
1               5

<210> SEQ ID NO 7
<211> LENGTH: 7
<212> TYPE: PRT
<213> ORGANISM: Artificial Sequence
<220> FEATURE:
<223> OTHER INFORMATION: Engineered enhanced sequon
<220> FEATURE:
<221> NAME/KEY: MISC_FEATURE
<222> LOCATION: (1)..(3)
<223> OTHER INFORMATION: SEQ ID NO:004 was mutated to replace first 3
      residues with Lys-Ile-Phe.

<400> SEQUENCE: 7

Lys Ile Phe Ala Asn Gly Thr
1               5

<210> SEQ ID NO 8
<211> LENGTH: 6
<212> TYPE: PRT
<213> ORGANISM: Artificial Sequence
<220> FEATURE:
<223> OTHER INFORMATION: engineered enhanced sequon sequence
<220> FEATURE:
<221> NAME/KEY: MISC_FEATURE
<222> LOCATION: (1)..(1)
<223> OTHER INFORMATION: Xaa at position 1 is Histidine, Phenylalanine,
      Tryptophan, or Tyrosine.
<220> FEATURE:
<221> NAME/KEY: MISC_FEATURE
<222> LOCATION: (2)..(2)
<223> OTHER INFORMATION: Xaa at residue 2 is Alanine, Cysteine, Aspartic
      Acid , Glutamic Acid, Glycine, Isoleucine, Lysine, Leucine,
      Methionine, Asparagine, Proline, Glutamine, Arginine, Serine,
      Threonine, or Valine.
<220> FEATURE:
<221> NAME/KEY: MISC_FEATURE
<222> LOCATION: (3)..(3)
<223> OTHER INFORMATION: Xaa at residue 3 is any amino acid residue
<220> FEATURE:
<221> NAME/KEY: MISC_FEATURE
<222> LOCATION: (5)..(5)
<223> OTHER INFORMATION: Xaa at residue 5 is is is Alanine, Cysteine,
      Aspartic Acid , Glutamic Acid, Phenylalanine, Glycine, Histidine,
      Isoleucine, Lysine, Leucine, Methionine, Asparagine, Glutamine,
      Arginine, Serine, Threonine, Valine, Tryptophan, or Tyrosine.
<220> FEATURE:
<221> NAME/KEY: MISC_FEATURE
<222> LOCATION: (6)..(6)
<223> OTHER INFORMATION: Xaa at residue 6 is Serine or Threonine.

<400> SEQUENCE: 8

Xaa Xaa Xaa Asn Xaa Xaa
1               5

<210> SEQ ID NO 9
<211> LENGTH: 5
<212> TYPE: PRT
<213> ORGANISM: Mus musculus
```

<400> SEQUENCE: 9

Asp Tyr Asn Ser Thr
1               5

<210> SEQ ID NO 10
<211> LENGTH: 5
<212> TYPE: PRT
<213> ORGANISM: Artificial Sequence
<220> FEATURE:
<223> OTHER INFORMATION: enhanced sequon in engineered Ibritumomab
      (Mouse Anti-CD20 Heavy chain 1)

<400> SEQUENCE: 10

Phe Tyr Asn Ser Thr
1               5

<210> SEQ ID NO 11
<211> LENGTH: 5
<212> TYPE: PRT
<213> ORGANISM: Mus musculus

<400> SEQUENCE: 11

Asp Ser Asp Gly Ser
1               5

<210> SEQ ID NO 12
<211> LENGTH: 5
<212> TYPE: PRT
<213> ORGANISM: Artificial Sequence
<220> FEATURE:
<223> OTHER INFORMATION: Engineered enhanced sequon in Ibritumomab
      (Mouse Anti-CD20 Heavy chain 1)

<400> SEQUENCE: 12

Tyr Ser Asn Gly Ser
1               5

<210> SEQ ID NO 13
<211> LENGTH: 5
<212> TYPE: PRT
<213> ORGANISM: Mus musculus

<400> SEQUENCE: 13

Asp Tyr Asn Ser Thr
1               5

<210> SEQ ID NO 14
<211> LENGTH: 5
<212> TYPE: PRT
<213> ORGANISM: Artificial Sequence
<220> FEATURE:
<223> OTHER INFORMATION: Engineered enhanced sequon in Ibritumomab
      (Mouse Anti-CD20 Heavy chain 2)

<400> SEQUENCE: 14

Phe Tyr Asn Ser Ser
1               5

<210> SEQ ID NO 15
<211> LENGTH: 5
<212> TYPE: PRT
<213> ORGANISM: Mus musculus

<400> SEQUENCE: 15

Asp Ser Asp Gly Ser

```
<210> SEQ ID NO 16
<211> LENGTH: 5
<212> TYPE: PRT
<213> ORGANISM: Artificial Sequence
<220> FEATURE:
<223> OTHER INFORMATION: Engineered enhanced sequon in Ibritumomab
      (Mouse Anti-CD20 Heavy chain 2)

<400> SEQUENCE: 16

Tyr Ser Asn Gly Thr
1               5

<210> SEQ ID NO 17
<211> LENGTH: 5
<212> TYPE: PRT
<213> ORGANISM: Homo sapiens

<400> SEQUENCE: 17

Gln Tyr Asn Ser Thr
1               5

<210> SEQ ID NO 18
<211> LENGTH: 5
<212> TYPE: PRT
<213> ORGANISM: Artificial Sequence
<220> FEATURE:
<223> OTHER INFORMATION: Engineered enhanced sequon in human IgG1

<400> SEQUENCE: 18

Tyr Tyr Asn Ser Thr
1               5

<210> SEQ ID NO 19
<211> LENGTH: 5
<212> TYPE: PRT
<213> ORGANISM: Homo sapiens

<400> SEQUENCE: 19

Asp Ser Asp Gly Ser
1               5

<210> SEQ ID NO 20
<211> LENGTH: 5
<212> TYPE: PRT
<213> ORGANISM: Artificial Sequence
<220> FEATURE:
<223> OTHER INFORMATION: Engineered enhanced sequon in IgG1

<400> SEQUENCE: 20

Tyr Ser Asn Gly Ser
1               5

<210> SEQ ID NO 21
<211> LENGTH: 5
<212> TYPE: PRT
<213> ORGANISM: Artificial Sequence
<220> FEATURE:
<223> OTHER INFORMATION: loop in dimeric fusion protein consisting of
      the extracellular ligand-binding portion of the human 75
      kilodalton (p75) tumor necrosis factor receptor (TNFR) linked to
      the Fc portion of human IgG1 (Etanercept)

<400> SEQUENCE: 21

Gln Tyr Asn Ser Thr
1               5
```

<210> SEQ ID NO 22
<211> LENGTH: 5
<212> TYPE: PRT
<213> ORGANISM: Artificial Sequence
<220> FEATURE:
<223> OTHER INFORMATION: Engineered enhanced sequon in Etanercept (TNF
      receptor 2 fused to human Fc of IgG1)

<400> SEQUENCE: 22

Trp Tyr Asn Ser Thr
1               5

<210> SEQ ID NO 23
<211> LENGTH: 5
<212> TYPE: PRT
<213> ORGANISM: Artificial Sequence
<220> FEATURE:
<223> OTHER INFORMATION: loop in dimeric fusion protein consisting of
      the extracellular ligand-binding portion of the human 75
      kilodalton (p75) tumor necrosis factor receptor (TNFR) linked to
      the Fc portion of human IgG1 (Etanercept)

<400> SEQUENCE: 23

Asp Ser Asp Gly Ser
1               5

<210> SEQ ID NO 24
<211> LENGTH: 5
<212> TYPE: PRT
<213> ORGANISM: Artificial Sequence
<220> FEATURE:
<223> OTHER INFORMATION: Engineered enhanced sequon in Etanercept (TNF
      receptor 2 fused to human Fc of IgG1)

<400> SEQUENCE: 24

His Ser Asn Gly Thr
1               5

<210> SEQ ID NO 25
<211> LENGTH: 5
<212> TYPE: PRT
<213> ORGANISM: Artificial Sequence
<220> FEATURE:
<223> OTHER INFORMATION: loop in recombinant DNA-derived humanized
      monoclonal antibody (Campath-1H) that is directed against the
      21-28 kD cell surface glycoprotein,CD52; Alemtuzumab.

<400> SEQUENCE: 25

Asp Ser Asp Gly Ser
1               5

<210> SEQ ID NO 26
<211> LENGTH: 5
<212> TYPE: PRT
<213> ORGANISM: Artificial Sequence
<220> FEATURE:
<223> OTHER INFORMATION: Engineered enhanced sequon in recombinant DNA-
      derived humanized monoclonal antibody (Campath-1H) that is
      directed against the 21-28 kD cell surface glycoprotein,CD52;
      Alemtuzumab.

<400> SEQUENCE: 26

Trp Ser Asn Gly Thr
1               5

<210> SEQ ID NO 27
<211> LENGTH: 5

```
<212> TYPE: PRT
<213> ORGANISM: Artificial Sequence
<220> FEATURE:
<223> OTHER INFORMATION: loop in recombinant DNA-derived humanized
      monoclonal antibody (Campath-1H) that is directed against the
      21-28 kD cell surface glycoprotein,CD52; Alemtuzumab.

<400> SEQUENCE: 27

Asp Ser Asp Gly Ser
1               5

<210> SEQ ID NO 28
<211> LENGTH: 5
<212> TYPE: PRT
<213> ORGANISM: Artificial Sequence
<220> FEATURE:
<223> OTHER INFORMATION: Engineered enhanced sequon in recombinant DNA-
      derived humanized monoclonal antibody (Campath-1H) that is
      directed against the 21-28 kD cell surface glycoprotein,CD52;
      Alemtuzumab.

<400> SEQUENCE: 28

Phe Ser Asn Gly Thr
1               5

<210> SEQ ID NO 29
<211> LENGTH: 5
<212> TYPE: PRT
<213> ORGANISM: Mus musculus

<400> SEQUENCE: 29

Asp Tyr Asn Ser Thr
1               5

<210> SEQ ID NO 30
<211> LENGTH: 5
<212> TYPE: PRT
<213> ORGANISM: Artificial Sequence
<220> FEATURE:
<223> OTHER INFORMATION: Engineered enhanced sequon in  in Arcitumomab
      heavy chain 1

<400> SEQUENCE: 30

Phe Tyr Asn Ser Thr
1               5

<210> SEQ ID NO 31
<211> LENGTH: 5
<212> TYPE: PRT
<213> ORGANISM: Mus musculus

<400> SEQUENCE: 31

Asp Ser Asp Gly Ser
1               5

<210> SEQ ID NO 32
<211> LENGTH: 5
<212> TYPE: PRT
<213> ORGANISM: Artificial Sequence
<220> FEATURE:
<223> OTHER INFORMATION: Engineered enhanced sequon in  in Arcitumomab
      heavy chain 1

<400> SEQUENCE: 32

Phe Ser Asn Gly Thr
1               5
```

```
<210> SEQ ID NO 33
<211> LENGTH: 5
<212> TYPE: PRT
<213> ORGANISM: Mus musculus

<400> SEQUENCE: 33

Asp Tyr Asn Ser Thr
1               5

<210> SEQ ID NO 34
<211> LENGTH: 5
<212> TYPE: PRT
<213> ORGANISM: Artificial Sequence
<220> FEATURE:
<223> OTHER INFORMATION: Engineered enhanced sequon in  in Arcitumomab
      heavy chain 2

<400> SEQUENCE: 34

Phe Tyr Asn Ser Thr
1               5

<210> SEQ ID NO 35
<211> LENGTH: 5
<212> TYPE: PRT
<213> ORGANISM: Mus musculus

<400> SEQUENCE: 35

Asp Ser Asp Gly Ser
1               5

<210> SEQ ID NO 36
<211> LENGTH: 5
<212> TYPE: PRT
<213> ORGANISM: Artificial Sequence
<220> FEATURE:
<223> OTHER INFORMATION: Engineered enhanced sequon in Arcitumomab heavy
      chain 2

<400> SEQUENCE: 36

Trp Ser Asn Gly Ser
1               5

<210> SEQ ID NO 37
<211> LENGTH: 5
<212> TYPE: PRT
<213> ORGANISM: Artificial Sequence
<220> FEATURE:
<223> OTHER INFORMATION: Loop in Omalizumab VH chain domain 1

<400> SEQUENCE: 37

Gln Tyr Asn Ser Thr
1               5

<210> SEQ ID NO 38
<211> LENGTH: 5
<212> TYPE: PRT
<213> ORGANISM: Artificial Sequence
<220> FEATURE:
<223> OTHER INFORMATION: Engineered enhanced sequon in loop of
      Omalizumab VH chain domain 1

<400> SEQUENCE: 38

Trp Tyr Asn Ser Thr
1               5

<210> SEQ ID NO 39
<211> LENGTH: 5
```

```
<212> TYPE: PRT
<213> ORGANISM: Artificial Sequence
<220> FEATURE:
<223> OTHER INFORMATION: Loop in Omalizumab VH chain domain 1

<400> SEQUENCE: 39

Asp Ser Asp Gly Ser
1               5

<210> SEQ ID NO 40
<211> LENGTH: 5
<212> TYPE: PRT
<213> ORGANISM: Artificial Sequence
<220> FEATURE:
<223> OTHER INFORMATION: Engineered enhanced sequon in loop of
      Omalizumab VH chain domain 1

<400> SEQUENCE: 40

Tyr Ser Asn Gly Thr
1               5

<210> SEQ ID NO 41
<211> LENGTH: 5
<212> TYPE: PRT
<213> ORGANISM: Artificial Sequence
<220> FEATURE:
<223> OTHER INFORMATION: Loop in Omalizumab VH chain domain 2

<400> SEQUENCE: 41

Gln Tyr Asn Ser Thr
1               5

<210> SEQ ID NO 42
<211> LENGTH: 5
<212> TYPE: PRT
<213> ORGANISM: Artificial Sequence
<220> FEATURE:
<223> OTHER INFORMATION: Engineered enhanced sequon in loop of
      Omalizumab VH chain domain 2

<400> SEQUENCE: 42

His Tyr Asn Ser Thr
1               5

<210> SEQ ID NO 43
<211> LENGTH: 5
<212> TYPE: PRT
<213> ORGANISM: Artificial Sequence
<220> FEATURE:
<223> OTHER INFORMATION: Loop in Omalizumab VH chain domain 2

<400> SEQUENCE: 43

Asp Ser Asp Gly Ser
1               5

<210> SEQ ID NO 44
<211> LENGTH: 5
<212> TYPE: PRT
<213> ORGANISM: Artificial Sequence
<220> FEATURE:
<223> OTHER INFORMATION: Engineered enhanced sequon in loop of
      Omalizumab VH chain domain 2

<400> SEQUENCE: 44

Tyr Ser Asn Gly Ser
1               5
```

```
<210> SEQ ID NO 45
<211> LENGTH: 5
<212> TYPE: PRT
<213> ORGANISM: Artificial Sequence
<220> FEATURE:
<223> OTHER INFORMATION: Loop in Satumomab Pendetide humanized murine
      antibody Heavy chain 1 B72.3

<400> SEQUENCE: 45

Asp Tyr Asn Ser Thr
1               5

<210> SEQ ID NO 46
<211> LENGTH: 5
<212> TYPE: PRT
<213> ORGANISM: Artificial Sequence
<220> FEATURE:
<223> OTHER INFORMATION: Engineered enhanced sequon in loop of Satumomab
      Pendetide humanized murine antibody Heavy chain 1 B72.3

<400> SEQUENCE: 46

Phe Tyr Asn Ser Thr
1               5

<210> SEQ ID NO 47
<211> LENGTH: 5
<212> TYPE: PRT
<213> ORGANISM: Artificial Sequence
<220> FEATURE:
<223> OTHER INFORMATION: Loop in Satumomab Pendetide humanized murine
      antibody Heavy chain 1 B72.3

<400> SEQUENCE: 47

Asp Ser Asp Gly Ser
1               5

<210> SEQ ID NO 48
<211> LENGTH: 5
<212> TYPE: PRT
<213> ORGANISM: Artificial Sequence
<220> FEATURE:
<223> OTHER INFORMATION: Engineered enhanced sequon in loop of Satumomab
      Pendetide humanized murine antibody Heavy chain 1 B72.3

<400> SEQUENCE: 48

His Ser Asn Gly Thr
1               5

<210> SEQ ID NO 49
<211> LENGTH: 5
<212> TYPE: PRT
<213> ORGANISM: Artificial Sequence
<220> FEATURE:
<223> OTHER INFORMATION: Loop in Satumomab Pendetide humanized murine
      antibody Heavy chain 2 B72.3

<400> SEQUENCE: 49

Asp Tyr Asn Ser Thr
1               5

<210> SEQ ID NO 50
<211> LENGTH: 5
<212> TYPE: PRT
<213> ORGANISM: Artificial Sequence
<220> FEATURE:
<223> OTHER INFORMATION: Engineered enhanced sequon in loop of Satumomab
      Pendetide humanized murine antibody Heavy chain 2 B72.3

<400> SEQUENCE: 50
```

Trp Tyr Asn Ser Thr
1               5

<210> SEQ ID NO 51
<211> LENGTH: 5
<212> TYPE: PRT
<213> ORGANISM: Artificial Sequence
<220> FEATURE:
<223> OTHER INFORMATION: Loop in Satumomab Pendetide humanized murine
      antibody Heavy chain 2 B72.3

<400> SEQUENCE: 51

Asp Ser Asp Gly Ser
1               5

<210> SEQ ID NO 52
<211> LENGTH: 5
<212> TYPE: PRT
<213> ORGANISM: Artificial Sequence
<220> FEATURE:
<223> OTHER INFORMATION: Engineered enhanced sequon in loop of Satumomab
      Pendetide humanized murine antibody Heavy chain 2 B72.3

<400> SEQUENCE: 52

Tyr Ser Asn Gly Thr
1               5

<210> SEQ ID NO 53
<211> LENGTH: 5
<212> TYPE: PRT
<213> ORGANISM: Artificial Sequence
<220> FEATURE:
<223> OTHER INFORMATION: loop in Alefacept; Human LFA fused to human Fc

<400> SEQUENCE: 53

Gln Tyr Asn Ser Thr
1               5

<210> SEQ ID NO 54
<211> LENGTH: 5
<212> TYPE: PRT
<213> ORGANISM: Artificial Sequence
<220> FEATURE:
<223> OTHER INFORMATION: Engineered enhanced sequon in loop of
      Alefacept; Human LFA fused to human Fc

<400> SEQUENCE: 54

Trp Tyr Asn Ser Thr
1               5

<210> SEQ ID NO 55
<211> LENGTH: 5
<212> TYPE: PRT
<213> ORGANISM: Artificial Sequence
<220> FEATURE:
<223> OTHER INFORMATION: loop in Alefacept; Human LFA fused to human Fc

<400> SEQUENCE: 55

Asp Ser Asp Gly Ser
1               5

<210> SEQ ID NO 56
<211> LENGTH: 5
<212> TYPE: PRT
<213> ORGANISM: Artificial Sequence
<220> FEATURE:
<223> OTHER INFORMATION: Engineered enhanced sequon in loop of Alefacept; Human LFA fused to human Fc

<400> SEQUENCE: 56

Tyr Ser Asn Gly Thr
1               5

<210> SEQ ID NO 57
<211> LENGTH: 5
<212> TYPE: PRT
<213> ORGANISM: Artificial Sequence
<220> FEATURE:
<223> OTHER INFORMATION: Loop in Daclizumab Humanized Anti-CD25 Heavy
      Chain 1

<400> SEQUENCE: 57

Gln Tyr Asn Ser Thr
1               5

<210> SEQ ID NO 58
<211> LENGTH: 5
<212> TYPE: PRT
<213> ORGANISM: Artificial Sequence
<220> FEATURE:
<223> OTHER INFORMATION: Engineered enhanced sequon in loop of
      Daclizumab Humanized Anti-CD25 Heavy Chain 1

<400> SEQUENCE: 58

Phe Tyr Asn Ser Thr
1               5

<210> SEQ ID NO 59
<211> LENGTH: 5
<212> TYPE: PRT
<213> ORGANISM: Artificial Sequence
<220> FEATURE:
<223> OTHER INFORMATION: Loop in Daclizumab Humanized Anti-CD25 Heavy
      Chain 1

<400> SEQUENCE: 59

Asp Ser Asp Gly Ser
1               5

<210> SEQ ID NO 60
<211> LENGTH: 5
<212> TYPE: PRT
<213> ORGANISM: Artificial Sequence
<220> FEATURE:
<223> OTHER INFORMATION: Engineered enhanced sequon in loop of
      Daclizumab Humanized Anti-CD25 Heavy Chain 1

<400> SEQUENCE: 60

Tyr Ser Asn Gly Ser
1               5

<210> SEQ ID NO 61
<211> LENGTH: 5
<212> TYPE: PRT
<213> ORGANISM: Artificial Sequence
<220> FEATURE:
<223> OTHER INFORMATION: Loop in Daclizumab Humanized Anti-CD25 Heavy
      Chain 2

<400> SEQUENCE: 61

Gln Tyr Asn Ser Thr
1               5

<210> SEQ ID NO 62

```
<211> LENGTH: 5
<212> TYPE: PRT
<213> ORGANISM: Artificial Sequence
<220> FEATURE:
<223> OTHER INFORMATION: Engineered enhanced sequon in loop of
      Daclizumab Humanized Anti-CD25 Heavy Chain 2

<400> SEQUENCE: 62

His Tyr Asn Ser Thr
1               5

<210> SEQ ID NO 63
<211> LENGTH: 5
<212> TYPE: PRT
<213> ORGANISM: Artificial Sequence
<220> FEATURE:
<223> OTHER INFORMATION: Loop in Daclizumab Humanized Anti-CD25 Heavy
      Chain 2

<400> SEQUENCE: 63

Asp Ser Asp Gly Ser
1               5

<210> SEQ ID NO 64
<211> LENGTH: 5
<212> TYPE: PRT
<213> ORGANISM: Artificial Sequence
<220> FEATURE:
<223> OTHER INFORMATION: Engineered enhanced sequon in loop of
      Daclizumab Humanized Anti-CD25 Heavy Chain 2

<400> SEQUENCE: 64

Phe Ser Asn Gly Ser
1               5

<210> SEQ ID NO 65
<211> LENGTH: 5
<212> TYPE: PRT
<213> ORGANISM: Artificial Sequence
<220> FEATURE:
<223> OTHER INFORMATION: Loop in Cetuximab Anti-EGFR heavy chain 1

<400> SEQUENCE: 65

Asp Ser Asp Gly Ser
1               5

<210> SEQ ID NO 66
<211> LENGTH: 5
<212> TYPE: PRT
<213> ORGANISM: Artificial Sequence
<220> FEATURE:
<223> OTHER INFORMATION: Engineered enhanced sequon in loop of
      Cetuximab Anti-EGFR heavy chain 1

<400> SEQUENCE: 66

Trp Ser Asn Gly Ser
1               5

<210> SEQ ID NO 67
<211> LENGTH: 5
<212> TYPE: PRT
<213> ORGANISM: Artificial Sequence
<220> FEATURE:
<223> OTHER INFORMATION: Loop in Cetuximab Anti-EGFR heavy chain 2

<400> SEQUENCE: 67

Asp Ser Asp Gly Ser
1               5
```

```
<210> SEQ ID NO 68
<211> LENGTH: 5
<212> TYPE: PRT
<213> ORGANISM: Artificial Sequence
<220> FEATURE:
<223> OTHER INFORMATION: Engineered enhanced sequon in loop of Cetuximab
      Anti-EGFR heavy chain 2

<400> SEQUENCE: 68

Trp Ser Asn Gly Thr
1               5

<210> SEQ ID NO 69
<211> LENGTH: 5
<212> TYPE: PRT
<213> ORGANISM: Artificial Sequence
<220> FEATURE:
<223> OTHER INFORMATION: Loop in Tositumomab Mouse-Human chimeric Anti-
      CD20 heavy chain 1

<400> SEQUENCE: 69

Gln Tyr Asn Ser Thr
1               5

<210> SEQ ID NO 70
<211> LENGTH: 5
<212> TYPE: PRT
<213> ORGANISM: Artificial Sequence
<220> FEATURE:
<223> OTHER INFORMATION: Engineered enhanced sequon in loop of
      Tositumomab Mouse-Human chimeric Anti-CD20 heavy chain 1

<400> SEQUENCE: 70

Phe Tyr Asn Ser Thr
1               5

<210> SEQ ID NO 71
<211> LENGTH: 5
<212> TYPE: PRT
<213> ORGANISM: Artificial Sequence
<220> FEATURE:
<223> OTHER INFORMATION: Loop in Tositumomab Mouse-Human chimeric Anti-
      CD20 heavy chain 1

<400> SEQUENCE: 71

Asp Ser Asp Gly Ser
1               5

<210> SEQ ID NO 72
<211> LENGTH: 5
<212> TYPE: PRT
<213> ORGANISM: Artificial Sequence
<220> FEATURE:
<223> OTHER INFORMATION: Engineered enhanced sequon in loop of
      Tositumomab Mouse-Human chimeric Anti-CD20 heavy chain 1

<400> SEQUENCE: 72

Phe Ser Asn Gly Thr
1               5

<210> SEQ ID NO 73
<211> LENGTH: 5
<212> TYPE: PRT
<213> ORGANISM: Artificial Sequence
<220> FEATURE:
<223> OTHER INFORMATION: Loop in Tositumomab Mouse-Human chimeric Anti-
      CD20 heavy chain 2
```

```
<400> SEQUENCE: 73

Gln Tyr Asn Ser Thr
1               5

<210> SEQ ID NO 74
<211> LENGTH: 5
<212> TYPE: PRT
<213> ORGANISM: Artificial Sequence
<220> FEATURE:
<223> OTHER INFORMATION: Engineered enhanced sequon in loop of
      Tositumomab Mouse-Human chimeric Anti-CD20 heavy chain 2

<400> SEQUENCE: 74

Phe Tyr Asn Ser Ser
1               5

<210> SEQ ID NO 75
<211> LENGTH: 5
<212> TYPE: PRT
<213> ORGANISM: Artificial Sequence
<220> FEATURE:
<223> OTHER INFORMATION: Loop in Tositumomab Mouse-Human chimeric Anti-
      CD20 heavy chain 2

<400> SEQUENCE: 75

Asp Ser Asp Gly Ser
1               5

<210> SEQ ID NO 76
<211> LENGTH: 5
<212> TYPE: PRT
<213> ORGANISM: Artificial Sequence
<220> FEATURE:
<223> OTHER INFORMATION: Engineered enhanced sequon in loop of
      Tositumomab Mouse-Human chimeric Anti-CD20 heavy chain 2

<400> SEQUENCE: 76

Trp Ser Asn Gly Thr
1               5

<210> SEQ ID NO 77
<211> LENGTH: 5
<212> TYPE: PRT
<213> ORGANISM: Artificial Sequence
<220> FEATURE:
<223> OTHER INFORMATION: Loop in Trastuzumab Anti-HER2 Heavy chain 1

<400> SEQUENCE: 77

Gln Tyr Asn Ser Thr
1               5

<210> SEQ ID NO 78
<211> LENGTH: 5
<212> TYPE: PRT
<213> ORGANISM: Artificial Sequence
<220> FEATURE:
<223> OTHER INFORMATION: Engineered enhanced sequon in loop of
      Trastuzumab Anti-HER2 Heavy chain 1

<400> SEQUENCE: 78

Phe Tyr Asn Ser Thr
1               5

<210> SEQ ID NO 79
<211> LENGTH: 5
<212> TYPE: PRT
```

<213> ORGANISM: Artificial Sequence
<220> FEATURE:
<223> OTHER INFORMATION: Loop in Trastuzumab Anti-HER2 Heavy chain 1

<400> SEQUENCE: 79

Asp Ser Asp Gly Ser
1               5

<210> SEQ ID NO 80
<211> LENGTH: 5
<212> TYPE: PRT
<213> ORGANISM: Artificial Sequence
<220> FEATURE:
<223> OTHER INFORMATION: Engineered enhanced sequon in loop of
      Trastuzumab Anti-HER2 Heavy chain 1

<400> SEQUENCE: 80

Trp Ser Asn Gly Ser
1               5

<210> SEQ ID NO 81
<211> LENGTH: 5
<212> TYPE: PRT
<213> ORGANISM: Artificial Sequence
<220> FEATURE:
<223> OTHER INFORMATION: Loop in Trastuzumab Anti-HER2 Heavy chain 2

<400> SEQUENCE: 81

Gln Tyr Asn Ser Thr
1               5

<210> SEQ ID NO 82
<211> LENGTH: 5
<212> TYPE: PRT
<213> ORGANISM: Artificial Sequence
<220> FEATURE:
<223> OTHER INFORMATION: Engineered enhanced sequon in loop of
      Trastuzumab Anti-HER2 Heavy chain 2

<400> SEQUENCE: 82

Phe Tyr Asn Ser Thr
1               5

<210> SEQ ID NO 83
<211> LENGTH: 5
<212> TYPE: PRT
<213> ORGANISM: Artificial Sequence
<220> FEATURE:
<223> OTHER INFORMATION: Loop in Trastuzumab Anti-HER2 Heavy chain 2

<400> SEQUENCE: 83

Asp Ser Asp Gly Ser
1               5

<210> SEQ ID NO 84
<211> LENGTH: 5
<212> TYPE: PRT
<213> ORGANISM: Artificial Sequence
<220> FEATURE:
<223> OTHER INFORMATION: Engineered enhanced sequon in loop of
      Trastuzumab Anti-HER2 Heavy chain 2

<400> SEQUENCE: 84

Trp Ser Asn Gly Ser
1               5

<210> SEQ ID NO 85

```
<211> LENGTH: 5
<212> TYPE: PRT
<213> ORGANISM: Mus musculus

<400> SEQUENCE: 85

Gln Tyr Asn Ser Thr
1               5

<210> SEQ ID NO 86
<211> LENGTH: 5
<212> TYPE: PRT
<213> ORGANISM: Artificial Sequence
<220> FEATURE:
<223> OTHER INFORMATION: Engineered enhanced sequon in Muromonab 1SY6:H
      OKT3 Heavy Chain 1

<400> SEQUENCE: 86

Trp Tyr Asn Ser Thr
1               5

<210> SEQ ID NO 87
<211> LENGTH: 5
<212> TYPE: PRT
<213> ORGANISM: Mus musculus

<400> SEQUENCE: 87

Asp Ser Asp Gly Ser
1               5

<210> SEQ ID NO 88
<211> LENGTH: 5
<212> TYPE: PRT
<213> ORGANISM: Artificial Sequence
<220> FEATURE:
<223> OTHER INFORMATION: Engineered enhanced sequon in Muromonab 1SY6:H
      OKT3 Heavy Chain 1

<400> SEQUENCE: 88

Phe Ser Asn Gly Ser
1               5

<210> SEQ ID NO 89
<211> LENGTH: 5
<212> TYPE: PRT
<213> ORGANISM: Mus musculus

<400> SEQUENCE: 89

Gln Tyr Asn Ser Thr
1               5

<210> SEQ ID NO 90
<211> LENGTH: 5
<212> TYPE: PRT
<213> ORGANISM: Artificial Sequence
<220> FEATURE:
<223> OTHER INFORMATION: Engineered enhanced sequon in Muromonab 1SY6:H
      OKT3 Heavy Chain 2

<400> SEQUENCE: 90

His Tyr Asn Ser Thr
1               5

<210> SEQ ID NO 91
<211> LENGTH: 5
<212> TYPE: PRT
<213> ORGANISM: Mus musculus
```

```
<400> SEQUENCE: 91

Asp Ser Asp Gly Ser
1               5

<210> SEQ ID NO 92
<211> LENGTH: 5
<212> TYPE: PRT
<213> ORGANISM: Artificial Sequence
<220> FEATURE:
<223> OTHER INFORMATION: Engineered enhanced sequon in Muromonab 1SY6:H
      OKT3 Heavy Chain 2

<400> SEQUENCE: 92

Tyr Ser Asn Gly Ser
1               5

<210> SEQ ID NO 93
<211> LENGTH: 5
<212> TYPE: PRT
<213> ORGANISM: Artificial Sequence
<220> FEATURE:
<223> OTHER INFORMATION: Loop in Abciximab 1TXV:H ReoPro-like antibody
      Heavy Chain 1

<400> SEQUENCE: 93

Gln Tyr Asn Ser Thr
1               5

<210> SEQ ID NO 94
<211> LENGTH: 5
<212> TYPE: PRT
<213> ORGANISM: Artificial Sequence
<220> FEATURE:
<223> OTHER INFORMATION: Engineered enhanced sequon in loop of Abciximab
      1TXV:H ReoPro-like antibody Heavy Chain 1

<400> SEQUENCE: 94

Trp Tyr Asn Ser Thr
1               5

<210> SEQ ID NO 95
<211> LENGTH: 5
<212> TYPE: PRT
<213> ORGANISM: Artificial Sequence
<220> FEATURE:
<223> OTHER INFORMATION: Loop in Abciximab 1TXV:H ReoPro-like antibody
      Heavy Chain 1

<400> SEQUENCE: 95

Asp Ser Asp Gly Ser
1               5

<210> SEQ ID NO 96
<211> LENGTH: 5
<212> TYPE: PRT
<213> ORGANISM: Artificial Sequence
<220> FEATURE:
<223> OTHER INFORMATION: Engineered enhanced sequon in loop of Abciximab
      1TXV:H ReoPro-like antibody Heavy Chain 1

<400> SEQUENCE: 96

Trp Ser Asn Gly Thr
1               5

<210> SEQ ID NO 97
<211> LENGTH: 5
<212> TYPE: PRT
```

```
<213> ORGANISM: Artificial Sequence
<220> FEATURE:
<223> OTHER INFORMATION: Loop in Abciximab 1TXV:H ReoPro-like antibody
      Heavy Chain 2

<400> SEQUENCE: 97

Gln Tyr Asn Ser Thr
1               5

<210> SEQ ID NO 98
<211> LENGTH: 5
<212> TYPE: PRT
<213> ORGANISM: Artificial Sequence
<220> FEATURE:
<223> OTHER INFORMATION: Engineered enhanced sequon in loop of Abciximab
      1TXV:H ReoPro-like antibody Heavy Chain 2

<400> SEQUENCE: 98

Phe Tyr Asn Ser Thr
1               5

<210> SEQ ID NO 99
<211> LENGTH: 5
<212> TYPE: PRT
<213> ORGANISM: Artificial Sequence
<220> FEATURE:
<223> OTHER INFORMATION: Loop in Abciximab 1TXV:H ReoPro-like antibody
      Heavy Chain 2

<400> SEQUENCE: 99

Asp Ser Asp Gly Ser
1               5

<210> SEQ ID NO 100
<211> LENGTH: 5
<212> TYPE: PRT
<213> ORGANISM: Artificial Sequence
<220> FEATURE:
<223> OTHER INFORMATION: Engineered enhanced sequon in loop of Abciximab
      1TXV:H ReoPro-like antibody Heavy Chain 2

<400> SEQUENCE: 100

Phe Ser Asn Gly Thr
1               5

<210> SEQ ID NO 101
<211> LENGTH: 5
<212> TYPE: PRT
<213> ORGANISM: Artificial Sequence
<220> FEATURE:
<223> OTHER INFORMATION: loop in Basiliximab 1MIM:H Anti-CD25 antibody
      heavy CHIMERIC chain 1

<400> SEQUENCE: 101

Gln Tyr Asn Ser Thr
1               5

<210> SEQ ID NO 102
<211> LENGTH: 5
<212> TYPE: PRT
<213> ORGANISM: Artificial Sequence
<220> FEATURE:
<223> OTHER INFORMATION: Engineered enhanced sequon in loop of
      Basiliximab 1MIM:H Anti-CD25 antibody heavy CHIMERIC chain 1

<400> SEQUENCE: 102

Tyr Tyr Asn Ser Thr
1               5
```

<210> SEQ ID NO 103
<211> LENGTH: 5
<212> TYPE: PRT
<213> ORGANISM: Artificial Sequence
<220> FEATURE:
<223> OTHER INFORMATION: loop in Basiliximab 1MIM:H Anti-CD25 antibody
      heavy CHIMERIC chain 1

<400> SEQUENCE: 103

Asp Ser Asp Gly Ser
1               5

<210> SEQ ID NO 104
<211> LENGTH: 5
<212> TYPE: PRT
<213> ORGANISM: Artificial Sequence
<220> FEATURE:
<223> OTHER INFORMATION: Engineered enhanced sequon in loop of
      Basiliximab 1MIM:H Anti-CD25 antibody heavy CHIMERIC chain 1

<400> SEQUENCE: 104

Phe Ser Asn Gly Thr
1               5

<210> SEQ ID NO 105
<211> LENGTH: 5
<212> TYPE: PRT
<213> ORGANISM: Artificial Sequence
<220> FEATURE:
<223> OTHER INFORMATION: loop in Basiliximab 1MIM:H Anti-CD25 antibody
      heavy CHIMERIC chain 2

<400> SEQUENCE: 105

Gln Tyr Asn Ser Thr
1               5

<210> SEQ ID NO 106
<211> LENGTH: 5
<212> TYPE: PRT
<213> ORGANISM: Artificial Sequence
<220> FEATURE:
<223> OTHER INFORMATION: Engineered enhanced sequon in loop of Basiliximab 1MIM:H Anti-CD25 antibody heavy CHIMERIC chain 2

<400> SEQUENCE: 106

Trp Tyr Asn Ser Thr
1 5

<210> SEQ ID NO 107
<211> LENGTH: 5
<212> TYPE: PRT
<213> ORGANISM: Artificial Sequence
<220> FEATURE:
<223> OTHER INFORMATION: loop in Basiliximab 1MIM:H Anti-CD25 antibody heavy CHIMERIC chain 2

<400> SEQUENCE: 107

Asp Ser Asp Gly Ser
1 5

<210> SEQ ID NO 108
<211> LENGTH: 5
<212> TYPE: PRT
<213> ORGANISM: Artificial Sequence
<220> FEATURE:
<223> OTHER INFORMATION: Engineered enhanced sequon in loop of Basiliximab 1MIM:H Anti-CD25 antibody heavy CHIMERIC chain 2

```
<400> SEQUENCE: 108

Phe Ser Asn Gly Ser
1               5

<210> SEQ ID NO 109
<211> LENGTH: 5
<212> TYPE: PRT
<213> ORGANISM: Artificial Sequence
<220> FEATURE:
<223> OTHER INFORMATION: Loop in Rituximab Mouse-Human chimeric Anti-
      CD20 Heavy Chain 1

<400> SEQUENCE: 109

Gln Tyr Asn Ser Thr
1               5

<210> SEQ ID NO 110
<211> LENGTH: 5
<212> TYPE: PRT
<213> ORGANISM: Artificial Sequence
<220> FEATURE:
<223> OTHER INFORMATION: Engineered enhanced sequon in loop of Rituximab
      Mouse-Human chimeric Anti-CD20 Heavy Chain 1

<400> SEQUENCE: 110

His Tyr Asn Ser Ser
1               5

<210> SEQ ID NO 111
<211> LENGTH: 5
<212> TYPE: PRT
<213> ORGANISM: Artificial Sequence
<220> FEATURE:
<223> OTHER INFORMATION: Loop in Rituximab Mouse-Human chimeric Anti-
      CD20 Heavy Chain 1

<400> SEQUENCE: 111

Asp Ser Asp Gly Ser
1               5

<210> SEQ ID NO 112
<211> LENGTH: 5
<212> TYPE: PRT
<213> ORGANISM: Artificial Sequence
<220> FEATURE:
<223> OTHER INFORMATION: Engineered enhanced sequon in loop of Rituximab
      Mouse-Human chimeric Anti-CD20 Heavy Chain 1

<400> SEQUENCE: 112

Tyr Ser Asn Gly Ser
1               5

<210> SEQ ID NO 113
<211> LENGTH: 5
<212> TYPE: PRT
<213> ORGANISM: Artificial Sequence
<220> FEATURE:
<223> OTHER INFORMATION: Loop in Rituximab Mouse-Human chimeric Anti-
      CD20 Heavy Chain 2

<400> SEQUENCE: 113

Gln Tyr Asn Ser Thr
1               5

<210> SEQ ID NO 114
<211> LENGTH: 5
```

```
<212> TYPE: PRT
<213> ORGANISM: Artificial Sequence
<220> FEATURE:
<223> OTHER INFORMATION: Engineered enhanced sequon in loop of Rituximab
      Mouse-Human chimeric Anti-CD20 Heavy Chain 2

<400> SEQUENCE: 114

Phe Tyr Asn Ser Ser
1               5

<210> SEQ ID NO 115
<211> LENGTH: 5
<212> TYPE: PRT
<213> ORGANISM: Artificial Sequence
<220> FEATURE:
<223> OTHER INFORMATION: Loop in Rituximab Mouse-Human chimeric Anti-
      CD20 Heavy Chain 2

<400> SEQUENCE: 115

Asp Ser Asp Gly Ser
1               5

<210> SEQ ID NO 116
<211> LENGTH: 5
<212> TYPE: PRT
<213> ORGANISM: Artificial Sequence
<220> FEATURE:
<223> OTHER INFORMATION: Engineered enhanced sequon in loop of
      Rituximab Mouse-Human chimeric Anti-CD20 Heavy Chain 2

<400> SEQUENCE: 116

Trp Ser Asn Gly Ser
1               5

<210> SEQ ID NO 117
<211> LENGTH: 5
<212> TYPE: PRT
<213> ORGANISM: Homo sapiens

<400> SEQUENCE: 117

Val Met Gly Gly Phe
1               5

<210> SEQ ID NO 118
<211> LENGTH: 5
<212> TYPE: PRT
<213> ORGANISM: Artificial Sequence
<220> FEATURE:
<223> OTHER INFORMATION: Engineered enhanced sequon in loop of
      Follitropin beta alpha chain

<400> SEQUENCE: 118

Phe Met Asn Gly Thr
1               5

<210> SEQ ID NO 119
<211> LENGTH: 5
<212> TYPE: PRT
<213> ORGANISM: Artificial Sequence
<220> FEATURE:
<223> OTHER INFORMATION: Engineered enhanced sequon in loop of
      Follitropin beta alpha chain

<400> SEQUENCE: 119

Trp Met Asn Gly Thr
1               5
```

```
<210> SEQ ID NO 120
<211> LENGTH: 5
<212> TYPE: PRT
<213> ORGANISM: Artificial Sequence
<220> FEATURE:
<223> OTHER INFORMATION: Engineered enhanced sequon in loop of
      Follitropin beta alpha chain

<400> SEQUENCE: 120

Tyr Met Asn Gly Thr
1               5

<210> SEQ ID NO 121
<211> LENGTH: 5
<212> TYPE: PRT
<213> ORGANISM: Artificial Sequence
<220> FEATURE:
<223> OTHER INFORMATION: Engineered enhanced sequon in loop of
      Follitropin beta alpha chain

<400> SEQUENCE: 121

His Met Asn Gly Thr
1               5

<210> SEQ ID NO 122
<211> LENGTH: 5
<212> TYPE: PRT
<213> ORGANISM: Artificial Sequence
<220> FEATURE:
<223> OTHER INFORMATION: Engineered enhanced sequon in loop of
      Follitropin beta alpha chain

<400> SEQUENCE: 122

Phe Met Asn Gly Ser
1               5

<210> SEQ ID NO 123
<211> LENGTH: 5
<212> TYPE: PRT
<213> ORGANISM: Artificial Sequence
<220> FEATURE:
<223> OTHER INFORMATION: Engineered enhanced sequon in loop of
      Follitropin beta alpha chain

<400> SEQUENCE: 123

Trp Met Asn Gly Ser
1               5

<210> SEQ ID NO 124
<211> LENGTH: 5
<212> TYPE: PRT
<213> ORGANISM: Artificial Sequence
<220> FEATURE:
<223> OTHER INFORMATION: Engineered enhanced sequon in loop of
      Follitropin beta alpha chain

<400> SEQUENCE: 124

Tyr Met Asn Gly Ser
1               5

<210> SEQ ID NO 125
<211> LENGTH: 5
<212> TYPE: PRT
<213> ORGANISM: Artificial Sequence
<220> FEATURE:
<223> OTHER INFORMATION: Engineered enhanced sequon in loop of
      Follitropin beta alpha chain

<400> SEQUENCE: 125
```

```
His Met Asn Gly Ser
1               5

<210> SEQ ID NO 126
<211> LENGTH: 5
<212> TYPE: PRT
<213> ORGANISM: Homo sapiens

<400> SEQUENCE: 126

His Pro Asp Gly Ser
1               5

<210> SEQ ID NO 127
<211> LENGTH: 5
<212> TYPE: PRT
<213> ORGANISM: Artificial Sequence
<220> FEATURE:
<223> OTHER INFORMATION: Engineered enhanced sequon in loop of
      Imiglucerase Human Beta-glucocidase

<400> SEQUENCE: 127

Phe Pro Asn Gly Thr
1               5

<210> SEQ ID NO 128
<211> LENGTH: 5
<212> TYPE: PRT
<213> ORGANISM: Artificial Sequence
<220> FEATURE:
<223> OTHER INFORMATION: Engineered enhanced sequon in loop of
      Imiglucerase Human Beta-glucocidase

<400> SEQUENCE: 128

Trp Pro Asn Gly Thr
1               5

<210> SEQ ID NO 129
<211> LENGTH: 5
<212> TYPE: PRT
<213> ORGANISM: Artificial Sequence
<220> FEATURE:
<223> OTHER INFORMATION: Engineered enhanced sequon in loop of
      Imiglucerase Human Beta-glucocidase

<400> SEQUENCE: 129

Tyr Pro Asn Gly Thr
1               5

<210> SEQ ID NO 130
<211> LENGTH: 5
<212> TYPE: PRT
<213> ORGANISM: Artificial Sequence
<220> FEATURE:
<223> OTHER INFORMATION: Engineered enhanced sequon in loop of
      Imiglucerase Human Beta-glucocidase

<400> SEQUENCE: 130

His Pro Asn Gly Thr
1               5

<210> SEQ ID NO 131
<211> LENGTH: 5
<212> TYPE: PRT
<213> ORGANISM: Artificial Sequence
<220> FEATURE:
<223> OTHER INFORMATION: Engineered enhanced sequon in loop of
      Imiglucerase Human Beta-glucocidase
```

```
<400> SEQUENCE: 131

Phe Pro Asn Gly Ser
1               5

<210> SEQ ID NO 132
<211> LENGTH: 5
<212> TYPE: PRT
<213> ORGANISM: Artificial Sequence
<220> FEATURE:
<223> OTHER INFORMATION: Engineered enhanced sequon in loop of
      Imiglucerase Human Beta-glucocidase

<400> SEQUENCE: 132

Trp Pro Asn Gly Ser
1               5

<210> SEQ ID NO 133
<211> LENGTH: 5
<212> TYPE: PRT
<213> ORGANISM: Artificial Sequence
<220> FEATURE:
<223> OTHER INFORMATION: Engineered enhanced sequon in loop of
      Imiglucerase Human Beta-glucocidase

<400> SEQUENCE: 133

Tyr Pro Asn Gly Ser
1               5

<210> SEQ ID NO 134
<211> LENGTH: 5
<212> TYPE: PRT
<213> ORGANISM: Artificial Sequence
<220> FEATURE:
<223> OTHER INFORMATION: Engineered enhanced sequon in loop of
      Imiglucerase Human Beta-glucocidase

<400> SEQUENCE: 134

His Pro Asn Gly Ser
1               5

<210> SEQ ID NO 135
<211> LENGTH: 6
<212> TYPE: PRT
<213> ORGANISM: Artificial Sequence
<220> FEATURE:
<223> OTHER INFORMATION: Enhanced sequon loop glycosylation sequence
<220> FEATURE:
<221> NAME/KEY: MISC_FEATURE
<222> LOCATION: (2)..(2)
<223> OTHER INFORMATION: Xaa in position 2 is Alanine, Cysteine,
      Aspartic Acid , Glutamic Acid, Glycine, Isoleucine, Lysine,
      Leucine, Methionine, Asparagine, Proline, Glutamine, Arginine,
      Serine, Threonine or Valine.
<220> FEATURE:
<221> NAME/KEY: MISC_FEATURE
<222> LOCATION: (3)..(3)
<223> OTHER INFORMATION: Xaa in position 3 is any amino acid residue
<220> FEATURE:
<221> NAME/KEY: MISC_FEATURE
<222> LOCATION: (5)..(5)
<223> OTHER INFORMATION: Xaa in position 5 is Alanine, Cysteine,
      Aspartic Acid , Glutamic Acid, Phenylalanine, Glycine, Histidine,
      Isoleucine, Lysine, Leucine, Methionine, Asparagine, Glutamine,
      Arginine, Serine, Threonine, Valine, Tryptophan, or Tyrosine.
<220> FEATURE:
<221> NAME/KEY: CARBOHYD
<222> LOCATION: (5)..(5)
<223> OTHER INFORMATION: The Asn at position 5 may be glycosylated

<400> SEQUENCE: 135
```

```
Phe Xaa Xaa Asn Xaa Thr
1               5

<210> SEQ ID NO 136
<211> LENGTH: 5
<212> TYPE: PRT
<213> ORGANISM: Artificial Sequence
<220> FEATURE:
<223> OTHER INFORMATION: Enhanced sequon loop glycosylation sequence
<220> FEATURE:
<221> NAME/KEY: MISC_FEATURE
<222> LOCATION: (2)..(2)
<223> OTHER INFORMATION: Xaa in position 2 is Alanine, Cysteine,
      Aspartic Acid , Glutamic Acid, Glycine, Isoleucine, Lysine,
      Leucine, Methionine, Asparagine, Proline, Glutamine, Arginine,
      Serine, Threonine, or Valine.
<220> FEATURE:
<221> NAME/KEY: MISC_FEATURE
<222> LOCATION: (4)..(4)
<223> OTHER INFORMATION: Xaa in position 4 is is Alanine, Cysteine,
      Aspartic Acid, Glutamic Acid, Phenylalanine, Glycine, Histidine,
      Isoleucine, Lysine, Leucine, Methionine, Asparagine, Glutamine,
      Arginine, Serine, Threonine, Valine, Tryptophan, or Tyrosine.

<400> SEQUENCE: 136

Phe Xaa Asn Xaa Thr
1               5

<210> SEQ ID NO 137
<211> LENGTH: 4
<212> TYPE: PRT
<213> ORGANISM: Artificial Sequence
<220> FEATURE:
<223> OTHER INFORMATION: Glycosylation sequon in loop 1 of Pin1 WW
      domain variant
<220> FEATURE:
<221> NAME/KEY: CARBOHYD
<222> LOCATION: (2)..(2)
<223> OTHER INFORMATION: The Asparagine at position 2 is glycosylated

<400> SEQUENCE: 137

Phe Asn Gly Thr
1

<210> SEQ ID NO 138
<211> LENGTH: 5
<212> TYPE: PRT
<213> ORGANISM: Artificial Sequence
<220> FEATURE:
<223> OTHER INFORMATION: Glycosylation sequon in loop 1 of Pin1 WW
      domain variant
<220> FEATURE:
<221> NAME/KEY: CARBOHYD
<222> LOCATION: (3)..(3)
<223> OTHER INFORMATION: The Asn at position 3 may be glycosylated

<400> SEQUENCE: 138

Phe Ala Asn Gly Thr
1               5

<210> SEQ ID NO 139
<211> LENGTH: 6
<212> TYPE: PRT
<213> ORGANISM: Artificial Sequence
<220> FEATURE:
<223> OTHER INFORMATION: Glycosylation sequon in loop 1 of Pin1 WW
      domain variant
<220> FEATURE:
<221> NAME/KEY: CARBOHYD
<222> LOCATION: (4)..(4)
<223> OTHER INFORMATION: Asn at position 4 may be glycosylated
```

<400> SEQUENCE: 139

Phe Arg Ser Asn Gly Thr
1               5

<210> SEQ ID NO 140
<211> LENGTH: 5
<212> TYPE: PRT
<213> ORGANISM: Artificial Sequence
<220> FEATURE:
<223> OTHER INFORMATION: Variant Pin 1 WW domain loop 1 reverse turn
      sequence
<220> FEATURE:
<221> NAME/KEY: CARBOHYD
<222> LOCATION: (3)..(3)
<223> OTHER INFORMATION: Asn at position 3 is not glycosylated.

<400> SEQUENCE: 140

Met Ser Asn Gly Arg
1               5

<210> SEQ ID NO 141
<211> LENGTH: 5
<212> TYPE: PRT
<213> ORGANISM: Artificial Sequence
<220> FEATURE:
<223> OTHER INFORMATION: Variant Pin 1 WW domain loop 1 reverse turn
      sequence
<220> FEATURE:
<221> NAME/KEY: CARBOHYD
<222> LOCATION: (3)..(3)
<223> OTHER INFORMATION: Asn at position 3 is glycosylated

<400> SEQUENCE: 141

Met Ser Asn Gly Arg
1               5

<210> SEQ ID NO 142
<211> LENGTH: 5
<212> TYPE: PRT
<213> ORGANISM: Artificial Sequence
<220> FEATURE:
<223> OTHER INFORMATION: Variant Pin 1 WW domain loop 1 reverse turn
      sequence

<400> SEQUENCE: 142

Met Phe Asn Gly Arg
1               5

<210> SEQ ID NO 143
<211> LENGTH: 5
<212> TYPE: PRT
<213> ORGANISM: Artificial Sequence
<220> FEATURE:
<223> OTHER INFORMATION: Variant Pin 1 WW domain loop 1 reverse turn
      sequence
<220> FEATURE:
<221> NAME/KEY: CARBOHYD
<222> LOCATION: (3)..(3)
<223> OTHER INFORMATION: Asn at position 3 is glycolsylated

<400> SEQUENCE: 143

Met Phe Asn Gly Arg
1               5

<210> SEQ ID NO 144
<211> LENGTH: 5
<212> TYPE: PRT
<213> ORGANISM: Artificial Sequence

```
<220> FEATURE:
<223> OTHER INFORMATION: Variant Pin 1 WW domain loop 1 reverse turn
      sequence

<400> SEQUENCE: 144

Met Ser Asn Gly Thr
1               5

<210> SEQ ID NO 145
<211> LENGTH: 5
<212> TYPE: PRT
<213> ORGANISM: Artificial Sequence
<220> FEATURE:
<223> OTHER INFORMATION: Variant Pin 1 WW domain loop 1 reverse turn
      sequence
<220> FEATURE:
<221> NAME/KEY: CARBOHYD
<222> LOCATION: (3)..(3)
<223> OTHER INFORMATION: Asn at position 3 is glycolsylated

<400> SEQUENCE: 145

Met Ser Asn Gly Thr
1               5

<210> SEQ ID NO 146
<211> LENGTH: 5
<212> TYPE: PRT
<213> ORGANISM: Artificial Sequence
<220> FEATURE:
<223> OTHER INFORMATION: Variant Pin 1 WW domain loop 1 reverse turn
      sequence

<400> SEQUENCE: 146

Met Phe Asn Gly Thr
1               5

<210> SEQ ID NO 147
<211> LENGTH: 5
<212> TYPE: PRT
<213> ORGANISM: Artificial Sequence
<220> FEATURE:
<223> OTHER INFORMATION: Variant Pin 1 WW domain loop 1 reverse turn
      sequence
<220> FEATURE:
<221> NAME/KEY: CARBOHYD
<222> LOCATION: (3)..(3)
<223> OTHER INFORMATION: Asn at position 3 is glycolsylated

<400> SEQUENCE: 147

Met Phe Asn Gly Thr
1               5

<210> SEQ ID NO 148
<211> LENGTH: 6
<212> TYPE: PRT
<213> ORGANISM: Artificial Sequence
<220> FEATURE:
<223> OTHER INFORMATION: Variant Pin 1 WW domain loop 1 reverse turn
      sequence

<400> SEQUENCE: 148

Met Ser Ala Asn Gly Arg
1               5

<210> SEQ ID NO 149
<211> LENGTH: 6
<212> TYPE: PRT
<213> ORGANISM: Artificial Sequence
<220> FEATURE:
```

```
<223> OTHER INFORMATION: Variant Pin 1 WW domain loop 1 reverse turn
      sequence
<220> FEATURE:
<221> NAME/KEY: CARBOHYD
<222> LOCATION: (4)..(4)
<223> OTHER INFORMATION: Asn at position 4 is glycolsylated

<400> SEQUENCE: 149

Met Ser Ala Asn Gly Arg
1               5

<210> SEQ ID NO 150
<211> LENGTH: 6
<212> TYPE: PRT
<213> ORGANISM: Artificial Sequence
<220> FEATURE:
<223> OTHER INFORMATION: Variant Pin 1 WW domain loop 1 reverse turn
      sequence

<400> SEQUENCE: 150

Met Phe Ala Asn Gly Arg
1               5

<210> SEQ ID NO 151
<211> LENGTH: 6
<212> TYPE: PRT
<213> ORGANISM: Artificial Sequence
<220> FEATURE:
<223> OTHER INFORMATION: Variant Pin 1 WW domain loop 1 reverse turn
      sequence
<220> FEATURE:
<221> NAME/KEY: CARBOHYD
<222> LOCATION: (4)..(4)
<223> OTHER INFORMATION: Asn at position 4 is glycolsylated

<400> SEQUENCE: 151

Met Phe Ala Asn Gly Arg
1               5

<210> SEQ ID NO 152
<211> LENGTH: 6
<212> TYPE: PRT
<213> ORGANISM: Artificial Sequence
<220> FEATURE:
<223> OTHER INFORMATION: Variant Pin 1 WW domain loop 1 reverse turn
      sequence

<400> SEQUENCE: 152

Met Ser Ala Asn Gly Thr
1               5

<210> SEQ ID NO 153
<211> LENGTH: 6
<212> TYPE: PRT
<213> ORGANISM: Artificial Sequence
<220> FEATURE:
<223> OTHER INFORMATION: Variant Pin 1 WW domain loop 1 reverse turn
      sequence
<220> FEATURE:
<221> NAME/KEY: CARBOHYD
<222> LOCATION: (4)..(4)
<223> OTHER INFORMATION: Asn at position 4 is glycolsylated

<400> SEQUENCE: 153

Met Ser Ala Asn Gly Thr
1               5

<210> SEQ ID NO 154
<211> LENGTH: 6
```

```
<212> TYPE: PRT
<213> ORGANISM: Artificial Sequence
<220> FEATURE:
<223> OTHER INFORMATION: Variant Pin 1 WW domain loop 1 reverse turn
      sequence

<400> SEQUENCE: 154

Met Phe Ala Asn Gly Thr
1               5

<210> SEQ ID NO 155
<211> LENGTH: 6
<212> TYPE: PRT
<213> ORGANISM: Artificial Sequence
<220> FEATURE:
<223> OTHER INFORMATION: Variant Pin 1 WW domain loop 1 reverse turn
      sequence
<220> FEATURE:
<221> NAME/KEY: misc_feature
<222> LOCATION: (4)..(4)
<223> OTHER INFORMATION: Asn at position 4 is glycolsylated

<400> SEQUENCE: 155

Met Phe Ala Asn Gly Thr
1               5

<210> SEQ ID NO 156
<211> LENGTH: 7
<212> TYPE: PRT
<213> ORGANISM: Artificial Sequence
<220> FEATURE:
<223> OTHER INFORMATION: Variant Pin 1 WW domain loop 1 reverse turn
      sequence

<400> SEQUENCE: 156

Met Ser Arg Ser Asn Gly Arg
1               5

<210> SEQ ID NO 157
<211> LENGTH: 7
<212> TYPE: PRT
<213> ORGANISM: Artificial Sequence
<220> FEATURE:
<223> OTHER INFORMATION: Variant Pin 1 WW domain loop 1 reverse turn
      sequence
<220> FEATURE:
<221> NAME/KEY: CARBOHYD
<222> LOCATION: (5)..(5)
<223> OTHER INFORMATION: Asn at position 5 is glycolsylated

<400> SEQUENCE: 157

Met Phe Arg Ser Asn Gly Arg
1               5

<210> SEQ ID NO 158
<211> LENGTH: 7
<212> TYPE: PRT
<213> ORGANISM: Artificial Sequence
<220> FEATURE:
<223> OTHER INFORMATION: Variant Pin 1 WW domain loop 1 reverse turn
      sequence

<400> SEQUENCE: 158

Met Phe Arg Ser Asn Gly Arg
1               5

<210> SEQ ID NO 159
<211> LENGTH: 7
<212> TYPE: PRT
```

```
<213> ORGANISM: Artificial Sequence
<220> FEATURE:
<223> OTHER INFORMATION: Variant Pin 1 WW domain loop 1 reverse turn
      sequence
<220> FEATURE:
<221> NAME/KEY: CARBOHYD
<222> LOCATION: (5)..(5)
<223> OTHER INFORMATION: Asn at position 5 is glycolsylated

<400> SEQUENCE: 159

Met Phe Arg Ser Asn Gly Arg
1               5

<210> SEQ ID NO 160
<211> LENGTH: 7
<212> TYPE: PRT
<213> ORGANISM: Artificial Sequence
<220> FEATURE:
<223> OTHER INFORMATION: Variant Pin 1 WW domain loop 1 reverse turn
      sequence

<400> SEQUENCE: 160

Met Ser Arg Ser Asn Gly Thr
1               5

<210> SEQ ID NO 161
<211> LENGTH: 7
<212> TYPE: PRT
<213> ORGANISM: Artificial Sequence
<220> FEATURE:
<223> OTHER INFORMATION: Variant Pin 1 WW domain loop 1 reverse turn
      sequence
<220> FEATURE:
<221> NAME/KEY: CARBOHYD
<222> LOCATION: (6)..(6)
<223> OTHER INFORMATION: Asn at position 6 is glucosylated

<400> SEQUENCE: 161

Met Ser Arg Ser Asn Gly Thr
1               5

<210> SEQ ID NO 162
<211> LENGTH: 7
<212> TYPE: PRT
<213> ORGANISM: Artificial Sequence
<220> FEATURE:
<223> OTHER INFORMATION: Variant Pin 1 WW domain loop 1 reverse turn
      sequence

<400> SEQUENCE: 162

Met Phe Arg Ser Asn Gly Thr
1               5

<210> SEQ ID NO 163
<211> LENGTH: 7
<212> TYPE: PRT
<213> ORGANISM: Artificial Sequence
<220> FEATURE:
<223> OTHER INFORMATION: Variant Pin 1 WW domain loop 1 reverse turn
      sequence
<220> FEATURE:
<221> NAME/KEY: CARBOHYD
<222> LOCATION: (5)..(5)
<223> OTHER INFORMATION: Asn at position 5 is glycolsylated

<400> SEQUENCE: 163

Met Phe Arg Ser Asn Gly Thr
1               5
```

```
<210> SEQ ID NO 164
<211> LENGTH: 4
<212> TYPE: PRT
<213> ORGANISM: Artificial Sequence
<220> FEATURE:
<223> OTHER INFORMATION: Enhanced aromatic sequon
<220> FEATURE:
<221> NAME/KEY: MISC_FEATURE
<222> LOCATION: (3)..(3)
<223> OTHER INFORMATION: Xaa at position 3 is Alanine, Cysteine,
      Aspartic Acid , Glutamic Acid, Phenylalanine, Glycine, Histidine,
      Isoleucine, Lysine, Leucine, Methionine, Asparagine, Glutamine,
      Arginine, Serine, Threonine, Valine, Tryptophan, or Tyrosine.

<400> SEQUENCE: 164

Phe Asn Xaa Thr
1

<210> SEQ ID NO 165
<211> LENGTH: 128
<212> TYPE: PRT
<213> ORGANISM: Artificial Sequence
<220> FEATURE:
<223> OTHER INFORMATION: Rat CD2 protein bearing N-terminal tags as
      described
<220> FEATURE:
<221> NAME/KEY: PROPEP
<222> LOCATION: (1)..(6)
<223> OTHER INFORMATION: 6x-His purification tag
<220> FEATURE:
<221> NAME/KEY: PROPEP
<222> LOCATION: (7)..(13)
<223> OTHER INFORMATION: Tobacco Etch Virus protease cleavage site
<220> FEATURE:
<221> NAME/KEY: PROPEP
<222> LOCATION: (14)..(22)
<223> OTHER INFORMATION: FLAG-tag
<220> FEATURE:
<221> NAME/KEY: PROPEP
<222> LOCATION: (22)..(25)
<223> OTHER INFORMATION: Factor Xa cleavage site
<220> FEATURE:
<221> NAME/KEY: mat_peptide
<222> LOCATION: (26)..(128)
<223> OTHER INFORMATION: Protein following cleavage of tags; A is
      position 3 of wild-type protein.

<400> SEQUENCE: 165

His His His His His His Glu Asn Leu Tyr Phe Gln Ser Asp Tyr Lys
-25                 -20                 -15                 -10

Asp Asp Asp Asp Lys Ile Glu Gly Arg Ala Asp Cys Arg Asp Ser Gly
 -5              -1   1               5

Thr Val Trp Gly Ala Leu Gly His Gly Ile Asn Leu Asn Ile Pro Asn
            10                  15                  20

Phe Gln Met Thr Asp Asp Ile Asp Glu Val Arg Trp Glu Arg Gly Ser
        25                  30                  35

Thr Leu Val Ala Glu Phe Lys Arg Lys Met Lys Pro Phe Leu Lys Ser
40                  45                  50                  55

Gly Ala Phe Glu Ile Leu Ala Asn Gly Asp Leu Lys Ile Lys Asn Leu
                60                  65                  70

Thr Arg Asp Asp Ser Gly Thr Tyr Asn Val Thr Val Tyr Ser Thr Asn
            75                  80                  85

Gly Thr Arg Ile Leu Asp Lys Ala Leu Asp Leu Arg Ile Leu Glu Met
            90                  95                  100

<210> SEQ ID NO 166
<211> LENGTH: 128
<212> TYPE: PRT
```

```
<213> ORGANISM: Artificial Sequence
<220> FEATURE:
<223> OTHER INFORMATION: Engineered version of RnCD2
<220> FEATURE:
<221> NAME/KEY: PROPEP
<222> LOCATION: (1)..(6)
<223> OTHER INFORMATION: 6xHis tag
<220> FEATURE:
<221> NAME/KEY: PROPEP
<222> LOCATION: (7)..(13)
<223> OTHER INFORMATION: Tobacco Etch Virus protease cleavage site
<220> FEATURE:
<221> NAME/KEY: PROPEP
<222> LOCATION: (14)..(22)
<223> OTHER INFORMATION: FLAG-tag
<220> FEATURE:
<221> NAME/KEY: PROPEP
<222> LOCATION: (22)..(25)
<223> OTHER INFORMATION: Factor Xa cleavage site
<220> FEATURE:
<221> NAME/KEY: mat_peptide
<222> LOCATION: (26)..(128)
<223> OTHER INFORMATION: Protein following cleavage of tags; A is
      position 3 of wild-type protein
<220> FEATURE:
<221> NAME/KEY: MISC_FEATURE
<222> LOCATION: (90)..(90)
<223> OTHER INFORMATION: Asp mutated to Thr
<220> FEATURE:
<221> NAME/KEY: MISC_FEATURE
<222> LOCATION: (95)..(95)
<223> OTHER INFORMATION: Asn mutated to Glu
<220> FEATURE:
<221> NAME/KEY: MISC_FEATURE
<222> LOCATION: (105)..(105)
<223> OTHER INFORMATION: Asn mutated to Glu
<220> FEATURE:
<221> NAME/KEY: MISC_FEATURE
<222> LOCATION: (112)..(112)
<223> OTHER INFORMATION: Asn mutated to Asp

<400> SEQUENCE: 166

His His His His His His Glu Asn Leu Tyr Phe Gln Ser Asp Tyr Lys
-25                 -20                 -15                 -10

Asp Asp Asp Asp Lys Ile Glu Gly Arg Ala Asp Cys Arg Asp Ser Gly
 -5              -1   1               5

Thr Val Trp Gly Ala Leu Gly His Gly Ile Asn Leu Asn Ile Pro Asn
             10                  15                  20

Phe Gln Met Thr Asp Asp Ile Asp Glu Val Arg Trp Glu Arg Gly Ser
         25                  30                  35

Thr Leu Val Ala Glu Phe Lys Arg Lys Met Lys Pro Phe Leu Lys Ser
 40                  45                  50                  55

Gly Ala Phe Glu Ile Leu Ala Asn Gly Thr Leu Lys Ile Lys Glu Leu
             60                  65                  70

Thr Arg Asp Asp Ser Gly Thr Tyr Glu Val Thr Val Tyr Ser Thr Asp
             75                  80                  85

Gly Thr Arg Ile Leu Asp Lys Ala Leu Asp Leu Arg Ile Leu Glu Met
         90                  95                  100

<210> SEQ ID NO 167
<211> LENGTH: 128
<212> TYPE: PRT
<213> ORGANISM: Artificial Sequence
<220> FEATURE:
<223> OTHER INFORMATION: Engineered version of RnCD2 bearing 61E->K
      mutation
<220> FEATURE:
<221> NAME/KEY: PROPEP
<222> LOCATION: (1)..(6)
<223> OTHER INFORMATION: 6x His tag
```

```
<220> FEATURE:
<221> NAME/KEY: PROPEP
<222> LOCATION: (7)..(13)
<223> OTHER INFORMATION: Tobacco Etch Virus protease cleavage signal
<220> FEATURE:
<221> NAME/KEY: PROPEP
<222> LOCATION: (14)..(22)
<223> OTHER INFORMATION: FLAG-tag
<220> FEATURE:
<221> NAME/KEY: PROPEP
<222> LOCATION: (22)..(25)
<223> OTHER INFORMATION: Factor Xa cleavage site
<220> FEATURE:
<221> NAME/KEY: mat_peptide
<222> LOCATION: (26)..(128)
<220> FEATURE:
<221> NAME/KEY: MISC_FEATURE
<222> LOCATION: (84)..(84)
<223> OTHER INFORMATION: site of 61E->K mutation

<400> SEQUENCE: 167

His His His His His His Glu Asn Leu Tyr Phe Gln Ser Asp Tyr Lys
-25                 -20                 -15                 -10

Asp Asp Asp Asp Lys Ile Glu Gly Arg Ala Asp Cys Arg Asp Ser Gly
-5              -1  1               5

Thr Val Trp Gly Ala Leu Gly His Gly Ile Asn Leu Asn Ile Pro Asn
            10                  15                  20

Phe Gln Met Thr Asp Asp Ile Asp Glu Val Arg Trp Glu Arg Gly Ser
        25                  30                  35

Thr Leu Val Ala Glu Phe Lys Arg Lys Met Lys Pro Phe Leu Lys Ser
40                  45                  50                  55

Gly Ala Phe Lys Ile Leu Ala Asn Gly Thr Leu Lys Ile Lys Glu Leu
                60                  65                  70

Thr Arg Asp Asp Ser Gly Thr Tyr Glu Val Thr Val Tyr Ser Thr Asp
                75                  80                  85

Gly Thr Arg Ile Leu Asp Lys Ala Leu Asp Leu Arg Ile Leu Glu Met
                90                  95                  100

<210> SEQ ID NO 168
<211> LENGTH: 128
<212> TYPE: PRT
<213> ORGANISM: Artificial Sequence
<220> FEATURE:
<223> OTHER INFORMATION: Engineered version of RnCD2 bearing 61E->K
      mutation and glycosylated N65
<220> FEATURE:
<221> NAME/KEY: PROPEP
<222> LOCATION: (1)..(6)
<223> OTHER INFORMATION: 6x His tag
<220> FEATURE:
<221> NAME/KEY: PROPEP
<222> LOCATION: (7)..(13)
<223> OTHER INFORMATION: Tobacco Etch Virus protease cleavage site
<220> FEATURE:
<221> NAME/KEY: PROPEP
<222> LOCATION: (14)..(22)
<223> OTHER INFORMATION: FLAG-tag
<220> FEATURE:
<221> NAME/KEY: PROPEP
<222> LOCATION: (22)..(25)
<223> OTHER INFORMATION: Factor Xa cleavage site
<220> FEATURE:
<221> NAME/KEY: mat_peptide
<222> LOCATION: (26)..(128)
<220> FEATURE:
<221> NAME/KEY: CARBOHYD
<222> LOCATION: (88)..(88)
<223> OTHER INFORMATION: Asn 65 (at position 88) is glycosylated

<400> SEQUENCE: 168
```

```
His His His His His His Glu Asn Leu Tyr Phe Gln Ser Asp Tyr Lys
-25                 -20                 -15                 -10

Asp Asp Asp Asp Lys Ile Glu Gly Arg Ala Asp Cys Arg Asp Ser Gly
 -5              -1   1               5

Thr Val Trp Gly Ala Leu Gly His Gly Ile Asn Leu Asn Ile Pro Asn
         10                  15                  20

Phe Gln Met Thr Asp Asp Ile Asp Glu Val Arg Trp Glu Arg Gly Ser
         25                  30                  35

Thr Leu Val Ala Glu Phe Lys Arg Lys Met Lys Pro Phe Leu Lys Ser
 40              45                  50                  55

Gly Ala Phe Lys Ile Leu Ala Asn Gly Thr Leu Lys Ile Lys Glu Leu
                 60                  65                  70

Thr Arg Asp Asp Ser Gly Thr Tyr Glu Val Thr Val Tyr Ser Thr Asp
             75                  80                  85

Gly Thr Arg Ile Leu Asp Lys Ala Leu Asp Leu Arg Ile Leu Glu Met
             90                  95                 100
```

<210> SEQ ID NO 169
<211> LENGTH: 128
<212> TYPE: PRT
<213> ORGANISM: Artificial Sequence
<220> FEATURE:
<223> OTHER INFORMATION: Engineered version of RnCD2* bearing 63L->F
      mutation
<220> FEATURE:
<221> NAME/KEY: PROPEP
<222> LOCATION: (1)..(6)
<223> OTHER INFORMATION: 6x His tag
<220> FEATURE:
<221> NAME/KEY: PROPEP
<222> LOCATION: (7)..(13)
<223> OTHER INFORMATION: Tobacco Etch Virus protease site
<220> FEATURE:
<221> NAME/KEY: PROPEP
<222> LOCATION: (14)..(22)
<223> OTHER INFORMATION: FLAG-tag
<220> FEATURE:
<221> NAME/KEY: PROPEP
<222> LOCATION: (22)..(25)
<223> OTHER INFORMATION: Factor Xa cleavage site
<220> FEATURE:
<221> NAME/KEY: mat_peptide
<222> LOCATION: (26)..(128)

<400> SEQUENCE: 169

```
His His His His His His Glu Asn Leu Tyr Phe Gln Ser Asp Tyr Lys
-25                 -20                 -15                 -10

Asp Asp Asp Asp Lys Ile Glu Gly Arg Ala Asp Cys Arg Asp Ser Gly
 -5              -1   1               5

Thr Val Trp Gly Ala Leu Gly His Gly Ile Asn Leu Asn Ile Pro Asn
         10                  15                  20

Phe Gln Met Thr Asp Asp Ile Asp Glu Val Arg Trp Glu Arg Gly Ser
         25                  30                  35

Thr Leu Val Ala Glu Phe Lys Arg Lys Met Lys Pro Phe Leu Lys Ser
 40              45                  50                  55

Gly Ala Phe Glu Ile Phe Ala Asn Gly Thr Leu Lys Ile Lys Glu Leu
                 60                  65                  70

Thr Arg Asp Asp Ser Gly Thr Tyr Glu Val Thr Val Tyr Ser Thr Asp
             75                  80                  85

Gly Thr Arg Ile Leu Asp Lys Ala Leu Asp Leu Arg Ile Leu Glu Met
             90                  95                 100
```

<210> SEQ ID NO 170
<211> LENGTH: 128
<212> TYPE: PRT
<213> ORGANISM: Artificial Sequence
<220> FEATURE:
<223> OTHER INFORMATION: Engineered version of RnCD2* bearing 63L->F
      mutation and glycosylated at N65
<220> FEATURE:
<221> NAME/KEY: PROPEP
<222> LOCATION: (1)..(6)
<223> OTHER INFORMATION: 6x-His tag
<220> FEATURE:
<221> NAME/KEY: PROPEP
<222> LOCATION: (7)..(13)
<223> OTHER INFORMATION: Tobacco Etch Virus protease cleavage site
<220> FEATURE:
<221> NAME/KEY: PROPEP
<222> LOCATION: (14)..(22)
<223> OTHER INFORMATION: FLAG-tag
<220> FEATURE:
<221> NAME/KEY: PROPEP
<222> LOCATION: (22)..(25)
<223> OTHER INFORMATION: Factor Xa cleavage site
<220> FEATURE:
<221> NAME/KEY: mat_peptide
<222> LOCATION: (26)..(128)
<220> FEATURE:
<221> NAME/KEY: MISC_FEATURE
<222> LOCATION: (86)..(86)
<223> OTHER INFORMATION: site of 63L->F mutation
<220> FEATURE:
<221> NAME/KEY: CARBOHYD
<222> LOCATION: (88)..(88)
<223> OTHER INFORMATION: Asn 65 (at position 88) is glycosylated

<400> SEQUENCE: 170

His His His His His His Glu Asn Leu Tyr Phe Gln Ser Asp Tyr Lys
-25                 -20                 -15                 -10

Asp Asp Asp Asp Lys Ile Glu Gly Arg Ala Asp Cys Arg Asp Ser Gly
 -5              -1   1               5

Thr Val Trp Gly Ala Leu Gly His Gly Ile Asn Leu Asn Ile Pro Asn
             10                  15                  20

Phe Gln Met Thr Asp Asp Ile Asp Glu Val Arg Trp Glu Arg Gly Ser
         25                  30                  35

Thr Leu Val Ala Glu Phe Lys Arg Lys Met Lys Pro Phe Leu Lys Ser
 40              45                  50                  55

Gly Ala Phe Glu Ile Phe Ala Asn Gly Thr Leu Lys Ile Lys Glu Leu
                 60                  65                  70

Thr Arg Asp Asp Ser Gly Thr Tyr Glu Val Thr Val Tyr Ser Thr Asp
             75                  80                  85

Gly Thr Arg Ile Leu Asp Lys Ala Leu Asp Leu Arg Ile Leu Glu Met
             90                  95                  100

<210> SEQ ID NO 171
<211> LENGTH: 128
<212> TYPE: PRT
<213> ORGANISM: Artificial Sequence
<220> FEATURE:
<223> OTHER INFORMATION: Engineered version of RnCD2* bearing 63L->F
      mutation and 61E->K mutation
<220> FEATURE:
<221> NAME/KEY: PROPEP
<222> LOCATION: (1)..(6)
<223> OTHER INFORMATION: 6x-His tag
<220> FEATURE:
<221> NAME/KEY: PROPEP
<222> LOCATION: (7)..(14)
<223> OTHER INFORMATION: Tobacco Etch VIrus protease cleavage site
<220> FEATURE:

```
<221> NAME/KEY: PROPEP
<222> LOCATION: (15)..(22)
<223> OTHER INFORMATION: FLAG-tag
<220> FEATURE:
<221> NAME/KEY: PROPEP
<222> LOCATION: (22)..(25)
<223> OTHER INFORMATION: Factor Xa cleavage site
<220> FEATURE:
<221> NAME/KEY: mat_peptide
<222> LOCATION: (26)..(128)

<400> SEQUENCE: 171
```

His His His His His His Glu Asn Leu Tyr Phe Gln Ser Asp Tyr Lys
-25                 -20                 -15                 -10

Asp Asp Asp Asp Lys Ile Glu Gly Arg Ala Asp Cys Arg Asp Ser Gly
-5              -1   1               5

Thr Val Trp Gly Ala Leu Gly His Gly Ile Asn Leu Asn Ile Pro Asn
            10                  15                  20

Phe Gln Met Thr Asp Asp Ile Asp Glu Val Arg Trp Glu Arg Gly Ser
        25                  30                  35

Thr Leu Val Ala Glu Phe Lys Arg Lys Met Lys Pro Phe Leu Lys Ser
40                  45                  50                  55

Gly Ala Phe Lys Ile Phe Ala Asn Gly Thr Leu Lys Ile Lys Glu Leu
                60                  65                  70

Thr Arg Asp Asp Ser Gly Thr Tyr Glu Val Thr Val Tyr Ser Thr Asp
            75                  80                  85

Gly Thr Arg Ile Leu Asp Lys Ala Leu Asp Leu Arg Ile Leu Glu Met
            90                  95                  100

```
<210> SEQ ID NO 172
<211> LENGTH: 128
<212> TYPE: PRT
<213> ORGANISM: Artificial Sequence
<220> FEATURE:
<223> OTHER INFORMATION: Engineered version of RnCD2* bearing 63L->F
      mutation and 61E->K mutation and glycosylated at N65 site
<220> FEATURE:
<221> NAME/KEY: PROPEP
<222> LOCATION: (1)..(6)
<223> OTHER INFORMATION: 6x-His tag
<220> FEATURE:
<221> NAME/KEY: PROPEP
<222> LOCATION: (7)..(13)
<223> OTHER INFORMATION: Tobacco Etch Virus protease cleavage site
<220> FEATURE:
<221> NAME/KEY: PROPEP
<222> LOCATION: (14)..(22)
<223> OTHER INFORMATION: FLAG-tag
<220> FEATURE:
<221> NAME/KEY: PROPEP
<222> LOCATION: (22)..(25)
<223> OTHER INFORMATION: Factor Xa cleavage site
<220> FEATURE:
<221> NAME/KEY: mat_peptide
<222> LOCATION: (26)..(128)
<220> FEATURE:
<221> NAME/KEY: CARBOHYD
<222> LOCATION: (88)..(88)
<223> OTHER INFORMATION: Asn65 at position 88 is glycosylated

<400> SEQUENCE: 172
```

His His His His His His Glu Asn Leu Tyr Phe Gln Ser Asp Tyr Lys
-25                 -20                 -15                 -10

Asp Asp Asp Asp Lys Ile Glu Gly Arg Ala Asp Cys Arg Asp Ser Gly
-5              -1   1               5

Thr Val Trp Gly Ala Leu Gly His Gly Ile Asn Leu Asn Ile Pro Asn
            10                  15                  20

```
Phe Gln Met Thr Asp Asp Ile Asp Glu Val Arg Trp Glu Arg Gly Ser
        25                  30                  35
Thr Leu Val Ala Glu Phe Lys Arg Lys Met Lys Pro Phe Leu Lys Ser
 40                  45                  50                  55
Gly Ala Phe Lys Ile Phe Ala Asn Gly Thr Leu Lys Ile Lys Glu Leu
                 60                  65                  70
Thr Arg Asp Asp Ser Gly Thr Tyr Glu Val Thr Val Tyr Ser Thr Asp
             75                  80                  85
Gly Thr Arg Ile Leu Asp Lys Ala Leu Asp Leu Arg Ile Leu Glu Met
         90                  95                 100
```

<210> SEQ ID NO 173
<211> LENGTH: 124
<212> TYPE: PRT
<213> ORGANISM: Artificial Sequence
<220> FEATURE:
<223> OTHER INFORMATION: AcyP2 amino acid sequence bearing N-terminal
      tags as described
<220> FEATURE:
<221> NAME/KEY: PROPEP
<222> LOCATION: (1)..(6)
<223> OTHER INFORMATION: 6x-His purification tag
<220> FEATURE:
<221> NAME/KEY: PROPEP
<222> LOCATION: (7)..(13)
<223> OTHER INFORMATION: Tobacco Etch Virus protease cleavage site
<220> FEATURE:
<221> NAME/KEY: PROPEP
<222> LOCATION: (14)..(21)
<223> OTHER INFORMATION: FLAG-tag
<220> FEATURE:
<221> NAME/KEY: PROPEP
<222> LOCATION: (23)..(25)
<223> OTHER INFORMATION: Factor Xa cleavage site
<220> FEATURE:
<221> NAME/KEY: mat_peptide
<222> LOCATION: (26)..(124)

<400> SEQUENCE: 173

```
His His His His His His Glu Asn Leu Tyr Phe Gln Ser Asp Tyr Lys
-25                 -20                 -15                 -10
Asp Asp Asp Asp Lys Ile Glu Gly Arg Met Ser Thr Ala Gln Ser Leu
 -5              -1   1                   5
Lys Ser Val Asp Tyr Glu Val Phe Gly Arg Val Gln Gly Val Cys Phe
             10                  15                  20
Arg Met Tyr Thr Glu Asp Glu Ala Arg Lys Ile Gly Val Val Gly Trp
        25                  30                  35
Val Lys Asn Thr Ser Lys Gly Thr Val Thr Gly Gln Val Gln Gly Pro
 40                  45                  50                  55
Glu Asp Lys Val Asn Ser Met Lys Ser Trp Leu Ser Lys Val Gly Ser
                 60                  65                  70
Pro Ser Ser Arg Ile Asp Arg Thr Asn Phe Ser Asn Glu Lys Thr Ile
             75                  80                  85
Ser Lys Leu Glu Tyr Ser Asn Phe Ser Ile Arg Tyr
         90                  95
```

<210> SEQ ID NO 174
<211> LENGTH: 124
<212> TYPE: PRT
<213> ORGANISM: Artificial Sequence
<220> FEATURE:
<223> OTHER INFORMATION: AcyP2 amino acid sequence bearing N-terminal
      tags as described and mutated to direct glycosylation to a single
      site

```
<220> FEATURE:
<221> NAME/KEY: PROPEP
<222> LOCATION: (1)..(6)
<223> OTHER INFORMATION: 6x His tag
<220> FEATURE:
<221> NAME/KEY: PROPEP
<222> LOCATION: (7)..(13)
<223> OTHER INFORMATION: Tobacco Etch Virus protease cleavage site
<220> FEATURE:
<221> NAME/KEY: PROPEP
<222> LOCATION: (14)..(22)
<223> OTHER INFORMATION: FLAG-tag
<220> FEATURE:
<221> NAME/KEY: PROPEP
<222> LOCATION: (22)..(25)
<223> OTHER INFORMATION: Factor Xa cleavage site
<220> FEATURE:
<221> NAME/KEY: mat_peptide
<222> LOCATION: (26)..(124)

<400> SEQUENCE: 174

His His His His His His Glu Asn Leu Tyr Phe Gln Ser Asp Tyr Lys
-25                 -20                 -15                 -10

Asp Asp Asp Asp Lys Ile Glu Gly Arg Met Ser Thr Ala Gln Ser Leu
 -5              -1   1               5

Lys Ser Val Asp Tyr Glu Val Phe Gly Arg Val Gln Gly Val Cys Phe
         10                  15                  20

Arg Met Tyr Thr Glu Asp Glu Ala Arg Lys Ile Gly Val Val Gly Trp
     25                  30                  35

Val Lys Asn Thr Ala Asn Gly Thr Val Thr Gly Gln Val Gln Gly Pro
 40                  45                  50                  55

Glu Asp Lys Val Asn Ser Met Lys Ser Trp Leu Ser Lys Val Gly Ser
                 60                  65                  70

Pro Ser Ser Arg Ile Asp Arg Thr Asn Phe Ala Asn Glu Lys Thr Ile
         75                  80                  85

Ser Lys Leu Glu Tyr Ser Asn Phe Ala Ile Arg Tyr
         90                  95

<210> SEQ ID NO 175
<211> LENGTH: 124
<212> TYPE: PRT
<213> ORGANISM: Artificial Sequence
<220> FEATURE:
<223> OTHER INFORMATION: AcyP2 amino acid sequence bearing N-terminal
      tags as described and mutated to direct glycosylation to a single
      site
<220> FEATURE:
<221> NAME/KEY: PROPEP
<222> LOCATION: (1)..(6)
<223> OTHER INFORMATION: 6x His tag
<220> FEATURE:
<221> NAME/KEY: PROPEP
<222> LOCATION: (7)..(13)
<223> OTHER INFORMATION: Tobacco Etch Virus protease cleavage site
<220> FEATURE:
<221> NAME/KEY: PROPEP
<222> LOCATION: (14)..(22)
<223> OTHER INFORMATION: FLAG-tag
<220> FEATURE:
<221> NAME/KEY: PROPEP
<222> LOCATION: (22)..(25)
<223> OTHER INFORMATION: Factor Xa cleavage site
<220> FEATURE:
<221> NAME/KEY: mat_peptide
<222> LOCATION: (22)..(25)
<220> FEATURE:
<221> NAME/KEY: CARBOHYD
<222> LOCATION: (70)..(70)
<223> OTHER INFORMATION: Asn45 (at position 70) is glycosylated
```

<400> SEQUENCE: 175

```
His His His His His His Glu Asn Leu Tyr Phe Gln Ser Asp Tyr Lys
-20                 -15                 -10
Asp Asp Asp Asp Lys Ile Glu Gly Arg Met Ser Thr Ala Gln Ser Leu
-5              -1  1               5                   10
Lys Ser Val Asp Tyr Glu Val Phe Gly Arg Val Gln Gly Val Cys Phe
                15                  20                  25
Arg Met Tyr Thr Glu Asp Glu Ala Arg Lys Ile Gly Val Val Gly Trp
            30                  35                  40
Val Lys Asn Thr Ala Asn Gly Thr Val Thr Gly Gln Val Gln Gly Pro
        45                  50                  55
Glu Asp Lys Val Asn Ser Met Lys Ser Trp Leu Ser Lys Val Gly Ser
60                  65                  70                  75
Pro Ser Ser Arg Ile Asp Arg Thr Asn Phe Ala Asn Glu Lys Thr Ile
                80                  85                  90
Ser Lys Leu Glu Tyr Ser Asn Phe Ala Ile Arg Tyr
            95                  100
```

<210> SEQ ID NO 176
<211> LENGTH: 124
<212> TYPE: PRT
<213> ORGANISM: Artificial Sequence
<220> FEATURE:
<223> OTHER INFORMATION: AcyP2 amino acid sequence bearing N-terminal
      tags as described and mutated to direct glycosylation to a single
      site, also bearing a T->F at mature position 43
<220> FEATURE:
<221> NAME/KEY: PROPEP
<222> LOCATION: (1)..(6)
<223> OTHER INFORMATION: 6x His tag
<220> FEATURE:
<221> NAME/KEY: PROPEP
<222> LOCATION: (7)..(13)
<223> OTHER INFORMATION: Tobacco Etch Virus protease cleavage site
<220> FEATURE:
<221> NAME/KEY: PROPEP
<222> LOCATION: (14)..(22)
<223> OTHER INFORMATION: FLAG-tag
<220> FEATURE:
<221> NAME/KEY: PROPEP
<222> LOCATION: (22)..(25)
<223> OTHER INFORMATION: Factor Xa cleavage site
<220> FEATURE:
<221> NAME/KEY: mat_peptide
<222> LOCATION: (22)..(25)
<220> FEATURE:
<221> NAME/KEY: MISC_FEATURE
<222> LOCATION: (68)..(68)
<223> OTHER INFORMATION: site of T->F mutation

<400> SEQUENCE: 176

```
His His His His His His Glu Asn Leu Tyr Phe Gln Ser Asp Tyr Lys
-20                 -15                 -10
Asp Asp Asp Asp Lys Ile Glu Gly Arg Met Ser Thr Ala Gln Ser Leu
-5              -1  1               5                   10
Lys Ser Val Asp Tyr Glu Val Phe Gly Arg Val Gln Gly Val Cys Phe
                15                  20                  25
Arg Met Tyr Thr Glu Asp Glu Ala Arg Lys Ile Gly Val Val Gly Trp
            30                  35                  40
Val Lys Asn Phe Ala Asn Gly Thr Val Thr Gly Gln Val Gln Gly Pro
        45                  50                  55
Glu Asp Lys Val Asn Ser Met Lys Ser Trp Leu Ser Lys Val Gly Ser
60                  65                  70                  75
```

Pro Ser Ser Arg Ile Asp Arg Thr Asn Phe Ala Asn Glu Lys Thr Ile
            80                  85                  90

Ser Lys Leu Glu Tyr Ser Asn Phe Ala Ile Arg Tyr
            95                  100

<210> SEQ ID NO 177
<211> LENGTH: 124
<212> TYPE: PRT
<213> ORGANISM: Artificial Sequence
<220> FEATURE:
<223> OTHER INFORMATION: AcyP2 amino acid sequence bearing N-terminal
      tags as described and mutated to direct glycosylation to a single
      site, also bearing a T->F at mature position 43
<220> FEATURE:
<221> NAME/KEY: PROPEP
<222> LOCATION: (1)..(6)
<223> OTHER INFORMATION: 6x His tag
<220> FEATURE:
<221> NAME/KEY: PROPEP
<222> LOCATION: (7)..(13)
<223> OTHER INFORMATION: Tobacco Etch Virus protease cleavage site
<220> FEATURE:
<221> NAME/KEY: PROPEP
<222> LOCATION: (14)..(22)
<223> OTHER INFORMATION: FLAG-tag
<220> FEATURE:
<221> NAME/KEY: PROPEP
<222> LOCATION: (22)..(25)
<223> OTHER INFORMATION: Factor Xa cleavage site
<220> FEATURE:
<221> NAME/KEY: mat_peptide
<222> LOCATION: (26)..(124)
<220> FEATURE:
<221> NAME/KEY: CARBOHYD
<222> LOCATION: (70)..(70)
<223> OTHER INFORMATION: Asn45 (position 70) is glycosylated

<400> SEQUENCE: 177

His His His His His His Glu Asn Leu Tyr Phe Gln Ser Asp Tyr Lys
-25                 -20                 -15                 -10

Asp Asp Asp Asp Lys Ile Glu Gly Arg Met Ser Thr Ala Gln Ser Leu
-5              -1  1               5

Lys Ser Val Asp Tyr Glu Val Phe Gly Arg Val Gln Gly Val Cys Phe
            10                  15                  20

Arg Met Tyr Thr Glu Asp Glu Ala Arg Lys Ile Gly Val Val Gly Trp
            25                  30                  35

Val Lys Asn Phe Ala Asn Gly Thr Val Thr Gly Gln Val Gln Gly Pro
40                  45                  50                  55

Glu Asp Lys Val Asn Ser Met Lys Ser Trp Leu Ser Lys Val Gly Ser
            60                  65                  70

Pro Ser Ser Arg Ile Asp Arg Thr Asn Phe Ala Asn Glu Lys Thr Ile
            75                  80                  85

Ser Lys Leu Glu Tyr Ser Asn Phe Ala Ile Arg Tyr
            90                  95

<210> SEQ ID NO 178
<211> LENGTH: 162
<212> TYPE: PRT
<213> ORGANISM: Homo sapiens
<220> FEATURE:
<221> NAME/KEY: DOMAIN
<222> LOCATION: (6)..(44)
<223> OTHER INFORMATION: WW domain of Pin1
<300> PUBLICATION INFORMATION:
<301> AUTHORS: Ranganathan R, Lu KP, Hunter T, Noel JP.
<302> TITLE: Structural and functional analysis of the mitotic rotamase
      Pin1 suggests substrate recognition is phosphorylation dependent.
<303> JOURNAL: Cell

<304> VOLUME: 89
<305> ISSUE: 6
<306> PAGES: 875-86
<307> DATE: 1997-06-13

<400> SEQUENCE: 178

```
Met Ala Asp Glu Glu Lys Leu Pro Pro Gly Trp Glu Lys Arg Met Ser
1               5                   10                  15

Arg Ser Ser Gly Val Tyr Tyr Phe Asn His Ile Thr Asn Ala Ser Gln
            20                  25                  30

Trp Glu Arg Pro Ser Gly Asn Ser Ser Gly Gly Lys Asn Gly Gln
        35                  40                  45

Gly Glu Pro Ala Arg Val Arg Cys Ser His Leu Leu Val Lys His Ser
    50                  55                  60

Gln Ser Arg Arg Pro Ser Ser Trp Arg Gln Glu Lys Ile Thr Arg Thr
65                  70                  75                  80

Lys Glu Glu Ala Leu Glu Leu Ile Asn Gly Tyr Ile Gln Lys Ile Lys
                85                  90                  95

Ser Gly Glu Glu Asp Phe Glu Ser Leu Ala Ser Gln Phe Ser Asp Cys
                100                 105                 110

Ser Ser Ala Lys Ala Arg Gly Asp Leu Gly Ala Phe Ser Arg Gly Gln
            115                 120                 125

Met Gln Lys Pro Phe Glu Asp Ala Ser Phe Ala Leu Arg Thr Gly Glu
130                 135                 140

Met Ser Gly Pro Val Phe Thr Asp Ser Gly Ile His Ile Ile Leu Arg
145                 150                 155                 160

Thr Glu
```

<210> SEQ ID NO 179
<211> LENGTH: 32
<212> TYPE: PRT
<213> ORGANISM: Artificial Sequence
<220> FEATURE:
<223> OTHER INFORMATION: WW loop domain corresponding to residues 6-39
     of wt protein

<400> SEQUENCE: 179

```
Lys Leu Pro Pro Gly Trp Glu Lys Arg Met Ser Asn Gly Arg Val Tyr
1               5                   10                  15

Tyr Phe Asn His Ile Thr Asn Ala Ser Gln Phe Glu Arg Pro Ser Gly
            20                  25                  30
```

<210> SEQ ID NO 180
<211> LENGTH: 32
<212> TYPE: PRT
<213> ORGANISM: Artificial Sequence
<220> FEATURE:
<223> OTHER INFORMATION: WW loop domain corresponding to residues 6-39
     of wt protein
<220> FEATURE:
<221> NAME/KEY: CARBOHYD
<222> LOCATION: (12)..(12)
<223> OTHER INFORMATION: Asn at position 12 is glycosylated

<400> SEQUENCE: 180

```
Lys Leu Pro Pro Gly Trp Glu Lys Arg Met Ser Asn Gly Arg Val Tyr
1               5                   10                  15

Tyr Phe Asn His Ile Thr Asn Ala Ser Gln Phe Glu Arg Pro Ser Gly
            20                  25                  30
```

<210> SEQ ID NO 181

<211> LENGTH: 32
<212> TYPE: PRT
<213> ORGANISM: Artificial Sequence
<220> FEATURE:
<223> OTHER INFORMATION: WW loop domain corresponding to residues 6-39 of wt protein

<400> SEQUENCE: 181

```
Lys Leu Pro Pro Gly Trp Glu Lys Arg Met Phe Asn Gly Arg Val Tyr
1               5                   10                  15
Tyr Phe Asn His Ile Thr Asn Ala Ser Gln Phe Glu Arg Pro Ser Gly
            20                  25                  30
```

<210> SEQ ID NO 182
<211> LENGTH: 32
<212> TYPE: PRT
<213> ORGANISM: Artificial Sequence
<220> FEATURE:
<223> OTHER INFORMATION: WW loop domain corresponding to residues 6-39 of wt protein
<220> FEATURE:
<221> NAME/KEY: CARBOHYD
<222> LOCATION: (12)..(12)
<223> OTHER INFORMATION: Asn at position 12 is glycosylated

<400> SEQUENCE: 182

```
Lys Leu Pro Pro Gly Trp Glu Lys Arg Met Phe Asn Gly Arg Val Tyr
1               5                   10                  15
Tyr Phe Asn His Ile Thr Asn Ala Ser Gln Phe Glu Arg Pro Ser Gly
            20                  25                  30
```

<210> SEQ ID NO 183
<211> LENGTH: 32
<212> TYPE: PRT
<213> ORGANISM: Artificial Sequence
<220> FEATURE:
<223> OTHER INFORMATION: WW loop domain corresponding to residues 6-39 of wt protein

<400> SEQUENCE: 183

```
Lys Leu Pro Pro Gly Trp Glu Lys Arg Met Ser Asn Gly Thr Val Tyr
1               5                   10                  15
Tyr Phe Asn His Ile Thr Asn Ala Ser Gln Phe Glu Arg Pro Ser Gly
            20                  25                  30
```

<210> SEQ ID NO 184
<211> LENGTH: 32
<212> TYPE: PRT
<213> ORGANISM: Artificial Sequence
<220> FEATURE:
<223> OTHER INFORMATION: WW loop domain corresponding to residues 6-39 of wt protein
<220> FEATURE:
<221> NAME/KEY: CARBOHYD
<222> LOCATION: (12)..(12)
<223> OTHER INFORMATION: Asn at position 12 is glycosylated

<400> SEQUENCE: 184

```
Lys Leu Pro Pro Gly Trp Glu Lys Arg Met Ser Asn Gly Thr Val Tyr
1               5                   10                  15
Tyr Phe Asn His Ile Thr Asn Ala Ser Gln Phe Glu Arg Pro Ser Gly
            20                  25                  30
```

<210> SEQ ID NO 185
<211> LENGTH: 32
<212> TYPE: PRT
<213> ORGANISM: Artificial Sequence

```
<220> FEATURE:
<223> OTHER INFORMATION: WW loop domain corresponding to residues 6-39
      of wt protein

<400> SEQUENCE: 185

Lys Leu Pro Pro Gly Trp Glu Lys Arg Met Phe Asn Gly Thr Val Tyr
1               5                   10                  15

Tyr Phe Asn His Ile Thr Asn Ala Ser Gln Phe Glu Arg Pro Ser Gly
                20                  25                  30

<210> SEQ ID NO 186
<211> LENGTH: 32
<212> TYPE: PRT
<213> ORGANISM: Artificial Sequence
<220> FEATURE:
<223> OTHER INFORMATION: WW loop domain corresponding to residues 6-39
      of wt protein
<220> FEATURE:
<221> NAME/KEY: CARBOHYD
<222> LOCATION: (12)..(12)
<223> OTHER INFORMATION: Asn at position 12 is glycosylated

<400> SEQUENCE: 186

Lys Leu Pro Pro Gly Trp Glu Lys Arg Met Phe Asn Gly Thr Val Tyr
1               5                   10                  15

Tyr Phe Asn His Ile Thr Asn Ala Ser Gln Phe Glu Arg Pro Ser Gly
                20                  25                  30

<210> SEQ ID NO 187
<211> LENGTH: 33
<212> TYPE: PRT
<213> ORGANISM: Artificial Sequence
<220> FEATURE:
<223> OTHER INFORMATION: WW loop domain corresponding to residues 6-39
      of wt protein

<400> SEQUENCE: 187

Lys Leu Pro Pro Gly Trp Glu Lys Arg Met Ser Ala Asn Gly Arg Val
1               5                   10                  15

Tyr Tyr Phe Asn His Ile Thr Asn Ala Ser Gln Phe Glu Arg Pro Ser
                20                  25                  30

Gly

<210> SEQ ID NO 188
<211> LENGTH: 33
<212> TYPE: PRT
<213> ORGANISM: Artificial Sequence
<220> FEATURE:
<223> OTHER INFORMATION: WW loop domain corresponding to residues 6-39
      of wt protein
<220> FEATURE:
<221> NAME/KEY: CARBOHYD
<222> LOCATION: (13)..(13)
<223> OTHER INFORMATION: Asn at position 13 is glycosylated

<400> SEQUENCE: 188

Lys Leu Pro Pro Gly Trp Glu Lys Arg Met Ser Ala Asn Gly Arg Val
1               5                   10                  15

Tyr Tyr Phe Asn His Ile Thr Asn Ala Ser Gln Phe Glu Arg Pro Ser
                20                  25                  30

Gly

<210> SEQ ID NO 189
<211> LENGTH: 33
<212> TYPE: PRT
```

```
<213> ORGANISM: Artificial Sequence
<220> FEATURE:
<223> OTHER INFORMATION: WW loop domain corresponding to residues 6-39
      of wt protein

<400> SEQUENCE: 189

Lys Leu Pro Pro Gly Trp Glu Lys Arg Met Phe Ala Asn Gly Arg Val
1               5                   10                  15

Tyr Tyr Phe Asn His Ile Thr Asn Ala Ser Gln Phe Glu Arg Pro Ser
            20                  25                  30

Gly

<210> SEQ ID NO 190
<211> LENGTH: 33
<212> TYPE: PRT
<213> ORGANISM: Artificial Sequence
<220> FEATURE:
<223> OTHER INFORMATION: WW loop domain corresponding to residues 6-39
      of wt protein
<220> FEATURE:
<221> NAME/KEY: CARBOHYD
<222> LOCATION: (13)..(13)
<223> OTHER INFORMATION: Asn at position 13 is glycosylated

<400> SEQUENCE: 190

Lys Leu Pro Pro Gly Trp Glu Lys Arg Met Phe Ala Asn Gly Arg Val
1               5                   10                  15

Tyr Tyr Phe Asn His Ile Thr Asn Ala Ser Gln Phe Glu Arg Pro Ser
            20                  25                  30

Gly

<210> SEQ ID NO 191
<211> LENGTH: 33
<212> TYPE: PRT
<213> ORGANISM: Artificial Sequence
<220> FEATURE:
<223> OTHER INFORMATION: WW loop domain corresponding to residues 6-39
      of wt protein

<400> SEQUENCE: 191

Lys Leu Pro Pro Gly Trp Glu Lys Arg Met Ser Ala Asn Gly Thr Val
1               5                   10                  15

Tyr Tyr Phe Asn His Ile Thr Asn Ala Ser Gln Phe Glu Arg Pro Ser
            20                  25                  30

Gly

<210> SEQ ID NO 192
<211> LENGTH: 33
<212> TYPE: PRT
<213> ORGANISM: Artificial Sequence
<220> FEATURE:
<223> OTHER INFORMATION: WW loop domain corresponding to residues 6-39
      of wt protein
<220> FEATURE:
<221> NAME/KEY: CARBOHYD
<222> LOCATION: (13)..(13)
<223> OTHER INFORMATION: Asn at position 13 is glycosylated

<400> SEQUENCE: 192

Lys Leu Pro Pro Gly Trp Glu Lys Arg Met Ser Ala Asn Gly Thr Val
1               5                   10                  15

Tyr Tyr Phe Asn His Ile Thr Asn Ala Ser Gln Phe Glu Arg Pro Ser
            20                  25                  30

Gly
```

<210> SEQ ID NO 193
<211> LENGTH: 33
<212> TYPE: PRT
<213> ORGANISM: Artificial Sequence
<220> FEATURE:
<223> OTHER INFORMATION: WW loop domain corresponding to residues 6-39
      of wt protein

<400> SEQUENCE: 193

Lys Leu Pro Pro Gly Trp Glu Lys Arg Met Phe Ala Asn Gly Thr Val
1               5                   10                  15

Tyr Tyr Phe Asn His Ile Thr Asn Ala Ser Gln Phe Glu Arg Pro Ser
            20                  25                  30

Gly

<210> SEQ ID NO 194
<211> LENGTH: 33
<212> TYPE: PRT
<213> ORGANISM: Artificial Sequence
<220> FEATURE:
<223> OTHER INFORMATION: WW loop domain corresponding to residues 6-39
      of wt protein
<220> FEATURE:
<221> NAME/KEY: CARBOHYD
<222> LOCATION: (13)..(13)
<223> OTHER INFORMATION: Asn at position 13 is glycosylated

<400> SEQUENCE: 194

Lys Leu Pro Pro Gly Trp Glu Lys Arg Met Phe Ala Asn Gly Thr Val
1               5                   10                  15

Tyr Tyr Phe Asn His Ile Thr Asn Ala Ser Gln Phe Glu Arg Pro Ser
            20                  25                  30

Gly

<210> SEQ ID NO 195
<211> LENGTH: 34
<212> TYPE: PRT
<213> ORGANISM: Artificial Sequence
<220> FEATURE:
<223> OTHER INFORMATION: WW loop domain corresponding to residues 6-39
      of wt protein

<400> SEQUENCE: 195

Lys Leu Pro Pro Gly Trp Glu Lys Arg Met Ser Arg Ser Asn Gly Arg
1               5                   10                  15

Val Tyr Tyr Phe Asn His Ile Thr Asn Ala Ser Gln Phe Glu Arg Pro
            20                  25                  30

Ser Gly

<210> SEQ ID NO 196
<211> LENGTH: 34
<212> TYPE: PRT
<213> ORGANISM: Artificial Sequence
<220> FEATURE:
<223> OTHER INFORMATION: WW loop domain corresponding to residues 6-39
      of wt protein
<220> FEATURE:
<221> NAME/KEY: CARBOHYD
<222> LOCATION: (14)..(14)
<223> OTHER INFORMATION: Asn at position 14 is glycosylated

<400> SEQUENCE: 196

Lys Leu Pro Pro Gly Trp Glu Lys Arg Met Ser Arg Ser Asn Gly Arg
1               5                   10                  15

-continued

Val Tyr Tyr Phe Asn His Ile Thr Asn Ala Ser Gln Phe Glu Arg Pro
            20                  25                  30

Ser Gly

<210> SEQ ID NO 197
<211> LENGTH: 34
<212> TYPE: PRT
<213> ORGANISM: Artificial Sequence
<220> FEATURE:
<223> OTHER INFORMATION: WW loop domain corresponding to residues 6-39
      of wt protein

<400> SEQUENCE: 197

Lys Leu Pro Pro Gly Trp Glu Lys Arg Met Phe Arg Ser Asn Gly Arg
1               5                   10                  15

Val Tyr Tyr Phe Asn His Ile Thr Asn Ala Ser Gln Phe Glu Arg Pro
            20                  25                  30

Ser Gly

<210> SEQ ID NO 198
<211> LENGTH: 34
<212> TYPE: PRT
<213> ORGANISM: Artificial Sequence
<220> FEATURE:
<223> OTHER INFORMATION: WW loop domain corresponding to residues 6-39
      of wt protein
<220> FEATURE:
<221> NAME/KEY: CARBOHYD
<222> LOCATION: (14)..(14)
<223> OTHER INFORMATION: Asn at position 14 is glycosylated

<400> SEQUENCE: 198

Lys Leu Pro Pro Gly Trp Glu Lys Arg Met Phe Arg Ser Asn Gly Arg
1               5                   10                  15

Val Tyr Tyr Phe Asn His Ile Thr Asn Ala Ser Gln Phe Glu Arg Pro
            20                  25                  30

Ser Gly

<210> SEQ ID NO 199
<211> LENGTH: 34
<212> TYPE: PRT
<213> ORGANISM: Artificial Sequence
<220> FEATURE:
<223> OTHER INFORMATION: WW loop domain corresponding to residues 6-39
      of wt protein

<400> SEQUENCE: 199

Lys Leu Pro Pro Gly Trp Glu Lys Arg Met Ser Arg Ser Asn Gly Thr
1               5                   10                  15

Val Tyr Tyr Phe Asn His Ile Thr Asn Ala Ser Gln Phe Glu Arg Pro
            20                  25                  30

Ser Gly

<210> SEQ ID NO 200
<211> LENGTH: 34
<212> TYPE: PRT
<213> ORGANISM: Artificial Sequence
<220> FEATURE:
<223> OTHER INFORMATION: WW loop domain corresponding to residues 6-39
      of wt protein
<220> FEATURE:
<221> NAME/KEY: CARBOHYD
<222> LOCATION: (14)..(14)
<223> OTHER INFORMATION: Asn at position 14 is glycosylated

```
<400> SEQUENCE: 200

Lys Leu Pro Pro Gly Trp Glu Lys Arg Met Ser Arg Ser Asn Gly Thr
1               5                   10                  15

Val Tyr Tyr Phe Asn His Ile Thr Asn Ala Ser Gln Phe Glu Arg Pro
            20                  25                  30

Ser Gly

<210> SEQ ID NO 201
<211> LENGTH: 34
<212> TYPE: PRT
<213> ORGANISM: Artificial Sequence
<220> FEATURE:
<223> OTHER INFORMATION: WW loop domain corresponding to residues 6-39
      of wt protein

<400> SEQUENCE: 201

Lys Leu Pro Pro Gly Trp Glu Lys Arg Met Phe Arg Ser Asn Gly Thr
1               5                   10                  15

Val Tyr Tyr Phe Asn His Ile Thr Asn Ala Ser Gln Phe Glu Arg Pro
            20                  25                  30

Ser Gly

<210> SEQ ID NO 202
<211> LENGTH: 34
<212> TYPE: PRT
<213> ORGANISM: Artificial Sequence
<220> FEATURE:
<223> OTHER INFORMATION: WW loop domain corresponding to residues 6-39
      of wt protein
<220> FEATURE:
<221> NAME/KEY: CARBOHYD
<222> LOCATION: (14)..(14)
<223> OTHER INFORMATION: Asn at position 14 is glycosylated

<400> SEQUENCE: 202

Lys Leu Pro Pro Gly Trp Glu Lys Arg Met Phe Arg Ser Asn Gly Thr
1               5                   10                  15

Val Tyr Tyr Phe Asn His Ile Thr Asn Ala Ser Gln Phe Glu Arg Pro
            20                  25                  30

Ser Gly

<210> SEQ ID NO 203
<211> LENGTH: 128
<212> TYPE: PRT
<213> ORGANISM: Artificial Sequence
<220> FEATURE:
<223> OTHER INFORMATION: Glycosylated version of RnCD2*
<220> FEATURE:
<221> NAME/KEY: PROPEP
<222> LOCATION: (1)..(6)
<223> OTHER INFORMATION: 6x His tag
<220> FEATURE:
<221> NAME/KEY: PROPEP
<222> LOCATION: (7)..(13)
<223> OTHER INFORMATION: Tobacco Etch Virus protease cleavage site
<220> FEATURE:
<221> NAME/KEY: PROPEP
<222> LOCATION: (14)..(22)
<223> OTHER INFORMATION: FLAG-tag
<220> FEATURE:
<221> NAME/KEY: PROPEP
<222> LOCATION: (22)..(25)
<223> OTHER INFORMATION: Factor Xa cleavage site
<220> FEATURE:
<221> NAME/KEY: mat_peptide
<222> LOCATION: (26)..(128)
```

```
<220> FEATURE:
<221> NAME/KEY: CARBOHYD
<222> LOCATION: (88)..(88)
<223> OTHER INFORMATION: Asn at posn 88 is glycosylated

<400> SEQUENCE: 203

His His His His His Glu Asn Leu Tyr Phe Gln Ser Asp Tyr Lys
-25             -20                 -15                 -10

Asp Asp Asp Asp Lys Ile Glu Gly Arg Ala Asp Cys Arg Asp Ser Gly
-5              -1  1                5

Thr Val Trp Gly Ala Leu Gly His Gly Ile Asn Leu Asn Ile Pro Asn
            10                  15                  20

Phe Gln Met Thr Asp Asp Ile Asp Glu Val Arg Trp Glu Arg Gly Ser
        25                  30                  35

Thr Leu Val Ala Glu Phe Lys Arg Lys Met Lys Pro Phe Leu Lys Ser
40                  45                  50                  55

Gly Ala Phe Glu Ile Leu Ala Asn Gly Thr Leu Lys Ile Lys Glu Leu
                60                  65                  70

Thr Arg Asp Asp Ser Gly Thr Tyr Glu Val Thr Val Tyr Ser Thr Asp
                75                  80                  85

Gly Thr Arg Ile Leu Asp Lys Ala Leu Asp Leu Arg Ile Leu Glu Met
                90                  95                  100

<210> SEQ ID NO 204
<211> LENGTH: 34
<212> TYPE: PRT
<213> ORGANISM: Artificial Sequence
<220> FEATURE:
<223> OTHER INFORMATION: WW loop domain corresponding to residues 6-39
      of wt Pin1 protein

<400> SEQUENCE: 204

Lys Leu Pro Pro Gly Trp Glu Lys Arg Met Ser Arg Ser Asn Gly Arg
1               5                   10                  15

Val Tyr Tyr Phe Asn His Ile Thr Asn Ala Ser Gln Phe Glu Arg Pro
            20                  25                  30

Ser Gly

<210> SEQ ID NO 205
<211> LENGTH: 34
<212> TYPE: PRT
<213> ORGANISM: Artificial Sequence
<220> FEATURE:
<223> OTHER INFORMATION: WW loop domain corresponding to residues 6-39
      of wt Pin1 protein, glycosylated at N19 (position 14)
<220> FEATURE:
<221> NAME/KEY: CARBOHYD
<222> LOCATION: (14)..(14)
<223> OTHER INFORMATION: Asn 14 is glycosylated

<400> SEQUENCE: 205

Lys Leu Pro Pro Gly Trp Glu Lys Arg Met Ser Arg Ser Asn Gly Arg
1               5                   10                  15

Val Tyr Tyr Phe Asn His Ile Thr Asn Ala Ser Gln Phe Glu Arg Pro
            20                  25                  30

Ser Gly

<210> SEQ ID NO 206
<211> LENGTH: 443
<212> TYPE: PRT
<213> ORGANISM: Mus musculus
<300> PUBLICATION INFORMATION:
```

<308> DATABASE ACCESSION NUMBER: drugbank/DB00078
<309> DATABASE ENTRY DATE: 2006-06-13
<313> RELEVANT RESIDUES IN SEQ ID NO: (1)..(443)

<400> SEQUENCE: 206

```
Gln Ala Tyr Leu Gln Gln Ser Gly Ala Glu Leu Val Arg Pro Gly Ala
1               5                   10                  15

Ser Val Lys Met Ser Cys Lys Ala Ser Gly Tyr Thr Phe Thr Ser Tyr
                20                  25                  30

Asn Met His Trp Val Lys Gln Thr Pro Arg Gln Gly Leu Glu Trp Ile
            35                  40                  45

Gly Ala Ile Tyr Pro Gly Asn Gly Asp Thr Ser Tyr Asn Gln Lys Phe
        50                  55                  60

Lys Gly Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Val Val Tyr Tyr Ser Asn Ser Tyr Trp Tyr Phe Asp Val Trp
            100                 105                 110

Gly Thr Gly Thr Thr Val Thr Val Ser Ala Pro Ser Val Tyr Pro Leu
        115                 120                 125

Ala Pro Val Cys Gly Asp Thr Thr Gly Ser Ser Val Thr Leu Gly Cys
    130                 135                 140

Leu Val Lys Gly Tyr Phe Pro Glu Pro Val Thr Leu Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Thr Ser Ser Thr Trp
            180                 185                 190

Pro Ser Gln Ser Ile Thr Cys Asn Val Ala His Pro Ala Ser Ser Thr
        195                 200                 205

Lys Val Asp Lys Lys Ile Glu Pro Arg Gly Pro Thr Ile Lys Pro Cys
    210                 215                 220

Pro Pro Cys Lys Cys Pro Ala Pro Asn Leu Leu Gly Gly Pro Ser Val
225                 230                 235                 240

Phe Ile Phe Pro Pro Lys Ile Lys Asp Val Leu Met Ile Ser Leu Ser
                245                 250                 255

Pro Ile Val Thr Cys Val Val Asp Val Ser Glu Asp Asp Pro Asp
            260                 265                 270

Val Gln Ile Ser Trp Phe Val Asn Asn Val Glu Val His Thr Ala Gln
        275                 280                 285

Thr Gln Thr His Arg Glu Asp Tyr Asn Ser Thr Leu Arg Val Val Ser
    290                 295                 300

Ala Leu Pro Ile Gln His Gln Asp Trp Met Ser Gly Lys Glu Phe Lys
305                 310                 315                 320

Cys Lys Val Asn Asn Lys Asp Leu Pro Ala Pro Ile Glu Arg Thr Ile
                325                 330                 335

Ser Lys Pro Lys Gly Ser Val Arg Ala Pro Gln Val Tyr Val Leu Pro
            340                 345                 350

Pro Pro Glu Glu Glu Met Thr Lys Lys Gln Val Thr Leu Thr Cys Met
        355                 360                 365

Val Thr Asp Phe Met Pro Glu Asp Ile Tyr Val Glu Trp Thr Asn Asn
    370                 375                 380

Gly Lys Thr Glu Leu Asn Tyr Lys Asn Thr Glu Pro Val Leu Asp Ser
```

```
                385                 390                 395                 400
Asp Gly Ser Tyr Phe Met Tyr Ser Lys Leu Arg Val Glu Lys Lys Asn
                        405                 410                 415

Trp Val Glu Arg Asn Ser Tyr Ser Cys Ser Val Val His Glu Gly Leu
                        420                 425                 430

His Asn His His Thr Thr Lys Ser Phe Ser Arg
                        435                 440

<210> SEQ ID NO 207
<211> LENGTH: 443
<212> TYPE: PRT
<213> ORGANISM: Mus musculus
<300> PUBLICATION INFORMATION:
<308> DATABASE ACCESSION NUMBER: PDB/DOI:10.2210/pdb1igt/pdb
<309> DATABASE ENTRY DATE: 1996-10-25
<313> RELEVANT RESIDUES IN SEQ ID NO: (1)..(443)
<300> PUBLICATION INFORMATION:
<308> DATABASE ACCESSION NUMBER: drugbank/DB00078
<309> DATABASE ENTRY DATE: 2006-06-13
<313> RELEVANT RESIDUES IN SEQ ID NO: (1)..(443)

<400> SEQUENCE: 207

Gln Ala Tyr Leu Gln Gln Ser Gly Ala Glu Leu Val Arg Pro Gly Ala
1               5                   10                  15

Ser Val Lys Met Ser Cys Lys Ala Ser Gly Tyr Thr Phe Thr Ser Tyr
                20                  25                  30

Asn Met His Trp Val Lys Gln Thr Pro Arg Gln Gly Leu Glu Trp Ile
                35                  40                  45

Gly Ala Ile Tyr Pro Gly Asn Gly Asp Thr Ser Tyr Asn Gln Lys Phe
            50                  55                  60

Lys Gly Lys Ala Thr Leu Thr Val Asp Lys Ser Ser Ser Thr Ala Tyr
65              70                  75                  80

Met Gln Leu Ser Ser Leu Thr Ser Glu Asp Ser Ala Val Tyr Phe Cys
                85                  90                  95

Ala Arg Val Val Tyr Tyr Ser Asn Ser Tyr Trp Tyr Phe Asp Val Trp
                100                 105                 110

Gly Thr Gly Thr Thr Val Thr Val Ser Ala Pro Ser Val Tyr Pro Leu
            115                 120                 125

Ala Pro Val Cys Gly Asp Thr Thr Gly Ser Ser Val Thr Leu Gly Cys
        130                 135                 140

Leu Val Lys Gly Tyr Phe Pro Glu Pro Val Thr Leu Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Thr Ser Ser Thr Trp
            180                 185                 190

Pro Ser Gln Ser Ile Thr Cys Asn Val Ala His Pro Ala Ser Ser Thr
        195                 200                 205

Lys Val Asp Lys Lys Ile Glu Pro Arg Gly Pro Thr Ile Lys Pro Cys
        210                 215                 220

Pro Pro Cys Lys Cys Pro Ala Pro Asn Leu Leu Gly Gly Pro Ser Val
225                 230                 235                 240

Phe Ile Phe Pro Pro Lys Ile Lys Asp Val Leu Met Ile Ser Leu Ser
                245                 250                 255

Pro Ile Val Thr Cys Val Val Val Asp Val Ser Glu Asp Asp Pro Asp
            260                 265                 270

Val Gln Ile Ser Trp Phe Val Asn Asn Val Glu Val His Thr Ala Gln
```

```
                275                 280                 285
Thr Gln Thr His Arg Glu Asp Tyr Asn Ser Thr Leu Arg Val Val Ser
    290                 295                 300
Ala Leu Pro Ile Gln His Gln Asp Trp Met Ser Gly Lys Glu Phe Lys
305                 310                 315                 320
Cys Lys Val Asn Asn Lys Asp Leu Pro Ala Pro Ile Glu Arg Thr Ile
                325                 330                 335
Ser Lys Pro Lys Gly Ser Val Arg Ala Pro Gln Val Tyr Val Leu Pro
                340                 345                 350
Pro Pro Glu Glu Glu Met Thr Lys Lys Gln Val Thr Leu Thr Cys Met
                355                 360                 365
Val Thr Asp Phe Met Pro Glu Asp Ile Tyr Val Glu Trp Thr Asn Asn
    370                 375                 380
Gly Lys Thr Glu Leu Asn Tyr Lys Asn Thr Glu Pro Val Leu Asp Ser
385                 390                 395                 400
Asp Gly Ser Tyr Phe Met Tyr Ser Lys Leu Arg Val Glu Lys Lys Asn
                405                 410                 415
Trp Val Glu Arg Asn Ser Tyr Ser Cys Ser Val Val His Glu Gly Leu
                420                 425                 430
His Asn His His Thr Thr Lys Ser Phe Ser Arg
                435                 440

<210> SEQ ID NO 208
<211> LENGTH: 209
<212> TYPE: PRT
<213> ORGANISM: Mus musculus
<300> PUBLICATION INFORMATION:
<308> DATABASE ACCESSION NUMBER: PDB/1IGT
<309> DATABASE ENTRY DATE: 1996-10-25
<313> RELEVANT RESIDUES IN SEQ ID NO: (1)..(209)
<300> PUBLICATION INFORMATION:
<308> DATABASE ACCESSION NUMBER: drugbank/DB00078
<309> DATABASE ENTRY DATE: 2005-06-13
<313> RELEVANT RESIDUES IN SEQ ID NO: (1)..(209)

<400> SEQUENCE: 208

Gln Ile Val Leu Ser Gln Ser Pro Ala Ile Leu Ser Ala Ser Pro Gly
1               5                   10                  15
Glu Lys Val Thr Met Thr Cys Arg Ala Ser Ser Ser Val Ser Tyr Met
                20                  25                  30
His Trp Tyr Gln Gln Lys Pro Gly Ser Ser Pro Lys Pro Trp Ile Tyr
            35                  40                  45
Ala Pro Ser Asn Leu Ala Ser Gly Val Pro Ala Arg Phe Ser Gly Ser
    50                  55                  60
Gly Ser Gly Thr Ser Tyr Ser Leu Thr Ile Ser Arg Val Glu Ala Glu
65                  70                  75                  80
Asp Ala Ala Thr Tyr Tyr Cys Gln Gln Trp Ser Phe Asn Pro Pro Thr
                85                  90                  95
Phe Gly Ala Gly Thr Lys Leu Glu Leu Lys Arg Ala Asp Ala Ala Pro
                100                 105                 110
Thr Val Phe Ile Phe Pro Pro Ser Asp Glu Gln Leu Lys Ser Gly Thr
                115                 120                 125
Ala Ser Val Val Cys Leu Leu Asn Asn Phe Tyr Pro Arg Glu Ala Lys
                130                 135                 140
Val Gln Trp Lys Val Asp Asn Ala Leu Gln Ser Gly Asn Ser Gln Glu
145                 150                 155                 160
Ser Val Thr Glu Gln Asp Ser Lys Asp Ser Thr Tyr Ser Leu Ser Ser
```

165                 170                 175
Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
            195                 200                 205

Asn

<210> SEQ ID NO 209
<211> LENGTH: 209
<212> TYPE: PRT
<213> ORGANISM: Mus musculus
<300> PUBLICATION INFORMATION:
<308> DATABASE ACCESSION NUMBER: PDB/1IGT
<309> DATABASE ENTRY DATE: 1996-10-25
<313> RELEVANT RESIDUES IN SEQ ID NO: (1)..(209)
<300> PUBLICATION INFORMATION:
<308> DATABASE ACCESSION NUMBER: drugbank/DB00078
<309> DATABASE ENTRY DATE: 2005-06-13
<313> RELEVANT RESIDUES IN SEQ ID NO: (1)..(209)

<400> SEQUENCE: 209

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
            20                  25                  30

His Trp Tyr Gln Gln Lys Pro Gly Ser Ser Pro Lys Pro Trp Ile Tyr
        35                  40                  45

Ala Pro Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Phe Asn Pro Pro Thr
                85                  90                  95

Phe Gly Ala Gly Thr Lys Leu Glu Leu Lys Arg Ala Asp Ala Ala Pro
            100                 105                 110

Thr Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn

<210> SEQ ID NO 210
<211> LENGTH: 644
<212> TYPE: PRT
<213> ORGANISM: Homo sapiens
<300> PUBLICATION INFORMATION:
<308> DATABASE ACCESSION NUMBER: PDB/1IGT
<309> DATABASE ENTRY DATE: 1996-10-25
<313> RELEVANT RESIDUES IN SEQ ID NO: (1)..(644)
<300> PUBLICATION INFORMATION:
<308> DATABASE ACCESSION NUMBER: drugbank/DB00028
<309> DATABASE ENTRY DATE: 2005-06-13

<313> RELEVANT RESIDUES IN SEQ ID NO: (1)..(644)

<400> SEQUENCE: 210

```
Pro Ser Ala Leu Thr Gln Pro Ser Ala Ser Gly Ser Leu Gly Gln
1               5                   10                  15

Ser Val Thr Ile Ser Cys Thr Gly Thr Ser Ser Asp Val Gly Gly Tyr
                20                  25                  30

Asn Tyr Val Ser Trp Tyr Gln Gln His Ala Gly Lys Ala Pro Lys Val
                35                  40                  45

Ile Ile Tyr Glu Val Asn Lys Arg Pro Ser Gly Val Pro Asp Arg Phe
        50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Glu Gly Ser
                85                  90                  95

Asp Asn Phe Val Phe Gly Thr Gly Thr Lys Val Thr Val Leu Gly Gln
                100                 105                 110

Pro Lys Ala Asn Pro Thr Val Thr Leu Phe Pro Pro Ser Ser Glu Glu
            115                 120                 125

Leu Gln Ala Asn Lys Ala Thr Glu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
                180                 185                 190

Arg Ser Tyr Ser Cys Gln Val Thr His Glu Gly Ser Thr Val Glu Lys
            195                 200                 205

Thr Val Ala Pro Thr Glu Cys Ser Pro Leu Val Leu Gln Glu Ser Gly
    210                 215                 220

Pro Gly Leu Val Lys Pro Ser Glu Ala Leu Ser Leu Thr Cys Thr Val
225                 230                 235                 240

Ser Gly Asp Ser Ile Asn Thr Ile Leu Tyr Tyr Trp Ser Trp Ile Arg
                245                 250                 255

Gln Pro Pro Gly Lys Gly Leu Glu Trp Ile Gly Tyr Ile Tyr Tyr Ser
            260                 265                 270

Gly Ser Thr Tyr Gly Asn Pro Ser Leu Lys Ser Arg Val Thr Ile Ser
            275                 280                 285

Val Asn Thr Ser Lys Asn Gln Phe Tyr Ser Lys Leu Ser Ser Val Thr
290                 295                 300

Ala Ala Asp Thr Ala Val Tyr Tyr Cys Ala Arg Val Pro Leu Val Val
305                 310                 315                 320

Asn Pro Trp Gly Gln Gly Thr Leu Val Thr Val Ser Ser Ala Ser Thr
                325                 330                 335

Lys Gly Pro Ser Val Phe Pro Leu Ala Pro Ser Ser Lys Ser Thr Ser
            340                 345                 350

Gly Gly Thr Ala Ala Leu Gly Cys Leu Val Lys Asp Tyr Phe Pro Gln
        355                 360                 365

Pro Val Thr Val Ser Trp Asn Ser Gly Ala Leu Thr Ser Gly Val His
    370                 375                 380

Thr Phe Pro Ala Val Leu Gln Ser Ser Gly Leu Tyr Ser Leu Ser Ser
385                 390                 395                 400
```

```
Val Val Thr Val Pro Ser Ser Leu Gly Thr Gln Thr Tyr Ile Cys
            405                 410                 415

Asn Val Asn His Lys Pro Ser Asn Thr Lys Val Asp Lys Arg Val Ala
            420                 425                 430

Pro Glu Leu Leu Gly Gly Pro Ser Val Phe Leu Phe Pro Pro Lys Pro
            435                 440                 445

Lys Asp Thr Leu Met Ile Ser Arg Thr Pro Glu Val Thr Cys Val Val
            450                 455                 460

Val Asp Val Ser His Glu Asp Pro Gln Val Lys Phe Asn Trp Tyr Val
465                 470                 475                 480

Asp Gly Val Gln Val His Asn Ala Lys Thr Lys Pro Arg Glu Gln Gln
                485                 490                 495

Tyr Asn Ser Thr Tyr Arg Val Val Ser Val Leu Thr Val Leu His Gln
                500                 505                 510

Asn Trp Leu Asp Gly Lys Glu Tyr Lys Cys Lys Val Ser Asn Lys Ala
            515                 520                 525

Leu Pro Ala Pro Ile Glu Lys Thr Ile Ser Lys Ala Lys Gly Gln Pro
            530                 535                 540

Arg Glu Pro Gln Val Tyr Thr Leu Pro Pro Ser Arg Glu Glu Met Thr
545                 550                 555                 560

Lys Asn Gln Val Ser Leu Thr Cys Leu Val Lys Gly Phe Tyr Pro Ser
                565                 570                 575

Asp Ile Ala Val Glu Trp Glu Ser Asn Gly Gln Pro Glu Asn Asn Tyr
            580                 585                 590

Lys Thr Thr Pro Pro Val Leu Asp Ser Asp Gly Ser Phe Phe Leu Tyr
            595                 600                 605

Ser Lys Leu Thr Val Asp Lys Ser Arg Trp Gln Gln Gly Asn Val Phe
            610                 615                 620

Ser Cys Ser Val Met His Glu Ala Leu His Asn His Tyr Thr Gln Lys
625                 630                 635                 640

Ser Leu Ser Leu

<210> SEQ ID NO 211
<211> LENGTH: 676
<212> TYPE: PRT
<213> ORGANISM: Homo sapiens
<300> PUBLICATION INFORMATION:
<308> DATABASE ACCESSION NUMBER: PDB/1IGT
<309> DATABASE ENTRY DATE: 1996-10-25
<313> RELEVANT RESIDUES IN SEQ ID NO: (1)..(675)
<300> PUBLICATION INFORMATION:
<308> DATABASE ACCESSION NUMBER: drugbank/DB00028
<309> DATABASE ENTRY DATE: 2005-06-13
<313> RELEVANT RESIDUES IN SEQ ID NO: (1)..(675)

<400> SEQUENCE: 211

Glu Leu Val Met Thr Gln Ser Pro Ser Ser Leu Ser Ala Ser Val Gly
1               5                   10                  15

Asp Arg Val Asn Ile Ala Cys Arg Ala Ser Gln Gly Ile Ser Ser Ala
                20                  25                  30

Leu Ala Trp Tyr Gln Gln Lys Pro Gly Lys Ala Pro Arg Leu Leu Ile
            35                  40                  45

Tyr Asp Ala Ser Asn Leu Glu Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Ile Tyr Tyr Cys Gln Gln Phe Asn Ser Tyr Pro Leu
```

```
                 85                  90                  95
Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gln Val Lys Leu Leu Glu Gln Ser Gly Ala
    210                 215                 220

Glu Val Lys Lys Pro Gly Ala Ser Val Lys Val Ser Cys Lys Ala Ser
225                 230                 235                 240

Gly Tyr Ser Phe Thr Ser Tyr Gly Leu His Trp Val Arg Gln Ala Pro
                245                 250                 255

Gly Gln Arg Leu Glu Trp Met Gly Trp Ile Ser Ala Gly Thr Gly Asn
            260                 265                 270

Thr Lys Tyr Ser Gln Lys Phe Arg Gly Arg Val Thr Phe Thr Arg Asp
        275                 280                 285

Thr Ser Ala Thr Thr Ala Tyr Met Gly Leu Ser Ser Leu Arg Pro Glu
    290                 295                 300

Asp Thr Ala Val Tyr Tyr Cys Ala Arg Asp Pro Tyr Gly Gly Gly Lys
305                 310                 315                 320

Ser Glu Phe Asp Tyr Trp Gly Gln Gly Thr Leu Val Thr Val Ser Ser
                325                 330                 335

Ala Ser Pro Thr Ser Pro Lys Val Phe Pro Leu Ser Leu Asp Ser Thr
            340                 345                 350

Pro Gln Asp Gly Asn Val Val Val Ala Cys Leu Val Gln Gly Phe Phe
        355                 360                 365

Pro Gln Glu Pro Leu Ser Val Thr Trp Ser Glu Ser Gly Gln Asn Val
    370                 375                 380

Thr Ala Arg Asn Phe Pro Pro Ser Gln Asp Ala Ser Gly Asp Leu Tyr
385                 390                 395                 400

Thr Thr Ser Ser Gln Leu Thr Leu Pro Ala Thr Gln Cys Pro Asp Gly
                405                 410                 415

Lys Ser Val Thr Cys His Val Lys His Tyr Thr Asn Pro Ser Gln Asp
            420                 425                 430

Val Thr Val Pro Cys Pro Val Pro Pro Pro Pro Cys Cys His Pro
        435                 440                 445

Arg Leu Ser Leu His Arg Pro Ala Leu Glu Asp Leu Leu Leu Gly Ser
    450                 455                 460

Glu Ala Asn Leu Thr Cys Thr Leu Thr Gly Leu Arg Asp Ala Ser Gly
465                 470                 475                 480

Ala Thr Phe Thr Trp Thr Pro Ser Ser Gly Lys Ser Ala Val Gln Gly
                485                 490                 495

Pro Pro Glu Arg Asp Leu Cys Gly Cys Tyr Ser Val Ser Ser Val Leu
            500                 505                 510
```

-continued

```
Pro Gly Cys Ala Gln Pro Trp Asn His Gly Glu Thr Phe Thr Cys Thr
        515                 520                 525

Ala Ala His Pro Glu Leu Lys Thr Pro Leu Thr Ala Asn Ile Thr Lys
    530                 535                 540

Ser Gly Asn Thr Phe Arg Pro Glu Val His Leu Leu Pro Pro Pro Ser
545                 550                 555                 560

Glu Glu Leu Ala Leu Asn Glu Leu Val Thr Leu Thr Cys Leu Ala Arg
                565                 570                 575

Gly Phe Ser Pro Lys Asp Val Leu Val Arg Trp Leu Gln Gly Ser Gln
                580                 585                 590

Glu Leu Pro Arg Glu Lys Tyr Leu Thr Trp Ala Ser Arg Gln Glu Pro
                595                 600                 605

Ser Gln Gly Thr Thr Thr Phe Ala Val Thr Ser Ile Leu Arg Val Ala
            610                 615                 620

Ala Glu Asp Trp Lys Lys Gly Asp Thr Phe Ser Cys Met Val Gly His
625                 630                 635                 640

Glu Ala Leu Pro Leu Ala Phe Thr Gln Lys Thr Ile Asp Arg Leu Ala
                645                 650                 655

Gly Lys Pro Thr His Val Asn Val Ser Val Val Met Ala Glu Val Asp
                660                 665                 670

Gly Thr Cys Tyr
            675

<210> SEQ ID NO 212
<211> LENGTH: 467
<212> TYPE: PRT
<213> ORGANISM: Artificial Sequence
<220> FEATURE:
<223> OTHER INFORMATION: Dimeric fusion protein consisting of the
      extracellular ligand-binding portion of the human 75 kilodalton
      (p75) tumor necrosis factor receptor (TNFR) linked to the Fc
      portion of human IgG1
<300> PUBLICATION INFORMATION:
<308> DATABASE ACCESSION NUMBER: drugbank/DB00005
<309> DATABASE ENTRY DATE: 2005-06-13
<313> RELEVANT RESIDUES IN SEQ ID NO: (1)..(467)

<400> SEQUENCE: 212

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
                20                  25                  30

Ser Lys Cys Ser Pro Gly Gln His Ala Lys Val Phe Cys Thr Lys Thr
            35                  40                  45

Ser Asp Thr Val Cys Asp Ser Cys Glu Asp Ser Thr Tyr Thr Gln Leu
50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
                100                 105                 110

Arg Leu Cys Ala Pro Leu Arg Lys Cys Arg Pro Gly Phe Gly Val Ala
            115                 120                 125

Arg Pro Gly Thr Glu Thr Ser Asp Val Val Cys Lys Pro Cys Ala Pro
        130                 135                 140

Gly Thr Phe Ser Asn Thr Thr Ser Ser Thr Asp Ile Cys Arg Pro His
```

```
                   145                 150                 155                 160
        Gln Ile Cys Asn Val Val Ala Ile Pro Gly Asn Ala Ser Met Asp Ala
                        165                 170                 175

Val Cys Thr Ser Thr Ser Pro Thr Arg Ser Met Ala Pro Gly Ala Val
                        180                 185                 190

His Leu Pro Gln Pro Val Ser Thr Arg Ser Gln His Thr Gln Pro Thr
                        195                 200                 205

Pro Glu Pro Ser Thr Ala Pro Ser Thr Ser Phe Leu Leu Pro Met Gly
        210                 215                 220

Pro Ser Pro Pro Ala Glu Gly Ser Thr Gly Asp Glu Pro Lys Ser Cys
        225                 230                 235                 240

Asp Lys Thr His Thr Cys Pro Pro Cys Pro Ala Pro Glu Leu Leu Gly
                        245                 250                 255

Gly Pro Ser Val Phe Leu Phe Pro Pro Lys Pro Lys Asp Thr Leu Met
                        260                 265                 270

Ile Ser Arg Thr Pro Glu Val Thr Cys Val Val Val Asp Val Ser His
                        275                 280                 285

Glu Asp Pro Gln Val Lys Phe Asn Trp Tyr Val Asp Gly Val Gln Val
        290                 295                 300

His Asn Ala Lys Thr Lys Pro Arg Glu Gln Gln Tyr Asn Ser Thr Tyr
        305                 310                 315                 320

Arg Val Val Ser Val Leu Thr Val Leu His Gln Asn Trp Leu Asp Gly
                        325                 330                 335

Lys Glu Tyr Lys Cys Lys Val Ser Asn Lys Ala Leu Pro Ala Pro Ile
                        340                 345                 350

Glu Lys Thr Ile Ser Lys Ala Lys Gly Gln Pro Arg Glu Pro Gln Val
                        355                 360                 365

Tyr Thr Leu Pro Pro Ser Arg Glu Glu Met Thr Lys Asn Gln Val Ser
                        370                 375                 380

Leu Thr Cys Leu Val Lys Gly Phe Tyr Pro Ser Asp Ile Ala Val Glu
        385                 390                 395                 400

Trp Glu Ser Asn Gly Gln Pro Glu Asn Asn Tyr Lys Thr Thr Pro Pro
                        405                 410                 415

Val Leu Asp Ser Asp Gly Ser Phe Phe Leu Tyr Ser Lys Leu Thr Val
                        420                 425                 430

Asp Lys Ser Arg Trp Gln Gln Gly Asn Val Phe Ser Cys Ser Val Met
                        435                 440                 445

His Glu Ala Leu His Asn His Tyr Thr Gln Lys Ser Leu Ser Leu Ser
        450                 455                 460

Pro Gly Lys
        465

<210> SEQ ID NO 213
<211> LENGTH: 451
<212> TYPE: PRT
<213> ORGANISM: Artificial Sequence
<220> FEATURE:
<223> OTHER INFORMATION: Humanized monoclonal antibody specific to
      lymphocyte antigens.
<300> PUBLICATION INFORMATION:
<308> DATABASE ACCESSION NUMBER: drugbank/DB00087
<309> DATABASE ENTRY DATE: 2005-06-13
<313> RELEVANT RESIDUES IN SEQ ID NO: (1)..(451)

<400> SEQUENCE: 213

Gln Val Gln Leu Gln Glu Ser Gly Pro Gly Leu Val Arg Pro Ser Gln
1               5                   10                  15
```

-continued

```
Thr Leu Ser Leu Thr Cys Thr Val Ser Gly Phe Thr Phe Thr Asp Phe
             20                  25                  30

Tyr Met Asn Trp Val Arg Gln Pro Gly Arg Gly Leu Glu Trp Ile
         35                  40                  45

Gly Phe Ile Arg Asp Lys Ala Lys Gly Tyr Thr Thr Glu Tyr Asn Pro
 50                  55                  60

Ser Val Lys Gly Arg Val Thr Met Leu Val Asp Thr Ser Lys Asn Gln
 65                  70                  75                  80

Phe Ser Leu Arg Leu Ser Ser Val Thr Ala Ala Asp Thr Ala Val Tyr
                 85                  90                  95

Tyr Cys Ala Arg Glu Gly His Thr Ala Ala Pro Phe Asp Tyr Trp Gly
            100                 105                 110

Gln Gly Ser Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430
```

His Glu Ala Leu His Asn His Tyr Thr Gln Lys Ser Leu Ser Leu Ser
            435                 440                 445

Pro Gly Lys
    450

<210> SEQ ID NO 214
<211> LENGTH: 451
<212> TYPE: PRT
<213> ORGANISM: Artificial Sequence
<220> FEATURE:
<223> OTHER INFORMATION: Humanized monoclonal antibody specific to
      lymphocyte antigens.
<300> PUBLICATION INFORMATION:
<308> DATABASE ACCESSION NUMBER: drugbank/DB00087
<309> DATABASE ENTRY DATE: 2005-06-13
<313> RELEVANT RESIDUES IN SEQ ID NO: (1)..(451)

<400> SEQUENCE: 214

Gln Val Gln Leu Gln Glu Ser Gly Pro Gly Leu Val Arg Pro Ser Gln
1               5                   10                  15

Thr Leu Ser Leu Thr Cys Thr Val Ser Gly Phe Thr Phe Thr Asp Phe
            20                  25                  30

Tyr Met Asn Trp Val Arg Gln Pro Pro Gly Arg Gly Leu Glu Trp Ile
        35                  40                  45

Gly Phe Ile Arg Asp Lys Ala Lys Gly Tyr Thr Thr Glu Tyr Asn Pro
    50                  55                  60

Ser Val Lys Gly Arg Val Thr Met Leu Val Asp Thr Ser Lys Asn Gln
65                  70                  75                  80

Phe Ser Leu Arg Leu Ser Ser Val Thr Ala Ala Asp Thr Ala Val Tyr
                85                  90                  95

Tyr Cys Ala Arg Glu Gly His Thr Ala Ala Pro Phe Asp Tyr Trp Gly
            100                 105                 110

Gln Gly Ser Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly

```
305                 310                 315                 320
Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 215
<211> LENGTH: 211
<212> TYPE: PRT
<213> ORGANISM: Artificial Sequence
<220> FEATURE:
<223> OTHER INFORMATION: Humanized monoclonal antibody specific to
      lymphocyte antigens.
<300> PUBLICATION INFORMATION:
<308> DATABASE ACCESSION NUMBER: drugbank/DB00087
<309> DATABASE ENTRY DATE: 2005-06-13
<313> RELEVANT RESIDUES IN SEQ ID NO: (1)..(211)

<400> SEQUENCE: 215

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asp Lys Tyr
            20                  25                  30

Leu Asn Trp Tyr Gln Gln Lys Pro Gly Lys Ala Pro Lys Leu Leu Ile
        35                  40                  45

Tyr Asn Thr Asn Asn Leu Gln Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln His Ile Ser Arg Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

```
Ala Cys Glu Val Thr His Gln Gly Leu Ser Ser Pro Val Thr Lys Ser
        195                 200                 205

Phe Asn Arg
    210
```

<210> SEQ ID NO 216
<211> LENGTH: 211
<212> TYPE: PRT
<213> ORGANISM: Artificial Sequence
<220> FEATURE:
<223> OTHER INFORMATION: Humanized monoclonal antibody specific to
      lymphocyte antigens.
<300> PUBLICATION INFORMATION:
<308> DATABASE ACCESSION NUMBER: drugbank/DB00087
<309> DATABASE ENTRY DATE: 2005-06-13
<313> RELEVANT RESIDUES IN SEQ ID NO: (1)..(211)

<400> SEQUENCE: 216

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asp Lys Tyr
            20                  25                  30

Leu Asn Trp Tyr Gln Gln Lys Pro Gly Lys Ala Pro Lys Leu Leu Ile
        35                  40                  45

Tyr Asn Thr Asn Asn Leu Gln Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln His Ile Ser Arg Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg
    210
```

<210> SEQ ID NO 217
<211> LENGTH: 213
<212> TYPE: PRT
<213> ORGANISM: Mus musculus
<300> PUBLICATION INFORMATION:
<308> DATABASE ACCESSION NUMBER: drugbank/DB00113
<309> DATABASE ENTRY DATE: 2005-06-13
<313> RELEVANT RESIDUES IN SEQ ID NO: (1)..(213)

<400> SEQUENCE: 217

```
Gln Thr Val Leu Ser Gln Ser Pro Ala Ile Leu Ser Ala Ser Pro Gly
1               5                   10                  15
```

Glu Lys Val Thr Met Thr Cys Arg Ala Ser Ser Ser Val Thr Tyr Ile
                20                  25                  30

His Trp Tyr Gln Gln Lys Pro Gly Ser Ser Pro Lys Ser Trp Ile Tyr
            35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln His Trp Ser Ser Lys Pro Pro Thr
                85                  90                  95

Phe Gly Gly Gly Thr Lys Leu Glu Ile Lys Arg Ala Asp Ala Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210

<210> SEQ ID NO 218
<211> LENGTH: 213
<212> TYPE: PRT
<213> ORGANISM: Mus musculus
<300> PUBLICATION INFORMATION:
<308> DATABASE ACCESSION NUMBER: drugbase/DB00113
<309> DATABASE ENTRY DATE: 2005-06-13
<313> RELEVANT RESIDUES IN SEQ ID NO: (1)..(213)

<400> SEQUENCE: 218

Gln Thr Val Leu Ser Gln Ser Pro Ala Ile Leu Ser Ala Ser Pro Gly
1               5                   10                  15

Glu Lys Val Thr Met Thr Cys Arg Ala Ser Ser Ser Val Thr Tyr Ile
                20                  25                  30

His Trp Tyr Gln Gln Lys Pro Gly Ser Ser Pro Lys Ser Trp Ile Tyr
            35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln His Trp Ser Ser Lys Pro Pro Thr
                85                  90                  95

Phe Gly Gly Gly Thr Lys Leu Glu Ile Lys Arg Ala Asp Ala Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn

```
             145                 150                 155                 160
Ser Trp Thr Asp Gln Asp Ser Lys Asp Ser Thr Tyr Ser Met Ser Ser
                    165                 170                 175

Thr Leu Thr Leu Thr Lys Asp Glu Tyr Glu Arg His Asn Ser Tyr Thr
                180                 185                 190

Cys Glu Ala Thr His Lys Thr Ser Thr Ser Pro Ile Val Lys Ser Phe
                195                 200                 205

Asn Arg Asn Glu Cys
            210

<210> SEQ ID NO 219
<211> LENGTH: 442
<212> TYPE: PRT
<213> ORGANISM: Mus musculus
<300> PUBLICATION INFORMATION:
<308> DATABASE ACCESSION NUMBER: drugbank/DB00113
<309> DATABASE ENTRY DATE: 2005-06-13
<313> RELEVANT RESIDUES IN SEQ ID NO: (1)..(442)

<400> SEQUENCE: 219

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
                20                  25                  30

Tyr Met Asn Trp Val Arg Gln Pro Pro Gly Lys Ala Leu Glu Trp Leu
            35                  40                  45

Gly Phe Ile Gly Asn Lys Ala Asn Gly Tyr Thr Thr Glu Tyr Ser Ala
        50                  55                  60

Ser Val Lys Gly Arg Phe Thr Ile Ser Arg Asp Lys Ser Gln Ser Ile
65                  70                  75                  80

Leu Tyr Leu Gln Met Asn Thr Leu Arg Ala Glu Asp Ser Ala Thr Tyr
                85                  90                  95

Tyr Cys Thr Arg Asp Arg Gly Leu Arg Phe Tyr Phe Asp Tyr Trp Gly
            100                 105                 110

Gln Gly Thr Thr Leu Thr Val Ser Ser Ala Lys Thr Thr Pro Pro Ser
        115                 120                 125

Val Tyr Pro Leu Ala Pro Gly Ser Ala Ala Gln Thr Asn Ser Met Val
    130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Pro
            180                 185                 190

Ser Ser Pro Arg Pro Ser Glu Thr Val Thr Cys Asn Val Ala His Pro
        195                 200                 205

Ala Ser Ser Thr Lys Val Asp Lys Lys Ile Val Pro Arg Asp Cys Pro
    210                 215                 220

Pro Cys Lys Cys Pro Ala Pro Asn Leu Leu Gly Gly Pro Ser Val Phe
225                 230                 235                 240

Ile Phe Pro Pro Lys Ile Lys Asp Val Leu Met Ile Ser Leu Ser Pro
                245                 250                 255

Ile Val Thr Cys Val Val Val Asp Val Ser Glu Asp Asp Pro Asp Val
            260                 265                 270

Gln Ile Ser Trp Phe Val Asn Asn Val Glu Val His Thr Ala Gln Thr
        275                 280                 285
```

```
Gln Thr His Arg Glu Asp Tyr Asn Ser Thr Leu Arg Val Val Ser Ala
    290                 295                 300

Leu Pro Ile Gln His Gln Asp Trp Met Ser Gly Lys Glu Phe Lys Cys
305                 310                 315                 320

Lys Val Asn Asn Lys Asp Leu Pro Ala Pro Ile Glu Arg Thr Ile Ser
                325                 330                 335

Lys Pro Lys Gly Ser Val Arg Ala Pro Gln Val Tyr Val Leu Pro Pro
                340                 345                 350

Pro Glu Glu Glu Met Thr Lys Lys Gln Val Thr Leu Thr Cys Met Val
                355                 360                 365

Thr Asp Phe Met Pro Glu Asp Ile Tyr Val Glu Trp Thr Asn Asn Gly
                370                 375                 380

Lys Thr Glu Leu Asn Tyr Lys Asn Thr Glu Pro Val Leu Asp Ser Asp
385                 390                 395                 400

Gly Ser Tyr Phe Met Tyr Ser Lys Leu Arg Val Glu Lys Lys Asn Trp
                405                 410                 415

Val Glu Arg Asn Ser Tyr Ser Cys Ser Val Val His Glu Gly Leu His
                420                 425                 430

Asn His His Thr Thr Lys Ser Phe Ser Arg
                435                 440

<210> SEQ ID NO 220
<211> LENGTH: 442
<212> TYPE: PRT
<213> ORGANISM: Mus musculus
<300> PUBLICATION INFORMATION:
<308> DATABASE ACCESSION NUMBER: drugbank/DB00113
<309> DATABASE ENTRY DATE: 2005-06-13
<313> RELEVANT RESIDUES IN SEQ ID NO: (1)..(442)

<400> SEQUENCE: 220

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
                20                  25                  30

Tyr Met Asn Trp Val Arg Gln Pro Pro Gly Lys Ala Leu Glu Trp Leu
                35                  40                  45

Gly Phe Ile Gly Asn Lys Ala Asn Gly Tyr Thr Thr Glu Tyr Ser Ala
        50                  55                  60

Ser Val Lys Gly Arg Phe Thr Ile Ser Arg Asp Lys Ser Gln Ser Ile
65                  70                  75                  80

Leu Tyr Leu Gln Met Asn Thr Leu Arg Ala Glu Asp Ser Ala Thr Tyr
                85                  90                  95

Tyr Cys Thr Arg Asp Arg Gly Leu Arg Phe Tyr Phe Asp Tyr Trp Gly
                100                 105                 110

Gln Gly Thr Thr Leu Thr Val Ser Ser Ala Lys Thr Thr Pro Pro Ser
            115                 120                 125

Val Tyr Pro Leu Ala Pro Gly Ser Ala Ala Gln Thr Asn Ser Met Val
            130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Pro
                180                 185                 190
```

-continued

```
Ser Ser Pro Arg Pro Ser Glu Thr Val Thr Cys Asn Val Ala His Pro
            195                 200                 205

Ala Ser Ser Thr Lys Val Asp Lys Lys Ile Val Pro Arg Asp Cys Pro
    210                 215                 220

Pro Cys Lys Cys Pro Ala Pro Asn Leu Leu Gly Gly Pro Ser Val Phe
225                 230                 235                 240

Ile Phe Pro Pro Lys Ile Lys Asp Val Leu Met Ile Ser Leu Ser Pro
                245                 250                 255

Ile Val Thr Cys Val Val Val Asp Val Ser Glu Asp Asp Pro Asp Val
            260                 265                 270

Gln Ile Ser Trp Phe Val Asn Asn Val Glu Val His Thr Ala Gln Thr
    275                 280                 285

Gln Thr His Arg Glu Asp Tyr Asn Ser Thr Leu Arg Val Val Ser Ala
290                 295                 300

Leu Pro Ile Gln His Gln Asp Trp Met Ser Gly Lys Glu Phe Lys Cys
305                 310                 315                 320

Lys Val Asn Asn Lys Asp Leu Pro Ala Pro Ile Glu Arg Thr Ile Ser
                325                 330                 335

Lys Pro Lys Gly Ser Val Arg Ala Pro Gln Val Tyr Val Leu Pro Pro
            340                 345                 350

Pro Glu Glu Glu Met Thr Lys Lys Gln Val Thr Leu Thr Cys Met Val
    355                 360                 365

Thr Asp Phe Met Pro Glu Asp Ile Tyr Val Glu Trp Thr Asn Asn Gly
370                 375                 380

Lys Thr Glu Leu Asn Tyr Lys Asn Thr Glu Pro Val Leu Asp Ser Asp
385                 390                 395                 400

Gly Ser Tyr Phe Met Tyr Ser Lys Leu Arg Val Glu Lys Lys Asn Trp
                405                 410                 415

Val Glu Arg Asn Ser Tyr Ser Cys Ser Val Val His Glu Gly Leu His
            420                 425                 430

Asn His His Thr Thr Lys Ser Phe Ser Arg
            435                 440

<210> SEQ ID NO 221
<211> LENGTH: 398
<212> TYPE: PRT
<213> ORGANISM: Homo sapiens
<300> PUBLICATION INFORMATION:
<308> DATABASE ACCESSION NUMBER: drugbank/DB00103
<309> DATABASE ENTRY DATE: 2005-06-13
<313> RELEVANT RESIDUES IN SEQ ID NO: (1)..(398)

<400> SEQUENCE: 221

Leu Asp Asn Gly Leu Ala Arg Thr Pro Thr Met Gly Trp Leu His Trp
1               5                   10                  15

Glu Arg Phe Met Cys Asn Leu Asp Cys Gln Glu Glu Pro Asp Ser Cys
            20                  25                  30

Ile Ser Glu Lys Leu Phe Met Glu Met Ala Glu Leu Met Val Ser Glu
        35                  40                  45

Gly Trp Lys Asp Ala Gly Tyr Glu Tyr Leu Cys Ile Asp Asp Cys Trp
    50                  55                  60

Met Ala Pro Gln Arg Asp Ser Glu Gly Arg Leu Gln Ala Asp Pro Gln
65                  70                  75                  80

Arg Phe Pro His Gly Ile Arg Gln Leu Ala Asn Tyr Val His Ser Lys
                85                  90                  95

Gly Leu Lys Leu Gly Ile Tyr Ala Asp Val Gly Asn Lys Thr Cys Ala
```

```
                100             105             110
Gly Phe Pro Gly Ser Phe Gly Tyr Tyr Asp Ile Asp Ala Gln Thr Phe
            115                 120                 125

Ala Asp Trp Gly Val Asp Leu Leu Lys Phe Asp Gly Cys Tyr Cys Asp
130                 135                 140

Ser Leu Glu Asn Leu Ala Asp Gly Tyr Lys His Met Ser Leu Ala Leu
145                 150                 155                 160

Asn Arg Thr Gly Arg Ser Ile Val Tyr Ser Cys Glu Trp Pro Leu Tyr
                165                 170                 175

Met Trp Pro Phe Gln Lys Pro Asn Tyr Thr Glu Ile Arg Gln Tyr Cys
            180                 185                 190

Asn His Trp Arg Asn Phe Ala Asp Ile Asp Asp Ser Trp Lys Ser Ile
        195                 200                 205

Lys Ser Ile Leu Asp Trp Thr Ser Phe Asn Gln Glu Arg Ile Val Asp
210                 215                 220

Val Ala Gly Pro Gly Gly Trp Asn Asp Pro Asp Met Leu Val Ile Gly
225                 230                 235                 240

Asn Phe Gly Leu Ser Trp Asn Gln Gln Val Thr Gln Met Ala Leu Trp
                245                 250                 255

Ala Ile Met Ala Ala Pro Leu Phe Met Ser Asn Asp Leu Arg His Ile
            260                 265                 270

Ser Pro Gln Ala Lys Ala Leu Leu Gln Asp Lys Asp Val Ile Ala Ile
        275                 280                 285

Asn Gln Asp Pro Leu Gly Lys Gln Gly Tyr Gln Leu Arg Gln Gly Asp
290                 295                 300

Asn Phe Glu Val Trp Glu Arg Pro Leu Ser Gly Leu Ala Trp Ala Val
305                 310                 315                 320

Ala Met Ile Asn Arg Gln Glu Ile Gly Gly Pro Arg Ser Tyr Thr Ile
                325                 330                 335

Ala Val Ala Ser Leu Gly Lys Gly Val Ala Cys Asn Pro Ala Cys Phe
            340                 345                 350

Ile Thr Gln Leu Leu Pro Val Lys Arg Lys Leu Gly Phe Tyr Glu Trp
        355                 360                 365

Thr Ser Arg Leu Arg Ser His Ile Asn Pro Thr Gly Thr Val Leu Leu
370                 375                 380

Gln Leu Glu Asn Thr Met Gln Met Ser Leu Lys Asp Leu Leu
385                 390                 395

<210> SEQ ID NO 222
<211> LENGTH: 585
<212> TYPE: PRT
<213> ORGANISM: Homo sapiens
<300> PUBLICATION INFORMATION:
<308> DATABASE ACCESSION NUMBER: drugbank/DB00064
<309> DATABASE ENTRY DATE: 2005-06-13
<313> RELEVANT RESIDUES IN SEQ ID NO: (1)..(585)
<300> PUBLICATION INFORMATION:
<308> DATABASE ACCESSION NUMBER: pdb/1HA2
<309> DATABASE ENTRY DATE: 2001-03-23
<313> RELEVANT RESIDUES IN SEQ ID NO: (1)..(585)

<400> SEQUENCE: 222

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
```

```
            35                  40                  45
Phe Ala Lys Thr Cys Val Ala Asp Glu Ser Ala Glu Asn Cys Asp Lys
 50                  55                  60
Ser Leu His Thr Leu Phe Gly Asp Lys Leu Cys Thr Val Ala Thr Leu
 65                      70                  75                  80
Arg Glu Thr Tyr Gly Glu Met Ala Asp Cys Cys Ala Lys Gln Glu Pro
                 85                  90                  95
Glu Arg Asn Glu Cys Phe Leu Gln His Lys Asp Asp Asn Pro Asn Leu
            100                 105                 110
Pro Arg Leu Val Arg Pro Glu Val Asp Val Met Cys Thr Ala Phe His
        115                 120                 125
Asp Asn Glu Glu Thr Phe Leu Lys Lys Tyr Leu Tyr Glu Ile Ala Arg
    130                 135                 140
Arg His Pro Tyr Phe Tyr Ala Pro Glu Leu Leu Phe Phe Ala Lys Arg
145                 150                 155                 160
Tyr Lys Ala Ala Phe Thr Glu Cys Cys Gln Ala Ala Asp Lys Ala Ala
                165                 170                 175
Cys Leu Leu Pro Lys Leu Asp Glu Leu Arg Asp Glu Gly Lys Ala Ser
            180                 185                 190
Ser Ala Lys Gln Arg Leu Lys Cys Ala Ser Leu Gln Lys Phe Gly Glu
        195                 200                 205
Arg Ala Phe Lys Ala Trp Ala Val Ala Arg Leu Ser Gln Arg Phe Pro
    210                 215                 220
Lys Ala Glu Phe Ala Glu Val Ser Lys Leu Val Thr Asp Leu Thr Lys
225                 230                 235                 240
Val His Thr Glu Cys Cys His Gly Asp Leu Leu Glu Cys Ala Asp Asp
                245                 250                 255
Arg Ala Asp Leu Ala Lys Tyr Ile Cys Glu Asn Gln Asp Ser Ile Ser
            260                 265                 270
Ser Lys Leu Lys Glu Cys Cys Glu Lys Pro Leu Leu Glu Lys Ser His
        275                 280                 285
Cys Ile Ala Glu Val Glu Asn Asp Glu Met Pro Ala Asp Leu Pro Ser
    290                 295                 300
Leu Ala Ala Asp Phe Val Glu Ser Lys Asp Val Cys Lys Asn Tyr Ala
305                 310                 315                 320
Glu Ala Lys Asp Val Phe Leu Gly Met Phe Leu Tyr Glu Tyr Ala Arg
                325                 330                 335
Arg His Pro Asp Tyr Ser Val Val Leu Leu Leu Arg Leu Ala Lys Thr
            340                 345                 350
Tyr Glu Thr Thr Leu Glu Lys Cys Cys Ala Ala Ala Asp Pro His Glu
        355                 360                 365
Cys Tyr Ala Lys Val Phe Asp Glu Phe Lys Pro Leu Val Glu Glu Pro
    370                 375                 380
Gln Asn Leu Ile Lys Gln Asn Cys Glu Leu Phe Glu Gln Leu Gly Glu
385                 390                 395                 400
Tyr Lys Phe Gln Asn Ala Leu Leu Val Arg Tyr Thr Lys Lys Val Pro
                405                 410                 415
Gln Val Ser Thr Pro Thr Leu Val Glu Val Ser Arg Asn Leu Gly Lys
            420                 425                 430
Val Gly Ser Lys Cys Cys Lys His Pro Glu Ala Lys Arg Met Pro Cys
        435                 440                 445
Ala Glu Asp Tyr Leu Ser Val Val Leu Asn Gln Leu Cys Val Leu His
    450                 455                 460
```

```
Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
            485                 490                 495

Tyr Val Pro Lys Glu Phe Asn Ala Glu Thr Phe Thr Phe His Ala Asp
        500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
        530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
            565                 570                 575

Ala Ala Ser Gln Ala Ala Leu Gly Leu
            580                 585

<210> SEQ ID NO 223
<211> LENGTH: 447
<212> TYPE: PRT
<213> ORGANISM: Artificial Sequence
<220> FEATURE:
<223> OTHER INFORMATION: humanized IgG1k monoclonal antibody that
      selectively binds to human immunoglobulin E (IgE)
<300> PUBLICATION INFORMATION:
<308> DATABASE ACCESSION NUMBER: drugbank/DB00043
<309> DATABASE ENTRY DATE: 2005-06-13
<313> RELEVANT RESIDUES IN SEQ ID NO: (1)..(447)

<400> SEQUENCE: 223

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Ser Ile Thr Ser Gly
            20                  25                  30

Tyr Ser Trp Asn Trp Ile Arg Gln Ala Pro Gly Lys Gly Leu Glu Trp
        35                  40                  45

Val Ala Ser Ile Thr Tyr Asp Gly Ser Thr Asn Tyr Ala Asp Ser Val
    50                  55                  60

Lys Gly Arg Phe Thr Ile Ser Arg Asp Asp Ser Lys Asn Thr Phe Tyr
65                  70                  75                  80

Leu Gln Met Asn Ser Leu Arg Ala Glu Asp Thr Ala Val Tyr Tyr Cys
            85                  90                  95

Ala Arg Gly Ser His Tyr Phe Gly His Trp His Phe Ala Val Trp Gly
        100                 105                 110

Gln Gly Thr Leu Val Thr Val Ser Ser Gly Pro Ser Val Phe Pro Leu
    115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
        180                 185                 190

Leu Gly Thr Gln Thr Tyr Ile Cys Asn Val Asn His Lys Pro Ser Asn
    195                 200                 205
```

```
Thr Lys Val Asp Lys Lys Ala Glu Pro Lys Ser Cys Asp Lys Thr His
    210                 215                 220
Thr Cys Pro Pro Cys Pro Ala Pro Glu Leu Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
            260                 265                 270
Val Lys Phe Asn Trp Tyr Val Asp Gly Val Glu Val His Asn Ala Lys
        275                 280                 285
Thr Lys Pro Arg Glu Glu Gln Tyr Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Arg Asp Glu Leu Thr Lys Asn Gln Val Ser Leu Thr Cys Leu
        355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Lys
        435                 440                 445

<210> SEQ ID NO 224
<211> LENGTH: 447
<212> TYPE: PRT
<213> ORGANISM: Artificial Sequence
<220> FEATURE:
<223> OTHER INFORMATION: humanized IgG1k monoclonal antibody that
      selectively binds to human immunoglobulin E (IgE)
<300> PUBLICATION INFORMATION:
<308> DATABASE ACCESSION NUMBER: drugbank/DB00043
<309> DATABASE ENTRY DATE: 2005-06-13
<313> RELEVANT RESIDUES IN SEQ ID NO: (1)..(447)

<400> SEQUENCE: 224

Glu Val Gln Leu Val Glu Ser Gly Gly Gly Leu Val Gln Pro Gly Gly
1               5                   10                  15
Ser Leu Arg Leu Ser Cys Ala Val Ser Gly Tyr Ser Ile Thr Ser Gly
            20                  25                  30
Tyr Ser Trp Asn Trp Ile Arg Gln Ala Pro Gly Lys Gly Leu Glu Trp
        35                  40                  45
Val Ala Ser Ile Thr Tyr Asp Gly Ser Thr Asn Tyr Ala Asp Ser Val
    50                  55                  60
Lys Gly Arg Phe Thr Ile Ser Arg Asp Asp Ser Lys Asn Thr Phe Tyr
65                  70                  75                  80
Leu Gln Met Asn Ser Leu Arg Ala Glu Asp Thr Ala Val Tyr Tyr Cys
                85                  90                  95
Ala Arg Gly Ser His Tyr Phe Gly His Trp His Phe Ala Val Trp Gly
```

```
                    100                 105                 110
Gln Gly Thr Leu Val Thr Val Ser Ser Gly Pro Ser Val Phe Pro Leu
                115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Ala Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 225
<211> LENGTH: 215
<212> TYPE: PRT
<213> ORGANISM: Artificial Sequence
<220> FEATURE:
<223> OTHER INFORMATION: humanized IgG1k monoclonal antibody that
      selectively binds to human immunoglobulin E (IgE)
<300> PUBLICATION INFORMATION:
<308> DATABASE ACCESSION NUMBER: drugbank/DB00043
<309> DATABASE ENTRY DATE: 2005-06-13
<313> RELEVANT RESIDUES IN SEQ ID NO: (1)..(215)

<400> SEQUENCE: 225
```

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Asp Tyr Asp
            20                  25                  30

Gly Asp Ser Tyr Met Asn Trp Tyr Gln Gln Lys Pro Gly Lys Ala Pro
        35                  40                  45

Lys Leu Leu Ile Tyr Ala Ala Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser His
                85                  90                  95

Glu Asp Pro Tyr Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg
    210                 215

<210> SEQ ID NO 226
<211> LENGTH: 215
<212> TYPE: PRT
<213> ORGANISM: Artificial Sequence
<220> FEATURE:
<223> OTHER INFORMATION: humanized IgG1k monoclonal antibody that
      selectively binds to human immunoglobulin E (IgE)
<300> PUBLICATION INFORMATION:
<308> DATABASE ACCESSION NUMBER: drugbank/DB00043
<309> DATABASE ENTRY DATE: 2005-06-13
<313> RELEVANT RESIDUES IN SEQ ID NO: (1)..(215)

<400> SEQUENCE: 226

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Asp Tyr Asp
            20                  25                  30

Gly Asp Ser Tyr Met Asn Trp Tyr Gln Gln Lys Pro Gly Lys Ala Pro
        35                  40                  45

Lys Leu Leu Ile Tyr Ala Ala Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser His
                85                  90                  95

Glu Asp Pro Tyr Thr Phe Gly Gln Gly Thr Lys Val Glu Ile Lys Arg
            100                 105                 110

-continued

```
Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg
    210                 215

<210> SEQ ID NO 227
<211> LENGTH: 415
<212> TYPE: PRT
<213> ORGANISM: Homo sapiens
<300> PUBLICATION INFORMATION:
<308> DATABASE ACCESSION NUMBER: drugbank/DB00100
<309> DATABASE ENTRY DATE: 2005-06-13
<313> RELEVANT RESIDUES IN SEQ ID NO: (1)..(415)

<400> SEQUENCE: 227

Tyr Asn Ser Gly Lys Leu Glu Glu Phe Val Gln Gly Asn Leu Glu Arg
1               5                   10                  15

Glu Cys Met Glu Glu Lys Cys Ser Phe Glu Glu Ala Arg Glu Val Phe
            20                  25                  30

Glu Asn Thr Glu Arg Thr Thr Glu Phe Trp Lys Gln Tyr Val Asp Gly
        35                  40                  45

Asp Gln Cys Glu Ser Asn Pro Cys Leu Asn Gly Gly Ser Cys Lys Asp
    50                  55                  60

Asp Ile Asn Ser Tyr Glu Cys Trp Cys Pro Phe Gly Phe Glu Gly Lys
65                  70                  75                  80

Asn Cys Glu Leu Asp Val Thr Cys Asn Ile Lys Asn Gly Arg Cys Glu
                85                  90                  95

Gln Phe Cys Lys Asn Ser Ala Asp Asn Lys Val Val Cys Ser Cys Thr
            100                 105                 110

Glu Gly Tyr Arg Leu Ala Glu Asn Gln Lys Ser Cys Glu Pro Ala Val
        115                 120                 125

Pro Phe Pro Cys Gly Arg Val Ser Val Ser Gln Thr Ser Lys Leu Thr
    130                 135                 140

Arg Ala Glu Ala Val Phe Pro Asp Val Asp Tyr Val Asn Ser Thr Glu
145                 150                 155                 160

Ala Glu Thr Ile Leu Asp Asn Ile Thr Gln Ser Thr Gln Ser Phe Asn
                165                 170                 175

Asp Phe Thr Arg Val Val Gly Gly Glu Asp Ala Lys Pro Gly Gln Phe
            180                 185                 190

Pro Trp Gln Val Val Leu Asn Gly Lys Val Asp Ala Phe Cys Gly Gly
        195                 200                 205

Ser Ile Val Asn Glu Lys Trp Ile Val Thr Ala Ala His Cys Val Glu
    210                 215                 220

Thr Gly Val Lys Ile Thr Val Val Ala Gly Glu His Asn Ile Glu Glu
225                 230                 235                 240

Thr Glu His Thr Glu Gln Lys Arg Asn Val Ile Arg Ile Ile Pro His
```

```
                        245                 250                 255

His Asn Tyr Asn Ala Ala Ile Asn Lys Tyr Asn His Asp Ile Ala Leu
                260                 265                 270

Leu Glu Leu Asp Glu Pro Leu Val Leu Asn Ser Tyr Val Thr Pro Ile
            275                 280                 285

Cys Ile Ala Asp Lys Glu Tyr Thr Asn Ile Phe Leu Lys Phe Gly Ser
        290                 295                 300

Gly Tyr Val Ser Gly Trp Gly Arg Val Phe His Lys Gly Arg Ser Ala
305                 310                 315                 320

Leu Val Leu Gln Tyr Leu Arg Val Pro Leu Val Asp Arg Ala Thr Cys
                325                 330                 335

Leu Arg Ser Thr Lys Phe Thr Ile Tyr Asn Asn Met Phe Cys Ala Gly
                340                 345                 350

Phe His Glu Gly Gly Arg Asp Ser Cys Gln Gly Asp Ser Gly Gly Pro
            355                 360                 365

His Val Thr Glu Val Glu Gly Thr Ser Phe Leu Thr Gly Ile Ile Ser
        370                 375                 380

Trp Gly Glu Glu Cys Ala Met Lys Gly Lys Tyr Gly Ile Tyr Thr Lys
385                 390                 395                 400

Val Ser Arg Tyr Val Asn Trp Ile Lys Glu Lys Thr Lys Leu Thr
                405                 410                 415

<210> SEQ ID NO 228
<211> LENGTH: 21
<212> TYPE: PRT
<213> ORGANISM: Homo sapiens
<300> PUBLICATION INFORMATION:
<308> DATABASE ACCESSION NUMBER: drugbase/DB00046
<309> DATABASE ENTRY DATE: 2005-06-13
<313> RELEVANT RESIDUES IN SEQ ID NO: (1)..(21)

<400> SEQUENCE: 228

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 229
<211> LENGTH: 30
<212> TYPE: PRT
<213> ORGANISM: Homo sapiens
<300> PUBLICATION INFORMATION:
<308> DATABASE ACCESSION NUMBER: drugbank/DB00046
<309> DATABASE ENTRY DATE: 2005-06-13
<313> RELEVANT RESIDUES IN SEQ ID NO: (1)..(30)

<400> SEQUENCE: 229

Phe Val Asn Gln His Leu Cys Gly Ser His Leu Val Glu Ala Leu Tyr
1               5                   10                  15

Leu Val Cys Gly Glu Arg Gly Phe Phe Tyr Thr Lys Pro Thr
            20                  25                  30

<210> SEQ ID NO 230
<211> LENGTH: 497
<212> TYPE: PRT
<213> ORGANISM: Homo sapiens
<300> PUBLICATION INFORMATION:
<308> DATABASE ACCESSION NUMBER: drugbank/DB00088
<309> DATABASE ENTRY DATE: 2005-06-13
<313> RELEVANT RESIDUES IN SEQ ID NO: (1)..(497)

<400> SEQUENCE: 230
```

```
Ala Arg Pro Cys Ile Pro Lys Ser Phe Gly Tyr Ser Ser Val Val Cys
1               5                   10                  15

Val Cys Asn Ala Thr Tyr Cys Asp Ser Phe Asp Pro Thr Phe Pro
            20                  25                  30

Ala Leu Gly Thr Phe Ser Arg Tyr Glu Ser Thr Arg Ser Gly Arg Arg
                35                  40                  45

Met Glu Leu Ser Met Gly Pro Ile Gln Ala Asn His Thr Gly Thr Gly
50                      55                  60

Leu Leu Leu Thr Leu Gln Pro Glu Gln Lys Phe Gln Lys Val Lys Gly
65                  70                  75                  80

Phe Gly Gly Ala Met Thr Asp Ala Ala Ala Leu Asn Ile Leu Ala Leu
                85                  90                  95

Ser Pro Pro Ala Gln Asn Leu Leu Lys Ser Tyr Phe Ser Glu Glu
            100                 105                 110

Gly Ile Gly Tyr Asn Ile Ile Arg Val Pro Met Ala Ser Cys Asp Phe
        115                 120                 125

Ser Ile Arg Thr Tyr Thr Tyr Ala Asp Thr Pro Asp Asp Phe Gln Leu
    130                 135                 140

His Asn Phe Ser Leu Pro Glu Glu Asp Thr Lys Leu Lys Ile Pro Leu
145                 150                 155                 160

Ile His Arg Ala Leu Gln Leu Ala Gln Arg Pro Val Ser Leu Leu Ala
                165                 170                 175

Ser Pro Trp Thr Ser Pro Thr Trp Leu Lys Thr Asn Gly Ala Val Asn
            180                 185                 190

Gly Lys Gly Ser Leu Lys Gly Gln Pro Gly Asp Ile Tyr His Gln Thr
        195                 200                 205

Trp Ala Arg Tyr Phe Val Lys Phe Leu Asp Ala Tyr Ala Glu His Lys
    210                 215                 220

Leu Gln Phe Trp Ala Val Thr Ala Glu Asn Glu Pro Ser Ala Gly Leu
225                 230                 235                 240

Leu Ser Gly Tyr Pro Phe Gln Cys Leu Gly Phe Thr Pro Glu His Gln
            245                 250                 255

Arg Asp Phe Ile Ala Arg Asp Leu Gly Pro Thr Leu Ala Asn Ser Thr
        260                 265                 270

His His Asn Val Arg Leu Leu Met Leu Asp Asp Gln Arg Leu Leu Leu
    275                 280                 285

Pro His Trp Ala Lys Val Val Leu Thr Asp Pro Glu Ala Ala Lys Tyr
290                 295                 300

Val His Gly Ile Ala Val His Trp Tyr Leu Asp Phe Leu Ala Pro Ala
305                 310                 315                 320

Lys Ala Thr Leu Gly Glu Thr His Arg Leu Phe Pro Asn Thr Met Leu
            325                 330                 335

Phe Ala Ser Glu Ala Cys Val Gly Ser Lys Phe Trp Glu Gln Ser Val
        340                 345                 350

Arg Leu Gly Ser Trp Asp Arg Gly Met Gln Tyr Ser His Ser Ile Ile
    355                 360                 365

Thr Asn Leu Leu Tyr His Val Val Gly Trp Thr Asp Trp Asn Leu Ala
370                 375                 380

Leu Asn Pro Glu Gly Gly Pro Asn Trp Val Arg Asn Phe Val Asp Ser
385                 390                 395                 400

Pro Ile Ile Val Asp Ile Thr Lys Asp Thr Phe Tyr Lys Gln Pro Met
            405                 410                 415
```

```
Phe Tyr His Leu Gly His Phe Ser Lys Phe Ile Pro Glu Gly Ser Gln
            420                 425                 430

Arg Val Gly Leu Val Ala Ser Gln Lys Asn Asp Leu Asp Ala Val Ala
            435                 440                 445

Leu Met His Pro Asp Gly Ser Ala Val Val Val Leu Asn Arg Ser
    450                 455                 460

Ser Lys Asp Val Pro Leu Thr Ile Lys Asp Pro Ala Val Gly Phe Leu
465                 470                 475                 480

Glu Thr Ile Ser Pro Gly Tyr Ser Ile His Thr Tyr Leu Trp Arg Arg
            485                 490                 495

Gln

<210> SEQ ID NO 231
<211> LENGTH: 166
<212> TYPE: PRT
<213> ORGANISM: Homo sapiens
<300> PUBLICATION INFORMATION:
<308> DATABASE ACCESSION NUMBER: drugbank/DB00015
<309> DATABASE ENTRY DATE: 2005-06-13
<313> RELEVANT RESIDUES IN SEQ ID NO: (1)..(166)

<400> SEQUENCE: 231

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 232
<211> LENGTH: 432
<212> TYPE: PRT
<213> ORGANISM: Mus musculus
<300> PUBLICATION INFORMATION:
<308> DATABASE ACCESSION NUMBER: drugbase/DB00057
<309> DATABASE ENTRY DATE: 2005-06-13
<313> RELEVANT RESIDUES IN SEQ ID NO: (1)..(432)

<400> SEQUENCE: 232

Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30
```

```
Ala Ile His Trp Ala Lys Gln Lys Pro Glu Gln Gly Leu Glu Trp Ile
         35                  40                  45
Gly Tyr Ile Ser Pro Gly Asn Asp Ile Lys Tyr Asn Glu Lys Phe
 50                  55                  60
Lys Gly Lys Ala Thr Leu Thr Ala Asp Lys Ser Ser Thr Ala Tyr
 65                  70                  75                  80
Met Gln Leu Asn Ser Leu Thr Ser Glu Asp Ser Ala Val Tyr Phe Cys
             85                  90                  95
Lys Arg Ser Tyr Tyr Gly His Trp Gly Gln Gly Thr Thr Leu Thr Val
                100                 105                 110
Ser Ser Ala Ser Thr Lys Gly Pro Ser Val Phe Pro Leu Ala Pro Cys
            115                 120                 125
Ser Arg Ser Thr Ser Glu Ser Thr Ala Ala Leu Gly Cys Leu Val Lys
        130                 135                 140
Asp Tyr Phe Pro Glu Pro Val Thr Val Ser Trp Asn Ser Gly Ala Leu
145                 150                 155                 160
Thr Ser Gly Val His Thr Phe Pro Ala Val Leu Gln Ser Ser Gly Leu
                165                 170                 175
Tyr Ser Leu Ser Ser Val Val Thr Val Pro Ser Ser Ser Leu Gly Thr
            180                 185                 190
Lys Thr Tyr Thr Cys Asn Val Asp His Lys Pro Ser Asn Thr Lys Val
        195                 200                 205
Asp Lys Arg Val Cys Pro Pro Cys Lys Cys Pro Ala Pro Asn Leu Leu
210                 215                 220
Gly Gly Pro Ser Val Phe Ile Phe Pro Pro Lys Ile Lys Asp Val Leu
225                 230                 235                 240
Met Ile Ser Leu Ser Pro Ile Val Thr Cys Val Val Val Asp Val Ser
                245                 250                 255
Glu Asp Asp Pro Asp Val Gln Ile Ser Trp Phe Val Asn Asn Val Glu
            260                 265                 270
Val His Thr Ala Gln Thr Gln Thr His Arg Glu Asp Tyr Asn Ser Thr
        275                 280                 285
Leu Arg Val Val Ser Ala Leu Pro Ile Gln His Gln Asp Trp Met Ser
290                 295                 300
Gly Lys Glu Phe Lys Cys Lys Val Asn Asn Lys Asp Leu Pro Ala Pro
305                 310                 315                 320
Ile Glu Arg Thr Ile Ser Lys Pro Lys Gly Ser Val Arg Ala Pro Gln
                325                 330                 335
Val Tyr Val Leu Pro Pro Pro Glu Glu Met Thr Lys Lys Gln Val
            340                 345                 350
Thr Leu Thr Cys Met Val Thr Asp Phe Met Pro Glu Asp Ile Tyr Val
        355                 360                 365
Glu Trp Thr Asn Asn Gly Lys Thr Glu Leu Asn Tyr Lys Asn Thr Glu
370                 375                 380
Pro Val Leu Asp Ser Asp Gly Ser Tyr Phe Met Tyr Ser Lys Leu Arg
385                 390                 395                 400
Val Glu Lys Lys Asn Trp Val Glu Arg Asn Ser Tyr Ser Cys Ser Val
                405                 410                 415
Val His Glu Gly Leu His Asn His His Thr Thr Lys Ser Phe Ser Arg
            420                 425                 430

<210> SEQ ID NO 233
<211> LENGTH: 432
```

```
<212> TYPE: PRT
<213> ORGANISM: Mus musculus
<300> PUBLICATION INFORMATION:
<308> DATABASE ACCESSION NUMBER: drugbase/DB00057
<309> DATABASE ENTRY DATE: 2005-06-13
<313> RELEVANT RESIDUES IN SEQ ID NO: (1)..(432)

<400> SEQUENCE: 233

Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
                20                  25                  30

Ala Ile His Trp Ala Lys Gln Lys Pro Glu Gln Gly Leu Glu Trp Ile
            35                  40                  45

Gly Tyr Ile Ser Pro Gly Asn Asp Asp Ile Lys Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Gln Leu Asn Ser Leu Thr Ser Glu Asp Ser Ala Val Tyr Phe Cys
                85                  90                  95

Lys Arg Ser Tyr Tyr Gly His Trp Gly Gln Gly Thr Thr Leu Thr Val
            100                 105                 110

Ser Ser Ala Ser Thr Lys Gly Pro Ser Val Phe Pro Leu Ala Pro Cys
    115                 120                 125

Ser Arg Ser Thr Ser Glu Ser Thr Ala Ala Leu Gly Cys Leu Val Lys
130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Lys Thr Tyr Thr Cys Asn Val Asp His Lys Pro Ser Asn Thr Lys Val
    195                 200                 205

Asp Lys Arg Val Cys Pro Pro Cys Lys Cys Pro Ala Pro Asn Leu Leu
210                 215                 220

Gly Gly Pro Ser Val Phe Ile Phe Pro Pro Lys Ile Lys Asp Val Leu
225                 230                 235                 240

Met Ile Ser Leu Ser Pro Ile Val Thr Cys Val Val Val Asp Val Ser
                245                 250                 255

Glu Asp Asp Pro Asp Val Gln Ile Ser Trp Phe Val Asn Asn Val Glu
            260                 265                 270

Val His Thr Ala Gln Thr Gln Thr His Arg Glu Asp Tyr Asn Ser Thr
    275                 280                 285

Leu Arg Val Val Ser Ala Leu Pro Ile Gln His Gln Asp Trp Met Ser
290                 295                 300

Gly Lys Glu Phe Lys Cys Lys Val Asn Asn Lys Asp Leu Pro Ala Pro
305                 310                 315                 320

Ile Glu Arg Thr Ile Ser Lys Pro Lys Gly Ser Val Arg Ala Pro Gln
                325                 330                 335

Val Tyr Val Leu Pro Pro Pro Glu Glu Glu Met Thr Lys Lys Gln Val
            340                 345                 350

Thr Leu Thr Cys Met Val Thr Asp Phe Met Pro Glu Asp Ile Tyr Val
    355                 360                 365

Glu Trp Thr Asn Asn Gly Lys Thr Glu Leu Asn Tyr Lys Asn Thr Glu
```

```
                370             375             380
Pro Val Leu Asp Ser Asp Gly Ser Tyr Phe Met Tyr Ser Lys Leu Arg
385                 390             395                 400

Val Glu Lys Lys Asn Trp Val Glu Arg Asn Ser Tyr Ser Cys Ser Val
                405             410                 415

Val His Glu Gly Leu His Asn His Thr Thr Lys Ser Phe Ser Arg
            420             425                 430
```

<210> SEQ ID NO 234
<211> LENGTH: 210
<212> TYPE: PRT
<213> ORGANISM: Mus musculus
<300> PUBLICATION INFORMATION:
<308> DATABASE ACCESSION NUMBER: drugbase/DB00057
<309> DATABASE ENTRY DATE: 2005-06-13
<313> RELEVANT RESIDUES IN SEQ ID NO: (1)..(210)

<400> SEQUENCE: 234

```
Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Gln Lys Gln Gly Lys Ser Pro Gln Leu Leu Val
        35                  40                  45

Tyr Ala Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Gly Thr Pro Tyr
                85                  90                  95

Thr Phe Gly Gly Gly Thr Arg Leu Glu Ile Lys Arg Ala Asp Ala Ala
            100                 105                 110

Pro Thr Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn
    210
```

<210> SEQ ID NO 235
<211> LENGTH: 210
<212> TYPE: PRT
<213> ORGANISM: Mus musculus
<300> PUBLICATION INFORMATION:
<308> DATABASE ACCESSION NUMBER: drugbank/DB00057
<309> DATABASE ENTRY DATE: 2005-06-13
<313> RELEVANT RESIDUES IN SEQ ID NO: (1)..(210)

<400> SEQUENCE: 235

```
Asp Ile Gln Met Thr Gln Ser Pro Ala Ser Leu Ser Val Ser Val Gly
1               5                   10                  15
```

```
Glu Thr Val Thr Ile Thr Cys Arg Ala Ser Glu Asn Ile Tyr Ser Asn
         20                  25                  30

Leu Ala Trp Tyr Gln Lys Gln Gly Lys Ser Pro Gln Leu Leu Val
         35                  40                  45

Tyr Ala Ala Thr Asn Leu Ala Asp Gly Val Pro Ser Arg Phe Ser Gly
 50                  55                  60

Ser Gly Ser Gly Thr Gln Tyr Ser Leu Lys Ile Asn Ser Leu Gln Ser
 65                  70                  75                  80

Glu Asp Phe Gly Ser Tyr Tyr Cys Gln His Phe Trp Gly Thr Pro Tyr
                 85                  90                  95

Thr Phe Gly Gly Gly Thr Arg Leu Glu Ile Lys Arg Ala Asp Ala Ala
                100                 105                 110

Pro Thr Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn
    210

<210> SEQ ID NO 236
<211> LENGTH: 257
<212> TYPE: PRT
<213> ORGANISM: Borrelia burgdorferi
<300> PUBLICATION INFORMATION:
<308> DATABASE ACCESSION NUMBER: drugbank/DB00045
<309> DATABASE ENTRY DATE: 2005-06-13
<313> RELEVANT RESIDUES IN SEQ ID NO: (1)..(257)

<400> SEQUENCE: 236

Cys Lys Gln Asn Val Ser Ser Leu Asp Glu Lys Asn Ser Val Ser Val
 1               5                  10                  15

Asp Leu Pro Gly Glu Met Asn Val Leu Val Ser Lys Glu Lys Asn Lys
         20                  25                  30

Asp Gly Lys Tyr Asp Leu Ile Ala Thr Val Asp Lys Leu Glu Leu Lys
         35                  40                  45

Gly Thr Ser Asp Lys Asn Asn Gly Ser Gly Val Leu Glu Gly Val Lys
 50                  55                  60

Ala Asp Lys Ser Lys Val Lys Leu Thr Ile Ser Asp Asp Leu Gly Gln
 65                  70                  75                  80

Thr Thr Leu Glu Val Phe Lys Glu Asp Gly Lys Thr Leu Val Ser Lys
                 85                  90                  95

Lys Val Thr Ser Lys Asp Lys Ser Ser Thr Glu Glu Lys Phe Asn Glu
                100                 105                 110

Lys Gly Glu Val Ser Glu Lys Ile Ile Thr Arg Ala Asp Gly Thr Arg
            115                 120                 125

Leu Glu Tyr Thr Glu Ile Lys Ser Asp Gly Ser Gly Lys Ala Lys Glu
130                 135                 140
```

-continued

```
Val Leu Lys Ser Tyr Val Leu Glu Gly Thr Leu Thr Ala Glu Lys Thr
145                 150                 155                 160

Thr Leu Val Val Lys Glu Gly Thr Val Thr Leu Ser Lys Asn Ile Ser
                165                 170                 175

Lys Ser Gly Glu Val Ser Val Glu Leu Asn Asp Thr Asp Ser Ser Ala
            180                 185                 190

Ala Thr Lys Lys Thr Ala Ala Trp Asn Ser Gly Thr Ser Thr Leu Thr
        195                 200                 205

Ile Thr Val Asn Ser Lys Lys Thr Lys Asp Leu Val Phe Thr Lys Glu
    210                 215                 220

Asn Thr Ile Thr Val Gln Gln Tyr Asp Ser Asn Gly Thr Lys Leu Glu
225                 230                 235                 240

Gly Ser Ala Val Glu Ile Thr Lys Leu Asp Glu Ile Lys Asn Ala Leu
                245                 250                 255

Lys

<210> SEQ ID NO 237
<211> LENGTH: 166
<212> TYPE: PRT
<213> ORGANISM: Homo sapiens
<300> PUBLICATION INFORMATION:
<308> DATABASE ACCESSION NUMBER: drugbank/DB00068
<309> DATABASE ENTRY DATE: 2005-06-13
<313> RELEVANT RESIDUES IN SEQ ID NO: (1)..(166)

<400> SEQUENCE: 237

Met Ser Tyr Asn Leu Leu Gly Phe Leu Gln Arg Ser Ser Asn Phe Gln
1               5                   10                  15

Ser Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 238
<211> LENGTH: 21
<212> TYPE: PRT
<213> ORGANISM: Artificial Sequence
<220> FEATURE:
<223> OTHER INFORMATION: analogue of human insulin made by replacing
      the asparagine residue at position A21 of the A-chain with glycine
      and adding two arginines to the C-terminus (positions B31 and 32)
      of the B-chain.
<300> PUBLICATION INFORMATION:
```

-continued

<308> DATABASE ACCESSION NUMBER: drugbase/DB00047
<309> DATABASE ENTRY DATE: 2005-06-13
<313> RELEVANT RESIDUES IN SEQ ID NO: (1)..(21)

<400> SEQUENCE: 238

Gly Ile Val Glu Gln Cys Cys Thr Ser Ile Cys Ser Leu Tyr Gln Leu
1               5                   10                  15

Glu Asn Tyr Cys Gly
            20

<210> SEQ ID NO 239
<211> LENGTH: 32
<212> TYPE: PRT
<213> ORGANISM: Artificial Sequence
<220> FEATURE:
<223> OTHER INFORMATION: analogue of human insulin made by replacing the
      asparagine residue at position A21 of the A-chain with glycine and
      adding two arginines to the C-terminus (positions B31 and 32) of
      the B-chain.
<300> PUBLICATION INFORMATION:
<308> DATABASE ACCESSION NUMBER: drugbase/DB00047
<309> DATABASE ENTRY DATE: 2005-06-13
<313> RELEVANT RESIDUES IN SEQ ID NO: (1)..(32)

<400> SEQUENCE: 239

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

<210> SEQ ID NO 240
<211> LENGTH: 457
<212> TYPE: PRT
<213> ORGANISM: Artificial Sequence
<220> FEATURE:
<223> OTHER INFORMATION: dimeric fusion protein that consists of the
      extracellular CD2-binding portion of the human leukocyte function
      antigen-3 (LFA-3) linked to the Fc (hinge, CH2 and CH3 domains)
      portion of human IgG1
<300> PUBLICATION INFORMATION:
<308> DATABASE ACCESSION NUMBER: drugbank/DB00092
<309> DATABASE ENTRY DATE: 2005-06-13
<313> RELEVANT RESIDUES IN SEQ ID NO: (1)..(457)

<400> SEQUENCE: 240

Cys Phe Ser Gln Gln Ile Tyr Gly Val Val Tyr Gly Asn Val Thr Phe
1               5                   10                  15

His Val Pro Ser Asn Val Pro Leu Lys Glu Val Leu Trp Lys Lys Gln
            20                  25                  30

Lys Asp Lys Val Ala Glu Leu Glu Asn Ser Glu Phe Arg Ala Phe Ser
        35                  40                  45

Ser Phe Lys Asn Arg Val Tyr Leu Asp Thr Val Ser Gly Ser Leu Thr
    50                  55                  60

Ile Tyr Asn Leu Thr Ser Ser Asp Glu Asp Glu Tyr Glu Met Glu Ser
65                  70                  75                  80

Pro Asn Ile Thr Asp Thr Met Lys Phe Phe Leu Tyr Val Leu Glu Ser
                85                  90                  95

Leu Pro Ser Pro Thr Leu Thr Cys Ala Leu Thr Asn Gly Ser Ile Glu
            100                 105                 110

Val Gln Cys Met Ile Pro Glu His Tyr Asn Ser His Arg Gly Leu Ile
        115                 120                 125

Met Tyr Ser Trp Asp Cys Pro Met Glu Gln Cys Lys Arg Asn Ser Thr
    130                 135                 140

Ser Ile Tyr Phe Lys Met Glu Asn Asp Leu Pro Gln Lys Ile Gln Cys
145                 150                 155                 160

Thr Leu Ser Asn Pro Leu Phe Asn Thr Thr Ser Ser Ile Ile Leu Thr
            165                 170                 175

Thr Cys Ile Pro Ser Ser Gly His Ser Arg His Arg Tyr Ala Leu Ile
        180                 185                 190

Pro Ile Pro Leu Ala Val Ile Thr Thr Cys Ile Val Leu Tyr Met Asn
    195                 200                 205

Gly Ile Leu Lys Cys Asp Arg Lys Pro Asp Arg Thr Asn Ser Asn Arg
210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
            245                 250                 255

Pro Lys Asp Thr Leu Met Ile Ser Arg Thr Pro Glu Val Thr Cys Val
        260                 265                 270

Val Val Asp Val Ser His Glu Asp Pro Gln Val Lys Phe Asn Trp Tyr
    275                 280                 285

Val Asp Gly Val Gln Val His Asn Ala Lys Thr Lys Pro Arg Glu Gln
290                 295                 300

Gln Tyr Asn Ser Thr Tyr Arg Val Val Ser Val Leu Thr Val Leu His
305                 310                 315                 320

Gln Asn Trp Leu Asp Gly Lys Glu Tyr Lys Cys Lys Val Ser Asn Lys
            325                 330                 335

Ala Leu Pro Ala Pro Ile Glu Lys Thr Ile Ser Lys Ala Lys Gly Gln
        340                 345                 350

Pro Arg Glu Pro Gln Val Tyr Thr Leu Pro Pro Ser Arg Glu Glu Met
    355                 360                 365

Thr Lys Asn Gln Val Ser Leu Thr Cys Leu Val Lys Gly Phe Tyr Pro
370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
            405                 410                 415

Tyr Ser Lys Leu Thr Val Asp Lys Ser Arg Trp Gln Gln Gly Asn Val
        420                 425                 430

Phe Ser Cys Ser Val Met His Glu Ala Leu His Asn His Tyr Thr Gln
    435                 440                 445

Lys Ser Leu Ser Leu Ser Pro Gly Lys
450                 455

<210> SEQ ID NO 241
<211> LENGTH: 165
<212> TYPE: PRT
<213> ORGANISM: Homo sapiens
<300> PUBLICATION INFORMATION:
<308> DATABASE ACCESSION NUMBER: drugbank/DB00011
<309> DATABASE ENTRY DATE: 2005-06-13
<313> RELEVANT RESIDUES IN SEQ ID NO: (1)..(165)

<400> SEQUENCE: 241

Cys Asp Leu Pro Gln Thr His Ser Leu Gly Ser Arg Arg Thr Leu Met
1               5                   10                  15

Leu Leu Ala Gln Met Arg Lys Ile Ser Leu Phe Ser Cys Leu Lys Asp
            20                  25                  30

Arg His Asp Phe Gly Phe Pro Gln Glu Glu Phe Gly Asn Gln Phe Gln

```
                35                  40                  45
Lys Ala Glu Thr Ile Pro Val Leu His Glu Met Ile Gln Gln Ile Phe
 50                  55                  60

Asn Leu Phe Ser Thr Lys Asp Ser Ser Ala Ala Trp Asp Glu Thr Leu
 65                  70                  75                  80

Leu Asp Lys Phe Tyr Thr Glu Leu Tyr Gln Gln Leu Asn Asp Leu Glu
                 85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 242
<211> LENGTH: 21
<212> TYPE: PRT
<213> ORGANISM: Homo sapiens
<300> PUBLICATION INFORMATION:
<308> DATABASE ACCESSION NUMBER: drugbase/DB00030
<309> DATABASE ENTRY DATE: 2005-06-13
<313> RELEVANT RESIDUES IN SEQ ID NO: (1)..(21)

<400> SEQUENCE: 242

Gly Ile Val Glu Gln Cys Cys Thr Ser Ile Cys Ser Leu Tyr Gln Leu
 1               5                  10                  15

Glu Asn Tyr Cys Asn
             20

<210> SEQ ID NO 243
<211> LENGTH: 30
<212> TYPE: PRT
<213> ORGANISM: Homo sapiens
<300> PUBLICATION INFORMATION:
<308> DATABASE ACCESSION NUMBER: drugbank/DB00030
<309> DATABASE ENTRY DATE: 2005-06-13
<313> RELEVANT RESIDUES IN SEQ ID NO: (1)..(30)

<400> SEQUENCE: 243

Phe Val Asn Gln His Leu Cys Gly Ser His Leu Val Glu Ala Leu Tyr
 1               5                  10                  15

Leu Val Cys Gly Glu Arg Gly Phe Phe Tyr Thr Pro Lys Thr
            20                  25                  30

<210> SEQ ID NO 244
<211> LENGTH: 303
<212> TYPE: PRT
<213> ORGANISM: Escherichia coli
<300> PUBLICATION INFORMATION:
<308> DATABASE ACCESSION NUMBER: drugbank/DB00023
<309> DATABASE ENTRY DATE: 2005-06-13
<313> RELEVANT RESIDUES IN SEQ ID NO: (1)..(303)

<400> SEQUENCE: 244

Gln Met Ser Leu Gln Gln Glu Leu Arg Tyr Ile Glu Ala Leu Ser Ala
 1               5                  10                  15

Ile Val Glu Thr Gly Gln Lys Met Leu Glu Ala Gly Glu Ser Ala Leu
            20                  25                  30
```

```
Asp Val Val Thr Glu Ala Val Arg Leu Leu Glu Glu Cys Pro Leu Phe
         35                  40                  45

Asn Ala Gly Ile Gly Ala Val Phe Thr Arg Asp Glu Thr His Glu Leu
 50                  55                  60

Asp Ala Cys Val Met Asp Gly Asn Thr Leu Lys Ala Gly Ala Val Ala
 65                  70                  75                  80

Gly Val Ser His Leu Arg Asn Pro Val Leu Ala Ala Arg Leu Val Met
                 85                  90                  95

Glu Gln Ser Pro His Val Met Met Ile Gly Glu Gly Ala Glu Asn Phe
                100                 105                 110

Ala Phe Ala Arg Gly Met Glu Arg Val Ser Pro Glu Ile Phe Ser Thr
                115                 120                 125

Ser Leu Arg Tyr Glu Gln Leu Leu Ala Ala Arg Lys Glu Gly Ala Thr
        130                 135                 140

Val Leu Asp His Ser Gly Ala Pro Leu Asp Glu Lys Gln Lys Met Gly
145                 150                 155                 160

Thr Val Gly Ala Val Ala Leu Asp Leu Asp Gly Asn Leu Ala Ala Ala
                    165                 170                 175

Thr Ser Thr Gly Gly Met Thr Asn Lys Leu Pro Gly Arg Val Gly Asp
                180                 185                 190

Ser Pro Leu Val Gly Ala Gly Cys Tyr Ala Asn Asn Ala Ser Val Ala
            195                 200                 205

Val Ser Cys Thr Gly Thr Gly Glu Val Phe Ile Arg Ala Leu Ala Ala
        210                 215                 220

Tyr Asp Ile Ala Ala Leu Met Asp Tyr Gly Gly Leu Ser Leu Ala Glu
225                 230                 235                 240

Ala Cys Glu Arg Val Val Met Glu Lys Leu Pro Ala Leu Gly Gly Ser
                    245                 250                 255

Gly Gly Leu Ile Ala Ile Asp His Glu Gly Asn Val Ala Leu Pro Phe
                260                 265                 270

Asn Thr Glu Gly Met Tyr Arg Ala Trp Gly Tyr Ala Gly Asp Thr Pro
            275                 280                 285

Thr Thr Gly Ile Tyr Arg Glu Lys Gly Asp Thr Val Ala Thr Gln
        290                 295                 300

<210> SEQ ID NO 245
<211> LENGTH: 92
<212> TYPE: PRT
<213> ORGANISM: Homo sapiens
<300> PUBLICATION INFORMATION:
<308> DATABASE ACCESSION NUMBER: drugbank/DB00024
<309> DATABASE ENTRY DATE: 2005-06-13
<313> RELEVANT RESIDUES IN SEQ ID NO: (1)..(92)

<400> SEQUENCE: 245

Ala Pro Asp Val Gln Asp Cys Pro Glu Cys Thr Leu Gln Glu Asn Pro
 1               5                  10                  15

Phe Phe Ser Gln Pro Gly Ala Pro Ile Leu Gln Cys Met Gly Cys Cys
                20                  25                  30

Phe Ser Arg Ala Tyr Pro Thr Pro Leu Arg Ser Lys Lys Thr Met Leu
            35                  40                  45

Val Gln Lys Asn Val Thr Ser Glu Ser Thr Cys Cys Val Ala Lys Ser
    50                  55                  60

Tyr Asn Arg Val Thr Val Met Gly Gly Phe Lys Val Glu Asn His Thr
65                  70                  75                  80
```

```
Ala Cys His Cys Ser Thr Cys Tyr Tyr His Lys Ser
                85                  90

<210> SEQ ID NO 246
<211> LENGTH: 111
<212> TYPE: PRT
<213> ORGANISM: Homo sapiens
<300> PUBLICATION INFORMATION:
<308> DATABASE ACCESSION NUMBER: drugbank/DB00024
<309> DATABASE ENTRY DATE: 2005-06-13
<313> RELEVANT RESIDUES IN SEQ ID NO: (1)..(111)

<400> SEQUENCE: 246

Asn Ser Cys Glu Leu Thr Asn Ile Thr Ile Ala Ile Glu Lys Glu Glu
1               5                   10                  15

Cys Arg Phe Cys Ile Ser Ile Asn Thr Thr Trp Cys Ala Gly Tyr Cys
                20                  25                  30

Tyr Thr Arg Asp Leu Val Tyr Lys Asp Pro Ala Arg Pro Lys Ile Gln
            35                  40                  45

Lys Thr Cys Thr Phe Lys Glu Leu Val Tyr Glu Thr Val Arg Val Pro
        50                  55                  60

Gly Cys Ala His His Ala Asp Ser Leu Tyr Thr Tyr Pro Val Ala Thr
65                  70                  75                  80

Gln Cys His Cys Gly Lys Cys Asp Ser Asp Ser Thr Asp Cys Thr Val
                85                  90                  95

Arg Gly Leu Gly Pro Ser Tyr Cys Ser Phe Gly Glu Met Lys Glu
            100                 105                 110

<210> SEQ ID NO 247
<211> LENGTH: 191
<212> TYPE: PRT
<213> ORGANISM: Homo sapiens
<300> PUBLICATION INFORMATION:
<308> DATABASE ACCESSION NUMBER: drugbank/DB00082
<309> DATABASE ENTRY DATE: 2005-06-13
<313> RELEVANT RESIDUES IN SEQ ID NO: (1)..(191)

<400> SEQUENCE: 247

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
                20                  25                  30

Glu Ala Tyr Ile Pro Lys Glu Gln Lys Tyr Ser Phe Leu Gln Asn Pro
            35                  40                  45

Gln Thr Ser Leu Cys Phe Ser Glu Ser Ile Pro Thr Pro Ser Asn Arg
        50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
        115                 120                 125

Glu Asp Gly Ser Pro Arg Thr Gly Gln Ile Phe Lys Gln Thr Tyr Ser
    130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
```

-continued

```
                    165                 170                 175

Leu Arg Ile Val Gln Cys Arg Ser Val Glu Gly Ser Cys Gly Phe
                180                 185                 190

<210> SEQ ID NO 248
<211> LENGTH: 276
<212> TYPE: PRT
<213> ORGANISM: Homo sapiens
<300> PUBLICATION INFORMATION:
<308> DATABASE ACCESSION NUMBER: drugbank/DB00013
<309> DATABASE ENTRY DATE: 2005-06-13
<313> RELEVANT RESIDUES IN SEQ ID NO: (1)..(276)

<400> SEQUENCE: 248

Lys Pro Ser Ser Pro Glu Glu Leu Lys Phe Gln Cys Gly Gln Lys
1               5                   10                  15

Thr Leu Arg Pro Arg Phe Lys Ile Ile Gly Gly Glu Phe Thr Thr Ile
            20                  25                  30

Glu Asn Gln Pro Trp Phe Ala Ala Ile Tyr Arg Arg His Arg Gly Gly
        35                  40                  45

Ser Val Thr Tyr Val Cys Gly Gly Ser Leu Met Ser Pro Cys Trp Val
    50                  55                  60

Ile Ser Ala Thr His Cys Phe Ile Asp Tyr Pro Lys Lys Glu Asp Tyr
65                  70                  75                  80

Ile Val Tyr Leu Gly Arg Ser Arg Leu Asn Ser Asn Thr Gln Gly Glu
                85                  90                  95

Met Lys Phe Glu Val Glu Asn Leu Ile Leu His Lys Asp Tyr Ser Ala
            100                 105                 110

Asp Thr Leu Ala His His Asn Asp Ile Ala Leu Leu Lys Ile Arg Ser
        115                 120                 125

Lys Glu Gly Arg Cys Ala Gln Pro Ser Arg Thr Ile Gln Thr Ile Cys
    130                 135                 140

Leu Pro Ser Met Tyr Asn Asp Pro Gln Phe Gly Thr Ser Cys Glu Ile
145                 150                 155                 160

Thr Gly Phe Gly Lys Glu Asn Ser Thr Asp Tyr Leu Tyr Pro Glu Gln
                165                 170                 175

Leu Lys Met Thr Val Val Lys Leu Ile Ser His Arg Glu Cys Gln Gln
            180                 185                 190

Pro His Tyr Tyr Gly Ser Glu Val Thr Thr Lys Met Leu Cys Ala Ala
        195                 200                 205

Asp Pro Gln Trp Lys Thr Asp Ser Cys Gln Gly Asp Ser Gly Gly Pro
    210                 215                 220

Leu Val Cys Ser Leu Gln Gly Arg Met Thr Leu Thr Gly Ile Val Ser
225                 230                 235                 240

Trp Gly Arg Gly Cys Ala Leu Lys Asp Lys Pro Gly Val Tyr Thr Arg
                245                 250                 255

Val Ser His Phe Leu Pro Trp Ile Arg Ser His Thr Lys Glu Glu Asn
            260                 265                 270

Gly Leu Ala Leu
        275

<210> SEQ ID NO 249
<211> LENGTH: 92
<212> TYPE: PRT
<213> ORGANISM: Homo sapiens
<300> PUBLICATION INFORMATION:
<308> DATABASE ACCESSION NUMBER: drugbank/DB00097
<309> DATABASE ENTRY DATE: 2005-06-13
```

<313> RELEVANT RESIDUES IN SEQ ID NO: (1)..(92)

<400> SEQUENCE: 249

Ala Pro Asp Val Gln Asp Cys Pro Glu Cys Thr Leu Gln Glu Asn Pro
1               5                   10                  15

Phe Phe Ser Gln Pro Gly Ala Pro Ile Leu Gln Cys Met Gly Cys Cys
            20                  25                  30

Phe Ser Arg Ala Tyr Pro Thr Pro Leu Arg Ser Lys Lys Thr Met Leu
        35                  40                  45

Val Gln Lys Asn Val Thr Ser Glu Ser Thr Cys Cys Val Ala Lys Ser
    50                  55                  60

Tyr Asn Arg Val Thr Val Met Gly Gly Phe Lys Val Glu Asn His Thr
65                  70                  75                  80

Ala Cys His Cys Ser Thr Cys Tyr Tyr His Lys Ser
                85                  90

<210> SEQ ID NO 250
<211> LENGTH: 145
<212> TYPE: PRT
<213> ORGANISM: Homo sapiens
<300> PUBLICATION INFORMATION:
<308> DATABASE ACCESSION NUMBER: drugbank/DB00097
<309> DATABASE ENTRY DATE: 2005-06-13
<313> RELEVANT RESIDUES IN SEQ ID NO: (1)..(145)

<400> SEQUENCE: 250

Ser Lys Glu Pro Leu Arg Pro Arg Cys Arg Pro Ile Asn Ala Thr Leu
1               5                   10                  15

Ala Val Glu Lys Glu Gly Cys Pro Val Cys Ile Thr Val Asn Thr Thr
            20                  25                  30

Ile Cys Ala Gly Tyr Cys Pro Thr Met Thr Arg Val Leu Gln Gly Val
        35                  40                  45

Leu Pro Ala Leu Pro Gln Val Val Cys Asn Tyr Arg Asp Val Arg Phe
    50                  55                  60

Glu Ser Ile Arg Leu Pro Gly Cys Pro Arg Gly Val Asn Pro Val Val
65                  70                  75                  80

Ser Tyr Ala Val Ala Leu Ser Cys Gln Cys Ala Leu Cys Arg Arg Ser
                85                  90                  95

Thr Thr Asp Cys Gly Gly Pro Lys Asp His Pro Leu Thr Cys Asp Asp
            100                 105                 110

Pro Arg Phe Gln Asp Ser Ser Ser Lys Ala Pro Pro Pro Ser Leu
        115                 120                 125

Pro Ser Pro Ser Arg Leu Pro Gly Pro Ser Asp Thr Pro Ile Leu Pro
    130                 135                 140

Gln
145

<210> SEQ ID NO 251
<211> LENGTH: 442
<212> TYPE: PRT
<213> ORGANISM: Artificial Sequence
<220> FEATURE:
<223> OTHER INFORMATION: Humanized IgG1 Mab that binds to the human
      interleukin-2 receptor
<300> PUBLICATION INFORMATION:
<308> DATABASE ACCESSION NUMBER: drugbank/DB00111
<309> DATABASE ENTRY DATE: 2005-06-13
<313> RELEVANT RESIDUES IN SEQ ID NO: (1)..(442)

<400> SEQUENCE: 251

-continued

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Arg Met His Trp Val Arg Gln Ala Pro Gly Gln Gly Leu Glu Trp Ile
        35                  40                  45

Gly Tyr Ile Asn Pro Ser Thr Gly Tyr Thr Glu Tyr Asn Gln Lys Phe
    50                  55                  60

Lys Asp Lys Ala Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Gly Val Phe Asp Tyr Trp Gly Gln Gly Thr Thr Leu
            100                 105                 110

Thr Val Ser Ser Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
        195                 200                 205

Lys Ala Glu Pro Lys Ser Cys Asp Lys Thr His Thr Cys Pro Pro Cys
210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Asp Glu
            340                 345                 350

Leu Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
```

```
                     420                 425                 430
Gln Lys Ser Leu Ser Leu Ser Pro Gly Lys
        435                 440

<210> SEQ ID NO 252
<211> LENGTH: 442
<212> TYPE: PRT
<213> ORGANISM: Artificial Sequence
<220> FEATURE:
<223> OTHER INFORMATION: Humanized IgG1 Mab that binds to the human
      interleukin-2 receptor
<300> PUBLICATION INFORMATION:
<308> DATABASE ACCESSION NUMBER: drugbank/DB00111
<309> DATABASE ENTRY DATE: 2005-06-13
<313> RELEVANT RESIDUES IN SEQ ID NO: (1)..(442)

<400> SEQUENCE: 252

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Arg Met His Trp Val Arg Gln Ala Pro Gly Gln Gly Leu Glu Trp Ile
        35                  40                  45

Gly Tyr Ile Asn Pro Ser Thr Gly Tyr Thr Glu Tyr Asn Gln Lys Phe
    50                  55                  60

Lys Asp Lys Ala Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Gly Val Phe Asp Tyr Trp Gly Gln Gly Thr Thr Leu
            100                 105                 110

Thr Val Ser Ser Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
        195                 200                 205

Lys Ala Glu Pro Lys Ser Cys Asp Lys Thr His Thr Cys Pro Pro Cys
    210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320
```

```
Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Asp Glu
            340                 345                 350

Leu Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly Lys
        435                 440
```

```
<210> SEQ ID NO 253
<211> LENGTH: 210
<212> TYPE: PRT
<213> ORGANISM: Artificial Sequence
<220> FEATURE:
<223> OTHER INFORMATION: Humanized IgG1 Mab that binds to the human
      interleukin-2 receptor
<300> PUBLICATION INFORMATION:
<308> DATABASE ACCESSION NUMBER: drugbank/DB00111
<309> DATABASE ENTRY DATE: 2005-06-13
<313> RELEVANT RESIDUES IN SEQ ID NO: (1)..(210)

<400> SEQUENCE: 253

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Ser Ile Ser Tyr Met
            20                  25                  30

His Trp Tyr Gln Gln Lys Pro Gly Lys Ala Pro Lys Leu Leu Ile Tyr
        35                  40                  45

Thr Thr Ser Asn Leu Ala Ser Gly Val Pro Ala Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys His Gln Arg Ser Thr Tyr Pro Leu Thr
                85                  90                  95

Phe Gly Ser Gly Thr Lys Val Glu Val Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205
```

Asn Arg
    210

<210> SEQ ID NO 254
<211> LENGTH: 210
<212> TYPE: PRT
<213> ORGANISM: Artificial Sequence
<220> FEATURE:
<223> OTHER INFORMATION: Humanized IgG1 Mab that binds to the human
      interleukin-2 receptor
<300> PUBLICATION INFORMATION:
<308> DATABASE ACCESSION NUMBER: drugbank/DB00111
<309> DATABASE ENTRY DATE: 2005-06-13
<313> RELEVANT RESIDUES IN SEQ ID NO: (1)..(210)

<400> SEQUENCE: 254

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Ser Ile Ser Tyr Met
            20                  25                  30

His Trp Tyr Gln Gln Lys Pro Gly Lys Ala Pro Lys Leu Leu Ile Tyr
        35                  40                  45

Thr Thr Ser Asn Leu Ala Ser Gly Val Pro Ala Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys His Gln Arg Ser Thr Tyr Pro Leu Thr
                85                  90                  95

Phe Gly Ser Gly Thr Lys Val Glu Val Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg
    210

<210> SEQ ID NO 255
<211> LENGTH: 165
<212> TYPE: PRT
<213> ORGANISM: Homo sapiens
<300> PUBLICATION INFORMATION:
<308> DATABASE ACCESSION NUMBER: drugbank/DB00034
<309> DATABASE ENTRY DATE: 2005-06-15
<313> RELEVANT RESIDUES IN SEQ ID NO: (1)..(165)

<400> SEQUENCE: 255

Cys Asp Leu Pro Gln Thr His Ser Leu Gly Ser Arg Arg Thr Leu Met
1               5                   10                  15

Leu Leu Ala Gln Met Arg Lys Ile Ser Leu Phe Ser Cys Leu Lys Asp
            20                  25                  30

Arg His Asp Phe Gly Phe Pro Gln Glu Glu Phe Gly Asn Gln Phe Gln

```
                35                  40                  45
Lys Ala Glu Thr Ile Pro Val Leu His Glu Met Ile Gln Gln Ile Phe
 50                  55                  60
Asn Leu Phe Ser Thr Lys Asp Ser Ser Ala Ala Trp Asp Glu Thr Leu
 65                  70                  75                  80
Leu Asp Lys Phe Tyr Thr Glu Leu Tyr Gln Gln Leu Asn Asp Leu Glu
                 85                  90                  95
Ala Cys Val Ile Gln Gly Val Gly Val Thr Glu Thr Pro Leu Met Lys
            100                 105                 110
Glu Asp Ser Ile Leu Ala Val Arg Lys Tyr Phe Gln Arg Ile Thr Leu
        115                 120                 125
Tyr Leu Lys Glu Lys Lys Tyr Ser Pro Cys Ala Trp Glu Val Val Arg
    130                 135                 140
Ala Glu Ile Met Arg Ser Phe Ser Leu Ser Thr Asn Leu Gln Glu Ser
145                 150                 155                 160
Leu Arg Ser Lys Glu
                165

<210> SEQ ID NO 256
<211> LENGTH: 585
<212> TYPE: PRT
<213> ORGANISM: Homo sapiens
<300> PUBLICATION INFORMATION:
<308> DATABASE ACCESSION NUMBER: drugbank/DB00096
<309> DATABASE ENTRY DATE: 2005-06-13
<313> RELEVANT RESIDUES IN SEQ ID NO: (1)..(585)

<400> SEQUENCE: 256

Asp Ala His Lys Ser Glu Val Ala His Arg Phe Lys Asp Leu Gly Glu
 1               5                  10                  15
Glu Asn Phe Lys Ala Leu Val Leu Ile Ala Phe Ala Gln Tyr Leu Gln
                 20                  25                  30
Gln Cys Pro Phe Glu Asp His Val Lys Leu Val Asn Glu Val Thr Glu
             35                  40                  45
Phe Ala Lys Thr Cys Val Ala Asp Glu Ser Ala Glu Asn Cys Asp Lys
 50                  55                  60
Ser Leu His Thr Leu Phe Gly Asp Lys Leu Cys Thr Val Ala Thr Leu
 65                  70                  75                  80
Arg Glu Thr Tyr Gly Glu Met Ala Asp Cys Cys Ala Lys Gln Glu Pro
                 85                  90                  95
Glu Arg Asn Glu Cys Phe Leu Gln His Lys Asp Asp Asn Pro Asn Leu
            100                 105                 110
Pro Arg Leu Val Arg Pro Glu Val Asp Val Met Cys Thr Ala Phe His
        115                 120                 125
Asp Asn Glu Glu Thr Phe Leu Lys Lys Tyr Leu Tyr Glu Ile Ala Arg
    130                 135                 140
Arg His Pro Tyr Phe Tyr Ala Pro Glu Leu Leu Phe Phe Ala Lys Arg
145                 150                 155                 160
Tyr Lys Ala Ala Phe Thr Glu Cys Cys Gln Ala Ala Asp Lys Ala Ala
                165                 170                 175
Cys Leu Leu Pro Lys Leu Asp Glu Leu Arg Asp Glu Gly Lys Ala Ser
            180                 185                 190
Ser Ala Lys Gln Arg Leu Lys Cys Ala Ser Leu Gln Lys Phe Gly Glu
        195                 200                 205
Arg Ala Phe Lys Ala Trp Ala Val Ala Arg Leu Ser Gln Arg Phe Pro
    210                 215                 220
```

```
Lys Ala Glu Phe Ala Glu Val Ser Lys Leu Val Thr Asp Leu Thr Lys
225                 230                 235                 240

Val His Thr Glu Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 257
<211> LENGTH: 65
<212> TYPE: PRT
<213> ORGANISM: Artificial Sequence
<220> FEATURE:
<223> OTHER INFORMATION: identical to natural hirudin except for
      substitution of leucine for isoleucine at the N-terminal end of
      the molecule and the absence of a sulfate group on the tyrosine
```

-continued

```
       at position 63
<300> PUBLICATION INFORMATION:
<308> DATABASE ACCESSION NUMBER: drugbank/DB00001
<309> DATABASE ENTRY DATE: 2005-06-13
<313> RELEVANT RESIDUES IN SEQ ID NO: (1)..(65)

<400> SEQUENCE: 257

Leu Val Tyr Thr Asp Cys Thr Glu Ser Gly Gln Asn Leu Cys Leu Cys
1               5                   10                  15

Glu Gly Ser Asn Val Cys Gly Gln Gly Asn Lys Cys Ile Leu Gly Ser
            20                  25                  30

Asp Gly Glu Lys Asn Gln Cys Val Thr Gly Glu Gly Thr Pro Lys Pro
        35                  40                  45

Gln Ser His Asn Asp Gly Asp Phe Glu Glu Ile Pro Glu Glu Tyr Leu
    50                  55                  60

Gln
65

<210> SEQ ID NO 258
<211> LENGTH: 92
<212> TYPE: PRT
<213> ORGANISM: Homo sapiens
<300> PUBLICATION INFORMATION:
<308> DATABASE ACCESSION NUMBER: drugbank/DB00044
<309> DATABASE ENTRY DATE: 2005-06-13
<313> RELEVANT RESIDUES IN SEQ ID NO: (1)..(92)

<400> SEQUENCE: 258

Ala Pro Asp Val Gln Asp Cys Pro Glu Cys Thr Leu Gln Glu Asn Pro
1               5                   10                  15

Phe Phe Ser Gln Pro Gly Ala Pro Ile Leu Gln Cys Met Gly Cys Cys
            20                  25                  30

Phe Ser Arg Ala Tyr Pro Thr Pro Leu Arg Ser Lys Lys Thr Met Leu
        35                  40                  45

Val Gln Lys Asn Val Thr Ser Glu Ser Thr Cys Cys Val Ala Lys Ser
    50                  55                  60

Tyr Asn Arg Val Thr Val Met Gly Gly Phe Lys Val Glu Asn His Thr
65                  70                  75                  80

Ala Cys His Cys Ser Thr Cys Tyr Tyr His Lys Ser
                85                  90

<210> SEQ ID NO 259
<211> LENGTH: 121
<212> TYPE: PRT
<213> ORGANISM: Homo sapiens
<300> PUBLICATION INFORMATION:
<308> DATABASE ACCESSION NUMBER: drugbank/DB00044
<309> DATABASE ENTRY DATE: 2005-06-13
<313> RELEVANT RESIDUES IN SEQ ID NO: (1)..(121)

<400> SEQUENCE: 259

Ser Arg Glu Pro Leu Arg Pro Trp Cys His Pro Ile Asn Ala Ile Leu
1               5                   10                  15

Ala Val Glu Lys Glu Gly Cys Pro Val Cys Ile Thr Val Asn Thr Thr
            20                  25                  30

Ile Cys Ala Gly Tyr Cys Pro Thr Met Met Arg Val Leu Gln Ala Val
        35                  40                  45

Leu Pro Pro Leu Pro Gln Val Val Cys Thr Tyr Arg Asp Val Arg Phe
    50                  55                  60

Glu Ser Ile Arg Leu Pro Gly Cys Pro Arg Gly Val Asp Pro Val Val
65                  70                  75                  80
```

Ser Phe Pro Val Ala Leu Ser Cys Arg Cys Gly Pro Cys Arg Arg Ser
                85                  90                  95

Thr Ser Asp Cys Gly Gly Pro Lys Asp His Pro Leu Thr Cys Asp His
            100                 105                 110

Pro Gln Leu Ser Gly Leu Leu Phe Leu
        115                 120

<210> SEQ ID NO 260
<211> LENGTH: 474
<212> TYPE: PRT
<213> ORGANISM: Ovis aries
<300> PUBLICATION INFORMATION:
<308> DATABASE ACCESSION NUMBER: drugbank/DB00070
<309> DATABASE ENTRY DATE: 2005-06-13
<313> RELEVANT RESIDUES IN SEQ ID NO: (1)..(474)

<400> SEQUENCE: 260

Leu Asn Phe Arg Ala Pro Pro Val Ile Pro Asn Val Pro Phe Leu Trp
1               5                   10                  15

Ala Trp Asn Ala Pro Ser Glu Phe Cys Leu Gly Lys Phe Asp Glu Pro
                20                  25                  30

Leu Asp Met Ser Leu Phe Ser Phe Ile Gly Ser Pro Arg Ile Asn Ala
            35                  40                  45

Thr Gly Gln Gly Val Thr Ile Phe Tyr Val Asp Arg Leu Gly Tyr Tyr
        50                  55                  60

Pro Tyr Ile Asp Ser Ile Thr Gly Val Thr Val Asn Gly Gly Ile Pro
65                  70                  75                  80

Gln Lys Ile Ser Leu Gln Asp His Leu Asp Lys Ala Lys Lys Asp Ile
                85                  90                  95

Thr Phe Tyr Met Pro Val Asp Asn Leu Gly Met Ala Val Ile Asp Trp
            100                 105                 110

Glu Glu Trp Arg Pro Thr Trp Ala Arg Asn Trp Lys Pro Lys Asp Val
        115                 120                 125

Tyr Lys Asn Arg Ser Ile Glu Leu Val Gln Gln Asn Val Gln Leu
    130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175

Pro Asn His Leu Trp Gly Tyr Tyr Leu Phe Pro Asp Cys Tyr Asn His
            180                 185                 190

His Tyr Lys Lys Pro Gly Tyr Asn Gly Ser Cys Phe Asn Val Glu Ile
        195                 200                 205

Lys Arg Asn Asp Asp Leu Ser Trp Leu Trp Asn Glu Ser Thr Ala Leu
    210                 215                 220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
                245                 250                 255

Pro Asp Ala Lys Ser Pro Leu Pro Val Phe Ala Tyr Thr Arg Ile Val
            260                 265                 270

Phe Thr Asp Gln Val Leu Lys Phe Leu Ser Gln Asp Glu Leu Val Tyr
        275                 280                 285

Thr Phe Gly Glu Thr Val Ala Leu Gly Ala Ser Gly Ile Val Ile Trp
    290                 295                 300

```
Gly Thr Leu Ser Ile Met Arg Ser Met Lys Ser Cys Leu Leu Leu Asp
305                 310                 315                 320

Asn Tyr Met Glu Thr Ile Leu Asn Pro Tyr Ile Ile Asn Val Thr Leu
            325                 330                 335

Ala Ala Lys Met Cys Ser Gln Val Leu Cys Gln Glu Gln Gly Val Cys
            340                 345                 350

Ile Arg Lys Asn Trp Asn Ser Ser Asp Tyr Leu His Leu Asn Pro Asp
            355                 360                 365

Asn Phe Ala Ile Gln Leu Glu Lys Gly Gly Lys Phe Thr Val Arg Gly
    370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys Ile Ala Asp Gly Val Cys Ile Asp Ala
                420                 425                 430

Phe Leu Lys Pro Pro Met Glu Thr Glu Glu Pro Gln Ile Phe Tyr Asn
            435                 440                 445

Ala Ser Pro Ser Thr Leu Ser Ala Thr Met Phe Ile Val Ser Ile Leu
450                 455                 460

Phe Leu Ile Ile Ser Ser Val Ala Ser Leu
465                 470
```

<210> SEQ ID NO 261
<211> LENGTH: 527
<212> TYPE: PRT
<213> ORGANISM: Artificial Sequence
<220> FEATURE:
<223> OTHER INFORMATION: Tenecteplase is a 527 amino acid glycoprotein
    developed by introducing the following modifications to the c
    omplementary DNA (cDNA) for natural human tPA: a substitution of
    threonine 103 with asparagine, and a substitution of asparagine
    117 with
<300> PUBLICATION INFORMATION:
<308> DATABASE ACCESSION NUMBER: drugbank/DB00031
<309> DATABASE ENTRY DATE: 2005-06-13
<313> RELEVANT RESIDUES IN SEQ ID NO: (1)..(527)

<400> SEQUENCE: 261

```
Ser Tyr Gln Val Ile Cys Arg Asp Glu Lys Thr Gln Met Ile Tyr Gln
1               5                   10                  15

Gln His Gln Ser Trp Leu Arg Pro Val Leu Arg Ser Asn Arg Val Glu
            20                  25                  30

Tyr Cys Trp Cys Asn Ser Gly Arg Ala Gln Cys His Ser Val Pro Val
        35                  40                  45

Lys Ser Cys Ser Glu Pro Arg Cys Phe Asn Gly Gly Thr Cys Gln Gln
50                  55                  60

Ala Leu Tyr Phe Ser Asp Phe Val Cys Gln Cys Pro Glu Gly Phe Ala
65                  70                  75                  80

Gly Lys Cys Cys Glu Ile Asp Thr Arg Ala Thr Cys Tyr Glu Asp Gln
                85                  90                  95

Gly Ile Ser Tyr Arg Gly Asn Trp Ser Thr Ala Glu Ser Gly Ala Glu
            100                 105                 110

Cys Thr Gln Trp Asn Ser Ser Ala Leu Ala Gln Lys Pro Tyr Ser Gly
        115                 120                 125

Arg Arg Pro Asp Ala Ile Arg Leu Gly Leu Gly Asn His Asn Tyr Cys
130                 135                 140

Arg Asn Pro Asp Arg Asp Ser Lys Pro Trp Cys Tyr Val Phe Lys Ala
```

```
            145                 150                 155                 160
Gly Lys Tyr Ser Ser Glu Phe Cys Ser Thr Pro Ala Cys Ser Glu Gly
                165                 170                 175

Asn Ser Asp Cys Tyr Phe Gly Asn Gly Ser Ala Tyr Arg Gly Thr His
                180                 185                 190

Ser Leu Thr Glu Ser Gly Ala Ser Cys Leu Pro Trp Asn Ser Met Ile
                195                 200                 205

Leu Ile Gly Lys Val Tyr Thr Ala Gln Asn Pro Ser Ala Gln Ala Leu
            210                 215                 220

Gly Leu Gly Lys His Asn Tyr Cys Arg Asn Pro Asp Gly Asp Ala Lys
225                 230                 235                 240

Pro Trp Cys His Val Leu Lys Asn Arg Arg Leu Thr Trp Glu Tyr Cys
                245                 250                 255

Asp Val Pro Ser Cys Ser Thr Cys Gly Leu Arg Gln Tyr Ser Gln Pro
                260                 265                 270

Gln Phe Arg Ile Lys Gly Gly Leu Phe Ala Asp Ile Ala Ser His Pro
            275                 280                 285

Trp Gln Ala Ala Ala Ala Lys His Arg Arg Ser Pro Gly Glu Arg
            290                 295                 300

Phe Leu Cys Gly Gly Ile Leu Ile Ser Ser Cys Trp Ile Leu Ser Ala
305                 310                 315                 320

Ala His Cys Phe Gln Glu Arg Phe Pro Pro His His Leu Thr Val Ile
                325                 330                 335

Leu Gly Arg Thr Tyr Arg Val Val Pro Gly Glu Glu Glu Gln Lys Phe
            340                 345                 350

Glu Val Glu Lys Tyr Ile Val His Lys Glu Phe Asp Asp Asp Thr Tyr
            355                 360                 365

Asp Asn Asp Ile Ala Leu Leu Gln Leu Lys Ser Asp Ser Ser Arg Cys
            370                 375                 380

Ala Gln Glu Ser Ser Val Val Arg Thr Val Cys Leu Pro Pro Ala Asp
385                 390                 395                 400

Leu Gln Leu Pro Asp Trp Thr Glu Cys Glu Leu Ser Gly Tyr Gly Lys
            405                 410                 415

His Glu Ala Leu Ser Pro Phe Tyr Ser Glu Arg Leu Lys Glu Ala His
            420                 425                 430

Val Arg Leu Tyr Pro Ser Ser Arg Cys Thr Ser Gln His Leu Leu Asn
            435                 440                 445

Arg Thr Val Thr Asp Asn Met Leu Cys Ala Gly Asp Thr Arg Ser Gly
            450                 455                 460

Gly Pro Gln Ala Asn Leu His Asp Ala Cys Gln Gly Asp Ser Gly Gly
465                 470                 475                 480

Pro Leu Val Cys Leu Asn Asp Gly Arg Met Thr Leu Val Gly Ile Ile
                485                 490                 495

Ser Trp Gly Leu Gly Cys Gly Gln Lys Asp Val Pro Gly Val Tyr Thr
                500                 505                 510

Lys Val Thr Asn Tyr Leu Asp Trp Ile Arg Asp Asn Met Arg Pro
            515                 520                 525

<210> SEQ ID NO 262
<211> LENGTH: 218
<212> TYPE: PRT
<213> ORGANISM: Ovis aries
<300> PUBLICATION INFORMATION:
<308> DATABASE ACCESSION NUMBER: drugbank/DB00076
<309> DATABASE ENTRY DATE: 2005-06-13
```

<313> RELEVANT RESIDUES IN SEQ ID NO: (1)..(218)

<400> SEQUENCE: 262

Glu Val Gln Leu Gln Gln Ser Gly Pro Glu Leu Val Lys Pro Gly Ala
1               5                   10                  15

Ser Val Arg Met Ser Cys Lys Ser Ser Gly Tyr Ile Phe Thr Asp Phe
            20                  25                  30

Tyr Met Asn Trp Val Arg Gln Ser His Gly Lys Ser Leu Asp Tyr Ile
        35                  40                  45

Gly Tyr Ile Ser Pro Tyr Ser Gly Val Thr Gly Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Gly Ser Ser Gly Asn Lys Trp Ala Met Asp Tyr Trp Gly His Gly
            100                 105                 110

Ala Ser Val Thr Val Ser Ser Ala Lys Thr Thr Ala Pro Ser Val Tyr
        115                 120                 125

Pro Leu Ala Pro Val Cys Gly Asp Thr Thr Gly Ser Ser Val Thr Leu
    130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Thr Ser Ser
            180                 185                 190

Thr Trp Pro Ser Gln Ser Ile Thr Cys Asn Val Ala His Pro Ala Ser
        195                 200                 205

Ser Thr Lys Val Asp Lys Lys Ile Glu Pro
    210                 215

<210> SEQ ID NO 263
<211> LENGTH: 219
<212> TYPE: PRT
<213> ORGANISM: Ovis aries
<300> PUBLICATION INFORMATION:
<308> DATABASE ACCESSION NUMBER: drugbank/DB00076
<309> DATABASE ENTRY DATE: 2005-06-13
<313> RELEVANT RESIDUES IN SEQ ID NO: (1)..(219)

<400> SEQUENCE: 263

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu Asn Trp Tyr Leu Gln Lys Ala Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Phe Cys Ser Gln Thr
                85                  90                  95

Thr His Val Pro Pro Thr Phe Gly Gly Gly Thr Lys Leu Glu Ile Lys
            100                 105                 110

```
Arg Ala Asp Ala Ala Pro Thr Val Ser Ile Phe Pro Pro Ser Ser Glu
            115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215

<210> SEQ ID NO 264
<211> LENGTH: 28
<212> TYPE: PRT
<213> ORGANISM: Homo sapiens
<300> PUBLICATION INFORMATION:
<308> DATABASE ACCESSION NUMBER: drugbank/DB04900
<309> DATABASE ENTRY DATE: 2007-10-21
<313> RELEVANT RESIDUES IN SEQ ID NO: (1)..(28)

<400> SEQUENCE: 264

Ser Asp Ala Ala Val Asp Thr Ser Ser Glu Ile Thr Thr Lys Asp Leu
1               5                   10                  15

Lys Glu Lys Lys Glu Val Val Glu Glu Ala Glu Asn
            20                  25

<210> SEQ ID NO 265
<211> LENGTH: 362
<212> TYPE: PRT
<213> ORGANISM: Bos taurus
<300> PUBLICATION INFORMATION:
<308> DATABASE ACCESSION NUMBER: drugbank/DB00061
<309> DATABASE ENTRY DATE: 2005-06-13
<313> RELEVANT RESIDUES IN SEQ ID NO: (1)..(362)

<400> SEQUENCE: 265

Ala Gln Thr Pro Ala Phe Asn Lys Pro Lys Val Glu Leu His Val His
1               5                   10                  15

Leu Asp Gly Ala Ile Lys Pro Glu Thr Ile Leu Tyr Tyr Gly Arg Lys
            20                  25                  30

Arg Gly Ile Ala Leu Pro Ala Asp Thr Pro Glu Glu Leu Gln Asn Ile
        35                  40                  45

Ile Gly Met Asp Lys Pro Leu Ser Leu Pro Glu Phe Leu Ala Lys Phe
    50                  55                  60

Asp Tyr Tyr Met Pro Ala Ile Ala Gly Cys Arg Glu Ala Val Lys Arg
65                  70                  75                  80

Ile Ala Tyr Glu Phe Val Glu Met Lys Ala Lys Asp Gly Val Val Tyr
                85                  90                  95

Val Glu Val Arg Tyr Ser Pro His Leu Leu Ala Asn Ser Lys Val Glu
            100                 105                 110

Pro Ile Pro Trp Asn Gln Ala Glu Gly Asp Leu Thr Pro Asp Glu Val
        115                 120                 125

Val Ser Leu Val Asn Gln Gly Leu Gln Glu Gly Glu Arg Asp Phe Gly
    130                 135                 140

Val Lys Val Arg Ser Ile Leu Cys Cys Met Arg His Gln Pro Ser Trp
```

```
145                 150                 155                 160

Ser Ser Glu Val Val Glu Leu Cys Lys Lys Tyr Arg Glu Gln Thr Val
                165                 170                 175

Val Ala Ile Asp Leu Ala Gly Asp Glu Thr Ile Glu Gly Ser Ser Leu
            180                 185                 190

Phe Pro Gly His Val Lys Ala Tyr Ala Glu Ala Val Lys Ser Gly Val
        195                 200                 205

His Arg Thr Val His Ala Gly Glu Val Gly Ser Ala Asn Val Val Lys
    210                 215                 220

Glu Ala Val Asp Thr Leu Lys Thr Glu Arg Leu Gly His Gly Tyr His
225                 230                 235                 240

Thr Leu Glu Asp Ala Thr Leu Tyr Asn Arg Leu Arg Gln Glu Asn Met
                245                 250                 255

His Phe Glu Val Cys Pro Trp Ser Ser Tyr Leu Thr Gly Ala Trp Lys
            260                 265                 270

Pro Asp Thr Glu His Pro Val Val Arg Phe Lys Asn Asp Gln Val Asn
        275                 280                 285

Tyr Ser Leu Asn Thr Asp Asp Pro Leu Ile Phe Lys Ser Thr Leu Asp
    290                 295                 300

Thr Asp Tyr Gln Met Thr Lys Asn Glu Met Gly Phe Thr Glu Glu Glu
305                 310                 315                 320

Phe Lys Arg Leu Asn Ile Asn Ala Ala Lys Ser Ser Phe Leu Pro Glu
                325                 330                 335

Asp Glu Lys Lys Glu Leu Leu Asp Leu Leu Tyr Lys Ala Tyr Gly Met
            340                 345                 350

Pro Ser Pro Ala Ser Ala Glu Gln Cys Leu
        355                 360

<210> SEQ ID NO 266
<211> LENGTH: 521
<212> TYPE: PRT
<213> ORGANISM: Artificial Sequence
<220> FEATURE:
<223> OTHER INFORMATION: composed of the amino acid sequences for
      diphtheria toxin fragments A and B (Met 1-Thr 387)-His followed
      by the sequences for interleukin-2 (IL-2; Ala 1-Thr 133)
<300> PUBLICATION INFORMATION:
<308> DATABASE ACCESSION NUMBER: drugbank/DB0004
<309> DATABASE ENTRY DATE: 2005-06-13
<313> RELEVANT RESIDUES IN SEQ ID NO: (1)..(521)

<400> SEQUENCE: 266

Met Gly Ala Asp Asp Val Val Asp Ser Ser Lys Ser Phe Val Met Glu
1               5                   10                  15

Asn Phe Ser Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
```

```
                    115                 120                 125
Gly Asp Gly Ala Ser Arg Val Val Leu Ser Leu Pro Phe Ala Glu Gly
130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ile Asp Ser Glu Thr Ala Asp Asn Leu Glu Lys Thr Thr Ala Ala
290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
        355                 360                 365

Phe Gln Val Val His Asn Ser Tyr Asn Arg Pro Ala Tyr Ser Pro Gly
370                 375                 380

His Lys Thr His Ala Pro Thr Ser Ser Ser Thr Lys Lys Thr Gln Leu
385                 390                 395                 400

Gln Leu Glu His Leu Leu Leu Asp Leu Gln Met Ile Leu Asn Gly Ile
                405                 410                 415

Asn Asn Tyr Lys Asn Pro Lys Leu Thr Arg Met Leu Thr Phe Lys Phe
            420                 425                 430

Tyr Met Pro Lys Lys Ala Thr Glu Leu Lys His Leu Gln Cys Leu Glu
        435                 440                 445

Glu Glu Leu Lys Pro Leu Glu Val Leu Asn Leu Ala Gln Ser Lys
450                 455                 460

Asn Phe His Leu Arg Pro Arg Asp Leu Ile Ser Asn Ile Asn Val Ile
465                 470                 475                 480

Val Leu Glu Leu Lys Gly Ser Glu Thr Thr Phe Met Cys Glu Tyr Ala
                485                 490                 495

Asp Glu Thr Ala Thr Ile Val Glu Phe Leu Asn Arg Trp Ile Thr Phe
            500                 505                 510

Cys Gln Ser Ile Ile Ser Thr Leu Thr
        515                 520

<210> SEQ ID NO 267
```

```
<211> LENGTH: 1291
<212> TYPE: PRT
<213> ORGANISM: Clostridium botulinum
<300> PUBLICATION INFORMATION:
<308> DATABASE ACCESSION NUMBER: drugbank/DB00042
<309> DATABASE ENTRY DATE: 2005-06-13
<313> RELEVANT RESIDUES IN SEQ ID NO: (1)..(1291)

<400> SEQUENCE: 267
```

Met Pro Val Thr Ile Asn Asn Phe Asn Tyr Asn Asp Pro Ile Asp Asn
1               5                   10                  15

Asn Asn Ile Ile Met Met Glu Pro Pro Phe Ala Arg Gly Thr Gly Arg
            20                  25                  30

Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
            260                 265                 270

Gly Gly Gln Asp Pro Ser Ile Ile Thr Pro Ser Thr Asp Lys Ser Ile
        275                 280                 285

Tyr Asp Lys Val Leu Gln Asn Phe Arg Gly Ile Val Asp Arg Leu Asn
    290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asp Lys Leu Tyr Lys Ser Leu
            340                 345                 350

Met Phe Gly Phe Thr Glu Thr Asn Ile Ala Glu Asn Tyr Lys Ile Lys
        355                 360                 365

```
Thr Arg Ala Ser Tyr Phe Ser Asp Ser Leu Pro Pro Val Lys Ile Lys
    370                 375                 380

Asn Leu Leu Asp Asn Glu Ile Tyr Thr Ile Glu Glu Gly Phe Asn Ile
385                 390                 395                 400

Ser Asp Lys Asp Met Glu Lys Glu Tyr Arg Gly Gln Asn Lys Ala Ile
                405                 410                 415

Asn Lys Gln Ala Tyr Glu Glu Ile Ser Lys Glu His Leu Ala Val Tyr
            420                 425                 430

Lys Ile Gln Met Cys Lys Ser Val Lys Ala Pro Gly Ile Cys Ile Asp
        435                 440                 445

Val Asp Asn Glu Asp Leu Phe Phe Ile Ala Asp Lys Asn Ser Phe Ser
450                 455                 460

Asp Asp Leu Ser Lys Asn Glu Arg Ile Glu Tyr Asn Thr Gln Ser Asn
465                 470                 475                 480

Tyr Ile Glu Asn Asp Phe Pro Ile Asn Glu Leu Ile Leu Asp Thr Asp
                485                 490                 495

Leu Ile Ser Lys Ile Glu Leu Pro Ser Glu Asn Thr Glu Ser Leu Thr
            500                 505                 510

Asp Phe Asn Val Asp Val Pro Val Tyr Glu Lys Gln Pro Ala Ile Lys
        515                 520                 525

Lys Ile Phe Thr Asp Glu Asn Thr Ile Phe Gln Tyr Leu Tyr Ser Gln
        530                 535                 540

Thr Phe Pro Leu Asp Ile Arg Asp Ile Ser Leu Thr Ser Ser Phe Asp
545                 550                 555                 560

Asp Ala Leu Leu Phe Ser Asn Lys Val Tyr Ser Phe Phe Ser Met Asp
                565                 570                 575

Tyr Ile Lys Thr Ala Asn Lys Val Val Glu Ala Gly Leu Phe Ala Gly
            580                 585                 590

Trp Val Lys Gln Ile Val Asn Asp Phe Val Ile Glu Ala Asn Lys Ser
        595                 600                 605

Asn Thr Met Asp Lys Ile Ala Asp Ile Ser Leu Ile Val Pro Tyr Ile
        610                 615                 620

Gly Leu Ala Leu Asn Val Gly Asn Glu Thr Ala Lys Gly Asn Phe Glu
625                 630                 635                 640

Asn Ala Phe Glu Ile Ala Gly Ala Ser Ile Leu Leu Glu Phe Ile Pro
                645                 650                 655

Glu Leu Leu Ile Pro Val Val Gly Ala Phe Leu Leu Glu Ser Tyr Ile
            660                 665                 670

Asp Asn Lys Asn Lys Ile Lys Thr Ile Asp Asn Ala Leu Thr Lys
        675                 680                 685

Arg Asn Glu Lys Trp Ser Asp Met Tyr Gly Leu Ile Val Ala Gln Trp
690                 695                 700

Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Glu Glu Ile Ile Lys Tyr
                725                 730                 735

Arg Tyr Asn Ile Tyr Ser Glu Lys Glu Lys Ser Asn Ile Asn Ile Asp
            740                 745                 750

Phe Asn Asp Ile Asn Ser Lys Leu Asn Glu Gly Ile Asn Gln Ala Ile
        755                 760                 765

Asp Asn Ile Asn Asn Phe Ile Asn Gly Cys Ser Val Ser Tyr Leu Met
        770                 775                 780

Lys Lys Met Ile Pro Leu Ala Val Glu Lys Leu Leu Asp Phe Asp Asn
```

-continued

```
            785                 790                 795                 800
        Thr Leu Lys Lys Asn Leu Leu Asn Tyr Ile Asp Glu Asn Lys Leu Tyr
                        805                 810                 815

Leu Ile Gly Ser Ala Glu Tyr Glu Lys Ser Lys Val Asn Lys Tyr Leu
                        820                 825                 830

Lys Thr Ile Met Pro Phe Asp Leu Ser Ile Tyr Thr Asn Asp Thr Ile
                        835                 840                 845

Leu Ile Glu Met Phe Asn Lys Tyr Asn Ser Glu Ile Leu Asn Asn Ile
                        850                 855                 860

Ile Leu Asn Leu Arg Tyr Lys Asp Asn Leu Ile Asp Leu Ser Gly
        865                 870                 875                 880

Tyr Gly Ala Lys Val Glu Val Tyr Asp Gly Val Glu Leu Asn Asp Lys
                        885                 890                 895

Asn Gln Phe Lys Leu Thr Ser Ser Ala Asn Ser Lys Ile Arg Val Thr
                        900                 905                 910

Gln Asn Gln Asn Ile Ile Phe Asn Ser Val Phe Leu Asp Phe Ser Val
                        915                 920                 925

Ser Phe Trp Ile Arg Ile Pro Lys Tyr Lys Asn Asp Gly Ile Gln Asn
                        930                 935                 940

Tyr Ile His Asn Glu Tyr Thr Ile Ile Asn Cys Met Lys Asn Asn Ser
        945                 950                 955                 960

Gly Trp Lys Ile Ser Ile Arg Gly Asn Arg Ile Ile Trp Thr Leu Ile
                        965                 970                 975

Asp Ile Asn Gly Lys Thr Lys Ser Val Phe Phe Glu Tyr Asn Ile Arg
                        980                 985                 990

Glu Asp Ile Ser Glu Tyr Ile Asn Arg Trp Phe Phe Val Thr Ile Thr
                        995                1000                1005

Asn Asn Leu Asn Asn Ala Lys Ile Tyr Ile Asn Gly Lys Leu Glu
                       1010                1015                1020

Ser Asn Thr Asp Ile Lys Asp Ile Arg Glu Val Ile Ala Asn Gly
                       1025                1030                1035

Glu Ile Ile Phe Lys Leu Asp Gly Asp Ile Asp Arg Thr Gln Phe
                       1040                1045                1050

Ile Trp Met Lys Tyr Phe Ser Ile Phe Asn Thr Glu Leu Ser Gln
                       1055                1060                1065

Ser Asn Ile Glu Glu Arg Tyr Lys Ile Gln Ser Tyr Ser Glu Tyr
                       1070                1075                1080

Leu Lys Asp Phe Trp Gly Asn Pro Leu Met Tyr Asn Lys Glu Tyr
                       1085                1090                1095

Tyr Met Phe Asn Ala Gly Asn Lys Asn Ser Tyr Ile Lys Leu Lys
                       1100                1105                1110

Lys Asp Ser Pro Val Gly Glu Ile Leu Thr Arg Ser Lys Tyr Asn
                       1115                1120                1125

Gln Asn Ser Lys Tyr Ile Asn Tyr Arg Asp Leu Tyr Ile Gly Glu
                       1130                1135                1140

Lys Phe Ile Ile Arg Arg Lys Ser Asn Ser Gln Ser Ile Asn Asp
                       1145                1150                1155

Asp Ile Val Arg Lys Glu Asp Tyr Ile Tyr Leu Asp Phe Phe Asn
                       1160                1165                1170

Leu Asn Gln Glu Trp Arg Val Tyr Thr Tyr Lys Tyr Phe Lys Lys
                       1175                1180                1185

Glu Glu Glu Lys Leu Phe Leu Ala Pro Ile Ser Asp Ser Asp Glu
                       1190                1195                1200
```

-continued

```
Phe Tyr Asn Thr Ile Gln Ile Lys Glu Tyr Asp Glu Gln Pro Thr
    1205                1210                1215

Tyr Ser Cys Gln Leu Leu Phe Lys Lys Asp Glu Glu Ser Thr Asp
    1220                1225                1230

Glu Ile Gly Leu Ile Gly Ile His Arg Phe Tyr Glu Ser Gly Ile
    1235                1240                1245

Val Phe Glu Glu Tyr Lys Asp Tyr Phe Cys Ile Ser Lys Trp Tyr
    1250                1255                1260

Leu Lys Glu Val Lys Arg Lys Pro Tyr Asn Leu Lys Leu Gly Cys
    1265                1270                1275

Asn Trp Gln Phe Ile Pro Lys Asp Glu Gly Trp Thr Glu
    1280                1285                1290

<210> SEQ ID NO 268
<211> LENGTH: 32
<212> TYPE: PRT
<213> ORGANISM: Homo sapiens
<300> PUBLICATION INFORMATION:
<308> DATABASE ACCESSION NUMBER: drugbank/DB04899
<309> DATABASE ENTRY DATE: 2007-10-21
<313> RELEVANT RESIDUES IN SEQ ID NO: (1)..(32)

<400> SEQUENCE: 268

Ser Pro Lys Met Val Gln Gly Ser Gly Cys Phe Gly Arg Lys Met Asp
1               5                   10                  15

Arg Ile Ser Ser Ser Ser Gly Leu Gly Cys Lys Val Leu Arg Arg His
            20                  25                  30

<210> SEQ ID NO 269
<211> LENGTH: 9
<212> TYPE: PRT
<213> ORGANISM: Homo sapiens
<300> PUBLICATION INFORMATION:
<308> DATABASE ACCESSION NUMBER: drugbank/DB00107
<309> DATABASE ENTRY DATE: 2005-06-13
<313> RELEVANT RESIDUES IN SEQ ID NO: (1)..(9)

<400> SEQUENCE: 269

Cys Tyr Ile Gln Asn Cys Pro Leu Gly
1               5

<210> SEQ ID NO 270
<211> LENGTH: 260
<212> TYPE: PRT
<213> ORGANISM: Homo sapiens
<300> PUBLICATION INFORMATION:
<308> DATABASE ACCESSION NUMBER: drugbank/DB00003
<309> DATABASE ENTRY DATE: 2005-06-13
<313> RELEVANT RESIDUES IN SEQ ID NO: (1)..(260)

<400> SEQUENCE: 270

Leu Lys Ile Ala Ala Phe Asn Ile Gln Thr Phe Gly Glu Thr Lys Met
1               5                   10                  15

Ser Asn Ala Thr Leu Val Ser Tyr Ile Val Gln Ile Leu Ser Arg Tyr
            20                  25                  30

Asp Ile Ala Leu Val Gln Glu Val Arg Asp Ser His Leu Thr Ala Val
        35                  40                  45

Gly Lys Leu Leu Asp Asn Leu Asn Gln Asp Ala Pro Asp Thr Tyr His
    50                  55                  60

Tyr Val Val Ser Glu Pro Leu Gly Arg Asn Ser Tyr Lys Glu Arg Tyr
65                  70                  75                  80
```

```
Leu Phe Val Tyr Arg Pro Asp Gln Val Ser Ala Val Asp Ser Tyr Tyr
                85                  90                  95

Tyr Asp Asp Gly Cys Glu Pro Cys Gly Asn Asp Thr Phe Asn Arg Glu
            100                 105                 110

Pro Ala Ile Val Arg Phe Phe Ser Arg Phe Thr Glu Val Arg Glu Phe
        115                 120                 125

Ala Ile Val Pro Leu His Ala Ala Pro Gly Asp Ala Val Ala Glu Ile
    130                 135                 140

Asp Ala Leu Tyr Asp Val Tyr Leu Asp Val Gln Glu Lys Trp Gly Leu
145                 150                 155                 160

Glu Asp Val Met Leu Met Gly Asp Phe Asn Ala Gly Cys Ser Tyr Val
                165                 170                 175

Arg Pro Ser Gln Trp Ser Ser Ile Arg Leu Trp Thr Ser Pro Thr Phe
            180                 185                 190

Gln Trp Leu Ile Pro Asp Ser Ala Asp Thr Thr Ala Thr Pro Thr His
        195                 200                 205

Cys Ala Tyr Asp Arg Ile Val Val Ala Gly Met Leu Leu Arg Gly Ala
    210                 215                 220

Val Val Pro Asp Ser Ala Leu Pro Phe Asn Phe Gln Ala Ala Tyr Gly
225                 230                 235                 240

Leu Ser Asp Gln Leu Ala Gln Ala Ile Ser Asp His Tyr Pro Val Glu
                245                 250                 255

Val Met Leu Lys
            260

<210> SEQ ID NO 271
<211> LENGTH: 452
<212> TYPE: PRT
<213> ORGANISM: Artificial Sequence
<220> FEATURE:
<223> OTHER INFORMATION: Fv (variable; antigen-binding) regions of the
      225 murine EGFr monoclonal antibody specific for the N-terminal
      portion of human EGFr with human IgG1 heavy and kappa light chain
      constant (framework) regions
<300> PUBLICATION INFORMATION:
<308> DATABASE ACCESSION NUMBER: drugbank/DB00002
<309> DATABASE ENTRY DATE: 2005-06-13
<313> RELEVANT RESIDUES IN SEQ ID NO: (1)..(452)

<400> SEQUENCE: 271

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140
```

-continued

```
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 272
<211> LENGTH: 452
<212> TYPE: PRT
<213> ORGANISM: Artificial Sequence
<220> FEATURE:
<223> OTHER INFORMATION: Fv (variable; antigen-binding) regions of the
      225 murine EGFr monoclonal antibody specific for the N-terminal
      portion of human EGFr with human IgG1 heavy and kappa light chain
      constant (framework) regions
<300> PUBLICATION INFORMATION:
<308> DATABASE ACCESSION NUMBER: drugbank/DB00002
<309> DATABASE ENTRY DATE: 2005-06-13
<313> RELEVANT RESIDUES IN SEQ ID NO: (1)..(452)

<400> SEQUENCE: 272

Gln Val Gln Leu Lys Gln Ser Gly Pro Gly Leu Val Gln Pro Ser Gln
```

-continued

```
  1               5                  10                 15
Ser Leu Ser Ile Thr Cys Thr Val Ser Gly Phe Ser Leu Thr Asn Tyr
            20                  25                 30
Gly Val His Trp Val Arg Gln Ser Pro Gly Lys Gly Leu Glu Trp Leu
            35                  40                 45
Gly Val Ile Trp Ser Gly Gly Asn Thr Asp Tyr Asn Thr Pro Phe Thr
            50                  55                 60
Ser Arg Leu Ser Ile Asn Lys Asp Asn Ser Lys Ser Gln Val Phe Phe
 65                  70                  75                 80
Lys Met Asn Ser Leu Gln Ser Asn Asp Thr Ala Ile Tyr Tyr Cys Ala
                85                  90                 95
Arg Ala Leu Thr Tyr Tyr Asp Tyr Glu Phe Ala Tyr Trp Gly Gln Gly
                100                 105                110
Thr Leu Val Thr Val Ser Ala Ala Ser Thr Lys Gly Pro Ser Val Phe
                115                 120                125
Pro Leu Ala Pro Ser Ser Lys Ser Thr Ser Gly Gly Thr Ala Ala Leu
            130                 135                140
Gly Cys Leu Val Lys Asp Tyr Phe Pro Glu Pro Val Thr Val Ser Trp
145                 150                 155                160
Asn Ser Gly Ala Leu Thr Ser Gly Val His Thr Phe Pro Ala Val Leu
                165                 170                175
Gln Ser Ser Gly Leu Tyr Ser Leu Ser Ser Val Val Thr Val Pro Ser
                180                 185                190
Ser Ser Leu Gly Thr Gln Thr Tyr Ile Cys Asn Val Asn His Lys Pro
            195                 200                205
Ser Asn Thr Lys Val Asp Lys Arg Val Glu Pro Lys Ser Pro Lys Ser
 210                 215                 220
Cys Asp Lys Thr His Thr Cys Pro Pro Cys Pro Ala Pro Glu Leu Leu
225                 230                 235                240
Gly Gly Pro Ser Val Phe Leu Phe Pro Pro Lys Pro Lys Asp Thr Leu
                245                 250                255
Met Ile Ser Arg Thr Pro Glu Val Thr Cys Val Val Val Asp Val Ser
                260                 265                270
His Glu Asp Pro Glu Val Lys Phe Asn Trp Tyr Val Asp Gly Val Glu
                275                 280                285
Val His Asn Ala Lys Thr Lys Pro Arg Glu Glu Gln Tyr Asn Ser Thr
                290                 295                300
Tyr Arg Val Val Ser Val Leu Thr Val Leu His Gln Asp Trp Leu Asn
305                 310                 315                320
Gly Lys Glu Tyr Lys Cys Lys Val Ser Asn Lys Ala Leu Pro Ala Pro
                325                 330                335
Ile Glu Lys Thr Ile Ser Lys Ala Lys Gly Gln Pro Arg Glu Pro Gln
                340                 345                350
Val Tyr Thr Leu Pro Pro Ser Arg Asp Glu Leu Thr Lys Asn Gln Val
            355                 360                365
Ser Leu Thr Cys Leu Val Lys Gly Phe Tyr Pro Ser Asp Ile Ala Val
 370                 375                 380
Glu Trp Glu Ser Asn Gly Gln Pro Glu Asn Asn Tyr Lys Thr Thr Pro
385                 390                 395                400
Pro Val Leu Asp Ser Asp Gly Ser Phe Phe Leu Tyr Ser Lys Leu Thr
                405                 410                415
Val Asp Lys Ser Arg Trp Gln Gln Gly Asn Val Phe Ser Cys Ser Val
            420                 425                430
```

```
Met His Glu Ala Leu His Asn His Tyr Thr Gln Lys Ser Leu Ser Leu
        435                 440                 445

Ser Pro Gly Lys
    450

<210> SEQ ID NO 273
<211> LENGTH: 213
<212> TYPE: PRT
<213> ORGANISM: Artificial Sequence
<220> FEATURE:
<223> OTHER INFORMATION: Fv (variable; antigen-binding) regions of the
      225 murine EGFr monoclonal antibody specific for the N-terminal
      portion of human EGFr with human IgG1 heavy and kappa light chain
      constant (framework) regions
<300> PUBLICATION INFORMATION:
<308> DATABASE ACCESSION NUMBER: drugbank/DB00002
<309> DATABASE ENTRY DATE: 2005-06-13
<313> RELEVANT RESIDUES IN SEQ ID NO: (1)..(213)

<400> SEQUENCE: 273

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Ala
    210

<210> SEQ ID NO 274
<211> LENGTH: 213
<212> TYPE: PRT
<213> ORGANISM: Artificial Sequence
<220> FEATURE:
<223> OTHER INFORMATION: Fv (variable; antigen-binding) regions of the
      225 murine EGFr monoclonal antibody specific for the N-terminal
      portion of human EGFr with human IgG1 heavy and kappa light chain
      constant (framework) regions
<300> PUBLICATION INFORMATION:
<308> DATABASE ACCESSION NUMBER: drugbank/DB00002
<309> DATABASE ENTRY DATE: 2005-06-13
```

<313> RELEVANT RESIDUES IN SEQ ID NO: (1)..(213)

<400> SEQUENCE: 274

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Ala
    210

<210> SEQ ID NO 275
<211> LENGTH: 175
<212> TYPE: PRT
<213> ORGANISM: Homo sapiens
<300> PUBLICATION INFORMATION:
<308> DATABASE ACCESSION NUMBER: drugbank/DB00019
<309> DATABASE ENTRY DATE: 2005-06-13
<313> RELEVANT RESIDUES IN SEQ ID NO: (1)..(175)

<400> SEQUENCE: 275

Met Thr Pro Leu Gly Pro Ala Ser Ser Leu Pro Gln Ser Phe Leu Leu
1               5                   10                  15

Lys Cys Leu Glu Gln Val Arg Lys Ile Gln Gly Asp Gly Ala Ala Leu
            20                  25                  30

Gln Glu Lys Leu Cys Ala Thr Tyr Lys Leu Cys His Pro Glu Glu Leu
        35                  40                  45

Val Leu Leu Gly His Ser Leu Gly Ile Pro Trp Ala Pro Leu Ser Ser
    50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
            100                 105                 110

-continued

```
Asp Phe Ala Thr Thr Ile Trp Gln Gln Met Glu Glu Leu Gly Met Ala
            115                 120                 125
Pro Ala Leu Gln Pro Thr Gln Gly Ala Met Pro Ala Phe Ala Ser Ala
        130                 135                 140
Phe Gln Arg Arg Ala Gly Gly Val Leu Val Ala Ser His Leu Gln Ser
145                 150                 155                 160
Phe Leu Glu Val Ser Tyr Arg Val Leu Arg His Leu Ala Gln Pro
                165                 170                 175

<210> SEQ ID NO 276
<211> LENGTH: 406
<212> TYPE: PRT
<213> ORGANISM: Homo sapiens
<300> PUBLICATION INFORMATION:
<308> DATABASE ACCESSION NUMBER: drugbank/DB00036
<309> DATABASE ENTRY DATE: 2005-06-13
<313> RELEVANT RESIDUES IN SEQ ID NO: (1)..(406)

<400> SEQUENCE: 276

Ala Asn Ala Phe Leu Glu Glu Leu Arg Pro Gly Ser Leu Glu Arg Glu
1               5                   10                  15
Cys Lys Glu Glu Gln Cys Ser Phe Glu Glu Ala Arg Glu Ile Phe Lys
            20                  25                  30
Asp Ala Glu Arg Thr Lys Leu Phe Trp Ile Ser Tyr Ser Asp Gly Asp
        35                  40                  45
Gln Cys Ala Ser Ser Pro Cys Gln Asn Gly Gly Ser Cys Lys Asp Gln
    50                  55                  60
Leu Gln Ser Tyr Ile Cys Phe Cys Leu Pro Ala Phe Glu Gly Arg Asn
65                  70                  75                  80
Cys Glu Thr His Lys Asp Asp Gln Leu Ile Cys Val Asn Glu Asn Gly
                85                  90                  95
Gly Cys Glu Gln Tyr Cys Ser Asp His Thr Gly Thr Lys Arg Ser Cys
            100                 105                 110
Arg Cys His Glu Gly Tyr Ser Leu Leu Ala Asp Gly Val Ser Cys Thr
        115                 120                 125
Pro Thr Val Glu Tyr Pro Cys Gly Lys Ile Pro Ile Leu Glu Lys Arg
    130                 135                 140
Asn Ala Ser Lys Pro Gln Gly Arg Ile Val Gly Gly Lys Val Cys Pro
145                 150                 155                 160
Lys Gly Glu Cys Pro Trp Gln Val Leu Leu Leu Val Asn Gly Ala Gln
                165                 170                 175
Leu Cys Gly Gly Thr Leu Ile Asn Thr Ile Trp Val Val Ser Ala Ala
            180                 185                 190
His Cys Phe Asp Lys Ile Lys Asn Trp Arg Asn Leu Ile Ala Val Leu
        195                 200                 205
Gly Glu His Asp Leu Ser Glu His Asp Gly Asp Glu Gln Ser Arg Arg
    210                 215                 220
Val Ala Gln Val Ile Ile Pro Ser Thr Tyr Val Pro Gly Thr Thr Asn
225                 230                 235                 240
His Asp Ile Ala Leu Leu Arg Leu His Gln Pro Val Val Leu Thr Asp
                245                 250                 255
His Val Val Pro Leu Cys Leu Pro Glu Arg Thr Phe Ser Glu Arg Thr
            260                 265                 270
Leu Ala Phe Val Arg Phe Ser Leu Val Ser Gly Trp Gly Gln Leu Leu
        275                 280                 285
Asp Arg Gly Ala Thr Ala Leu Glu Leu Met Val Leu Asn Val Pro Arg
```

```
            290                 295                 300
Leu Met Thr Gln Asp Cys Leu Gln Gln Ser Arg Lys Val Gly Asp Ser
305                 310                 315                 320

Pro Asn Ile Thr Glu Tyr Met Phe Cys Ala Gly Tyr Ser Asp Gly Ser
                325                 330                 335

Lys Asp Ser Cys Lys Gly Asp Ser Gly Pro His Ala Thr His Tyr
            340                 345                 350

Arg Gly Thr Trp Tyr Leu Thr Gly Ile Val Ser Trp Gly Gln Gly Cys
                355                 360                 365

Ala Thr Val Gly His Phe Gly Val Tyr Thr Arg Val Ser Gln Tyr Ile
            370                 375                 380

Glu Trp Leu Gln Lys Leu Met Arg Ser Glu Pro Arg Pro Gly Val Leu
385                 390                 395                 400

Leu Arg Ala Pro Phe Pro
                405

<210> SEQ ID NO 277
<211> LENGTH: 447
<212> TYPE: PRT
<213> ORGANISM: Artificial Sequence
<220> FEATURE:
<223> OTHER INFORMATION: human-murine chimeric antibody
<300> PUBLICATION INFORMATION:
<308> DATABASE ACCESSION NUMBER: drugbank/DB00081
<309> DATABASE ENTRY DATE: 2005-06-13
<313> RELEVANT RESIDUES IN SEQ ID NO: (1)..(447)

<400> SEQUENCE: 277

Gln Ala Tyr Leu Gln Gln Ser Gly Ala Glu Leu Val Arg Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Arg Gln Gly Leu Glu Trp Ile
        35                  40                  45

Gly Ala Ile Tyr Pro Gly Asn Gly Asp Thr Ser Tyr Asn Gln Lys Phe
50                  55                  60

Lys Gly Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Val Val Tyr Tyr Ser Asn Ser Tyr Trp Tyr Phe Asp Val Trp
            100                 105                 110

Gly Thr Gly Thr Thr Val Thr Val Ser Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Ala Glu Pro Lys Ser Cys Asp Lys Thr His
        210                 215                 220
```

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser His Glu Asp Pro Glu
        260                 265                 270

Val Lys Phe Asn Trp Tyr Val Asp Gly Val Glu Val His Asn Ala Lys
    275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
            325                 330                 335

Ser Lys Ala Lys Gly Gln Pro Arg Glu Pro Gln Val Tyr Thr Leu Pro
        340                 345                 350

Pro Ser Arg Asp Glu Leu Thr Lys Asn Gln Val Ser Leu Thr Cys Leu
    355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
        420                 425                 430

His Asn His Tyr Thr Gln Lys Ser Leu Ser Leu Ser Pro Gly Lys
    435                 440                 445

<210> SEQ ID NO 278
<211> LENGTH: 447
<212> TYPE: PRT
<213> ORGANISM: Artificial Sequence
<220> FEATURE:
<223> OTHER INFORMATION: human-murine chimeric antibody
<300> PUBLICATION INFORMATION:
<308> DATABASE ACCESSION NUMBER: drugbank/DB00081
<309> DATABASE ENTRY DATE: 2005-06-13
<313> RELEVANT RESIDUES IN SEQ ID NO: (1)..(447)

<400> SEQUENCE: 278

Gln Ala Tyr Leu Gln Gln Ser Gly Ala Glu Leu Val Arg Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Arg Gln Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Phe Cys
            85                  90                  95

Ala Arg Val Val Tyr Tyr Ser Asn Ser Tyr Trp Tyr Phe Asp Val Trp
        100                 105                 110

Gly Thr Gly Thr Thr Val Thr Val Ser Gly Pro Ser Val Phe Pro Leu
    115                 120                 125

```
Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Ala Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
            435                 440                 445

<210> SEQ ID NO 279
<211> LENGTH: 210
<212> TYPE: PRT
<213> ORGANISM: Artificial Sequence
<220> FEATURE:
<223> OTHER INFORMATION: human-murine chimeric antibody
<300> PUBLICATION INFORMATION:
<308> DATABASE ACCESSION NUMBER: drugbank/DB00081
<309> DATABASE ENTRY DATE: 2005-06-13
<313> RELEVANT RESIDUES IN SEQ ID NO: (1)..(210)

<400> SEQUENCE: 279

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
```

```
                   20                  25                  30

His Trp Tyr Gln Gln Lys Pro Gly Ser Ser Pro Lys Pro Trp Ile Tyr
            35                  40                  45

Ala Pro Ser Asn Leu Ala Ser Gly Val Pro Ala Arg Phe Ser Gly Ser
         50                  55                  60

Gly Ser Gly Thr Ser Tyr Ser Leu Thr Ile Ser Arg Val Glu Ala Glu
 65                  70                  75                  80

Asp Ala Ala Thr Tyr Tyr Cys Gln Gln Trp Ser Phe Asn Pro Pro Thr
                 85                  90                  95

Phe Gly Ala Gly Thr Lys Leu Glu Leu Lys Arg Thr Val Ala Ala Pro
             100                 105                 110

Ser Val Phe Ile Phe Pro Pro Ser Asp Glu Gln Leu Lys Ser Gly Thr
         115                 120                 125

Ala Ser Val Val Cys Leu Leu Asn Asn Phe Tyr Pro Arg Glu Ala Lys
     130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                 165                 170                 175

Thr Leu Thr Leu Ser Lys Ala Asp Tyr Glu Lys His Lys Val Tyr Ala
             180                 185                 190

Cys Glu Val Thr His Gln Gly Leu Ser Ser Pro Val Thr Lys Ser Phe
         195                 200                 205

Asn Arg
    210

<210> SEQ ID NO 280
<211> LENGTH: 210
<212> TYPE: PRT
<213> ORGANISM: Artificial Sequence
<220> FEATURE:
<223> OTHER INFORMATION: human-murine chimeric antibody
<300> PUBLICATION INFORMATION:
<308> DATABASE ACCESSION NUMBER: drugbank/DB00081
<309> DATABASE ENTRY DATE: 2005-06-13
<313> RELEVANT RESIDUES IN SEQ ID NO: (1)..(210)

<400> SEQUENCE: 280

Gln Ile Val Leu Ser Gln Ser Pro Ala Ile Leu Ser Ala Ser Pro Gly
 1               5                  10                  15

Glu Lys Val Thr Met Thr Cys Arg Ala Ser Ser Ser Val Ser Tyr Met
             20                  25                  30

His Trp Tyr Gln Gln Lys Pro Gly Ser Ser Pro Lys Pro Trp Ile Tyr
         35                  40                  45

Ala Pro Ser Asn Leu Ala Ser Gly Val Pro Ala Arg Phe Ser Gly Ser
     50                  55                  60

Gly Ser Gly Thr Ser Tyr Ser Leu Thr Ile Ser Arg Val Glu Ala Glu
 65                  70                  75                  80

Asp Ala Ala Thr Tyr Tyr Cys Gln Gln Trp Ser Phe Asn Pro Pro Thr
                 85                  90                  95

Phe Gly Ala Gly Thr Lys Leu Glu Leu Lys Arg Thr Val Ala Ala Pro
             100                 105                 110

Ser Val Phe Ile Phe Pro Pro Ser Asp Glu Gln Leu Lys Ser Gly Thr
         115                 120                 125

Ala Ser Val Val Cys Leu Leu Asn Asn Phe Tyr Pro Arg Glu Ala Lys
     130                 135                 140
```

```
Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg
    210

<210> SEQ ID NO 281
<211> LENGTH: 585
<212> TYPE: PRT
<213> ORGANISM: Homo sapiens
<300> PUBLICATION INFORMATION:
<308> DATABASE ACCESSION NUMBER: drugbank/DB00062
<309> DATABASE ENTRY DATE: 2005-06-13
<313> RELEVANT RESIDUES IN SEQ ID NO: (1)..(585)

<400> SEQUENCE: 281

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
```

```
                275                 280                 285
Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
                340                 345                 350

Tyr Glu Thr Thr Leu Glu Lys Cys Cys Ala Ala Ala Asp Pro His Glu
                355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
                420                 425                 430

Val Gly Ser Lys Cys Cys Lys His Pro Glu Ala Lys Arg Met Pro Cys
                435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
                500                 505                 510

Ile Cys Thr Leu Ser Glu Lys Glu Arg Gln Ile Lys Lys Gln Thr Ala
                515                 520                 525

Leu Val Glu Leu Val Lys His Lys Pro Lys Ala Thr Lys Glu Gln Leu
                530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
                580                 585

<210> SEQ ID NO 282
<211> LENGTH: 70
<212> TYPE: PRT
<213> ORGANISM: Homo sapiens
<300> PUBLICATION INFORMATION:
<308> DATABASE ACCESSION NUMBER: drugbank/DB01277
<309> DATABASE ENTRY DATE: 2007-05-16
<313> RELEVANT RESIDUES IN SEQ ID NO: (1)..(70)

<400> SEQUENCE: 282

Gly Pro Glu Ile Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
                20                  25                  30

Ser Ser Ser Arg Arg Ala Pro Gln Thr Gly Ile Val Asp Glu Cys Cys
                35                  40                  45
```

```
Phe Arg Ser Cys Asp Leu Arg Arg Leu Glu Met Tyr Cys Ala Pro Leu
    50                  55                  60

Lys Pro Ala Lys Ser Ala
 65                  70

<210> SEQ ID NO 283
<211> LENGTH: 132
<212> TYPE: PRT
<213> ORGANISM: Artificial Sequence
<220> FEATURE:
<223> OTHER INFORMATION: differs from human interleukin-2 in the
      following ways: a) Aldesleukin is not glycosylated because it is
      derived from E. coli; b) the molecule has no N-terminal alanine;
      the codon for this amino acid was deleted during the genetic
      engineering
<300> PUBLICATION INFORMATION:
<308> DATABASE ACCESSION NUMBER: drugbank/DB00041
<309> DATABASE ENTRY DATE: 2005-06-13
<313> RELEVANT RESIDUES IN SEQ ID NO: (1)..(132)

<400> SEQUENCE: 283

Pro Thr Ser Ser Ser Thr Lys Lys Thr Gln Leu Gln Leu Glu His Leu
 1               5                  10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
 65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ala Gln Ser Ile Ile
        115                 120                 125

Ser Thr Leu Thr
    130

<210> SEQ ID NO 284
<211> LENGTH: 527
<212> TYPE: PRT
<213> ORGANISM: Homo sapiens
<300> PUBLICATION INFORMATION:
<308> DATABASE ACCESSION NUMBER: drugbank/DB00029
<309> DATABASE ENTRY DATE: 2005-06-13
<313> RELEVANT RESIDUES IN SEQ ID NO: (1)..(527)

<400> SEQUENCE: 284

Ser Tyr Gln Val Ile Cys Arg Asp Glu Lys Thr Gln Met Ile Tyr Gln
 1               5                  10                  15

Gln His Gln Ser Trp Leu Arg Pro Val Leu Arg Ser Asn Arg Val Glu
            20                  25                  30

Tyr Cys Trp Cys Asn Ser Gly Arg Ala Gln Cys His Ser Val Pro Val
        35                  40                  45

Lys Ser Cys Ser Glu Pro Arg Cys Phe Asn Gly Gly Thr Cys Gln Gln
    50                  55                  60

Ala Leu Tyr Phe Ser Asp Phe Val Cys Gln Cys Pro Glu Gly Phe Ala
 65                  70                  75                  80
```

```
Gly Lys Cys Cys Glu Ile Asp Thr Arg Ala Thr Cys Tyr Glu Asp Gln
                 85                  90                  95

Gly Ile Ser Tyr Arg Gly Thr Trp Ser Thr Ala Glu Ser Gly Ala Glu
            100                 105                 110

Cys Thr Asn Trp Asn Ser Ser Ala Leu Ala Gln Lys Pro Tyr Ser Gly
            115                 120                 125

Arg Arg Pro Asp Ala Ile Arg Leu Gly Leu Gly Asn His Asn Tyr Cys
            130                 135                 140

Arg Asn Pro Asp Arg Asp Ser Lys Pro Trp Cys Tyr Val Phe Lys Ala
145                 150                 155                 160

Gly Lys Tyr Ser Ser Glu Phe Cys Ser Thr Pro Ala Cys Ser Glu Gly
                165                 170                 175

Asn Ser Asp Cys Tyr Phe Gly Asn Gly Ser Ala Tyr Arg Gly Thr His
                180                 185                 190

Ser Leu Thr Glu Ser Gly Ala Ser Cys Leu Pro Trp Asn Ser Met Ile
            195                 200                 205

Leu Ile Gly Lys Val Tyr Thr Ala Gln Asn Pro Ser Ala Gln Ala Leu
            210                 215                 220

Gly Leu Gly Lys His Asn Tyr Cys Arg Asn Pro Asp Gly Asp Ala Lys
225                 230                 235                 240

Pro Trp Cys His Val Leu Lys Asn Arg Arg Leu Thr Trp Glu Tyr Cys
                245                 250                 255

Asp Val Pro Ser Cys Ser Thr Cys Gly Leu Arg Gln Tyr Ser Gln Pro
                260                 265                 270

Gln Phe Arg Ile Lys Gly Gly Leu Phe Ala Asp Ile Ala Ser His Pro
            275                 280                 285

Trp Gln Ala Ala Ile Phe Ala Lys His Arg Arg Ser Pro Gly Glu Arg
            290                 295                 300

Phe Leu Cys Gly Gly Ile Leu Ile Ser Ser Cys Trp Ile Leu Ser Ala
305                 310                 315                 320

Ala His Cys Phe Gln Glu Arg Phe Pro Pro His His Leu Thr Val Ile
                325                 330                 335

Leu Gly Arg Thr Tyr Arg Val Val Pro Gly Glu Glu Glu Gln Lys Phe
            340                 345                 350

Glu Val Glu Lys Tyr Ile Val His Lys Glu Phe Asp Asp Asp Thr Tyr
            355                 360                 365

Asp Asn Asp Ile Ala Leu Leu Gln Leu Lys Ser Asp Ser Ser Arg Cys
            370                 375                 380

Ala Gln Glu Ser Ser Val Val Arg Thr Val Cys Leu Pro Pro Ala Asp
385                 390                 395                 400

Leu Gln Leu Pro Asp Trp Thr Glu Cys Glu Leu Ser Gly Tyr Gly Lys
            405                 410                 415

His Glu Ala Leu Ser Pro Phe Tyr Ser Glu Arg Leu Lys Glu Ala His
            420                 425                 430

Val Arg Leu Tyr Pro Ser Ser Arg Cys Thr Ser Gln His Leu Leu Asn
            435                 440                 445

Arg Thr Val Thr Asp Asn Met Leu Cys Ala Gly Asp Thr Arg Ser Gly
            450                 455                 460

Gly Pro Gln Ala Asn Leu His Asp Ala Cys Gln Gly Asp Ser Gly Gly
465                 470                 475                 480

Pro Leu Val Cys Leu Asn Asp Gly Arg Met Thr Leu Val Gly Ile Ile
                485                 490                 495

Ser Trp Gly Leu Gly Cys Gly Gln Lys Asp Val Pro Gly Val Tyr Thr
```

```
                    500                 505                 510
Lys Val Thr Asn Tyr Leu Asp Trp Ile Arg Asp Asn Met Arg Pro
            515                 520                 525

<210> SEQ ID NO 285
<211> LENGTH: 21
<212> TYPE: PRT
<213> ORGANISM: Sus scrofa
<300> PUBLICATION INFORMATION:
<308> DATABASE ACCESSION NUMBER: drugbank/DB00071
<309> DATABASE ENTRY DATE: 2005-06-13
<313> RELEVANT RESIDUES IN SEQ ID NO: (1)..(21)

<400> SEQUENCE: 285

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 286
<211> LENGTH: 30
<212> TYPE: PRT
<213> ORGANISM: Sus scrofa
<300> PUBLICATION INFORMATION:
<308> DATABASE ACCESSION NUMBER: drugbank/DB00071
<309> DATABASE ENTRY DATE: 2005-06-13
<313> RELEVANT RESIDUES IN SEQ ID NO: (1)..(30)

<400> SEQUENCE: 286

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 287
<211> LENGTH: 2332
<212> TYPE: PRT
<213> ORGANISM: Homo sapiens
<300> PUBLICATION INFORMATION:
<308> DATABASE ACCESSION NUMBER: drugbank/DB00025
<309> DATABASE ENTRY DATE: 2005-06-13
<313> RELEVANT RESIDUES IN SEQ ID NO: (1)..(2332)

<400> SEQUENCE: 287

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140
```

```
Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Leu Thr Asp
            340                 345                 350

Ser Glu Met Asp Val Val Arg Phe Asp Asp Asn Ser Pro Ser Phe
        355                 360                 365

Ile Gln Ile Arg Ser Val Ala Lys Lys His Pro Lys Thr Trp Val His
    370                 375                 380

Tyr Ile Ala Ala Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
        515                 520                 525

Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Val Asp
545                 550                 555                 560
```

-continued

```
Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
        675                 680                 685

Ile Leu Gly Cys His Asn Ser Asp Phe Arg Asn Arg Gly Met Thr Ala
    690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Ser Arg His Pro Ser Thr Arg
            740                 745                 750

Gln Lys Gln Phe Asn Ala Thr Thr Ile Pro Glu Asn Asp Ile Glu Lys
        755                 760                 765

Thr Asp Pro Trp Phe Ala His Arg Thr Pro Met Pro Lys Ile Gln Asn
    770                 775                 780

Val Ser Ser Ser Asp Leu Leu Met Leu Leu Arg Gln Ser Pro Thr Pro
785                 790                 795                 800

His Gly Leu Ser Leu Ser Asp Leu Gln Glu Ala Lys Tyr Glu Thr Phe
                805                 810                 815

Ser Asp Asp Pro Ser Pro Gly Ala Ile Asp Ser Asn Asn Ser Leu Ser
            820                 825                 830

Glu Met Thr His Phe Arg Pro Gln Leu His His Ser Gly Asp Met Val
        835                 840                 845

Phe Thr Pro Glu Ser Gly Leu Gln Leu Arg Leu Asn Glu Lys Leu Gly
    850                 855                 860

Thr Thr Ala Ala Thr Glu Leu Lys Lys Leu Asp Phe Lys Val Ser Ser
865                 870                 875                 880

Thr Ser Asn Asn Leu Ile Ser Thr Ile Pro Ser Asp Asn Leu Ala Ala
                885                 890                 895

Gly Thr Asp Asn Thr Ser Ser Leu Gly Pro Pro Ser Met Pro Val His
            900                 905                 910

Tyr Asp Ser Gln Leu Asp Thr Thr Leu Phe Gly Lys Lys Ser Ser Pro
        915                 920                 925

Leu Thr Glu Ser Gly Gly Pro Leu Ser Leu Ser Glu Glu Asn Asn Asp
    930                 935                 940

Ser Lys Leu Leu Glu Ser Gly Leu Met Asn Ser Gln Glu Ser Ser Trp
945                 950                 955                 960

Gly Lys Asn Val Ser Ser Thr Glu Ser Gly Arg Leu Phe Lys Gly Lys
                965                 970                 975

Arg Ala His Gly Pro Ala Leu Leu Thr Lys Asp Asn Ala Leu Phe Lys
```

-continued

```
                980             985             990
Val Ser Ile Ser Leu Leu Lys Thr Asn Lys Thr Ser Asn Asn Ser Ala
            995             1000            1005
Thr Asn Arg Lys Thr His Ile Asp Gly Pro Ser Leu Leu Ile Glu
    1010            1015            1020
Asn Ser Pro Ser Val Trp Gln Asn Ile Leu Glu Ser Asp Thr Glu
    1025            1030            1035
Phe Lys Lys Val Thr Pro Leu Ile His Asp Arg Met Leu Met Asp
    1040            1045            1050
Lys Asn Ala Thr Ala Leu Arg Leu Asn His Met Ser Asn Lys Thr
    1055            1060            1065
Thr Ser Ser Lys Asn Met Glu Met Val Gln Gln Lys Lys Glu Gly
    1070            1075            1080
Pro Ile Pro Pro Asp Ala Gln Asn Pro Asp Met Ser Phe Phe Lys
    1085            1090            1095
Met Leu Phe Leu Pro Glu Ser Ala Arg Trp Ile Gln Arg Thr His
    1100            1105            1110
Gly Lys Asn Ser Leu Asn Ser Gly Gln Gly Pro Ser Pro Lys Gln
    1115            1120            1125
Leu Val Ser Leu Gly Pro Glu Lys Ser Val Glu Gly Gln Asn Phe
    1130            1135            1140
Leu Ser Glu Lys Asn Lys Val Val Val Gly Lys Gly Glu Phe Thr
    1145            1150            1155
Lys Asp Val Gly Leu Lys Glu Met Val Phe Pro Ser Ser Arg Asn
    1160            1165            1170
Leu Phe Leu Thr Asn Leu Asp Asn Leu His Glu Asn Asn Thr His
    1175            1180            1185
Asn Gln Glu Lys Lys Ile Gln Glu Glu Ile Glu Lys Lys Glu Thr
    1190            1195            1200
Leu Ile Gln Glu Asn Val Val Leu Pro Gln Ile His Thr Val Thr
    1205            1210            1215
Gly Thr Lys Asn Phe Met Lys Asn Leu Phe Leu Leu Ser Thr Arg
    1220            1225            1230
Gln Asn Val Glu Gly Ser Tyr Asp Gly Ala Tyr Ala Pro Val Leu
    1235            1240            1245
Gln Asp Phe Arg Ser Leu Asn Asp Ser Thr Asn Arg Thr Lys Lys
    1250            1255            1260
His Thr Ala His Phe Ser Lys Lys Gly Glu Glu Asn Leu Glu
    1265            1270            1275
Gly Leu Gly Asn Gln Thr Lys Gln Ile Val Glu Lys Tyr Ala Cys
    1280            1285            1290
Thr Thr Arg Ile Ser Pro Asn Thr Ser Gln Gln Asn Phe Val Thr
    1295            1300            1305
Gln Arg Ser Lys Arg Ala Leu Lys Gln Phe Arg Leu Pro Leu Glu
    1310            1315            1320
Glu Thr Glu Leu Glu Lys Arg Ile Ile Val Asp Asp Thr Ser Thr
    1325            1330            1335
Gln Trp Ser Lys Asn Met Lys His Leu Thr Pro Ser Thr Leu Thr
    1340            1345            1350
Gln Ile Asp Tyr Asn Glu Lys Glu Lys Gly Ala Ile Thr Gln Ser
    1355            1360            1365
Pro Leu Ser Asp Cys Leu Thr Arg Ser His Ser Ile Pro Gln Ala
    1370            1375            1380
```

-continued

```
Asn Arg Ser Pro Leu Pro Ile Ala Lys Val Ser Ser Phe Pro Ser
    1385            1390            1395

Ile Arg Pro Ile Tyr Leu Thr Arg Val Leu Phe Gln Asp Asn Ser
    1400            1405            1410

Ser His Leu Pro Ala Ala Ser Tyr Arg Lys Lys Asp Ser Gly Val
    1415            1420            1425

Gln Glu Ser Ser His Phe Leu Gln Gly Ala Lys Lys Asn Asn Leu
    1430            1435            1440

Ser Leu Ala Ile Leu Thr Leu Glu Met Thr Gly Asp Gln Arg Glu
    1445            1450            1455

Val Gly Ser Leu Gly Thr Ser Ala Thr Asn Ser Val Thr Tyr Lys
    1460            1465            1470

Lys Val Glu Asn Thr Val Leu Pro Lys Pro Asp Leu Pro Lys Thr
    1475            1480            1485

Ser Gly Lys Val Glu Leu Leu Pro Lys Val His Ile Tyr Gln Lys
    1490            1495            1500

Asp Leu Phe Pro Thr Glu Thr Ser Asn Gly Ser Pro Gly His Leu
    1505            1510            1515

Asp Leu Val Glu Gly Ser Leu Leu Gln Gly Thr Glu Gly Ala Ile
    1520            1525            1530

Lys Trp Asn Glu Ala Asn Arg Pro Gly Lys Val Pro Phe Leu Arg
    1535            1540            1545

Val Ala Thr Glu Ser Ser Ala Lys Thr Pro Ser Lys Leu Leu Asp
    1550            1555            1560

Pro Leu Ala Trp Asp Asn His Tyr Gly Thr Gln Ile Pro Lys Glu
    1565            1570            1575

Glu Trp Lys Ser Gln Glu Lys Ser Pro Glu Lys Thr Ala Phe Lys
    1580            1585            1590

Lys Lys Asp Thr Ile Leu Ser Leu Asn Ala Cys Glu Ser Asn His
    1595            1600            1605

Ala Ile Ala Ala Ile Asn Glu Gly Gln Asn Lys Pro Glu Ile Glu
    1610            1615            1620

Val Thr Trp Ala Lys Gln Gly Arg Thr Glu Arg Leu Cys Ser Gln
    1625            1630            1635

Asn Pro Pro Val Leu Lys Arg His Gln Arg Glu Ile Thr Arg Thr
    1640            1645            1650

Thr Leu Gln Ser Asp Gln Glu Glu Ile Asp Tyr Asp Asp Thr Ile
    1655            1660            1665

Ser Val Glu Met Lys Lys Glu Asp Phe Asp Ile Tyr Asp Glu Asp
    1670            1675            1680

Glu Asn Gln Ser Pro Arg Ser Phe Gln Lys Lys Thr Arg His Tyr
    1685            1690            1695

Phe Ile Ala Ala Val Glu Arg Leu Trp Asp Tyr Gly Met Ser Ser
    1700            1705            1710

Ser Pro His Val Leu Arg Asn Arg Ala Gln Ser Gly Ser Val Pro
    1715            1720            1725

Gln Phe Lys Lys Val Val Phe Gln Glu Phe Thr Asp Gly Ser Phe
    1730            1735            1740

Thr Gln Pro Leu Tyr Arg Gly Glu Leu Asn Glu His Leu Gly Leu
    1745            1750            1755

Leu Gly Pro Tyr Ile Arg Ala Glu Val Glu Asp Asn Ile Met Val
    1760            1765            1770
```

```
Thr Phe Arg Asn Gln Ala Ser Arg Pro Tyr Ser Phe Tyr Ser Ser
    1775                1780                1785

Leu Ile Ser Tyr Glu Glu Asp Gln Arg Gln Gly Ala Glu Pro Arg
    1790                1795                1800

Lys Asn Phe Val Lys Pro Asn Glu Thr Lys Thr Tyr Phe Trp Lys
    1805                1810                1815

Val Gln His His Met Ala Pro Thr Lys Asp Glu Phe Asp Cys Lys
    1820                1825                1830

Ala Trp Ala Tyr Phe Ser Asp Val Asp Leu Glu Lys Asp Val His
    1835                1840                1845

Ser Gly Leu Ile Gly Pro Leu Leu Val Cys His Thr Asn Thr Leu
    1850                1855                1860

Asn Pro Ala His Gly Arg Gln Val Thr Val Gln Glu Phe Ala Leu
    1865                1870                1875

Phe Phe Thr Ile Phe Asp Glu Thr Lys Ser Trp Tyr Phe Thr Glu
    1880                1885                1890

Asn Met Glu Arg Asn Cys Arg Ala Pro Cys Asn Ile Gln Met Glu
    1895                1900                1905

Asp Pro Thr Phe Lys Glu Asn Tyr Arg Phe His Ala Ile Asn Gly
    1910                1915                1920

Tyr Ile Met Asp Thr Leu Pro Gly Leu Val Met Ala Gln Asp Gln
    1925                1930                1935

Arg Ile Arg Trp Tyr Leu Leu Ser Met Gly Ser Asn Glu Asn Ile
    1940                1945                1950

His Ser Ile His Phe Ser Gly His Val Phe Thr Val Arg Lys Lys
    1955                1960                1965

Glu Glu Tyr Lys Met Ala Leu Tyr Asn Leu Tyr Pro Gly Val Phe
    1970                1975                1980

Glu Thr Val Glu Met Leu Pro Ser Lys Ala Gly Ile Trp Arg Val
    1985                1990                1995

Glu Cys Leu Ile Gly Glu His Leu His Ala Gly Met Ser Thr Leu
    2000                2005                2010

Phe Leu Val Tyr Ser Asn Lys Cys Gln Thr Pro Leu Gly Met Ala
    2015                2020                2025

Ser Gly His Ile Arg Asp Phe Gln Ile Thr Ala Ser Gly Gln Tyr
    2030                2035                2040

Gly Gln Trp Ala Pro Lys Leu Ala Arg Leu His Tyr Ser Gly Ser
    2045                2050                2055

Ile Asn Ala Trp Ser Thr Lys Glu Pro Phe Ser Trp Ile Lys Val
    2060                2065                2070

Asp Leu Leu Ala Pro Met Ile Ile His Gly Ile Lys Thr Gln Gly
    2075                2080                2085

Ala Arg Gln Lys Phe Ser Ser Leu Tyr Ile Ser Gln Phe Ile Ile
    2090                2095                2100

Met Tyr Ser Leu Asp Gly Lys Lys Trp Gln Thr Tyr Arg Gly Asn
    2105                2110                2115

Ser Thr Gly Thr Leu Met Val Phe Phe Gly Asn Val Asp Ser Ser
    2120                2125                2130

Gly Ile Lys His Asn Ile Phe Asn Pro Pro Ile Ile Ala Arg Tyr
    2135                2140                2145

Ile Arg Leu His Pro Thr His Tyr Ser Ile Arg Ser Thr Leu Arg
    2150                2155                2160

Met Glu Leu Met Gly Cys Asp Leu Asn Ser Cys Ser Met Pro Leu
```

-continued

```
                  2165                2170                2175

Gly Met Glu Ser Lys Ala Ile Ser Asp Ala Gln Ile Thr Ala Ser
            2180                2185                2190

Ser Tyr Phe Thr Asn Met Phe Ala Thr Trp Ser Pro Ser Lys Ala
    2195                2200                2205

Arg Leu His Leu Gln Gly Arg Ser Asn Ala Trp Arg Pro Gln Val
2210                2215                2220

Asn Asn Pro Lys Glu Trp Leu Gln Val Asp Phe Gln Lys Thr Met
    2225                2230                2235

Lys Val Thr Gly Val Thr Thr Gln Gly Val Lys Ser Leu Leu Thr
        2240                2245                2250

Ser Met Tyr Val Lys Glu Phe Leu Ile Ser Ser Ser Gln Asp Gly
            2255                2260                2265

His Gln Trp Thr Leu Phe Phe Gln Asn Gly Lys Val Lys Val Phe
                2270                2275                2280

Gln Gly Asn Gln Asp Ser Phe Thr Pro Val Val Asn Ser Leu Asp
            2285                2290                2295

Pro Pro Leu Leu Thr Arg Tyr Leu Arg Ile His Pro Gln Ser Trp
        2300                2305                2310

Val His Gln Ile Ala Leu Arg Met Glu Val Leu Gly Cys Glu Ala
    2315                2320                2325

Gln Asp Leu Tyr
    2330

<210> SEQ ID NO 288
<211> LENGTH: 303
<212> TYPE: PRT
<213> ORGANISM: Escherichia coli
<300> PUBLICATION INFORMATION:
<308> DATABASE ACCESSION NUMBER: drugbank/DB00059
<309> DATABASE ENTRY DATE: 2005-06-13
<313> RELEVANT RESIDUES IN SEQ ID NO: (1)..(303)

<400> SEQUENCE: 288

Gln Met Ser Leu Gln Gln Glu Leu Arg Tyr Ile Glu Ala Leu Ser Ala
1               5                   10                  15

Ile Val Glu Thr Gly Gln Lys Met Leu Glu Ala Gly Glu Ser Ala Leu
                20                  25                  30

Asp Val Val Thr Glu Ala Val Arg Leu Leu Glu Cys Pro Leu Phe
            35                  40                  45

Asn Ala Gly Ile Gly Ala Val Phe Thr Arg Asp Glu Thr His Glu Leu
    50                  55                  60

Asp Ala Cys Val Met Asp Gly Asn Thr Leu Lys Ala Gly Ala Val Ala
65                  70                  75                  80

Gly Val Ser His Leu Arg Asn Pro Val Leu Ala Ala Arg Leu Val Met
                85                  90                  95

Glu Gln Ser Pro His Val Met Met Ile Gly Glu Gly Ala Glu Asn Phe
            100                 105                 110

Ala Phe Ala Arg Gly Met Glu Arg Val Ser Pro Glu Ile Phe Ser Thr
        115                 120                 125

Ser Leu Arg Tyr Glu Gln Leu Leu Ala Ala Arg Lys Glu Gly Ala Thr
    130                 135                 140

Val Leu Asp His Ser Gly Ala Pro Leu Asp Glu Lys Gln Lys Met Gly
145                 150                 155                 160

Thr Val Gly Ala Val Ala Leu Asp Leu Asp Gly Asn Leu Ala Ala Ala
                165                 170                 175
```

```
Thr Ser Thr Gly Gly Met Thr Asn Lys Leu Pro Gly Arg Val Gly Asp
            180                 185                 190

Ser Pro Leu Val Gly Ala Gly Cys Tyr Ala Asn Asn Ala Ser Val Ala
            195                 200                 205

Val Ser Cys Thr Gly Thr Gly Glu Val Phe Ile Arg Ala Leu Ala Ala
210                 215                 220

Tyr Asp Ile Ala Ala Leu Met Asp Tyr Gly Gly Leu Ser Leu Ala Glu
225                 230                 235                 240

Ala Cys Glu Arg Val Val Met Glu Lys Leu Pro Ala Leu Gly Gly Ser
            245                 250                 255

Gly Gly Leu Ile Ala Ile Asp His Glu Gly Asn Val Ala Leu Pro Phe
            260                 265                 270

Asn Thr Glu Gly Met Tyr Arg Ala Trp Gly Tyr Ala Gly Asp Thr Pro
            275                 280                 285

Thr Thr Gly Ile Tyr Arg Glu Lys Gly Asp Thr Val Ala Thr Gln
            290                 295                 300

<210> SEQ ID NO 289
<211> LENGTH: 527
<212> TYPE: PRT
<213> ORGANISM: Homo sapiens
<300> PUBLICATION INFORMATION:
<308> DATABASE ACCESSION NUMBER: drugbase/DB00009
<309> DATABASE ENTRY DATE: 2005-06-13
<313> RELEVANT RESIDUES IN SEQ ID NO: (1)..(527)

<400> SEQUENCE: 289

Ser Tyr Gln Val Ile Cys Arg Asp Glu Lys Thr Gln Met Ile Tyr Gln
1               5                   10                  15

Gln His Gln Ser Trp Leu Arg Pro Val Leu Arg Ser Asn Arg Val Glu
            20                  25                  30

Tyr Cys Trp Cys Asn Ser Gly Arg Ala Gln Cys His Ser Val Pro Val
        35                  40                  45

Lys Ser Cys Ser Glu Pro Arg Cys Phe Asn Gly Gly Thr Cys Gln Gln
    50                  55                  60

Ala Leu Tyr Phe Ser Asp Phe Val Cys Gln Cys Pro Glu Gly Phe Ala
65                  70                  75                  80

Gly Lys Cys Cys Glu Ile Asp Thr Arg Ala Thr Cys Tyr Glu Asp Gln
                85                  90                  95

Gly Ile Ser Tyr Arg Gly Thr Trp Ser Thr Ala Glu Ser Gly Ala Glu
            100                 105                 110

Cys Thr Asn Trp Asn Ser Ser Ala Leu Ala Gln Lys Pro Tyr Ser Gly
        115                 120                 125

Arg Arg Pro Asp Ala Ile Arg Leu Gly Leu Gly Asn His Asn Tyr Cys
    130                 135                 140

Arg Asn Pro Asp Arg Asp Ser Lys Pro Trp Cys Tyr Val Phe Lys Ala
145                 150                 155                 160

Gly Lys Tyr Ser Ser Glu Phe Cys Ser Thr Pro Ala Cys Ser Glu Gly
                165                 170                 175

Asn Ser Asp Cys Tyr Phe Gly Asn Gly Ser Ala Tyr Arg Gly Thr His
            180                 185                 190

Ser Leu Thr Glu Ser Gly Ala Ser Cys Leu Pro Trp Asn Ser Met Ile
        195                 200                 205

Leu Ile Gly Lys Val Tyr Thr Ala Gln Asn Pro Ser Ala Gln Ala Leu
    210                 215                 220
```

```
Gly Leu Gly Lys His Asn Tyr Cys Arg Asn Pro Asp Gly Asp Ala Lys
225                 230                 235                 240

Pro Trp Cys His Val Leu Lys Asn Arg Arg Leu Thr Trp Glu Tyr Cys
                245                 250                 255

Asp Val Pro Ser Cys Ser Thr Cys Gly Leu Arg Gln Tyr Ser Gln Pro
            260                 265                 270

Gln Phe Arg Ile Lys Gly Gly Leu Phe Ala Asp Ile Ala Ser His Pro
        275                 280                 285

Trp Gln Ala Ala Ile Phe Ala Lys His Arg Arg Ser Pro Gly Glu Arg
    290                 295                 300

Phe Leu Cys Gly Gly Ile Leu Ile Ser Cys Trp Ile Leu Ser Ala
305                 310                 315                 320

Ala His Cys Phe Gln Glu Arg Phe Pro Pro His His Leu Thr Val Ile
                325                 330                 335

Leu Gly Arg Thr Tyr Arg Val Val Pro Gly Glu Glu Gln Lys Phe
            340                 345                 350

Glu Val Glu Lys Tyr Ile Val His Lys Glu Phe Asp Asp Thr Tyr
        355                 360                 365

Asp Asn Asp Ile Ala Leu Leu Gln Leu Lys Ser Asp Ser Ser Arg Cys
370                 375                 380

Ala Gln Glu Ser Ser Val Val Arg Thr Val Cys Leu Pro Pro Ala Asp
385                 390                 395                 400

Leu Gln Leu Pro Asp Trp Thr Glu Cys Glu Leu Ser Gly Tyr Gly Lys
                405                 410                 415

His Glu Ala Leu Ser Pro Phe Tyr Ser Glu Arg Leu Lys Glu Ala His
            420                 425                 430

Val Arg Leu Tyr Pro Ser Ser Arg Cys Thr Ser Gln His Leu Leu Asn
        435                 440                 445

Arg Thr Val Thr Asp Asn Met Leu Cys Ala Gly Asp Thr Arg Ser Gly
    450                 455                 460

Gly Pro Gln Ala Asn Leu His Asp Ala Cys Gln Gly Asp Ser Gly Gly
465                 470                 475                 480

Pro Leu Val Cys Leu Asn Asp Gly Arg Met Thr Leu Val Gly Ile Ile
                485                 490                 495

Ser Trp Gly Leu Gly Cys Gly Gln Lys Asp Val Pro Gly Val Tyr Thr
            500                 505                 510

Lys Val Thr Asn Tyr Leu Asp Trp Ile Arg Asp Asn Met Arg Pro
        515                 520                 525

<210> SEQ ID NO 290
<211> LENGTH: 58
<212> TYPE: PRT
<213> ORGANISM: Bos taurus
<300> PUBLICATION INFORMATION:
<308> DATABASE ACCESSION NUMBER: drugbank/DB06692
<309> DATABASE ENTRY DATE: 2009-02-12
<313> RELEVANT RESIDUES IN SEQ ID NO: (1)..(58)

<400> SEQUENCE: 290

Arg Pro Asp Phe Cys Leu Glu Pro Pro Tyr Thr Gly Pro Cys Lys Ala
1               5                   10                  15

Arg Ile Ile Arg Tyr Phe Tyr Asn Ala Lys Ala Gly Leu Cys Gln Thr
            20                  25                  30

Phe Val Tyr Gly Gly Cys Arg Ala Lys Arg Asn Asn Phe Lys Ser Ala
        35                  40                  45

Glu Asp Cys Met Arg Thr Cys Gly Gly Ala
```

-continued

```
              50                  55

<210> SEQ ID NO 291
<211> LENGTH: 139
<212> TYPE: PRT
<213> ORGANISM: Homo sapiens
<300> PUBLICATION INFORMATION:
<308> DATABASE ACCESSION NUMBER: drugbase/DB00039
<309> DATABASE ENTRY DATE: 2005-06-15
<313> RELEVANT RESIDUES IN SEQ ID NO: (1)..(139)

<400> SEQUENCE: 291

Tyr Asp Tyr Met Glu Gly Gly Asp Ile Arg Val Arg Arg Leu Phe Cys
1               5                   10                  15

Arg Thr Gln Trp Tyr Leu Arg Ile Asp Lys Arg Gly Lys Val Lys Gly
            20                  25                  30

Thr Gln Glu Met Lys Asn Asn Tyr Asn Ile Met Glu Ile Arg Thr Val
        35                  40                  45

Ala Val Gly Ile Val Ala Ile Lys Gly Val Glu Ser Glu Phe Tyr Leu
    50                  55                  60

Ala Met Asn Lys Glu Gly Lys Leu Tyr Ala Lys Lys Glu Cys Asn Glu
65                  70                  75                  80

Asp Cys Asn Phe Lys Glu Leu Ile Leu Glu Asn His Tyr Asn Thr Tyr
                85                  90                  95

Ala Ser Ala Lys Trp Thr His Asn Gly Gly Glu Met Phe Val Ala Leu
            100                 105                 110

Asn Gln Lys Gly Ile Pro Val Arg Gly Lys Lys Thr Lys Lys Glu Gln
        115                 120                 125

Lys Thr Ala His Phe Leu Pro Met Ala Ile Thr
    130                 135

<210> SEQ ID NO 292
<211> LENGTH: 451
<212> TYPE: PRT
<213> ORGANISM: Artificial Sequence
<220> FEATURE:
<223> OTHER INFORMATION: recombinant IgG1 kappa, humanized monoclonal
      antibody
<300> PUBLICATION INFORMATION:
<308> DATABASE ACCESSION NUMBER: drugbase/DB00072
<309> DATABASE ENTRY DATE: 2005-06-13
<313> RELEVANT RESIDUES IN SEQ ID NO: (1)..(451)

<400> SEQUENCE: 292

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125
```

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 293
<211> LENGTH: 451
<212> TYPE: PRT
<213> ORGANISM: Artificial Sequence
<220> FEATURE:
<223> OTHER INFORMATION: recombinant IgG1 kappa, humanized monoclonal
      antibody
<300> PUBLICATION INFORMATION:
<308> DATABASE ACCESSION NUMBER: drugbase/DB00072
<309> DATABASE ENTRY DATE: 2005-06-13
<313> RELEVANT RESIDUES IN SEQ ID NO: (1)..(451)

<400> SEQUENCE: 293

-continued

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
```

```
                         420                 425                 430
His Glu Ala Leu His Asn His Tyr Thr Gln Lys Ser Leu Ser Leu Ser
            435                 440                 445

Pro Gly Lys
        450

<210> SEQ ID NO 294
<211> LENGTH: 214
<212> TYPE: PRT
<213> ORGANISM: Artificial Sequence
<220> FEATURE:
<223> OTHER INFORMATION: recombinant IgG1 kappa, humanized monoclonal
      antibody
<300> PUBLICATION INFORMATION:
<308> DATABASE ACCESSION NUMBER: drugbank/DB00072
<309> DATABASE ENTRY DATE: 2005-06-13
<313> RELEVANT RESIDUES IN SEQ ID NO: (1)..(214)

<400> SEQUENCE: 294

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 295
<211> LENGTH: 214
<212> TYPE: PRT
<213> ORGANISM: Artificial Sequence
<220> FEATURE:
<223> OTHER INFORMATION: recombinant IgG1 kappa, humanized monoclonal
      antibody
<300> PUBLICATION INFORMATION:
<308> DATABASE ACCESSION NUMBER: drugbase/DB00072
<309> DATABASE ENTRY DATE: 2005-06-13
<313> RELEVANT RESIDUES IN SEQ ID NO: (1)..(214)

<400> SEQUENCE: 295
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 296
<211> LENGTH: 450
<212> TYPE: PRT
<213> ORGANISM: Mus musculus
<300> PUBLICATION INFORMATION:
<308> DATABASE ACCESSION NUMBER: drugbank/DB00075
<309> DATABASE ENTRY DATE: 2005-06-13
<313> RELEVANT RESIDUES IN SEQ ID NO: (1)..(450)

<400> SEQUENCE: 296

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Ala Lys Thr Thr Ala Pro Ser Val Tyr
        115                 120                 125

-continued

```
Pro Leu Ala Pro Val Cys Gly Gly Thr Thr Gly Ser Ser Val Thr Leu
130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
            165                 170                 175

Gln Ser Asp Leu Tyr Thr Leu Ser Ser Val Thr Val Thr Ser Ser
        180                 185                 190

Thr Trp Pro Ser Gln Ser Ile Thr Cys Asn Val Ala His Pro Ala Ser
        195                 200                 205

Ser Thr Lys Val Asp Lys Lys Ile Glu Pro Arg Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 297
<211> LENGTH: 450
<212> TYPE: PRT
<213> ORGANISM: Mus musculus
<300> PUBLICATION INFORMATION:
<308> DATABASE ACCESSION NUMBER: drugbank/DB00075
<309> DATABASE ENTRY DATE: 2005-06-13
<313> RELEVANT RESIDUES IN SEQ ID NO: (1)..(450)

<400> SEQUENCE: 297

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
```

-continued

```
                20                  25                  30
Thr Met His Trp Val Lys Gln Arg Pro Gly Gln Gly Leu Glu Trp Ile
            35                  40                  45
Gly Tyr Ile Asn Pro Ser Arg Gly Tyr Thr Asn Tyr Asn Gln Lys Phe
        50                  55                  60
Lys Asp Lys Ala Thr Leu Thr Thr Asp Lys Ser Ser Thr Ala Tyr
65                  70                  75                  80
Met Gln Leu Ser Ser Leu Thr Ser Glu Asp Ser Ala Val Tyr Tyr Cys
                85                  90                  95
Ala Arg Tyr Tyr Asp Asp His Tyr Cys Leu Asp Tyr Trp Gly Gln Gly
            100                 105                 110
Thr Thr Leu Thr Val Ser Ser Ala Lys Thr Thr Ala Pro Ser Val Tyr
        115                 120                 125
Pro Leu Ala Pro Val Cys Gly Thr Thr Gly Ser Ser Val Thr Leu
130                 135                 140
Gly Cys Leu Val Lys Gly Tyr Phe Pro Glu Pro Val Thr Leu Thr Trp
145                 150                 155                 160
Asn Ser Gly Ser Leu Ser Ser Gly Val His Thr Phe Pro Ala Val Leu
                165                 170                 175
Gln Ser Asp Leu Tyr Thr Leu Ser Ser Ser Val Thr Val Thr Ser Ser
            180                 185                 190
Thr Trp Pro Ser Gln Ser Ile Thr Cys Asn Val Ala His Pro Ala Ser
        195                 200                 205
Ser Thr Lys Val Asp Lys Lys Ile Glu Pro Arg Pro Lys Ser Cys Asp
210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
```

Gly Lys
    450

<210> SEQ ID NO 298
<211> LENGTH: 213
<212> TYPE: PRT
<213> ORGANISM: Mus musculus
<300> PUBLICATION INFORMATION:
<308> DATABASE ACCESSION NUMBER: drugbank/DB00075
<309> DATABASE ENTRY DATE: 2005-06-13
<313> RELEVANT RESIDUES IN SEQ ID NO: (1)..(213)

<400> SEQUENCE: 298

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn Arg Ala Asp Thr Ala Pro
            100                 105                 110

Thr Val Ser Ile Phe Pro Pro Ser Glu Gln Leu Thr Ser Gly Gly
        115                 120                 125

Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210

<210> SEQ ID NO 299
<211> LENGTH: 213
<212> TYPE: PRT
<213> ORGANISM: Mus musculus
<300> PUBLICATION INFORMATION:
<308> DATABASE ACCESSION NUMBER: drugbank/DB00075
<309> DATABASE ENTRY DATE: 2005-06-13
<313> RELEVANT RESIDUES IN SEQ ID NO: (1)..(213)

<400> SEQUENCE: 299

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Leu Ala Ser Gly Val Pro Ala His Phe Arg Gly Ser
50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn Arg Ala Asp Thr Ala Pro
            100                 105                 110

Thr Val Ser Ile Phe Pro Pro Ser Glu Gln Leu Thr Ser Gly Gly
            115                 120                 125

Ala Ser Val Val Cys Phe Leu Asn Asn Phe Tyr Pro Lys Asp Ile Asn
130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
            195                 200                 205

Asn Arg Asn Glu Cys
            210

<210> SEQ ID NO 300
<211> LENGTH: 165
<212> TYPE: PRT
<213> ORGANISM: Homo sapiens
<300> PUBLICATION INFORMATION:
<308> DATABASE ACCESSION NUMBER: drugbank/DB00008
<309> DATABASE ENTRY DATE: 2005-06-13
<313> RELEVANT RESIDUES IN SEQ ID NO: (1)..(165)

<400> SEQUENCE: 300

Cys Asp Leu Pro Gln Thr His Ser Leu Gly Ser Arg Arg Thr Leu Met
1               5                   10                  15

Leu Leu Ala Gln Met Arg Lys Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
130                 135                 140

Ala Glu Ile Met Arg Ser Phe Ser Leu Ser Thr Asn Leu Gln Glu Ser
145                 150                 155                 160

Leu Arg Ser Lys Glu
            165

-continued

```
<210> SEQ ID NO 301
<211> LENGTH: 34
<212> TYPE: PRT
<213> ORGANISM: Homo sapiens
<300> PUBLICATION INFORMATION:
<308> DATABASE ACCESSION NUMBER: drugbank/DB06285
<309> DATABASE ENTRY DATE: 2008-03-19
<313> RELEVANT RESIDUES IN SEQ ID NO: (1)..(34)

<400> SEQUENCE: 301
```

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

```
<210> SEQ ID NO 302
<211> LENGTH: 450
<212> TYPE: PRT
<213> ORGANISM: Artificial Sequence
<220> FEATURE:
<223> OTHER INFORMATION: Fab fragment of the chimeric human-murine
      monoclonal antibody 7E3
<300> PUBLICATION INFORMATION:
<308> DATABASE ACCESSION NUMBER: drugbank/DB00054
<309> DATABASE ENTRY DATE: 2005-06-13
<313> RELEVANT RESIDUES IN SEQ ID NO: (1)..(450)

<400> SEQUENCE: 302
```

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Val His Trp Val Lys Gln Arg Pro Glu Gln Gly Leu Glu Trp Ile
        35                  40                  45

Gly Arg Ile Asp Pro Ala Asn Gly Tyr Thr Lys Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Val Arg Pro Leu Tyr Asp Tyr Tyr Ala Met Asp Tyr Trp Gly Gln Gly
            100                 105                 110

Thr Ser Val Thr Val Ser Ser Ala Lys Thr Thr Ala Pro Ser Val Tyr
        115                 120                 125

Pro Leu Ala Pro Val Cys Gly Asp Thr Thr Gly Ser Ser Val Thr Leu
    130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Thr Ser Ser
            180                 185                 190

Thr Trp Pro Ser Gln Ser Ile Thr Cys Asn Val Ala His Pro Ala Ser
        195                 200                 205

Ser Thr Lys Val Asp Lys Lys Ile Glu Pro Arg Pro Lys Ser Cys Asp
    210                 215                 220

Lys Thr His Thr Cys Pro Pro Cys Pro Ala Pro Glu Leu Leu Gly Gly
225                 230                 235                 240

```
Pro Ser Val Phe Leu Phe Pro Pro Lys Pro Lys Asp Thr Leu Met Ile
            245                 250                 255

Ser Arg Thr Pro Glu Val Thr Cys Val Val Asp Val Ser His Glu
        260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 303
<211> LENGTH: 450
<212> TYPE: PRT
<213> ORGANISM: Artificial Sequence
<220> FEATURE:
<223> OTHER INFORMATION: Fab fragment of the chimeric human-murine
      monoclonal antibody 7E3

<400> SEQUENCE: 303

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Val His Trp Val Lys Gln Arg Pro Glu Gln Gly Leu Glu Trp Ile
        35                  40                  45

Gly Arg Ile Asp Pro Ala Asn Gly Tyr Thr Lys Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Val Arg Pro Leu Tyr Asp Tyr Tyr Ala Met Asp Tyr Trp Gly Gln Gly
            100                 105                 110

Thr Ser Val Thr Val Ser Ser Ala Lys Thr Thr Ala Pro Ser Val Tyr
        115                 120                 125

Pro Leu Ala Pro Val Cys Gly Asp Thr Thr Gly Ser Ser Val Thr Leu
    130                 135                 140
```

```
Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
            165                 170                 175

Gln Ser Asp Leu Tyr Thr Leu Ser Ser Val Thr Val Thr Ser Ser
        180                 185                 190

Thr Trp Pro Ser Gln Ser Ile Thr Cys Asn Val Ala His Pro Ala Ser
            195                 200                 205

Ser Thr Lys Val Asp Lys Lys Ile Glu Pro Arg Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 304
<211> LENGTH: 214
<212> TYPE: PRT
<213> ORGANISM: Artificial Sequence
<220> FEATURE:
<223> OTHER INFORMATION: Fab fragment of the chimeric human-murine
      monoclonal antibody 7E3
<300> PUBLICATION INFORMATION:
<308> DATABASE ACCESSION NUMBER: drugbank/DB00054
<309> DATABASE ENTRY DATE: 2005-06-13
<313> RELEVANT RESIDUES IN SEQ ID NO: (1)..(214)

<400> SEQUENCE: 304

Asp Ile Leu Met Thr Gln Ser Pro Ser Ser Met Ser Val Ser Leu Gly
1               5                   10                  15
```

```
Asp Thr Val Ser Ile Thr Cys His Ala Ser Gln Gly Ile Ser Ser Asn
            20                  25                  30

Ile Gly Trp Leu Gln Gln Lys Pro Gly Lys Ser Phe Met Gly Leu Ile
            35                  40                  45

Tyr Tyr Gly Thr Asn Leu Val Asp Gly Val Pro Ser Arg Phe Ser Gly
 50                  55                  60

Ser Gly Ser Gly Ala Asp Tyr Ser Leu Thr Ile Ser Ser Leu Asp Ser
 65                  70                  75                  80

Glu Asp Phe Ala Asp Tyr Tyr Cys Val Gln Tyr Ala Gln Leu Pro Tyr
                 85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
            115                 120                 125

Gly Ala Ser Val Val Cys Phe Leu Asn Asn Phe Tyr Pro Lys Asp Ile
            130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
            195                 200                 205

Phe Asn Arg Asn Glu Cys
    210
```

<210> SEQ ID NO 305
<211> LENGTH: 214
<212> TYPE: PRT
<213> ORGANISM: Artificial Sequence
<220> FEATURE:
<223> OTHER INFORMATION: Fab fragment of the chimeric human-murine
      monoclonal antibody 7E3
<300> PUBLICATION INFORMATION:
<308> DATABASE ACCESSION NUMBER: drugbank/DB00054
<309> DATABASE ENTRY DATE: 2005-06-13
<313> RELEVANT RESIDUES IN SEQ ID NO: (1)..(214)

<400> SEQUENCE: 305

```
Asp Ile Leu Met Thr Gln Ser Pro Ser Ser Met Ser Val Ser Leu Gly
 1               5                  10                  15

Asp Thr Val Ser Ile Thr Cys His Ala Ser Gln Gly Ile Ser Ser Asn
            20                  25                  30

Ile Gly Trp Leu Gln Gln Lys Pro Gly Lys Ser Phe Met Gly Leu Ile
            35                  40                  45

Tyr Tyr Gly Thr Asn Leu Val Asp Gly Val Pro Ser Arg Phe Ser Gly
 50                  55                  60

Ser Gly Ser Gly Ala Asp Tyr Ser Leu Thr Ile Ser Ser Leu Asp Ser
 65                  70                  75                  80

Glu Asp Phe Ala Asp Tyr Tyr Cys Val Gln Tyr Ala Gln Leu Pro Tyr
                 85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
            115                 120                 125

Gly Ala Ser Val Val Cys Phe Leu Asn Asn Phe Tyr Pro Lys Asp Ile
```

```
              130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 306
<211> LENGTH: 92
<212> TYPE: PRT
<213> ORGANISM: Homo sapiens
<300> PUBLICATION INFORMATION:
<308> DATABASE ACCESSION NUMBER: drugbank/DB00094
<309> DATABASE ENTRY DATE: 2005-06-13
<313> RELEVANT RESIDUES IN SEQ ID NO: (1)..(92)

<400> SEQUENCE: 306

Ala Pro Asp Val Gln Asp Cys Pro Glu Cys Thr Leu Gln Glu Asn Pro
1               5                   10                  15

Phe Phe Ser Gln Pro Gly Ala Pro Ile Leu Gln Cys Met Gly Cys Cys
            20                  25                  30

Phe Ser Arg Ala Tyr Pro Thr Pro Leu Arg Ser Lys Lys Thr Met Leu
        35                  40                  45

Val Gln Lys Asn Val Thr Ser Glu Ser Thr Cys Cys Val Ala Lys Ser
    50                  55                  60

Tyr Asn Arg Val Thr Val Met Gly Gly Phe Lys Val Glu Asn His Thr
65                  70                  75                  80

Ala Cys His Cys Ser Thr Cys Tyr Tyr His Lys Ser
                85                  90

<210> SEQ ID NO 307
<211> LENGTH: 111
<212> TYPE: PRT
<213> ORGANISM: Homo sapiens
<300> PUBLICATION INFORMATION:
<308> DATABASE ACCESSION NUMBER: drugbank/DR00094
<309> DATABASE ENTRY DATE: 2005-06-13
<313> RELEVANT RESIDUES IN SEQ ID NO: (1)..(111)

<400> SEQUENCE: 307

Asn Ser Cys Glu Leu Thr Asn Ile Thr Ile Ala Ile Glu Lys Glu Glu
1               5                   10                  15

Cys Arg Phe Cys Ile Ser Ile Asn Thr Thr Trp Cys Ala Gly Tyr Cys
            20                  25                  30

Tyr Thr Arg Asp Leu Val Tyr Lys Asp Pro Ala Arg Pro Lys Ile Gln
        35                  40                  45

Lys Thr Cys Thr Phe Lys Glu Leu Val Tyr Glu Thr Val Arg Val Pro
    50                  55                  60

Gly Cys Ala His His Ala Asp Ser Leu Tyr Thr Tyr Pro Val Ala Thr
65                  70                  75                  80

Gln Cys His Cys Gly Lys Cys Asp Ser Asp Ser Thr Asp Cys Thr Val
                85                  90                  95

Arg Gly Leu Gly Pro Ser Tyr Cys Ser Phe Gly Glu Met Lys Glu
                100                 105                 110
```

<210> SEQ ID NO 308
<211> LENGTH: 146
<212> TYPE: PRT
<213> ORGANISM: Homo sapiens
<300> PUBLICATION INFORMATION:
<308> DATABASE ACCESSION NUMBER: drugbank/DB00033
<309> DATABASE ENTRY DATE: 2005-06-13
<313> RELEVANT RESIDUES IN SEQ ID NO: (1)..(146)

<400> SEQUENCE: 308

Cys Tyr Cys Gln Asp Pro Tyr Val Lys Glu Ala Glu Asn Leu Lys Lys
1               5                   10                  15

Tyr Phe Asn Ala Gly His Ser Asp Val Ala Asp Asn Gly Thr Leu Phe
            20                  25                  30

Leu Gly Ile Leu Lys Asn Trp Lys Glu Glu Ser Asp Arg Lys Ile Met
        35                  40                  45

Gln Ser Gln Ile Val Ser Phe Tyr Phe Lys Leu Phe Lys Asn Phe Lys
    50                  55                  60

Asp Asp Gln Ser Ile Gln Lys Ser Val Glu Thr Ile Lys Glu Asp Met
65                  70                  75                  80

Asn Val Lys Phe Phe Asn Ser Asn Lys Lys Arg Asp Asp Phe Glu
                85                  90                  95

Lys Leu Thr Asn Tyr Ser Val Thr Asp Leu Asn Val Gln Arg Lys Ala
            100                 105                 110

Ile His Glu Leu Ile Gln Val Met Ala Glu Leu Ser Pro Ala Ala Lys
        115                 120                 125

Thr Gly Lys Arg Lys Arg Ser Gln Met Leu Phe Arg Gly Arg Arg Ala
    130                 135                 140

Ser Gln
145

<210> SEQ ID NO 309
<211> LENGTH: 153
<212> TYPE: PRT
<213> ORGANISM: Homo sapiens
<300> PUBLICATION INFORMATION:
<308> DATABASE ACCESSION NUMBER: drugbank/DB00026
<309> DATABASE ENTRY DATE: 2005-06-13
<313> RELEVANT RESIDUES IN SEQ ID NO: (1)..(153)

<400> SEQUENCE: 309

Met Arg Pro Ser Gly Arg Lys Ser Ser Lys Met Gln Ala Phe Arg Ile
1               5                   10                  15

Trp Asp Val Asn Gln Lys Thr Phe Tyr Leu Arg Asn Asn Gln Leu Val
            20                  25                  30

Ala Gly Tyr Leu Gln Gly Pro Asn Val Asn Leu Glu Glu Lys Ile Asp
        35                  40                  45

Val Val Pro Ile Glu Pro His Ala Leu Phe Leu Gly Ile His Gly Gly
    50                  55                  60

Lys Met Cys Leu Ser Cys Val Lys Ser Gly Asp Glu Thr Arg Leu Gln
65                  70                  75                  80

Leu Glu Ala Val Asn Ile Thr Asp Leu Ser Glu Asn Arg Lys Gln Asp
                85                  90                  95

Lys Arg Phe Ala Phe Ile Arg Ser Asp Ser Gly Pro Thr Thr Ser Phe
            100                 105                 110

Glu Ser Ala Ala Cys Pro Gly Trp Phe Leu Cys Thr Ala Met Glu Ala
        115                 120                 125

```
Asp Gln Pro Val Ser Leu Thr Asn Met Pro Asp Glu Gly Val Met Val
    130                 135                 140

Thr Lys Phe Tyr Phe Gln Glu Asp Glu
145                 150

<210> SEQ ID NO 310
<211> LENGTH: 27
<212> TYPE: PRT
<213> ORGANISM: Homo sapiens
<300> PUBLICATION INFORMATION:
<308> DATABASE ACCESSION NUMBER: drugbank/DB00021
<309> DATABASE ENTRY DATE: 2005-06-13
<313> RELEVANT RESIDUES IN SEQ ID NO: (1)..(27)

<400> SEQUENCE: 310

His Ser Asp Gly Thr Phe Thr Ser Glu Leu Ser Arg Leu Arg Asp Ser
1               5                   10                  15

Ala Arg Leu Gln Arg Leu Leu Gln Gly Leu Val
            20                  25

<210> SEQ ID NO 311
<211> LENGTH: 20
<212> TYPE: PRT
<213> ORGANISM: Artificial Sequence
<220> FEATURE:
<223> OTHER INFORMATION: synthetic 20 residue peptide (thrombin
      inhibitor) which reversibly inhibits thrombin
<300> PUBLICATION INFORMATION:
<308> DATABASE ACCESSION NUMBER: drugbank/DB00006
<309> DATABASE ENTRY DATE: 2005-06-13
<313> RELEVANT RESIDUES IN SEQ ID NO: (1)..(20)

<400> SEQUENCE: 311

Phe Pro Arg Pro Gly Gly Gly Gly Asn Gly Asp Phe Glu Glu Ile Pro
1               5                   10                  15

Glu Glu Tyr Leu
            20

<210> SEQ ID NO 312
<211> LENGTH: 39
<212> TYPE: PRT
<213> ORGANISM: Artificial Sequence
<220> FEATURE:
<223> OTHER INFORMATION: ACTH 1-39
<300> PUBLICATION INFORMATION:
<308> DATABASE ACCESSION NUMBER: drugbank/DB01285
<309> DATABASE ENTRY DATE: 2007-05-23
<313> RELEVANT RESIDUES IN SEQ ID NO: (1)..(39)

<400> SEQUENCE: 312

Ser Tyr Ser Met Glu His Phe Arg Trp Gly Lys Pro Val Gly Lys Lys
1               5                   10                  15

Arg Arg Pro Val Lys Val Tyr Pro Asp Gly Ala Glu Asp Gln Leu Ala
            20                  25                  30

Glu Ala Phe Pro Leu Glu Phe
        35

<210> SEQ ID NO 313
<211> LENGTH: 446
<212> TYPE: PRT
<213> ORGANISM: Artificial Sequence
<220> FEATURE:
<223> OTHER INFORMATION: recombinant chimeric (murine/human) monoclonal
      antibody (IgG1k) binding to and blocking the interleukin-2
      receptor a-chain (IL-2R alpha, also known as CD25 antigen)
<300> PUBLICATION INFORMATION:
<308> DATABASE ACCESSION NUMBER: drugbank/DB00074
```

<309> DATABASE ENTRY DATE: 2005-06-13
<313> RELEVANT RESIDUES IN SEQ ID NO: (1)..(446)

<400> SEQUENCE: 313

```
Gln Leu Gln Gln Ser Gly Thr Val Leu Ala Arg Pro Gly Ala Ser Val
1               5                   10                  15

Lys Met Ser Cys Lys Ala Ser Gly Tyr Ser Phe Thr Arg Tyr Trp Met
            20                  25                  30

His Trp Ile Lys Gln Arg Pro Gly Gln Gly Leu Glu Trp Ile Gly Ala
        35                  40                  45

Ile Tyr Pro Gly Asn Ser Asp Thr Ser Tyr Asn Gln Lys Phe Glu Gly
    50                  55                  60

Lys Ala Lys Leu Thr Ala Val Thr Ser Ala Ser Thr Ala Tyr Met Glu
65                  70                  75                  80

Leu Ser Ser Leu Thr His Glu Asp Ser Ala Val Tyr Tyr Cys Ser Arg
                85                  90                  95

Asp Tyr Gly Tyr Tyr Phe Asp Phe Trp Gly Gln Gly Thr Thr Leu Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Trp Glu Ser Asn Gly
    370                 375                 380

Gln Pro Glu Asn Asn Tyr Lys Thr Thr Pro Pro Val Leu Asp Ser Asp
385                 390                 395                 400
```

```
Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 314
<211> LENGTH: 446
<212> TYPE: PRT
<213> ORGANISM: Artificial Sequence
<220> FEATURE:
<223> OTHER INFORMATION: recombinant chimeric (murine/human) monoclonal
      antibody (IgG1k) binding to and blocking the interleukin-2
      receptor a-chain (IL-2R alpha, also known as CD25 antigen)
<300> PUBLICATION INFORMATION:
<308> DATABASE ACCESSION NUMBER: drugbank/DB00074
<309> DATABASE ENTRY DATE: 2005-06-13
<313> RELEVANT RESIDUES IN SEQ ID NO: (1)..(446)

<400> SEQUENCE: 314

Gln Leu Gln Gln Ser Gly Thr Val Leu Ala Arg Pro Gly Ala Ser Val
1               5                   10                  15

Lys Met Ser Cys Lys Ala Ser Gly Tyr Ser Phe Thr Arg Tyr Trp Met
            20                  25                  30

His Trp Ile Lys Gln Arg Pro Gly Gln Gly Leu Glu Trp Ile Gly Ala
        35                  40                  45

Ile Tyr Pro Gly Asn Ser Asp Thr Ser Tyr Asn Gln Lys Phe Glu Gly
    50                  55                  60

Lys Ala Lys Leu Thr Ala Val Thr Ser Ala Ser Thr Ala Tyr Met Glu
65                  70                  75                  80

Leu Ser Ser Leu Thr His Glu Asp Ser Ala Val Tyr Tyr Cys Ser Arg
                85                  90                  95

Asp Tyr Gly Tyr Tyr Phe Asp Phe Trp Gly Gln Gly Thr Thr Leu Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285
```

-continued

```
Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 315
<211> LENGTH: 210
<212> TYPE: PRT
<213> ORGANISM: Artificial Sequence
<220> FEATURE:
<223> OTHER INFORMATION: recombinant chimeric (murine/human) monoclonal
      antibody (IgG1k) binding to and blocking the interleukin-2
      receptor a-chain (IL-2R alpha, also known as CD25 antigen)
<300> PUBLICATION INFORMATION:
<308> DATABASE ACCESSION NUMBER: drugbank/DB00074
<309> DATABASE ENTRY DATE: 2005-06-13
<313> RELEVANT RESIDUES IN SEQ ID NO: (1)..(210)

<400> SEQUENCE: 315

Gln Ile Val Ser Thr Gln Ser Pro Ala Ile Met Ser Ala Ser Pro Gly
1               5                   10                  15

Glu Lys Val Thr Met Thr Cys Ser Ala Ser Ser Ser Arg Ser Tyr Met
                20                  25                  30

Gln Trp Tyr Gln Gln Lys Pro Gly Thr Ser Pro Lys Arg Trp Ile Tyr
            35                  40                  45

Asp Thr Ser Lys Leu Ala Ser Gly Val Pro Ala Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys His Gln Arg Ser Ser Tyr Thr Phe Gly
                85                  90                  95

Gly Gly Thr Lys Leu Glu Ile Lys Arg Thr Val Ala Ala Pro Ser Val
            100                 105                 110

Phe Ile Phe Pro Pro Ser Asp Glu Gln Leu Lys Ser Gly Thr Ala Ser
        115                 120                 125

Val Val Cys Leu Leu Asn Asn Phe Tyr Pro Arg Glu Ala Lys Val Gln
    130                 135                 140

Trp Lys Val Asp Asn Ala Leu Gln Ser Gly Asn Ser Gln Glu Ser Val
145                 150                 155                 160

Thr Glu Gln Asp Ser Lys Asp Ser Thr Tyr Ser Leu Ser Ser Thr Leu
                165                 170                 175
```

```
Thr Leu Ser Lys Ala Asp Tyr Glu Lys His Lys Val Tyr Ala Cys Glu
            180                 185                 190

Val Thr His Gln Gly Leu Ser Ser Pro Val Thr Lys Ser Phe Asn Arg
        195                 200                 205

Gly Glu
    210

<210> SEQ ID NO 316
<211> LENGTH: 210
<212> TYPE: PRT
<213> ORGANISM: Artificial Sequence
<220> FEATURE:
<223> OTHER INFORMATION: recombinant chimeric (murine/human) monoclonal
      antibody (IgG1k) binding to and blocking the interleukin-2
      receptor a-chain (IL-2R alpha, also known as CD25 antigen)
<300> PUBLICATION INFORMATION:
<308> DATABASE ACCESSION NUMBER: drugbank/DB00074
<309> DATABASE ENTRY DATE: 2005-06-13
<313> RELEVANT RESIDUES IN SEQ ID NO: (1)..(210)

<400> SEQUENCE: 316

Gln Ile Val Ser Thr Gln Ser Pro Ala Ile Met Ser Ala Ser Pro Gly
1               5                   10                  15

Glu Lys Val Thr Met Thr Cys Ser Ala Ser Ser Ser Arg Ser Tyr Met
            20                  25                  30

Gln Trp Tyr Gln Gln Lys Pro Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys His Gln Arg Ser Ser Tyr Thr Phe Gly
                85                  90                  95

Gly Gly Thr Lys Leu Glu Ile Lys Arg Thr Val Ala Ala Pro Ser Val
            100                 105                 110

Phe Ile Phe Pro Pro Ser Asp Glu Gln Leu Lys Ser Gly Thr Ala Ser
        115                 120                 125

Val Val Cys Leu Leu Asn Asn Phe Tyr Pro Arg Glu Ala Lys Val Gln
    130                 135                 140

Trp Lys Val Asp Asn Ala Leu Gln Ser Gly Asn Ser Gln Glu Ser Val
145                 150                 155                 160

Thr Glu Gln Asp Ser Lys Asp Ser Thr Tyr Ser Leu Ser Ser Thr Leu
                165                 170                 175

Thr Leu Ser Lys Ala Asp Tyr Glu Lys His Lys Val Tyr Ala Cys Glu
            180                 185                 190

Val Thr His Gln Gly Leu Ser Ser Pro Val Thr Lys Ser Phe Asn Arg
        195                 200                 205

Gly Glu
    210

<210> SEQ ID NO 317
<211> LENGTH: 39
<212> TYPE: PRT
<213> ORGANISM: Artificial Sequence
<220> FEATURE:
<223> OTHER INFORMATION: synthetic version of exendin-4 from the saliva
      of Heloderm suspectum
<300> PUBLICATION INFORMATION:
<308> DATABASE ACCESSION NUMBER: drugbank/DB01276
<309> DATABASE ENTRY DATE: 2007-05-16
```

<313> RELEVANT RESIDUES IN SEQ ID NO: (1)..(39)

<400> SEQUENCE: 317

```
His Gly Glu Gly Thr Phe Thr Ser Asp Leu Ser Lys Gln Met Glu Glu
1               5                   10                  15
Glu Ala Val Arg Leu Phe Ile Glu Trp Leu Lys Asn Gly Gly Pro Ser
            20                  25                  30
Ser Gly Ala Pro Pro Ser
        35
```

<210> SEQ ID NO 318
<211> LENGTH: 447
<212> TYPE: PRT
<213> ORGANISM: Artificial Sequence
<220> FEATURE:
<223> OTHER INFORMATION: chimeric murine/human monoclonal antibody
      directed against the CD20 antigen
<300> PUBLICATION INFORMATION:
<308> DATABASE ACCESSION NUMBER: drugbank/DB00073
<309> DATABASE ENTRY DATE: 2005-06-13
<313> RELEVANT RESIDUES IN SEQ ID NO: (1)..(447)

<400> SEQUENCE: 318

```
Gln Ala Tyr Leu Gln Gln Ser Gly Ala Glu Leu Val Arg Pro Gly Ala
1               5                   10                  15
Ser Val Lys Met Ser Cys Lys Ala Ser Gly Tyr Thr Phe Thr Ser Tyr
            20                  25                  30
Asn Met His Trp Val Lys Gln Thr Pro Arg Gln Gly Leu Glu Trp Ile
        35                  40                  45
Gly Ala Ile Tyr Pro Gly Asn Gly Asp Thr Ser Tyr Asn Gln Lys Phe
    50                  55                  60
Lys Gly Lys Ala Thr Leu Thr Val Asp Lys Ser Ser Ser Thr Ala Tyr
65                  70                  75                  80
Met Gln Leu Ser Ser Leu Thr Ser Glu Asp Ser Ala Val Tyr Phe Cys
                85                  90                  95
Ala Arg Val Val Tyr Tyr Ser Asn Ser Tyr Trp Tyr Phe Asp Val Trp
            100                 105                 110
Gly Thr Gly Thr Thr Val Thr Val Ser Gly Pro Ser Val Phe Pro Leu
        115                 120                 125
Ala Pro Ser Ser Lys Ser Thr Ser Gly Gly Thr Ala Ala Leu Gly Cys
    130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
            180                 185                 190
Leu Gly Thr Gln Thr Tyr Ile Cys Asn Val Asn His Lys Pro Ser Asn
        195                 200                 205
Thr Lys Val Asp Lys Lys Ala Glu Pro Lys Ser Cys Asp Lys Thr His
    210                 215                 220
Thr Cys Pro Pro Cys Pro Ala Pro Glu Leu Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
            260                 265                 270
```

```
Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 319
<211> LENGTH: 447
<212> TYPE: PRT
<213> ORGANISM: Artificial Sequence
<220> FEATURE:
<223> OTHER INFORMATION: chimeric murine/human monoclonal antibody
      directed against the CD20 antigen
<300> PUBLICATION INFORMATION:
<308> DATABASE ACCESSION NUMBER: drugbank/DB00073
<309> DATABASE ENTRY DATE: 2005-06-13
<313> RELEVANT RESIDUES IN SEQ ID NO: (1)..(447)

<400> SEQUENCE: 319

Gln Ala Tyr Leu Gln Gln Ser Gly Ala Glu Leu Val Arg Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Arg Gln Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Val Val Tyr Tyr Ser Asn Ser Tyr Trp Tyr Phe Asp Val Trp
            100                 105                 110

Gly Thr Gly Thr Thr Val Thr Val Ser Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
```

```
                165                 170                 175
Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Ala Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 320
<211> LENGTH: 210
<212> TYPE: PRT
<213> ORGANISM: Artificial Sequence
<220> FEATURE:
<223> OTHER INFORMATION: chimeric murine/human monoclonal antibody
      directed against the CD20 antigen
<300> PUBLICATION INFORMATION:
<308> DATABASE ACCESSION NUMBER: drugbank/DB00073
<309> DATABASE ENTRY DATE: 2005-06-13
<313> RELEVANT RESIDUES IN SEQ ID NO: (1)..(210)

<400> SEQUENCE: 320

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
            20                  25                  30

His Trp Tyr Gln Gln Lys Pro Gly Ser Ser Pro Lys Pro Trp Ile Tyr
        35                  40                  45

Ala Pro Ser Asn Leu Ala Ser Gly Val Pro Ala Arg Phe Ser Gly Ser
    50                  55                  60
```

```
Gly Ser Gly Thr Ser Tyr Ser Leu Thr Ile Ser Arg Val Glu Ala Glu
 65                  70                  75                  80

Asp Ala Ala Thr Tyr Tyr Cys Gln Gln Trp Ser Phe Asn Pro Pro Thr
                 85                  90                  95

Phe Gly Ala Gly Thr Lys Leu Glu Leu Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg
    210

<210> SEQ ID NO 321
<211> LENGTH: 210
<212> TYPE: PRT
<213> ORGANISM: Artificial Sequence
<220> FEATURE:
<223> OTHER INFORMATION: chimeric murine/human monoclonal antibody
      directed against the CD20 antigen
<300> PUBLICATION INFORMATION:
<308> DATABASE ACCESSION NUMBER: drugbank/DB00073
<309> DATABASE ENTRY DATE: 2005-06-13
<313> RELEVANT RESIDUES IN SEQ ID NO: (1)..(210)

<400> SEQUENCE: 321

Gln Ile Val Leu Ser Gln Ser Pro Ala Ile Leu Ser Ala Ser Pro Gly
  1               5                  10                  15

Glu Lys Val Thr Met Thr Cys Arg Ala Ser Ser Ser Val Ser Tyr Met
                 20                  25                  30

His Trp Tyr Gln Gln Lys Pro Gly Ser Ser Pro Lys Pro Trp Ile Tyr
             35                  40                  45

Ala Pro Ser Asn Leu Ala Ser Gly Val Pro Ala Arg Phe Ser Gly Ser
         50                  55                  60

Gly Ser Gly Thr Ser Tyr Ser Leu Thr Ile Ser Arg Val Glu Ala Glu
 65                  70                  75                  80

Asp Ala Ala Thr Tyr Tyr Cys Gln Gln Trp Ser Phe Asn Pro Pro Thr
                 85                  90                  95

Phe Gly Ala Gly Thr Lys Leu Glu Leu Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175
```

```
Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg
    210

<210> SEQ ID NO 322
<211> LENGTH: 250
<212> TYPE: PRT
<213> ORGANISM: Homo sapiens
<300> PUBLICATION INFORMATION:
<308> DATABASE ACCESSION NUMBER: drugbank/DB00055
<309> DATABASE ENTRY DATE: 2005-06-13
<313> RELEVANT RESIDUES IN SEQ ID NO: (1)..(250)

<400> SEQUENCE: 322

Leu Ile Asp Gly Lys Met Thr Arg Arg Gly Asp Ser Pro Trp Gln Val
1               5                   10                  15

Val Leu Leu Asp Ser Lys Lys Lys Leu Ala Cys Gly Ala Val Leu Ile
            20                  25                  30

His Pro Ser Trp Val Leu Thr Ala Ala His Cys Met Asp Glu Ser Lys
        35                  40                  45

Lys Leu Leu Val Arg Leu Gly Glu Tyr Asp Leu Arg Arg Trp Glu Lys
    50                  55                  60

Trp Glu Leu Asp Leu Asp Ile Lys Glu Val Phe Val His Pro Asn Tyr
65                  70                  75                  80

Ser Lys Ser Thr Thr Asp Asn Asp Ile Ala Leu Leu His Leu Ala Gln
                85                  90                  95

Pro Ala Thr Leu Ser Gln Thr Ile Val Pro Ile Cys Leu Pro Asp Ser
            100                 105                 110

Gly Leu Ala Glu Arg Glu Leu Asn Gln Ala Gly Gln Glu Thr Leu Val
        115                 120                 125

Thr Gly Trp Gly Tyr His Ser Ser Arg Glu Lys Glu Ala Lys Arg Asn
    130                 135                 140

Arg Thr Phe Val Leu Asn Phe Ile Lys Ile Pro Val Val Pro His Asn
145                 150                 155                 160

Glu Cys Ser Glu Val Met Ser Asn Met Val Ser Glu Asn Met Leu Cys
                165                 170                 175

Ala Gly Ile Leu Gly Asp Arg Gln Asp Ala Cys Glu Gly Asp Ser Gly
            180                 185                 190

Gly Pro Met Val Ala Ser Phe His Gly Thr Trp Phe Leu Val Gly Leu
        195                 200                 205

Val Ser Trp Gly Glu Gly Cys Gly Leu Leu His Asn Tyr Gly Val Tyr
    210                 215                 220

Thr Lys Val Ser Arg Tyr Leu Asp Trp Ile His Gly His Ile Arg Asp
225                 230                 235                 240

Lys Glu Ala Pro Gln Lys Ser Trp Ala Pro
                245                 250

<210> SEQ ID NO 323
<211> LENGTH: 114
<212> TYPE: PRT
<213> ORGANISM: Homo sapiens
<220> FEATURE:
<221> NAME/KEY: misc_feature
<222> LOCATION: (30)..(30)
<223> OTHER INFORMATION: Xaa can be any naturally occurring amino acid
<300> PUBLICATION INFORMATION:
```

-continued

```
<308> DATABASE ACCESSION NUMBER: drugbank/DB)))55
<309> DATABASE ENTRY DATE: 2005-06-13
<313> RELEVANT RESIDUES IN SEQ ID NO: (1)..(114)

<400> SEQUENCE: 323

Ser Lys His Val Asp Gly Asp Gln Cys Leu Val Leu Pro Leu Glu His
1               5                   10                  15

Pro Cys Ala Ser Leu Cys Cys Gly His Gly Thr Cys Ile Xaa Gly Ile
            20                  25                  30

Gly Ser Phe Ser Cys Asp Cys Arg Ser Gly Trp Glu Gly Arg Phe Cys
        35                  40                  45

Gln Arg Glu Val Ser Phe Leu Asn Cys Ser Leu Asp Asn Gly Gly Cys
    50                  55                  60

Thr His Tyr Cys Leu Glu Glu Val Gly Trp Arg Arg Cys Ser Cys Ala
65                  70                  75                  80

Pro Gly Tyr Lys Leu Gly Asp Asp Leu Leu Gln Cys His Pro Ala Val
                85                  90                  95

Lys Phe Pro Cys Gly Arg Pro Trp Lys Arg Met Glu Lys Arg Ser
            100                 105                 110

His Leu

<210> SEQ ID NO 324
<211> LENGTH: 92
<212> TYPE: PRT
<213> ORGANISM: Homo sapiens
<300> PUBLICATION INFORMATION:
<308> DATABASE ACCESSION NUMBER: drugbank/DB00066
<309> DATABASE ENTRY DATE: 2005-06-13
<313> RELEVANT RESIDUES IN SEQ ID NO: (1)..(92)

<400> SEQUENCE: 324

Ala Pro Asp Val Gln Asp Cys Pro Glu Cys Thr Leu Gln Glu Asn Pro
1               5                   10                  15

Phe Phe Ser Gln Pro Gly Ala Pro Ile Leu Gln Cys Met Gly Cys Cys
            20                  25                  30

Phe Ser Arg Ala Tyr Pro Thr Pro Leu Arg Ser Lys Lys Thr Met Leu
        35                  40                  45

Val Gln Lys Asn Val Thr Ser Glu Ser Thr Cys Cys Val Ala Lys Ser
    50                  55                  60

Tyr Asn Arg Val Thr Val Met Gly Gly Phe Lys Val Glu Asn His Thr
65                  70                  75                  80

Ala Cys His Cys Ser Thr Cys Tyr Tyr His Lys Ser
            85                  90

<210> SEQ ID NO 325
<211> LENGTH: 111
<212> TYPE: PRT
<213> ORGANISM: Homo sapiens
<300> PUBLICATION INFORMATION:
<308> DATABASE ACCESSION NUMBER: drugbank/DB00066
<309> DATABASE ENTRY DATE: 2005-06-13
<313> RELEVANT RESIDUES IN SEQ ID NO: (1)..(111)

<400> SEQUENCE: 325

Asn Ser Cys Glu Leu Thr Asn Ile Thr Ile Ala Ile Glu Lys Glu Glu
1               5                   10                  15

Cys Arg Phe Cys Ile Ser Ile Asn Thr Thr Trp Cys Ala Gly Tyr Cys
            20                  25                  30

Tyr Thr Arg Asp Leu Val Tyr Lys Asp Pro Ala Arg Pro Lys Ile Gln
        35                  40                  45
```

```
Lys Thr Cys Thr Phe Lys Glu Leu Val Tyr Glu Thr Arg Val Pro
 50                  55                  60

Gly Cys Ala His His Ala Asp Ser Leu Tyr Thr Tyr Pro Val Ala Thr
 65                  70                  75                  80

Gln Cys His Cys Gly Lys Cys Asp Ser Asp Ser Thr Asp Cys Thr Val
                 85                  90                  95

Arg Gly Leu Gly Pro Ser Tyr Cys Ser Phe Gly Glu Met Lys Glu
            100                 105                 110

<210> SEQ ID NO 326
<211> LENGTH: 497
<212> TYPE: PRT
<213> ORGANISM: Homo sapiens
<300> PUBLICATION INFORMATION:
<308> DATABASE ACCESSION NUMBER: drugbank/DB00053
<309> DATABASE ENTRY DATE: 2005-06-13
<313> RELEVANT RESIDUES IN SEQ ID NO: (1)..(407)

<400> SEQUENCE: 326

Ala Arg Pro Cys Ile Pro Lys Ser Phe Gly Tyr Ser Ser Val Val Cys
  1               5                  10                  15

Val Cys Asn Ala Thr Tyr Cys Asp Ser Phe Asp Pro Pro Thr Phe Pro
                 20                  25                  30

Ala Leu Gly Thr Phe Ser Arg Tyr Glu Ser Thr Arg Ser Gly Arg Arg
             35                  40                  45

Met Glu Leu Ser Met Gly Pro Ile Gln Ala Asn His Thr Gly Thr Gly
 50                  55                  60

Leu Leu Leu Thr Leu Gln Pro Glu Gln Lys Phe Gln Lys Val Lys Gly
 65                  70                  75                  80

Phe Gly Gly Ala Met Thr Asp Ala Ala Ala Leu Asn Ile Leu Ala Leu
                 85                  90                  95

Ser Pro Pro Ala Gln Asn Leu Leu Leu Lys Ser Tyr Phe Ser Glu Glu
            100                 105                 110

Gly Ile Gly Tyr Asn Ile Ile Arg Val Pro Met Ala Ser Cys Asp Phe
        115                 120                 125

Ser Ile Arg Thr Tyr Thr Tyr Ala Asp Thr Pro Asp Asp Phe Gln Leu
130                 135                 140

His Asn Phe Ser Leu Pro Glu Glu Asp Thr Lys Leu Lys Ile Pro Leu
145                 150                 155                 160

Ile His Arg Ala Leu Gln Leu Ala Gln Arg Pro Val Ser Leu Leu Ala
                165                 170                 175

Ser Pro Trp Thr Ser Pro Thr Trp Leu Lys Thr Asn Gly Ala Val Asn
            180                 185                 190

Gly Lys Gly Ser Leu Lys Gly Gln Pro Gly Asp Ile Tyr His Gln Thr
        195                 200                 205

Trp Ala Arg Tyr Phe Val Lys Phe Leu Asp Ala Tyr Ala Glu His Lys
210                 215                 220

Leu Gln Phe Trp Ala Val Thr Ala Glu Asn Glu Pro Ser Ala Gly Leu
225                 230                 235                 240

Leu Ser Gly Tyr Pro Phe Gln Cys Leu Gly Phe Thr Pro Glu His Gln
                245                 250                 255

Arg Asp Phe Ile Ala Arg Asp Leu Gly Pro Thr Leu Ala Asn Ser Thr
            260                 265                 270

His His Asn Val Arg Leu Leu Met Leu Asp Asp Gln Arg Leu Leu Leu
        275                 280                 285
```

```
Pro His Trp Ala Lys Val Val Leu Thr Asp Pro Glu Ala Ala Lys Tyr
290                 295                 300

Val His Gly Ile Ala Val His Trp Tyr Leu Asp Phe Leu Ala Pro Ala
305                 310                 315                 320

Lys Ala Thr Leu Gly Glu Thr His Arg Leu Phe Pro Asn Thr Met Leu
                325                 330                 335

Phe Ala Ser Glu Ala Cys Val Gly Ser Lys Phe Trp Glu Gln Ser Val
            340                 345                 350

Arg Leu Gly Ser Trp Asp Arg Gly Met Gln Tyr Ser His Ser Ile Ile
        355                 360                 365

Thr Asn Leu Leu Tyr His Val Val Gly Trp Thr Asp Trp Asn Leu Ala
370                 375                 380

Leu Asn Pro Glu Gly Gly Pro Asn Trp Val Arg Asn Phe Val Asp Ser
385                 390                 395                 400

Pro Ile Ile Val Asp Ile Thr Lys Asp Thr Phe Tyr Lys Gln Pro Met
                405                 410                 415

Phe Tyr His Leu Gly His Phe Ser Lys Phe Ile Pro Glu Gly Ser Gln
            420                 425                 430

Arg Val Gly Leu Val Ala Ser Gln Lys Asn Asp Leu Asp Ala Val Ala
        435                 440                 445

Leu Met His Pro Asp Gly Ser Ala Val Val Val Leu Asn Arg Ser
450                 455                 460

Ser Lys Asp Val Pro Leu Thr Ile Lys Asp Pro Ala Val Gly Phe Leu
465                 470                 475                 480

Glu Thr Ile Ser Pro Gly Tyr Ser Ile His Thr Tyr Leu Trp Arg Arg
                485                 490                 495

Gln

<210> SEQ ID NO 327
<211> LENGTH: 13
<212> TYPE: PRT
<213> ORGANISM: Artificial Sequence
<220> FEATURE:
<223> OTHER INFORMATION: Engineered enhanced sequon
<220> FEATURE:
<221> NAME/KEY: MISC_FEATURE
<222> LOCATION: (2)..(4)
<223> OTHER INFORMATION: Xaa at positions 2-4 are present or absent and
      if present are any amino acid residue
<220> FEATURE:
<221> NAME/KEY: MISC_FEATURE
<222> LOCATION: (5)..(5)
<223> OTHER INFORMATION: Xaa at residue 5 is Histidine, Phenylalanine,
      Tryptophan, or Tyrosine
<220> FEATURE:
<221> NAME/KEY: MISC_FEATURE
<222> LOCATION: (6)..(9)
<223> OTHER INFORMATION: Xaa at residues 6-9 are present or absent and
      if present are Alanine, Cysteine, Aspartic Acid , Glutamic Acid,
      Glycine, Isoleucine, Lysine, Leucine, Methionine, Asparagine,
      Proline, Glutamine, Arginine, Serine, Threonine, or Valine.
<220> FEATURE:
<221> NAME/KEY: MISC_FEATURE
<222> LOCATION: (10)..(10)
<223> OTHER INFORMATION: Xaa at residue 10 is any amino acid residue
<220> FEATURE:
<221> NAME/KEY: MISC_FEATURE
<222> LOCATION: (12)..(12)
<223> OTHER INFORMATION: Xaa at residue 12 is Alanine, Cysteine,
      Aspartic Acid , Glutamic Acid, Phenylalanine, Glycine, Histidine,
      Isoleucine, Lysine, Leucine, Methionine, Asparagine, Glutamine,
      Arginine, Serine, Threonine, Valine, Tryptophan, or Tyrosine.
<220> FEATURE:
<221> NAME/KEY: MISC_FEATURE
<222> LOCATION: (13)..(13)
```

```
<223> OTHER INFORMATION: Xaa at residue 13 is Threonine or Serine.

<400> SEQUENCE: 327

Lys Xaa Xaa Xaa Xaa Xaa Xaa Xaa Xaa Xaa Asn Xaa Xaa
1               5                   10
```

What is claimed is:

1. A chimeric therapeutic polypeptide of a pre-existing therapeutic antibody, said pre-existing therapeutic antibody exhibiting a secondary structure that comprises at least one tight turn containing a sequence of four to about seven amino acid residues in which at least two amino acid side chains extend on the same side of the tight turn and are within less than about 7 Å of each other, said preexisting therapeutic antibody lacking the sequon within that sequence of four to about seven amino acid residues, in the direction from left to right and from N-terminus to C-terminus, Aro-(Xxx)n-(Zzz)p-Asn-Yyy-Thr/Ser, (SEQ ID NO:001) wherein Aro is an aromatic amino acid residue, n is zero, 1, 2, 3 or 4, Xxx is an amino acid residue other than an aromatic residue, P is zero or 1, Zzz is any amino acid residue, Asn is asparagine, Yyy is any amino acid residue other than proline, and Thr/Ser is one or the other of the amino acid residues threonine and serine, said chimeric therapeutic polypeptide having substantially the same length, at least one tight turn and substantially the same sequence as the pre-existing therapeutic polypeptide, the two sequences differing by the presence in the chimeric therapeutic polypeptide of said sequon, Aro-(Xxx)n-(Zzz)p-Asn-Yyy-Thr/Ser (SEQ ID NO:001), and said sequon being located at the same position in said tight turn as said sequence of four to about seven amino acid residues such that the side chains of the Aro, Asn and Thr/Ser amino acid residues project on the same side of the turn and are within less than about 7 Å of each other.

2. The chimeric therapeutic polypeptide of a pre-existing therapeutic antibody according to claim 1, wherein said chimeric therapeutic polypeptide, when said sequon is glycosylated, exhibits a folding stabilization enhanced by about −0.5 to about −4 kcal/mol compared to said pre-existing therapeutic polypeptide in non-glycosylated form.

3. The chimeric therapeutic polypeptide of a pre-existing therapeutic antibody according to claim 1, wherein said aromatic amino acid residue is Phe, Trp, Tyr or His.

4. The chimeric therapeutic polypeptide of a pre-existing therapeutic antibody according to claim 1, wherein n is 1.

5. The chimeric therapeutic polypeptide of a pre-existing therapeutic antibody according to claim 1, wherein Thr/Ser is threonine.

6. The chimeric therapeutic polypeptide of a pre-existing therapeutic antibody according to claim 1, wherein said antibody is OKT3.

7. The chimeric therapeutic polypeptide of a pre-existing therapeutic antibody according to claim 1 that has a length of about 25 to about 500 amino acid residues.

8. The chimeric therapeutic polypeptide of a pre-existing therapeutic antibody according to claim 1, wherein Asn occupies the i+2 position of a five-residue type I β-bulge turn that spans from Aro at the i position to Ser/Thr at the i+4 position.

9. The chimeric therapeutic polypeptide of a pre-existing therapeutic antibody according to claim 1, wherein Asn occupies the i+1 position of a five-residue type I' β-turn that spans from Aro at the i position to Ser/Thr at the i+3.

10. The chimeric therapeutic polypeptide of a pre-existing therapeutic antibody according to claim 1, wherein Asn occupies the i+3 position of a six-residue 4:6 hairpin loop turn that spans from Aro at the i position to Ser/Thr at the i+5 position.

11. The chimeric therapeutic polypeptide of a pre-existing therapeutic antibody according to claim 1, wherein said sequon has the sequence Lys-(Zzz)m-Aro-(Xxx)n-Zzz-Asn-Yyy-Thr/Ser, [SEQ ID NO:327]

wherein m is zero to three, and

Lys is lysine.

12. The chimeric therapeutic polypeptide of a pre-existing therapeutic antibody according to claim 1, wherein said sequon has the sequence Aro-Xxx-Zzz-Asn-Yyy-Thr/Ser (SEQ ID NO:008).

13. The chimeric therapeutic polypeptide of a pre-existing therapeutic antibody according to claim 1, wherein said sequon has the sequence Aro-Xxx-Asn-Yyy-Thr/Ser (SEQ ID NO:002).

14. The chimeric therapeutic polypeptide of a pre-existing therapeutic antibody according to claim 1, wherein said sequon has the sequence Aro-Asn-Yyy-Thr/Ser (SEQ ID NO:003).

15. The chimeric therapeutic polypeptide of a pre-existing therapeutic antibody according to claim 1, wherein the Asn of said sequon is glycosylated.

16. A method of enhancing folded stabilization of a chimeric therapeutic polypeptide compared to a pre-existing therapeutic polypeptide, wherein said pre-existing therapeutic polypeptide comprises a sequence of a pre-existing therapeutic antibody and exhibits a secondary structure that comprises at least one tight turn in which the side chains of two residues in a sequence of four to about seven amino acid residues within said tight turn project on the same side of the turn and are within less than about 7 Å of each other, said sequence of four to about seven amino acid residues free of the sequon Aro-(Xxx)n-(Zzz)p-Asn(Glycan)-Yyy-Thr/Ser (SEQ ID NO:005), as defined below, said method comprising the step of:

preparing a therapeutic chimeric polypeptide of substantially the same length and substantially same sequence as the therapeutic polypeptide that exhibits a secondary structure comprising at least one tight turn at the same sequence position within the tight turn of said therapeutic polypeptide except that said sequence of four to about seven amino acid residues is replaced with the sequon, in the direction from left to right and from N-terminus to C-terminus, Aro-(Xxx)n-(Zzz)p-Asn(Glycan)-Yyy-Thr/Ser (SEQ ID NO:005), wherein
- Aro is an aromatic amino acid residue,
- n is zero, 1, 2, 3 or 4,
- Xxx is an amino acid residue other than an aromatic residue,
- p is zero or 1,
- Zzz is any amino acid residue,
- Asn(Glycan) is glycosylated asparagine,
- Yyy is any amino acid residue other than proline,
- Thr/Ser is one or the other of the amino acid residues threonine and serine, and
- the side chains of the Aro, Asn(Glycan) and Thr/Ser amino acid residues project on the same side of the turn and are within less than about 7 Å of each other.

17. The method according to claim 16, wherein Asn(Glycan) is a 2-(acetylamino)-deoxy-2-β-glucopyranosyl]-L-asparaginyl residue [Asn(GlcNAc)1].

18. The method according to claim 16, wherein Asn(Glycan) is Asn(GlcNAc)2.

19. The method according to claim 16, wherein Asn(Glycan) is $Asn(GlcNAc)_2Man_1$.

20. The method according to claim 16, wherein the glycan of Asn(Glycan) is paucimannose.

21. The method according to claim 16, wherein said therapeutic chimeric polypeptide is prepared by expressing a nucleic acid sequence that encodes the polypeptide sequence of said chimeric therapeutic polypeptide of a pre-existing therapeutic antibody in a host cell that glycosylates the amino acid sequence Aro-(Xxx)n-(Zzz)p-Asn(Glycan)-Yyy-Thr/Ser (SEQ ID NO:005) when present in a polypeptide sequence expressed therein.

22. The method according to claim 16, wherein said therapeutic chimeric polypeptide is prepared by in vitro peptide synthesis.

23. The method according to claim 22, wherein said in vitro peptide synthesis is by solid phase means.

24. The method according to claim 16, wherein said sequence of four to about seven amino acid residues within said tight turn of said therapeutic polypeptide of a pre-existing therapeutic antibody are glycosylation-free.

25. A pharmaceutical composition comprising a pharmaceutically acceptable diluent having dissolved or dispersed therein an effective amount of a chimeric therapeutic polypeptide of a pre-existing therapeutic antibody according to claim 1 in which